DESIGN# United States Patent
Park et al.

(10) Patent No.: US 12,195,538 B2
(45) Date of Patent: Jan. 14, 2025

(54) ANTI-PD-L1/ANTI-4-1BB BISPECIFIC ANTIBODIES AND USES THEREOF

(71) Applicants: ABL BIO INC., Seongnam-si (KR); I-MAB BIOPHARMA US LIMITED, Rockville, MD (US)

(72) Inventors: Eunyoung Park, Seongnam-si (KR); Yangsoon Lee, Seongnam-si (KR); Hyejin Chung, Seongnam-si (KR); Eunsil Sung, Seongnam-si (KR); Jiseon Yoo, Seongnam-si (KR); Minji Park, Seongnam-si (KR); Yong-Gyu Son, Seongnam-si (KR); Hyoju Choi, Seongnam-si (KR); Eunjung Kim, Seongnam-si (KR); Jaeho Jung, Seongnam-si (KR); Weon-Kyoo You, Seongnam-si (KR); Sang Hoon Lee, Seongnam-si (KR); Lei Fang, Shanghai (CN); Wenqing Jiang, Shanghai (CN)

(73) Assignees: ABL BIO INC., Seongnam-si (KR); I-MAB BIOPHARMA US LIMITED, Rockville, MD (US)

( * ) Notice: Subject to any disclaimer, the term of this patent is extended or adjusted under 35 U.S.C. 154(b) by 823 days.

(21) Appl. No.: 17/298,741

(22) PCT Filed: Feb. 15, 2019

(86) PCT No.: PCT/CN2019/075180
§ 371 (c)(1),
(2) Date: Jun. 1, 2021

(87) PCT Pub. No.: WO2020/107715
PCT Pub. Date: Jun. 4, 2020

(65) Prior Publication Data
US 2022/0056136 A1 Feb. 24, 2022

Related U.S. Application Data

(60) Provisional application No. 62/773,239, filed on Nov. 30, 2018.

(51) Int. Cl.
*C07K 16/28* (2006.01)
*A61P 35/00* (2006.01)
*C07K 16/46* (2006.01)

(52) U.S. Cl.
CPC .......... *C07K 16/2827* (2013.01); *A61P 35/00* (2018.01); *C07K 16/2878* (2013.01); *C07K 16/468* (2013.01); *C07K 2317/21* (2013.01); *C07K 2317/24* (2013.01); *C07K 2317/31* (2013.01); *C07K 2317/34* (2013.01); *C07K 2317/565* (2013.01); *C07K 2317/622* (2013.01); *C07K 2317/64* (2013.01); *C07K 2317/75* (2013.01); *C07K 2317/92* (2013.01)

(58) Field of Classification Search
None
See application file for complete search history.

(56) References Cited

U.S. PATENT DOCUMENTS

2014/0302039 A1* 10/2014 Jeong ............... C07K 16/22
424/138.1
2017/0198050 A1 7/2017 Eckelman et al.

FOREIGN PATENT DOCUMENTS

| CN | 107326014 A | 11/2017 |
|----|-------------|---------|
| WO | 2016/061142 A1 | 4/2016 |
| WO | 2017/215590 A1 | 12/2017 |
| WO | 2017/220988 A1 | 12/2017 |
| WO | 2018/045110 A1 | 3/2018 |

OTHER PUBLICATIONS

Chang-ling Gu, et al., "Bispecific antibody simultaneously targeting PD1 and HER2 inhibits tumor growth via direct tumor cell killing in combination with PD1/PDL1 blockade and HER2 inhibition", Acta Pharmacologica Sinica, 2021, vol. 43, No. 3, 672-680 (9 pages).
Communication dated Sep. 20, 2023 in European Application No. 19 890 398.1.
Elisabeth Pérez-Ruiz, et al., "Anti-CD137 and PD-1/PD-L1 Antibodies En Route toward Clinical Synergy", Clinical Cancer Research, Aug. 8, 2017, pp. 5326-5328, vol. 23, No. 18.
Shu-Juan Zhou, et al., "Strategies for Bispecific Single Chain Antibody in Cancer Immunotherapy", Journal of Cancer, Oct. 17, 2017, pp. 3689-3696, vol. 8.
International Search Report for PCT/CN2019/075180 dated Aug. 27, 2019 [PCT/ISA/210].
Written Opinion for PCT/CN2019/075180 dated Aug. 27, 2019 [PCT/ISA/237].
Alexey Berezhnoy et al., "Converting PD-L1-induced T-lymphocyte Inhibition into CD137-mediated Costimulation via PD-L1 x CD137 Bispecific DART Molecules", MacroGenics, 2018, Presented at the 30th EORTC/AACR/NCI Symposium, Nov. 13-16, 0218, Dublin, Ireland (1 page total).

* cited by examiner

*Primary Examiner* — Daniel E Kolker
*Assistant Examiner* — Maureen Varina Driscoll
(74) *Attorney, Agent, or Firm* — Sughrue Mion, PLLC

(57) ABSTRACT

The present disclosure provides an anti-PD-L1/anti-4-1BB bispecific antibody capable to effectively block the interactions between PD-L1 and its receptor PD-1 and between 4-1BB and its ligand. The bispecific antibody may have high binding affinity to both of a PD-L1 protein and a 4-1BB protein.

10 Claims, 11 Drawing Sheets

Specification includes a Sequence Listing.

DACE

DACE

SEQUENCE LISTING

```
<160> NUMBER OF SEQ ID NOS: 272

<210> SEQ ID NO 1
<211> LENGTH: 5
<212> TYPE: PRT
<213> ORGANISM: Artificial Sequence
<220> FEATURE:
<223> OTHER INFORMATION: VH CDR1 of anti-PD-L1 antibody

<400> SEQUENCE: 1

Ser Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: VH CDR2 of anti-PD-L1 antibody

<400> SEQUENCE: 2

Thr Ile Ser Asp Ala Gly Gly Tyr Ile Tyr Tyr Ser Asp Ser Val Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: VH CDR2 of anti-PD-L1 antibody
```

<400> SEQUENCE: 3

Thr Ile Ser Asp Ala Gly Gly Tyr Ile Tyr Tyr Arg Asp Ser Val Lys
1               5                   10                  15
Gly

<210> SEQ ID NO 4
<211> LENGTH: 10
<212> TYPE: PRT
<213> ORGANISM: Artificial Sequence
<220> FEATURE:
<223> OTHER INFORMATION: VH CDR3 of anti-PD-L1 antibody

<400> SEQUENCE: 4

Glu Phe Gly Lys Arg Tyr Ala Leu Asp Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: VH CDR3 of anti-PD-L1 antibody

<400> SEQUENCE: 5

Glu Leu Pro Trp Arg Tyr Ala Leu Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: VL CDR1 of anti-PD-L1 antibody

<400> SEQUENCE: 6

Lys Ala Ser Gln Asp Val Thr Pro Ala Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: VL CDR2 of anti-PD-L1 antibody

<400> SEQUENCE: 7

Ser Thr Ser Ser Arg Tyr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: VL CDR3 of anti-PD-L1 antibody

<400> SEQUENCE: 8

Gln Gln His Tyr Thr Thr Pro Leu Thr
1               5

<210> SEQ ID NO 9
<211> LENGTH: 255
<212> TYPE: PRT
<213> ORGANISM: Homo sapiens

<400> SEQUENCE: 9

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 10
<211> LENGTH: 5
<212> TYPE: PRT
<213> ORGANISM: Artificial Sequence
<220> FEATURE:
<223> OTHER INFORMATION: VH CDR1 of anti-4-1BB antibody

<400> SEQUENCE: 10

Ser Tyr Asp Met Ser
1               5

<210> SEQ ID NO 11
<211> LENGTH: 5
<212> TYPE: PRT
<213> ORGANISM: Artificial Sequence
<220> FEATURE:
<223> OTHER INFORMATION: VH CDR1 of anti-4-1BB antibody

<400> SEQUENCE: 11

Gly Tyr Asp Met Ser
1               5

<210> SEQ ID NO 12
<211> LENGTH: 17
<212> TYPE: PRT
```

```
<213> ORGANISM: Artificial Sequence
<220> FEATURE:
<223> OTHER INFORMATION: VH CDR2 of anti-4-1BB antibody

<400> SEQUENCE: 12

Trp Ile Ser Tyr Ser Gly Gly Ser Ile Tyr Tyr Ala Asp Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: VH CDR2 of anti-4-1BB antibody

<400> SEQUENCE: 13

Val Ile Tyr Pro Asp Asp Gly Asn Thr Tyr Tyr Ala Asp Ser Val Lys
1               5                   10                  15

Gly

<210> SEQ ID NO 14
<211> LENGTH: 12
<212> TYPE: PRT
<213> ORGANISM: Artificial Sequence
<220> FEATURE:
<223> OTHER INFORMATION: VH CDR3 of anti-4-1BB antibody

<400> SEQUENCE: 14

Asp Gly Gln Arg Asn Ser Met Arg Glu Phe Asp Tyr
1               5                   10

<210> SEQ ID NO 15
<211> LENGTH: 18
<212> TYPE: PRT
<213> ORGANISM: Artificial Sequence
<220> FEATURE:
<223> OTHER INFORMATION: VH CDR3 of anti-4-1BB antibody

<400> SEQUENCE: 15

His Gly Gly Gln Lys Pro Thr Thr Lys Ser Ser Ser Ala Tyr Gly Met
1               5                   10                  15

Asp Gly

<210> SEQ ID NO 16
<211> LENGTH: 12
<212> TYPE: PRT
<213> ORGANISM: Artificial Sequence
<220> FEATURE:
<223> OTHER INFORMATION: VH CDR3 of anti-4-1BB antibody

<400> SEQUENCE: 16

Asp Ala Gln Arg Asn Ser Met Arg Glu Phe Asp Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: VH CDR3 of anti-4-1BB antibody

<400> SEQUENCE: 17

Asp Ala Gln Arg Gln Ser Met Arg Glu Phe Asp Tyr
1               5                   10
```

<210> SEQ ID NO 18
<211> LENGTH: 13
<212> TYPE: PRT
<213> ORGANISM: Artificial Sequence
<220> FEATURE:
<223> OTHER INFORMATION: VL CDR1 of anti-4-1BB antibody

<400> SEQUENCE: 18

Ser Gly Ser Ser Ser Asn Ile Gly Asn Asn Tyr Val Thr
1               5                   10

<210> SEQ ID NO 19
<211> LENGTH: 7
<212> TYPE: PRT
<213> ORGANISM: Artificial Sequence
<220> FEATURE:
<223> OTHER INFORMATION: VL CDR2 of anti-4-1BB antibody

<400> SEQUENCE: 19

Ala Asp Ser His Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: VL CDR3 of anti-4-1BB antibody

<400> SEQUENCE: 20

Ala Thr Trp Asp Tyr Ser Leu Ser Gly Tyr Val
1               5                   10

<210> SEQ ID NO 21
<211> LENGTH: 121
<212> TYPE: PRT
<213> ORGANISM: Artificial Sequence
<220> FEATURE:
<223> OTHER INFORMATION: heavy chain variable region of the anti-4-1BB
      antibody in the bispecific antibody

<400> SEQUENCE: 21

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 22
<211> LENGTH: 127
<212> TYPE: PRT

<213> ORGANISM: Artificial Sequence
<220> FEATURE:
<223> OTHER INFORMATION: heavy chain variable region of the anti-4-1BB
      antibody in the bispecific antibody

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ala Tyr
            100                 105                 110

Gly Met Asp Gly Trp Gly Gln Thr Leu Val Thr Val Ser Ser
            115                 120                 125

<210> SEQ ID NO 23
<211> LENGTH: 121
<212> TYPE: PRT
<213> ORGANISM: Artificial Sequence
<220> FEATURE:
<223> OTHER INFORMATION: heavy chain variable region of the anti-4-1BB
      antibody in the bispecific antibody

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
            115                 120

<210> SEQ ID NO 24
<211> LENGTH: 121
<212> TYPE: PRT
<213> ORGANISM: Artificial Sequence
<220> FEATURE:
<223> OTHER INFORMATION: heavy chain variable region of the anti-4-1BB
      antibody in the bispecific antibody

<400> SEQUENCE: 24

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Ser Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Tyr Trp Gly
            100                 105                 110

Gln Gly Thr Leu Val Thr Val Ser Ser
        115                 120

<210> SEQ ID NO 25
<211> LENGTH: 110
<212> TYPE: PRT
<213> ORGANISM: Artificial Sequence
<220> FEATURE:
<223> OTHER INFORMATION: light chain variable region of the anti-4-1BB
      antibody in the bispecific antibody

<400> SEQUENCE: 25

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 26
<211> LENGTH: 110
<212> TYPE: PRT
<213> ORGANISM: Artificial Sequence
<220> FEATURE:
<223> OTHER INFORMATION: light chain variable region of the anti-4-1BB
      antibody in the bispecific antibody

<400> SEQUENCE: 26

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80
```

-continued

Ser Glu Asp Glu Ala Asp Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 27
<211> LENGTH: 715
<212> TYPE: PRT
<213> ORGANISM: Artificial Sequence
<220> FEATURE:
<223> OTHER INFORMATION: Heavy component of ABLPNB.01

<400> SEQUENCE: 27

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
        515                 520                 525

Gly Ser Lys Ser Gly Thr Ser Ala Ser Leu Ala Ile Ser Gly Leu Arg
    530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
                565                 570                 575

Gly Gly Ser Gly Gly Gly Ser Gly Gly Gly Ser Gly Gly Gly
            580                 585                 590

Gly Ser Glu Val Gln Leu Leu Glu Ser Gly Gly Leu Val Gln Pro
    595                 600                 605

Gly Gly Ser Leu Arg Leu Ser Cys Ala Ala Ser Gly Phe Thr Phe Ser
610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
        675                 680                 685

Tyr Cys Ala Arg Asp Gly Gln Arg Asn Ser Met Arg Glu Phe Asp Tyr
    690                 695                 700

Trp Gly Gln Gly Thr Leu Val Thr Val Ser Ser
705                 710                 715

<210> SEQ ID NO 28
<211> LENGTH: 214
<212> TYPE: PRT
<213> ORGANISM: Artificial Sequence
<220> FEATURE:
```

<223> OTHER INFORMATION: Light component of ABLPNB.01

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 715
<212> TYPE: PRT
<213> ORGANISM: Artificial Sequence
<220> FEATURE:
<223> OTHER INFORMATION: Heavy component of ABLPNB.02

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Ser Gly Gly Gly Gly Ser
    450                 455                 460

Gln Ser Val Leu Thr Gln Pro Pro Ser Ala Ser Gly Thr Pro Gly Gln
465                 470                 475                 480

Arg Val Thr Ile Ser Cys Ser Gly Ser Ser Ser Asn Ile Gly Asn Asn
                485                 490                 495

Tyr Val Thr Trp Tyr Gln Gln Leu Pro Gly Thr Ala Pro Lys Leu Leu
                500                 505                 510

Ile Tyr Ala Asp Ser His Arg Pro Ser Gly Val Pro Asp Arg Phe Ser
            515                 520                 525

Gly Ser Lys Ser Gly Thr Ser Ala Ser Leu Ala Ile Ser Gly Leu Arg
    530                 535                 540
```

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
            565                 570                 575

Gly Gly Ser Gly Gly Gly Gly Ser Gly Gly Gly Gly Ser Gly Gly Gly
        580                 585                 590

Gly Ser Glu Val Gln Leu Leu Glu Ser Gly Gly Gly Leu Val Gln Pro
    595                 600                 605

Gly Gly Ser Leu Arg Leu Ser Cys Ala Ala Ser Gly Phe Thr Phe Ser
        610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
        675                 680                 685

Tyr Cys Ala Arg Asp Ala Gln Arg Asn Ser Met Arg Glu Phe Asp Tyr
690                 695                 700

Trp Gly Gln Gly Thr Leu Val Thr Val Ser Ser
705                 710                 715

<210> SEQ ID NO 30
<211> LENGTH: 214
<212> TYPE: PRT
<213> ORGANISM: Artificial Sequence
<220> FEATURE:
<223> OTHER INFORMATION: Light component of ABLPNB.02

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 31
<211> LENGTH: 721
<212> TYPE: PRT
<213> ORGANISM: Artificial Sequence
<220> FEATURE:
<223> OTHER INFORMATION: Heavy component of ABLPNB.03

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
            450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
            515                 520                 525

Gly Ser Lys Ser Gly Thr Ser Ala Ser Leu Ala Ile Ser Gly Leu Arg
530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
                565                 570                 575

Gly Gly Ser Gly Gly Gly Gly Ser Gly Gly Gly Gly Ser Gly Gly Gly
            580                 585                 590

Gly Ser Glu Val Gln Leu Leu Glu Ser Gly Gly Gly Leu Val Gln Pro
            595                 600                 605

Gly Gly Ser Leu Arg Leu Ser Cys Ala Ala Ser Gly Phe Thr Phe Ser
610                 615                 620

Gly Tyr Asp Met Ser Trp Val Arg Gln Ala Pro Gly Lys Cys Leu Glu
625                 630                 635                 640

Trp Val Ser Val Ile Tyr Pro Asp Asp Gly Asn Thr Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Ala Ala Val Tyr
            675                 680                 685

Tyr Cys Ala Lys His Gly Gly Gln Lys Pro Thr Thr Lys Ser Ser Ser
690                 695                 700

Ala Tyr Gly Met Asp Gly Trp Gly Gln Gly Thr Leu Val Thr Val Ser
705                 710                 715                 720

Ser

<210> SEQ ID NO 32
<211> LENGTH: 214
<212> TYPE: PRT
<213> ORGANISM: Artificial Sequence

```
<220> FEATURE:
<223> OTHER INFORMATION: Light component of ABLPNB.03

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 715
<212> TYPE: PRT
<213> ORGANISM: Artificial Sequence
<220> FEATURE:
<223> OTHER INFORMATION: Heavy component of ABLPNB.04

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
```

```
                115                 120                 125
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Ser Gly Gly Gly Ser Gly Gly Gly Ser
    450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Val Pro Asp Arg Phe Ser
        515                 520                 525

Gly Ser Lys Ser Gly Thr Ser Ala Ser Leu Ala Ile Ser Gly Leu Arg
    530                 535                 540
```

```
Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
            565                 570                 575

Gly Gly Ser Gly Gly Gly Ser Gly Gly Gly Ser Gly Gly Gly
        580                 585                 590

Gly Ser Glu Val Gln Leu Leu Glu Ser Gly Gly Gly Leu Val Gln Pro
        595                 600                 605

Gly Gly Ser Leu Arg Leu Ser Cys Ala Ala Ser Gly Phe Thr Phe Ser
        610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
        675                 680                 685

Tyr Cys Ala Arg Asp Gly Gln Arg Asn Ser Met Arg Glu Phe Asp Tyr
690                 695                 700

Trp Gly Gln Gly Thr Leu Val Thr Val Ser Ser
705                 710                 715

<210> SEQ ID NO 34
<211> LENGTH: 214
<212> TYPE: PRT
<213> ORGANISM: Artificial Sequence
<220> FEATURE:
<223> OTHER INFORMATION: Light component of ABLPNB.04

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 35
<211> LENGTH: 715
<212> TYPE: PRT
<213> ORGANISM: Artificial Sequence
<220> FEATURE:
<223> OTHER INFORMATION: Heavy component of ABLPNB.05

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
        515                 520                 525

Gly Ser Lys Ser Gly Thr Ser Ala Ser Leu Ala Ile Ser Gly Leu Arg
    530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
                565                 570                 575

Gly Gly Ser Gly Gly Gly Ser Gly Gly Gly Ser Gly Gly Gly
            580                 585                 590

Gly Ser Glu Val Gln Leu Leu Glu Ser Gly Gly Gly Leu Val Gln Pro
        595                 600                 605

Gly Gly Ser Leu Arg Leu Ser Cys Ala Ala Ser Gly Phe Thr Phe Ser
    610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
        675                 680                 685

Tyr Cys Ala Arg Asp Ala Gln Arg Asn Ser Met Arg Glu Phe Asp Tyr
    690                 695                 700

Trp Gly Gln Gly Thr Leu Val Thr Val Ser Ser
705                 710                 715

<210> SEQ ID NO 36
<211> LENGTH: 214
<212> TYPE: PRT
<213> ORGANISM: Artificial Sequence
<220> FEATURE:

<223> OTHER INFORMATION: Light component of ABLPNB.05

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 715
<212> TYPE: PRT
<213> ORGANISM: Artificial Sequence
<220> FEATURE:
<223> OTHER INFORMATION: Heavy component of ABLPNB.06

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
    435                 440                 445

Lys Gly Gly Gly Gly Ser Gly Gly Gly Gly Ser Gly Gly Gly Gly Ser
450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Asn Ile Gly Asn Asn
                485                 490                 495

Tyr Val Thr Trp Tyr Gln Gln Leu Pro Gly Thr Ala Pro Lys Leu Leu
                500                 505                 510

Ile Tyr Ala Asp Ser His Arg Pro Ser Gly Val Pro Asp Arg Phe Ser
            515                 520                 525

Gly Ser Lys Ser Gly Thr Ser Ala Ser Leu Ala Ile Ser Gly Leu Arg
    530                 535                 540
```

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
            565                 570                 575

Gly Gly Ser Gly Gly Gly Gly Ser Gly Gly Gly Gly Ser Gly Gly Gly
        580                 585                 590

Gly Ser Glu Val Gln Leu Leu Glu Ser Gly Gly Gly Leu Val Gln Pro
    595                 600                 605

Gly Gly Ser Leu Arg Leu Ser Cys Ala Ala Ser Gly Phe Thr Phe Ser
610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
        675                 680                 685

Tyr Cys Ala Arg Asp Ala Gln Arg Gln Ser Met Arg Glu Phe Asp Tyr
690                 695                 700

Trp Gly Gln Gly Thr Leu Val Thr Val Ser Ser
705                 710                 715

<210> SEQ ID NO 38
<211> LENGTH: 214
<212> TYPE: PRT
<213> ORGANISM: Artificial Sequence
<220> FEATURE:
<223> OTHER INFORMATION: Light component of ABLPNB.06

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

-continued

```
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 39
<211> LENGTH: 715
<212> TYPE: PRT
<213> ORGANISM: Artificial Sequence
<220> FEATURE:
<223> OTHER INFORMATION: Heavy component of ABLPNB.07

<400> SEQUENCE: 39

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met Ser Trp Val Arg Gln Ala Pro Gly Lys Ser Leu Glu Trp Val
        35                  40                  45
Ala Thr Ile Ser Asp Ala Gly Gly Tyr Ile Tyr Tyr Arg Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Asp Glu Asp Thr Ala Val Tyr Ile Cys
                85                  90                  95
Ala Arg Glu Leu Pro Trp Arg Tyr Ala Leu Asp Tyr Trp Gly Gln Gly
            100                 105                 110
Thr Thr Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Ala Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
```

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
            450                 455                 460

Gln Ser Val Leu Thr Gln Pro Pro Ser Ala Ser Gly Thr Pro Gly Gln
465                 470                 475                 480

Arg Val Thr Ile Ser Cys Ser Gly Ser Ser Ser Asn Ile Gly Asn Asn
            485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
            515                 520                 525

Gly Ser Lys Ser Gly Thr Ser Ala Ser Leu Ala Ile Ser Gly Leu Arg
            530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
            565                 570                 575

Gly Gly Ser Gly Gly Gly Gly Ser Gly Gly Gly Gly Ser Gly Gly Gly
            580                 585                 590

Gly Ser Glu Val Gln Leu Leu Glu Ser Gly Gly Gly Leu Val Gln Pro
            595                 600                 605

Gly Gly Ser Leu Arg Leu Ser Cys Ala Ala Ser Gly Phe Thr Phe Ser
            610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
            645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
            675                 680                 685

Tyr Cys Ala Arg Asp Ala Gln Arg Asn Ser Met Arg Glu Phe Asp Tyr
            690                 695                 700

Trp Gly Gln Gly Thr Leu Val Thr Val Ser Ser
705                 710                 715

<210> SEQ ID NO 40
<211> LENGTH: 214
<212> TYPE: PRT
<213> ORGANISM: Artificial Sequence
<220> FEATURE:
<223> OTHER INFORMATION: Light component of ABLPNB.07

-continued

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 715
<212> TYPE: PRT
<213> ORGANISM: Artificial Sequence
<220> FEATURE:
<223> OTHER INFORMATION: Heavy component of ABLPNB.08

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Ala Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Gly Gly Gly Ser Gly Gly Gly Gly Ser Gly Gly Gly Gly Ser
    450                 455                 460
Gln Ser Val Leu Thr Gln Pro Pro Ser Ala Ser Gly Thr Pro Gly Gln
465                 470                 475                 480
Arg Val Thr Ile Ser Cys Ser Gly Ser Ser Ser Asn Ile Gly Asn Asn
                485                 490                 495
Tyr Val Thr Trp Tyr Gln Gln Leu Pro Gly Thr Ala Pro Lys Leu Leu
            500                 505                 510
Ile Tyr Ala Asp Ser His Arg Pro Ser Gly Val Pro Asp Arg Phe Ser
        515                 520                 525
Gly Ser Lys Ser Gly Thr Ser Ala Ser Leu Ala Ile Ser Gly Leu Arg
    530                 535                 540
Ser Glu Asp Glu Ala Asp Tyr Tyr Cys Ala Thr Trp Asp Tyr Ser Leu
```

```
                   545                 550                 555                 560
Ser Gly Tyr Val Phe Gly Cys Gly Thr Lys Leu Thr Val Leu Gly Gly
                565                 570                 575

Gly Gly Ser Gly Gly Gly Ser Gly Gly Gly Ser Gly Gly
            580                 585                 590

Gly Ser Glu Val Gln Leu Leu Glu Ser Gly Gly Leu Val Gln Pro
            595                 600                 605

Gly Gly Ser Leu Arg Leu Ser Cys Ala Ala Ser Gly Phe Thr Phe Ser
610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
            675                 680                 685

Tyr Cys Ala Arg Asp Ala Gln Arg Gln Ser Met Arg Glu Phe Asp Tyr
690                 695                 700

Trp Gly Gln Gly Thr Leu Val Thr Val Ser Ser
705                 710                 715
```

<210> SEQ ID NO 42
<211> LENGTH: 214
<212> TYPE: PRT
<213> ORGANISM: Artificial Sequence
<220> FEATURE:
<223> OTHER INFORMATION: Light component of ABLPNB.08

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
            35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

195                 200                 205
Phe Asn Arg Gly Glu Cys
    210

<210> SEQ ID NO 43
<211> LENGTH: 721
<212> TYPE: PRT
<213> ORGANISM: Artificial Sequence
<220> FEATURE:
<223> OTHER INFORMATION: Heavy component of ABLPNB.09

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr

```
                  340                 345                 350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
        515                 520                 525

Gly Ser Lys Ser Gly Thr Ser Ala Ser Leu Ala Ile Ser Gly Leu Arg
530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
                565                 570                 575

Gly Gly Ser Gly Gly Gly Gly Ser Gly Gly Gly Gly Ser Gly Gly Gly
            580                 585                 590

Gly Ser Glu Val Gln Leu Leu Glu Ser Gly Gly Gly Leu Val Gln Pro
        595                 600                 605

Gly Gly Ser Leu Arg Leu Ser Cys Ala Ala Ser Gly Phe Thr Phe Ser
610                 615                 620

Gly Tyr Asp Met Ser Trp Val Arg Gln Ala Pro Gly Lys Cys Leu Glu
625                 630                 635                 640

Trp Val Ser Val Ile Tyr Pro Asp Asp Gly Asn Thr Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Ala Ala Val Tyr
        675                 680                 685

Tyr Cys Ala Lys His Gly Gly Gln Lys Pro Thr Thr Lys Ser Ser Ser
690                 695                 700

Ala Tyr Gly Met Asp Gly Trp Gly Gln Gly Thr Leu Val Thr Val Ser
705                 710                 715                 720

Ser

<210> SEQ ID NO 44
<211> LENGTH: 214
<212> TYPE: PRT
<213> ORGANISM: Artificial Sequence
<220> FEATURE:
```

<223> OTHER INFORMATION: Light component of ABLPNB.09

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 357
<212> TYPE: DNA
<213> ORGANISM: Artificial Sequence
<220> FEATURE:
<223> OTHER INFORMATION: HL1210-3 VH

<400> SEQUENCE: 45
gaagtgaaac tggtggagtc tgggggagac ttagtgaagc ctggagggtc cctgaaactc      60
tcctgtgcag cctctggatt cactttcagt agctatgaca tgtcttgggt tcgccagact     120
ccggagaaga gtctggagtg ggtcgcaacc attagtgatg gtggtggtta catctactat     180
tcagacagtg tgaaggggcg attaccatc tccagagaca tgccaagaa caacctgtac      240
ctgcaaatga gcagtctgag gtctgaggac acggccttgt atatttgtgc aagagaattt     300
ggtaagcgct atgctttgga ctactgggt caaggaacct cagtcaccgt ctcctca         357

<210> SEQ ID NO 46
<211> LENGTH: 116
<212> TYPE: PRT
<213> ORGANISM: Artificial Sequence
<220> FEATURE:
<223> OTHER INFORMATION: HL1210-3 VH

<400> SEQUENCE: 46

Glu Val Lys Leu Val Glu Ser Gly Gly Asp Leu Val Lys Pro Gly Gly

```
             1               5                  10                 15
            Ser Leu Lys Leu Ser Cys Ala Ala Ser Gly Phe Thr Phe Ser Ser Tyr
                        20                  25                  30

Asp Met Ser Trp Val Arg Gln Thr Pro Glu Lys Ser Leu Glu Trp Val
                        35                  40                  45

Ala Thr Ile Ser Asp Gly Gly Tyr Ile Tyr Tyr Ser Asp Ser Val
                        50                  55                  60

Lys Gly Arg Phe Thr Ile Ser Arg Asp Asn Ala Lys Asn Asn Leu Tyr
             65                  70                  75                  80

Leu Gln Met Ser Ser Leu Arg Ser Glu Asp Thr Ala Leu Tyr Ile Cys
                        85                  90                  95

Ala Arg Glu Phe Gly Lys Arg Tyr Ala Leu Asp Tyr Trp Gly Gln Gly
                        100                 105                 110

Thr Ser Val Thr
                        115

<210> SEQ ID NO 47
<211> LENGTH: 321
<212> TYPE: DNA
<213> ORGANISM: Artificial Sequence
<220> FEATURE:
<223> OTHER INFORMATION: HL1210-3 VL

<400> SEQUENCE: 47
gacattgtga tgacccagtc tcacaaattc atgtccacat cggtaggaga cagggtcagc      60
atctcctgca aggccagtca ggatgtgact cctgctgtcg cctggtatca acagaagcca    120
ggacaatctc ctaaactact gatttactcc acatcctccc ggtacactgg agtccctgat    180
cgcttcactg gcagtggatc tgggacggat ttcacttttca ccatcagcag tgtgcaggct    240
gaagacctgg cagtttatta ctgtcagcaa cattatacta ctccgctcac gttcggtgct    300
gggaccaagc tggagctgaa a                                               321

<210> SEQ ID NO 48
<211> LENGTH: 107
<212> TYPE: PRT
<213> ORGANISM: Artificial Sequence
<220> FEATURE:
<223> OTHER INFORMATION: HL1210-3 VL

<400> SEQUENCE: 48

Asp Ile Val Met Thr Gln Ser His Lys Phe Met Ser Thr Ser Val Gly
             1               5                  10                  15

Asp Arg Val Ser Ile Ser Cys Lys Ala Ser Gln Asp Val Thr Pro Ala
                        20                  25                  30

Val Ala Trp Tyr Gln Gln Lys Pro Gly Gln Ser Pro Lys Leu Leu Ile
                        35                  40                  45

Tyr Ser Thr Ser Ser Arg Tyr Thr Gly Val Pro Asp Arg Phe Thr Gly
                        50                  55                  60

Ser Gly Ser Gly Thr Asp Phe Thr Phe Thr Ile Ser Ser Val Gln Ala
             65                  70                  75                  80

Glu Asp Leu Ala Val Tyr Tyr Cys Gln Gln His Tyr Thr Thr Pro Leu
                        85                  90                  95

Thr Phe Gly Ala Gly Thr Lys Leu Glu Leu Lys
                        100                 105

<210> SEQ ID NO 49
<211> LENGTH: 119
```

```
<212> TYPE: PRT
<213> ORGANISM: Artificial Sequence
<220> FEATURE:
<223> OTHER INFORMATION: HL1210-VH

<400> SEQUENCE: 49

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Ile Cys
                85                  90                  95

Ala Arg Glu Phe Gly Lys Arg Tyr Ala Leu Asp Tyr Trp Gly Gln Gly
            100                 105                 110

Thr Ser Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Hu1210 VH.1

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Hu1210 VH.1a

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
```

```
                    20                  25                  30
Asp Met Ser Trp Val Arg Gln Ala Pro Gly Lys Gly Leu Glu Trp Val
            35                  40                  45

Ala Thr Ile Ser Asp Gly Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115

<210> SEQ ID NO 52
<211> LENGTH: 119
<212> TYPE: PRT
<213> ORGANISM: Artificial Sequence
<220> FEATURE:
<223> OTHER INFORMATION: Hu1210 VH.1b

<400> SEQUENCE: 52

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Gly Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115

<210> SEQ ID NO 53
<211> LENGTH: 119
<212> TYPE: PRT
<213> ORGANISM: Artificial Sequence
<220> FEATURE:
<223> OTHER INFORMATION: Hu1210 VH.2

<400> SEQUENCE: 53

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Ile Arg Gln Ala Pro Gly Lys Gly Leu Glu Trp Val
            35                  40                  45

Ser Thr Ile Ser Asp Gly Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
 65                 70                  75                  80
```

```
Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Hu1210 VH.2a

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Ile Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: Hu1210 VH.2b

<400> SEQUENCE: 55

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 56
```

```
<211> LENGTH: 119
<212> TYPE: PRT
<213> ORGANISM: Artificial Sequence
<220> FEATURE:
<223> OTHER INFORMATION: Hu1210 VH.3

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Gly Tyr Ile Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: Hu1210 VH.3a

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: Hu1210 VH.4

<400> SEQUENCE: 58

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Phe Gly Lys Arg Tyr Ala Leu Asp Tyr Trp Gly Gln Gly
                100                 105                 110

Thr Thr Val Thr Val Ser Ser
            115

<210> SEQ ID NO 59
<211> LENGTH: 119
<212> TYPE: PRT
<213> ORGANISM: Artificial Sequence
<220> FEATURE:
<223> OTHER INFORMATION: Hu1210 VH.4a

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Phe Gly Lys Arg Tyr Ala Leu Asp Tyr Trp Gly Gln Gly
                100                 105                 110

Thr Thr Val Thr Val Ser Ser
            115

<210> SEQ ID NO 60
<211> LENGTH: 119
<212> TYPE: PRT
<213> ORGANISM: Artificial Sequence
<220> FEATURE:
<223> OTHER INFORMATION: Hu1210 VH.4b

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80
```

-continued

```
Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 61
<211> LENGTH: 119
<212> TYPE: PRT
<213> ORGANISM: Artificial Sequence
<220> FEATURE:
<223> OTHER INFORMATION: Hu1210 VH.4c

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Glu Gly Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 62
<211> LENGTH: 119
<212> TYPE: PRT
<213> ORGANISM: Artificial Sequence
<220> FEATURE:
<223> OTHER INFORMATION: Hu1210 VH.4d(H12 VH)

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115
```

```
<210> SEQ ID NO 63
<211> LENGTH: 119
<212> TYPE: PRT
<213> ORGANISM: Artificial Sequence
<220> FEATURE:
<223> OTHER INFORMATION: Hu1210 VH.4e

<400> SEQUENCE: 63
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Val Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

```
<210> SEQ ID NO 64
<211> LENGTH: 119
<212> TYPE: PRT
<213> ORGANISM: Artificial Sequence
<220> FEATURE:
<223> OTHER INFORMATION: Hu1210 VH.5

<400> SEQUENCE: 64
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115

```
<210> SEQ ID NO 65
<211> LENGTH: 119
<212> TYPE: PRT
<213> ORGANISM: Artificial Sequence
<220> FEATURE:
<223> OTHER INFORMATION: HU1210 VH.5a

<400> SEQUENCE: 65
```

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
        20                  25                  30

Asp Met Ser Trp Val Arg Gln Ala Pro Gly Lys Gly Leu Glu Trp Val
            35                  40                  45

Ala Thr Ile Ser Asp Gly Gly Tyr Ile Tyr Tyr Ser Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115
```

<210> SEQ ID NO 66
<211> LENGTH: 119
<212> TYPE: PRT
<213> ORGANISM: Artificial Sequence
<220> FEATURE:
<223> OTHER INFORMATION: HU1210 VH.5b

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Asp Met Ser Trp Val Arg Gln Ala Pro Gly Lys Gly Leu Glu Trp Val
            35                  40                  45

Ala Thr Ile Ser Asp Gly Gly Tyr Ile Tyr Tyr Ser Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115
```

<210> SEQ ID NO 67
<211> LENGTH: 119
<212> TYPE: PRT
<213> ORGANISM: Artificial Sequence
<220> FEATURE:
<223> OTHER INFORMATION: HU1210 VH.5C

<400> SEQUENCE: 67

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Asp Met Ser Trp Val Arg Gln Ala Pro Gly Lys Gly Leu Glu Trp Val
            35                  40                  45

Ala Thr Ile Ser Asp Gly Gly Tyr Ile Tyr Tyr Ser Asp Ser Val
50                      55                  60

Lys Gly Arg Phe Thr Ile Ser Arg Asp Asn Ala Lys Asn Asn Leu Tyr
```

65                  70                  75                  80
Leu Gln Met Asn Ser Leu Arg Ala Glu Asp Thr Ala Val Tyr Ile Cys
                    85                  90                  95

Ala Arg Glu Phe Gly Lys Arg Tyr Ala Leu Asp Tyr Trp Gly Gln Gly
                100                 105                 110

Thr Leu Val Thr Val Ser Ser
            115

<210> SEQ ID NO 68
<211> LENGTH: 119
<212> TYPE: PRT
<213> ORGANISM: Artificial Sequence
<220> FEATURE:
<223> OTHER INFORMATION: HU1210 VH.5d

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Thr Pro Glu Lys Ser Leu Glu Trp Val
            35                  40                  45

Ala Thr Ile Ser Asp Gly Gly Tyr Ile Tyr Tyr Ser Asp Ser Val
        50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Ile Cys
                    85                  90                  95

Ala Arg Glu Phe Gly Lys Arg Tyr Ala Leu Asp Tyr Trp Gly Gln Gly
                100                 105                 110

Thr Leu Val Thr Val Ser Ser
            115

<210> SEQ ID NO 69
<211> LENGTH: 107
<212> TYPE: PRT
<213> ORGANISM: Artificial Sequence
<220> FEATURE:
<223> OTHER INFORMATION: HL1210-VK

<400> SEQUENCE: 69

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Thr Pro Ala
                20                  25                  30

Val Ala Trp Tyr Gln Gln Lys Pro Gly Gln Ser Pro Lys Leu Leu Ile
            35                  40                  45

Tyr Ser Thr Ser Ser Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                    85                  90                  95

Thr Phe Gly Ala Gly Thr Lys Leu Glu Leu Lys
                100                 105

<210> SEQ ID NO 70
<211> LENGTH: 107

```
<212> TYPE: PRT
<213> ORGANISM: Artificial Sequence
<220> FEATURE:
<223> OTHER INFORMATION: Hu1210 VK.1 (H12 VL)

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Hu1210 VK.1a

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ser Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 72
<211> LENGTH: 108
<212> TYPE: PRT
<213> ORGANISM: Artificial Sequence
<220> FEATURE:
<223> OTHER INFORMATION: Hu1210 VK.2

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
```

```
                    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Leu
                     85                  90                  95

Thr Phe Gly Gln Gly Thr Lys Leu Glu Ile Lys Arg
                100                 105
```

<210> SEQ ID NO 73
<211> LENGTH: 108
<212> TYPE: PRT
<213> ORGANISM: Artificial Sequence
<220> FEATURE:
<223> OTHER INFORMATION: Hu1210 VK.2a

<400> SEQUENCE: 73

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Thr Pro Ala
                 20                  25                  30

Val Ala Trp Tyr Gln Gln Lys Pro Gly Lys Ala Pro Lys Leu Leu Ile
             35                  40                  45

Tyr Ser Thr Ser Ser Arg Tyr Thr Gly Val Pro Asp Arg Phe Thr Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Leu
                     85                  90                  95

Thr Phe Gly Gln Gly Thr Lys Leu Glu Ile Lys Arg
                100                 105
```

<210> SEQ ID NO 74
<211> LENGTH: 108
<212> TYPE: PRT
<213> ORGANISM: Artificial Sequence
<220> FEATURE:
<223> OTHER INFORMATION: Hu1210 VK.2b

<400> SEQUENCE: 74

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Thr Pro Ala
                 20                  25                  30

Val Ala Trp Tyr Gln Gln Lys Pro Gly Gln Ser Pro Lys Leu Leu Ile
             35                  40                  45

Tyr Ser Thr Ser Ser Arg Tyr Thr Gly Val Pro Asp Arg Phe Thr Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Leu
                     85                  90                  95

Thr Phe Gly Gln Gly Thr Lys Leu Glu Ile Lys Arg
                100                 105
```

<210> SEQ ID NO 75
<211> LENGTH: 108
<212> TYPE: PRT
<213> ORGANISM: Artificial Sequence
<220> FEATURE:

-continued

<223> OTHER INFORMATION: Hu1210 VK.2c

<400> SEQUENCE: 75

Asp Ile Gln Met Thr Gln Ser Pro Ser Ser Leu Ser Ala Ser Val Gly
1               5                   10                  15

Asp Arg Val Thr Ile Ser Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
                85                  90                  95

Thr Phe Gly Gln Gly Thr Lys Leu Glu Ile Lys Arg
            100                 105

<210> SEQ ID NO 76
<211> LENGTH: 357
<212> TYPE: DNA
<213> ORGANISM: Artificial Sequence
<220> FEATURE:
<223> OTHER INFORMATION: HL1210 VH

<400> SEQUENCE: 76
gaggtgaagc tggtggagag cggcggagat ctggtgaagc ctggcggcag cctgaagctg      60
agctgtgccg ccagcggctt caccttcagc agctacgaca tgagctgggt gaggcagacc     120
cccgagaaga gcctggagtg ggtggccacc atcagcgatg cggcggcta catctactac      180 agcgacagcg tgaagggcag gttcaccatc agcagggaca acgccaagaa caacctgtac     240
ctgcagatga gcagcctgag gagcgaggac accgccctgt acatctgcgc cagggagttc     300
ggcaagaggt acgccctgga ctactgggga cagggcacca gcgtgaccgt gagcagc        357

<210> SEQ ID NO 77
<211> LENGTH: 357
<212> TYPE: DNA
<213> ORGANISM: Artificial Sequence
<220> FEATURE:
<223> OTHER INFORMATION: Hu1210 VH.1

<400> SEQUENCE: 77
gaggtgcagc tggtggagag cggaggagga ctggtgaagc ccggaggcag cctgagactg      60
agctgcgctg ccagcggctt caccttcagc agctacgaca tgagctgggt gagacaggcc     120
cctggcaaag gcctggagtg ggtgagcacc atctccgatg cggcggcta catctattac      180 tccgacagcg tgaagggcag gttcaccatc agcagggaca acgccaagaa cagcctgtac     240
ctgcagatga acagcctgag ggccgaggac accgccgtgt actactgcgc cagggagttc     300
ggcaaaaggt acgccctgga ctactggggc cagggcacaa ccgtgaccgt gagcagc        357

<210> SEQ ID NO 78
<211> LENGTH: 357
<212> TYPE: DNA
<213> ORGANISM: Artificial Sequence
<220> FEATURE:
<223> OTHER INFORMATION: Hu1210 VH.1a

<400> SEQUENCE: 78

```
gaggtgcagc tggtggagag cggaggagga ctggtgaagc ccggaggcag cctgagactg    60
agctgcgctg ccagcggctt caccttcagc agctacgaca tgagctgggt gagacaggcc   120
cctggcaaag gcctggagtg ggtggccacc atctccgatg gcggcggcta catctattac   180
tccgacagcg tgaagggcag gttcaccatc agcagggaca cgccaagaa cagcctgtac   240 ctgcagatga acagcctgag gccgaggac accgccgtgt actactgcgc cagggagttc   300
ggcaaaaggt acgccctgga ctactggggc cagggcacaa ccgtgaccgt gagcagc      357

<210> SEQ ID NO 79
<211> LENGTH: 357
<212> TYPE: DNA
<213> ORGANISM: Artificial Sequence
<220> FEATURE:
<223> OTHER INFORMATION: Hu1210 VH.1b

<400> SEQUENCE: 79
gaggtgcagc tggtggagag cggaggagga ctggtgaagc ccggaggcag cctgagactg    60
agctgcgctg ccagcggctt caccttcagc agctacgaca tgagctgggt gagacaggcc   120
cctggcaaaa gcctggagtg ggtggccacc atctccgatg gcggcggcta catctattac   180
tccgacagcg tgaagggcag gttcaccatc agcagggaca cgccaagaa cagcctgtac   240 ctgcagatga acagcctgag gccgaggac accgccgtgt acatctgcgc cagggagttc   300
ggcaaaaggt acgccctgga ctactggggc cagggcacaa ccgtgaccgt gagcagc      357

<210> SEQ ID NO 80
<211> LENGTH: 357
<212> TYPE: DNA
<213> ORGANISM: Artificial Sequence
<220> FEATURE:
<223> OTHER INFORMATION: Hu1210 VH.2

<400> SEQUENCE: 80
gaggtgcagc tggtggagag cggaggagga ctggtgaagc ccggaggcag cctgagactg    60
agctgcgctg ccagcggctt caccttcagc agctacgaca tgagctggat cagacaggcc   120
cctggcaaag gcctggagtg ggtgagcacc atctccgatg gcggcggcta catctattac   180
tccgacagcg tgaagggcag gttcaccatc agcagggaca cgccaagaa cagcctgtac   240 ctgcagatga acagcctgag gccgaggac accgccgtgt actactgcgc cagggagttc   300
ggcaaaaggt acgccctgga ctactggggc cagggcacaa ccgtgaccgt gagcagc      357

<210> SEQ ID NO 81
<211> LENGTH: 357
<212> TYPE: DNA
<213> ORGANISM: Artificial Sequence
<220> FEATURE:
<223> OTHER INFORMATION: Hu1210 VH.2a

<400> SEQUENCE: 81
gaggtgcagc tggtggagag cggaggagga ctggtgaagc ccggaggcag cctgagactg    60
agctgcgctg ccagcggctt caccttcagc agctacgaca tgagctggat cagacaggcc   120
cctggcaaag gcctggagtg ggtggccacc atctccgatg gcggcggcta catctattac   180
tccgacagcg tgaagggcag gttcaccatc agcagggaca cgccaagaa cagcctgtac   240 ctgcagatga acagcctgag gccgaggac accgccgtgt actactgcgc cagggagttc   300
ggcaaaaggt acgccctgga ctactggggc cagggcacaa ccgtgaccgt gagcagc      357
```

```
<210> SEQ ID NO 82
<211> LENGTH: 357
<212> TYPE: DNA
<213> ORGANISM: Artificial Sequence
<220> FEATURE:
<223> OTHER INFORMATION: Hu1210 VH.2b

<400> SEQUENCE: 82
gaggtgcagc tggtggagag cggaggagga ctggtgaagc ccggaggcag cctgagactg      60
agctgcgctg ccagcggctt caccttcagc agctacgaca tgagctgggt gagacaggcc     120
cctggcaaaa gcctggagtg ggtggccacc atctccgatg cggcggcta  catctattac     180 tccgacagcg tgaagggcag gttcaccatc agcagggaca cgccaagaa  cagcctgtac     240 ctgcagatga acagcctgag ggccgaggac accgccgtgt acatctgcgc cagggagttc     300
ggcaaaaggt acgccctgga ctactggggc cagggcacaa ccgtgaccgt gagcagc        357

<210> SEQ ID NO 83
<211> LENGTH: 357
<212> TYPE: DNA
<213> ORGANISM: Artificial Sequence
<220> FEATURE:
<223> OTHER INFORMATION: Hu1210 VH.3

<400> SEQUENCE: 83
gaggtgcagc tgctggagag cggaggagga ctggtgcaac ccggaggcag cctgagactg      60
agctgcgctg ccagcggctt caccttcagc agctacgaca tgagctgggt gagacaggcc     120
cctggcaaag gcctggagtg ggtgagcacc atctccgatg cggcggcta  catctattac     180 tccgacagcg tgaagggcag gttcaccatc agcagggaca acagcaagaa cacccctgtac    240 ctgcagatga acagcctgag ggccgaggac accgccgtgt actactgcgc cagggagttc     300
ggcaaaaggt acgccctgga ctactggggc cagggcacaa ccgtgaccgt gagcagc        357

<210> SEQ ID NO 84
<211> LENGTH: 357
<212> TYPE: DNA
<213> ORGANISM: Artificial Sequence
<220> FEATURE:
<223> OTHER INFORMATION: Hu1210 VH.3a

<400> SEQUENCE: 84
gaggtgcagc tgctggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgatg cggcggcta  catctattac     180 tccgacagcg tgaagggcag gttcaccatc agcagggaca acagcaagaa cacccctgtac    240 ctgcagatga acagcctgag ggccgaggac accgccgtgt acatctgcgc cagggagttc     300
ggcaaaaggt acgccctgga ctactggggc cagggcacaa ccgtgaccgt gagcagc        357

<210> SEQ ID NO 85
<211> LENGTH: 357
<212> TYPE: DNA
<213> ORGANISM: Artificial Sequence
<220> FEATURE:
<223> OTHER INFORMATION: Hu1210 VH.4

<400> SEQUENCE: 85
gaggtgcagc tggtggagag cggaggagga ctggtgcaac ccggaggcag cctgagactg      60
agctgcgctg ccagcggctt caccttcagc agctacgaca tgagctgggt gagacaggcc     120
```

```
cctggcaaag gcctggagtg ggtgagcacc atctccgatg gcggcggcta catctattac    180
tccgacagcg tgaagggcag gttcaccatc agcagggaca cgccaagaa cagcctgtac     240 ctgcagatga acagcctgag ggatgaggac accgccgtgt actactgcgc cagggagttc   300
ggcaaaaggt acgccctgga ctactggggc cagggcacaa ccgtgaccgt gagcagc       357
```

<210> SEQ ID NO 86
<211> LENGTH: 357
<212> TYPE: DNA
<213> ORGANISM: Artificial Sequence
<220> FEATURE:
<223> OTHER INFORMATION: Hu1210 VH.4a

<400> SEQUENCE: 86

```
gaggtgcagc tggtggagag cggaggagga ctggtgcaac ccggaggcag cctgagactg    60
agctgcgctg ccagcggctt caccttcagc agctacgaca tgagctgggt gagacaggcc   120
cctggcaaag gcctggagtg ggtggccacc atctccgatg gcggcggcta catctattac   180
tccgacagcg tgaagggcag gttcaccatc agcagggaca cgccaagaa cagcctgtac    240 ctgcagatga acagcctgag ggatgaggac accgccgtgt actactgcgc cagggagttc   300
ggcaaaaggt acgccctgga ctactggggc cagggcacaa ccgtgaccgt gagcagc      357
```

<210> SEQ ID NO 87
<211> LENGTH: 357
<212> TYPE: DNA
<213> ORGANISM: Artificial Sequence
<220> FEATURE:
<223> OTHER INFORMATION: Hu1210 VH.4b

<400> SEQUENCE: 87

```
gaggtgcagc tggtggagag cggaggagga ctggtgcaac ccggaggcag cctgagactg    60
agctgcgctg ccagcggctt caccttcagc agctacgaca tgagctgggt gagacaggcc   120
cctggcaaaa gcctggagtg ggtggccacc atctccgatg gcggcggcta catctattac   180
tccgacagcg tgaagggcag gttcaccatc agcagggaca cgccaagaa cagcctgtac    240 ctgcagatga acagcctgag ggatgaggac accgccgtgt acatctgcgc cagggagttc   300
ggcaaaaggt acgccctgga ctactggggc cagggcacaa ccgtgaccgt gagcagc      357
```

<210> SEQ ID NO 88
<211> LENGTH: 357
<212> TYPE: DNA
<213> ORGANISM: Artificial Sequence
<220> FEATURE:
<223> OTHER INFORMATION: Hu1210 VH.4c

<400> SEQUENCE: 88

```
gaggtgcagc tggtggagag cggaggagga ctggtgcaac ccggaggcag cctgagactg    60
agctgcgctg ccagcggctt caccttcagc agctacgaca tgagctgggt gagacaggcc   120
cctggcaaaa gcctggagtg ggtggccacc atctccgaag gcggcggcta catctattac   180
tccgacagcg tgaagggcag gttcaccatc agcagggaca cgccaagaa cagcctgtac    240 ctgcagatga acagcctgag ggatgaggac accgccgtgt acatctgcgc cagggagttc   300
ggcaaaaggt acgccctgga ctactggggc cagggcacaa ccgtgaccgt gagcagc      357
```

<210> SEQ ID NO 89
<211> LENGTH: 357
<212> TYPE: DNA
<213> ORGANISM: Artificial Sequence
<220> FEATURE:
<223> OTHER INFORMATION: Hu1210 VH.4d

<400> SEQUENCE: 89

| | | |
|---|---|---|
| gaggtgcagc tggtggagag cggaggagga ctggtgcaac ccggaggcag cctgagactg | 60 |
| agctgcgctg ccagcggctt caccttcagc agctacgaca tgagctgggt gagacaggcc | 120 |
| cctggcaaaa gcctggagtg ggtggccacc atctccgatg cgggcggcta catctattac | 180 |
| tccgacagcg tgaagggcag gttcaccatc agcagggaca cgccaagaa cagcctgtac | 240 |
| ctgcagatga acagcctgag ggatgaggac accgccgtgt acatctgcgc cagggagttc | 300 |
| ggcaaaaggt acgccctgga ctactggggc cagggcacaa ccgtgaccgt gagcagc | 357 |

<210> SEQ ID NO 90
<211> LENGTH: 357
<212> TYPE: DNA
<213> ORGANISM: Artificial Sequence
<220> FEATURE:
<223> OTHER INFORMATION: Hu1210 VH.4e

<400> SEQUENCE: 90

| | | |
|---|---|---|
| gaggtgcagc tggtggagag cggaggagga ctggtgcaac ccggaggcag cctgagactg | 60 |
| agctgcgctg ccagcggctt caccttcagc agctacgaca tgagctgggt gagacaggcc | 120 |
| cctggcaaaa gcctggagtg ggtggccacc atctccgatg ttggcggcta catctattac | 180 |
| tccgacagcg tgaagggcag gttcaccatc agcagggaca cgccaagaa cagcctgtac | 240 |
| ctgcagatga acagcctgag ggatgaggac accgccgtgt acatctgcgc cagggagttc | 300 |
| ggcaaaaggt acgccctgga ctactggggc cagggcacaa ccgtgaccgt gagcagc | 357 |

<210> SEQ ID NO 91
<211> LENGTH: 357
<212> TYPE: DNA
<213> ORGANISM: Artificial Sequence
<220> FEATURE:
<223> OTHER INFORMATION: Hu1210 VH.5

<400> SEQUENCE: 91

| | | |
|---|---|---|
| gaggtgcagc tggtggagtc cggaggaggc ctggtgcaac ctggaggctc cctgaggctg | 60 |
| tcctgtgccg cttccggctt caccttcagc tcctacgata tgagctgggt gaggcaggct | 120 |
| cctggaaagg gcctggagtg ggtggccacc atctccgacg gaggcggcta catctactac | 180 |
| tccgactccg tgaagggcag gttcaccatc tcccgggaca cgccaagaa ctccctgtac | 240 |
| ctgcagatga actctctcag ggctgaggac accgccgtgt attactgcgc cagggagttt | 300 |
| ggcaagaggt acgccctgga ttactggggc cagggcacac tggtgacagt gagctcc | 357 |

<210> SEQ ID NO 92
<211> LENGTH: 357
<212> TYPE: DNA
<213> ORGANISM: Artificial Sequence
<220> FEATURE:
<223> OTHER INFORMATION: Hu1210 VH.5a

<400> SEQUENCE: 92

| | | |
|---|---|---|
| gaggtgcagc tggtggagtc cggaggaggc ctggtgcaac ctggaggctc cctgaggctg | 60 |
| tcctgtgccg cttccggctt caccttcagc tcctacgata tgagctgggt gaggcaggct | 120 |
| cctggaaagg gcctggagtg ggtggccacc atctccgacg gaggcggcta catctactac | 180 |
| tccgactccg tgaagggcag gttcaccatc tcccgggaca cgccaagaa ctccctgtac | 240 | ctgcagatga actctctcag ggctgaggac accgccgtgt atatctgcgc agggagttt     300 ggcaagaggt acgccctgga ttactggggc cagggcacac tggtgacagt gagctcc      357

<210> SEQ ID NO 93
<211> LENGTH: 357
<212> TYPE: DNA
<213> ORGANISM: Artificial Sequence
<220> FEATURE:
<223> OTHER INFORMATION: Hu1210 VH.5b

<400> SEQUENCE: 93
gaggtgcagc tggtggagtc cggaggaggc ctggtgcaac tggaggctc cctgaggctg    60 tcctgtgccg cttccggctt caccttcagc tcctacgata tgagctgggt gaggcaggct   120
cctggaaagg gcctggagtg ggtggccacc atctccgacg gaggcggcta catctactac   180
tccgactccg tgaagggcag gttcaccatc tcccgggaca acgccaagaa caacctgtac   240
ctgcagatga actctctcag ggctgaggac accgccgtgt atatctgcgc agggagttt    300 ggcaagaggt acgccctgga ttactggggc cagggcacac tggtgacagt gagctcc      357

<210> SEQ ID NO 94
<211> LENGTH: 357
<212> TYPE: DNA
<213> ORGANISM: Artificial Sequence
<220> FEATURE:
<223> OTHER INFORMATION: Hu1210 VH.5c

<400> SEQUENCE: 94
gaggtgcagc tggtggagtc cggaggaggc ctggtgcaac tggaggctc cctgaggctg    60 tcctgtgccg cttccggctt caccttcagc tcctacgata tgagctgggt gaggcagacc   120
cctgagaaga gcctggagtg ggtggccacc atctccgacg gaggcggcta catctactac   180
tccgactccg tgaagggcag gttcaccatc tcccgggaca acgccaagaa caacctgtac   240
ctgcagatga actctctcag ggctgaggac accgccgtgt atatctgcgc agggagttt    300 ggcaagaggt acgccctgga ttactggggc cagggcacac tggtgacagt gagctcc      357

<210> SEQ ID NO 95
<211> LENGTH: 357
<212> TYPE: DNA
<213> ORGANISM: Artificial Sequence
<220> FEATURE:
<223> OTHER INFORMATION: Hu1210 VH.5d

<400> SEQUENCE: 95
gaggtgcagc tggtggagtc cggaggaggc ctggtgcaac tggaggctc cctgaggctg    60 tcctgtgccg cttccggctt caccttcagc tcctacgata tgagctgggt gaggcaggct   120
cctggaaagg gcctggagtg ggtggccacc atctccgacg gaggcggcta catctactac   180
tccgactccg tgaagggcag gttcaccatc tcccgggaca acgccaagaa ctccctgtac   240
ctgcagatga actctctcag ggctgaggac accgccgtgt atatctgcgc agggagttt    300 ggcaagaggt acgccctgga ttactggggc cagggcacaa ccgtgacagt gagctcc      357

<210> SEQ ID NO 96
<211> LENGTH: 321
<212> TYPE: DNA
<213> ORGANISM: Artificial Sequence
<220> FEATURE:
<223> OTHER INFORMATION: HL1210 VK

<400> SEQUENCE: 96

```
gacatcgtga tgacccagag ccacaagttc atgagcacca gcgtgggcga tagggtgagc      60
atcagctgca aggccagcca ggatgtgacc cctgccgtgg cctggtacca gcagaagccc     120
ggccagagcc ccaagctgct gatctacagc accagcagca ggtacaccgg cgtgcccgac     180
aggttcacag gaagcggcag cggcaccgac ttcaccttca ccatcagcag cgtgcaggcc     240
gaggacctgg ccgtgtacta ctgccagcag cactacacca cccctctgac cttcggcgcc     300
ggcaccaagc tggagctgaa g                                               321
```

<210> SEQ ID NO 97
<211> LENGTH: 321
<212> TYPE: DNA
<213> ORGANISM: Artificial Sequence
<220> FEATURE:
<223> OTHER INFORMATION: Hu1210 VK.1

<400> SEQUENCE: 97

```
gacatccaga tgacccagag ccctagcagc ctgagcgcta gcgtgggcga cagggtgacc      60
atcacctgca aggccagcca ggatgtgacc cctgccgtgg cctggtacca gcagaagccc     120
ggcaaggccc ccaagctgct gatctacagc accagcagca ggtacaccgg cgtgcccagc     180
aggtttagcg gaagcggcag cggcaccgac ttcaccttca ccatcagcag cctgcagccc     240
gaggacatcg ccacctacta ctgccagcag cactacacca cccctctgac cttcggccag     300
ggcaccaagc tggagatcaa g                                               321
```

<210> SEQ ID NO 98
<211> LENGTH: 321
<212> TYPE: DNA
<213> ORGANISM: Artificial Sequence
<220> FEATURE:
<223> OTHER INFORMATION: Hu1210 VK.1a

<400> SEQUENCE: 98

```
gacatccaga tgacccagag ccctagcagc ctgagcgcta gcgtgggcga cagggtgacc      60
atcacctgca aggccagcca ggatgtgacc cctgccgtgg cctggtacca gcagaagccc     120
ggcaagtccc ccaagctgct gatctacagc accagcagca ggtacaccgg cgtgcccagc     180
aggtttagcg gaagcggcag cggcaccgac ttcaccttca ccatcagcag cctgcagccc     240
gaggacatcg ccacctacta ctgccagcag cactacacca cccctctgac cttcggccag     300
ggcaccaagc tggagatcaa g                                               321
```

<210> SEQ ID NO 99
<211> LENGTH: 324
<212> TYPE: DNA
<213> ORGANISM: Artificial Sequence
<220> FEATURE:
<223> OTHER INFORMATION: Hu1210 VK.2

<400> SEQUENCE: 99

```
gacattcaga tgacccagtc ccctagcagc ctgtccgctt ccgtgggcga cagggtgacc      60
atcacctgca aggccagcca ggacgtgaca cctgctgtgg cctggtatca acagaagcct     120
ggcaaggctc ctaagctcct gatctacagc acatcctccc ggtacaccgg agtgccctcc     180
aggtttagcg gcagcggctc cggcaccgat ttcaccctga ccatttcctc cctgcagccc     240
gaggacttcg ccacctacta ctgccagcag cactacacca caccccctgac cttcggccag     300 ggcaccaagc tggagatcaa gcgg                                            324
```

<210> SEQ ID NO 100
<211> LENGTH: 324
<212> TYPE: DNA
<213> ORGANISM: Artificial Sequence
<220> FEATURE:
<223> OTHER INFORMATION: Hu1210 VK.2a

<400> SEQUENCE: 100

```
gacattcaga tgacccagtc ccctagcagc ctgtccgctt ccgtgggcga cagggtgacc      60
atcacctgca aggccagcca ggacgtgaca cctgctgtgg cctggtatca acagaagcct     120
ggcaaggctc ctaagctcct gatctacagc acatcctccc ggtacaccgg agtgcccgac     180
aggtttaccg gcagcggctc cggcaccgat ttcaccctga ccatttcctc cctgcagccc     240
gaggacttcg ccacctacta ctgccagcag cactacacca caccctgac cttcggccag      300
ggcaccaagc tggagatcaa gcgg                                             324
```

<210> SEQ ID NO 101
<211> LENGTH: 324
<212> TYPE: DNA
<213> ORGANISM: Artificial Sequence
<220> FEATURE:
<223> OTHER INFORMATION: Hu1210 VK.2b

<400> SEQUENCE: 101

```
gacattcaga tgacccagtc ccctagcagc ctgtccgctt ccgtgggcga cagggtgacc      60
atcacctgca aggccagcca ggacgtgaca cctgctgtgg cctggtatca acagaagcct     120
ggccagagcc ctaagctcct gatctacagc acatcctccc ggtacaccgg agtgcccgac     180
aggtttaccg gcagcggctc cggcaccgat ttcaccctga ccatttcctc cctgcagccc     240
gaggacttcg ccacctacta ctgccagcag cactacacca caccctgac cttcggccag      300
ggcaccaagc tggagatcaa gcgg                                             324
```

<210> SEQ ID NO 102
<211> LENGTH: 324
<212> TYPE: DNA
<213> ORGANISM: Artificial Sequence
<220> FEATURE:
<223> OTHER INFORMATION: Hu1210 VK.2c

<400> SEQUENCE: 102

```
gacattcaga tgacccagtc ccctagcagc ctgtccgctt ccgtgggcga cagggtgacc      60
atcagctgca aggccagcca ggacgtgaca cctgctgtgg cctggtatca acagaagcct     120
ggccagagcc ctaagctcct gatctacagc acatcctccc ggtacaccgg agtgcccgac     180
aggtttaccg gcagcggctc cggcaccgat ttcaccctga ccatttcctc cctgcagccc     240
gaggacttcg ccacctacta ctgccagcag cactacacca caccctgac cttcggccag      300
ggcaccaagc tggagatcaa gcgg                                             324
```

<210> SEQ ID NO 103
<211> LENGTH: 119
<212> TYPE: PRT
<213> ORGANISM: Artificial Sequence
<220> FEATURE:
<223> OTHER INFORMATION: Heavy chain variable region of H12

<400> SEQUENCE: 103

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115

<210> SEQ ID NO 104
<211> LENGTH: 119
<212> TYPE: PRT
<213> ORGANISM: Artificial Sequence
<220> FEATURE:
<223> OTHER INFORMATION: Heavy chain variable region of B6

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser
            115

<210> SEQ ID NO 105
<211> LENGTH: 107
<212> TYPE: PRT
<213> ORGANISM: Artificial Sequence
<220> FEATURE:
<223> OTHER INFORMATION: Light chain variable region of H12

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
            35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Light chain variable region of B6

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 107
<211> LENGTH: 5
<212> TYPE: PRT
<213> ORGANISM: Artificial Sequence
<220> FEATURE:
<223> OTHER INFORMATION: WT of CDR-H1

<400> SEQUENCE: 107

Ser Tyr Asp Met Ser
1               5

<210> SEQ ID NO 108
<211> LENGTH: 5
<212> TYPE: PRT
<213> ORGANISM: Artificial Sequence
<220> FEATURE:
<223> OTHER INFORMATION: B3 of CDR-H1

<400> SEQUENCE: 108

Ser Tyr Asp Met Ser
1               5

<210> SEQ ID NO 109
<211> LENGTH: 5
<212> TYPE: PRT
<213> ORGANISM: Artificial Sequence
<220> FEATURE:
<223> OTHER INFORMATION: C4 of CDR-H1

<400> SEQUENCE: 109

Ser Tyr Asp Met Ser
1               5

<210> SEQ ID NO 110

```
<211> LENGTH: 5
<212> TYPE: PRT
<213> ORGANISM: Artificial Sequence
<220> FEATURE:
<223> OTHER INFORMATION: B1 of CDR-H1

<400> SEQUENCE: 110

Ser Tyr Asp Met Ser
1               5

<210> SEQ ID NO 111
<211> LENGTH: 5
<212> TYPE: PRT
<213> ORGANISM: Artificial Sequence
<220> FEATURE:
<223> OTHER INFORMATION: B6 of CDR-H1

<400> SEQUENCE: 111

Ser Tyr Asp Met Ser
1               5

<210> SEQ ID NO 112
<211> LENGTH: 5
<212> TYPE: PRT
<213> ORGANISM: Artificial Sequence
<220> FEATURE:
<223> OTHER INFORMATION: C3 of CDR-H1

<400> SEQUENCE: 112

Ser Tyr Asp Met Ser
1               5

<210> SEQ ID NO 113
<211> LENGTH: 5
<212> TYPE: PRT
<213> ORGANISM: Artificial Sequence
<220> FEATURE:
<223> OTHER INFORMATION: C6 of CDR-H1

<400> SEQUENCE: 113

Ser Tyr Asp Met Ser
1               5

<210> SEQ ID NO 114
<211> LENGTH: 5
<212> TYPE: PRT
<213> ORGANISM: Artificial Sequence
<220> FEATURE:
<223> OTHER INFORMATION: A1 of CDR-H1

<400> SEQUENCE: 114

Ser Tyr Asp Met Ser
1               5

<210> SEQ ID NO 115
<211> LENGTH: 5
<212> TYPE: PRT
<213> ORGANISM: Artificial Sequence
<220> FEATURE:
<223> OTHER INFORMATION: A2 of CDR-H1

<400> SEQUENCE: 115

Ser Tyr Asp Met Ser
1               5

<210> SEQ ID NO 116
<211> LENGTH: 5
```

```
<212> TYPE: PRT
<213> ORGANISM: Artificial Sequence
<220> FEATURE:
<223> OTHER INFORMATION: A3 of CDR-H1

<400> SEQUENCE: 116

Ser Tyr Asp Met Ser
1               5

<210> SEQ ID NO 117
<211> LENGTH: 17
<212> TYPE: PRT
<213> ORGANISM: Artificial Sequence
<220> FEATURE:
<223> OTHER INFORMATION: WT of CDR-H2

<400> SEQUENCE: 117

Thr Ile Ser Asp Ala Gly Gly Tyr Ile Tyr Tyr Ser Asp Ser Val Lys
1               5                  10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: B3 of CDR-H2

<400> SEQUENCE: 118

Thr Ile Ser Asp Ala Gly Gly Tyr Ile Tyr Tyr Arg Asp Ser Val Lys
1               5                  10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: C4 of CDR-H2

<400> SEQUENCE: 119

Thr Ile Ser Asp Ala Gly Gly Tyr Ile Tyr Tyr Arg Asp Ser Val Lys
1               5                  10                  15

Gly

<210> SEQ ID NO 120
<211> LENGTH: 17
<212> TYPE: PRT
<213> ORGANISM: Artificial Sequence
<220> FEATURE:
<223> OTHER INFORMATION: B1 of CDR-H2

<400> SEQUENCE: 120

Thr Ile Ser Asp Ala Gly Gly Tyr Ile Tyr Tyr Arg Asp Ser Val Lys
1               5                  10                  15

Gly

<210> SEQ ID NO 121
<211> LENGTH: 17
<212> TYPE: PRT
<213> ORGANISM: Artificial Sequence
<220> FEATURE:
<223> OTHER INFORMATION: B6 of CDR-H2

<400> SEQUENCE: 121
```

Thr Ile Ser Asp Ala Gly Gly Tyr Ile Tyr Tyr Arg Asp Ser Val Lys
1               5                   10                  15

Gly

<210> SEQ ID NO 122
<211> LENGTH: 17
<212> TYPE: PRT
<213> ORGANISM: Artificial Sequence
<220> FEATURE:
<223> OTHER INFORMATION: C3 of CDR-H2

<400> SEQUENCE: 122

Thr Ile Ser Asp Ala Gly Gly Tyr Ile Tyr Tyr Arg Asp Ser Val Lys
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: C6 of CDR-H2

<400> SEQUENCE: 123

Thr Ile Ser Asp Ala Gly Gly Tyr Ile Tyr Tyr Arg Asp Ser Val Lys
1               5                   10                  15

Gly

<210> SEQ ID NO 124
<211> LENGTH: 17
<212> TYPE: PRT
<213> ORGANISM: Artificial Sequence
<220> FEATURE:
<223> OTHER INFORMATION: A1 of CDR-H2

<400> SEQUENCE: 124

Thr Ile Ser Asp Ala Gly Gly Tyr Ile Tyr Tyr Arg Asp Ser Val Lys
1               5                   10                  15

Gly

<210> SEQ ID NO 125
<211> LENGTH: 17
<212> TYPE: PRT
<213> ORGANISM: Artificial Sequence
<220> FEATURE:
<223> OTHER INFORMATION: A2 of CDR-H2

<400> SEQUENCE: 125

Thr Ile Ser Asp Ala Gly Gly Tyr Ile Tyr Tyr Arg Asp Ser Val Lys
1               5                   10                  15

Gly

<210> SEQ ID NO 126
<211> LENGTH: 17
<212> TYPE: PRT
<213> ORGANISM: Artificial Sequence
<220> FEATURE:
<223> OTHER INFORMATION: A3 of CDR-H2

<400> SEQUENCE: 126

Thr Ile Ser Asp Ala Gly Gly Tyr Ile Tyr Tyr Arg Asp Ser Val Lys
1               5                   10                  15

Gly

```
<210> SEQ ID NO 127
<211> LENGTH: 10
<212> TYPE: PRT
<213> ORGANISM: Artificial Sequence
<220> FEATURE:
<223> OTHER INFORMATION: WT of CDR-H3

<400> SEQUENCE: 127

Glu Phe Gly Lys Arg Tyr Ala Leu Asp Tyr
1               5                   10

<210> SEQ ID NO 128
<211> LENGTH: 10
<212> TYPE: PRT
<213> ORGANISM: Artificial Sequence
<220> FEATURE:
<223> OTHER INFORMATION: B3 of CDR-H3

<400> SEQUENCE: 128

Glu Phe Gly Lys Arg Tyr Ala Leu Asp Tyr
1               5                   10

<210> SEQ ID NO 129
<211> LENGTH: 10
<212> TYPE: PRT
<213> ORGANISM: Artificial Sequence
<220> FEATURE:
<223> OTHER INFORMATION: C4 of CDR-H3

<400> SEQUENCE: 129

Glu Phe Gly Lys Arg Tyr Ala Leu Asp Ser
1               5                   10

<210> SEQ ID NO 130
<211> LENGTH: 10
<212> TYPE: PRT
<213> ORGANISM: Artificial Sequence
<220> FEATURE:
<223> OTHER INFORMATION: B1 of CDR-H3

<400> SEQUENCE: 130

Glu Ile Phe Asn Arg Tyr Ala Leu Asp Tyr
1               5                   10

<210> SEQ ID NO 131
<211> LENGTH: 10
<212> TYPE: PRT
<213> ORGANISM: Artificial Sequence
<220> FEATURE:
<223> OTHER INFORMATION: B6 of CDR-H3

<400> SEQUENCE: 131

Glu Leu Pro Trp Arg Tyr Ala Leu Asp Tyr
1               5                   10

<210> SEQ ID NO 132
<211> LENGTH: 10
<212> TYPE: PRT
<213> ORGANISM: Artificial Sequence
<220> FEATURE:
<223> OTHER INFORMATION: C3 of CDR-H3

<400> SEQUENCE: 132

Glu Leu His Phe Arg Tyr Ala Leu Asp Tyr
1               5                   10
```

```
<210> SEQ ID NO 133
<211> LENGTH: 10
<212> TYPE: PRT
<213> ORGANISM: Artificial Sequence
<220> FEATURE:
<223> OTHER INFORMATION: C6 of CDR-H3

<400> SEQUENCE: 133

Glu Leu Tyr Phe Arg Tyr Ala Leu Asp Tyr
1               5                   10

<210> SEQ ID NO 134
<211> LENGTH: 10
<212> TYPE: PRT
<213> ORGANISM: Artificial Sequence
<220> FEATURE:
<223> OTHER INFORMATION: A1 of CDR-H3

<400> SEQUENCE: 134

Glu Leu Leu His Arg Tyr Ala Leu Asp Tyr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: A2 of CDR-H3

<400> SEQUENCE: 135

Glu Leu Arg Gly Arg Tyr Ala Leu Asp Tyr
1               5                   10

<210> SEQ ID NO 136
<211> LENGTH: 10
<212> TYPE: PRT
<213> ORGANISM: Artificial Sequence
<220> FEATURE:
<223> OTHER INFORMATION: A3 of CDR-H3

<400> SEQUENCE: 136

Glu Phe Gly Lys Arg Tyr Ala Leu Asp Tyr
1               5                   10

<210> SEQ ID NO 137
<211> LENGTH: 11
<212> TYPE: PRT
<213> ORGANISM: Artificial Sequence
<220> FEATURE:
<223> OTHER INFORMATION: WT of CDR-L1

<400> SEQUENCE: 137

Lys Ala Ser Gln Asp Val Thr Pro Ala Val Ala
1               5                   10

<210> SEQ ID NO 138
<211> LENGTH: 11
<212> TYPE: PRT
<213> ORGANISM: Artificial Sequence
<220> FEATURE:
<223> OTHER INFORMATION: B3 of CDR-L1

<400> SEQUENCE: 138

Lys Ala Lys Gln Asp Val Thr Pro Ala Val Ala
1               5                   10
```

```
<210> SEQ ID NO 139
<211> LENGTH: 11
<212> TYPE: PRT
<213> ORGANISM: Artificial Sequence
<220> FEATURE:
<223> OTHER INFORMATION: C4 of CDR-L1

<400> SEQUENCE: 139

Lys Ala Ser Gln Asp Val Trp Pro Ala Val Ala
1               5                   10

<210> SEQ ID NO 140
<211> LENGTH: 11
<212> TYPE: PRT
<213> ORGANISM: Artificial Sequence
<220> FEATURE:
<223> OTHER INFORMATION: B1 of CDR-L1

<400> SEQUENCE: 140

Lys Ala Ser Gln Asp Val Thr Pro Ala Val Ala
1               5                   10

<210> SEQ ID NO 141
<211> LENGTH: 11
<212> TYPE: PRT
<213> ORGANISM: Artificial Sequence
<220> FEATURE:
<223> OTHER INFORMATION: B6 of CDR-L1

<400> SEQUENCE: 141

Lys Ala Ser Gln Asp Val Thr Pro Ala Val Ala
1               5                   10

<210> SEQ ID NO 142
<211> LENGTH: 11
<212> TYPE: PRT
<213> ORGANISM: Artificial Sequence
<220> FEATURE:
<223> OTHER INFORMATION: C3 of CDR-L1

<400> SEQUENCE: 142

Lys Ala Ser Gln Asp Val Thr Pro Ala Val Ala
1               5                   10

<210> SEQ ID NO 143
<211> LENGTH: 11
<212> TYPE: PRT
<213> ORGANISM: Artificial Sequence
<220> FEATURE:
<223> OTHER INFORMATION: C6 of CDR-L1

<400> SEQUENCE: 143

Lys Ala Ser Gln Asp Val Thr Pro Ala Val Ala
1               5                   10

<210> SEQ ID NO 144
<211> LENGTH: 11
<212> TYPE: PRT
<213> ORGANISM: Artificial Sequence
<220> FEATURE:
<223> OTHER INFORMATION: A1 of CDR-L1

<400> SEQUENCE: 144

Lys Ala Ser Gln Asp Val Thr Pro Ala Val Ala
1               5                   10
```

```
<210> SEQ ID NO 145
<211> LENGTH: 11
<212> TYPE: PRT
<213> ORGANISM: Artificial Sequence
<220> FEATURE:
<223> OTHER INFORMATION: A2 of CDR-L1

<400> SEQUENCE: 145

Lys Ala Ser Gln Asp Val Thr Pro Ala Val Ala
1               5                   10

<210> SEQ ID NO 146
<211> LENGTH: 11
<212> TYPE: PRT
<213> ORGANISM: Artificial Sequence
<220> FEATURE:
<223> OTHER INFORMATION: A3 of CDR-L1

<400> SEQUENCE: 146

Lys Ala Ser Gln Asp Val Thr Pro Ala Val Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: WT of CDR-L2

<400> SEQUENCE: 147

Ser Thr Ser Ser Arg Tyr Thr
1               5

<210> SEQ ID NO 148
<211> LENGTH: 7
<212> TYPE: PRT
<213> ORGANISM: Artificial Sequence
<220> FEATURE:
<223> OTHER INFORMATION: B3 of CDR-L2

<400> SEQUENCE: 148

Ser Thr Ser Ser Arg Tyr Thr
1               5

<210> SEQ ID NO 149
<211> LENGTH: 7
<212> TYPE: PRT
<213> ORGANISM: Artificial Sequence
<220> FEATURE:
<223> OTHER INFORMATION: C4 of CDR-L2

<400> SEQUENCE: 149

Ser Thr Ser Ser Arg Tyr Thr
1               5

<210> SEQ ID NO 150
<211> LENGTH: 7
<212> TYPE: PRT
<213> ORGANISM: Artificial Sequence
<220> FEATURE:
<223> OTHER INFORMATION: B1 of CDR-L2

<400> SEQUENCE: 150

Ser Thr Ser Ser Arg Tyr Thr
1               5

<210> SEQ ID NO 151
```

```
<211> LENGTH: 7
<212> TYPE: PRT
<213> ORGANISM: Artificial Sequence
<220> FEATURE:
<223> OTHER INFORMATION: B6 of CDR-L2

<400> SEQUENCE: 151

Ser Thr Ser Ser Arg Tyr Thr
1               5

<210> SEQ ID NO 152
<211> LENGTH: 7
<212> TYPE: PRT
<213> ORGANISM: Artificial Sequence
<220> FEATURE:
<223> OTHER INFORMATION: C3 of CDR-L2

<400> SEQUENCE: 152

Ser Thr Ser Ser Arg Tyr Thr
1               5

<210> SEQ ID NO 153
<211> LENGTH: 7
<212> TYPE: PRT
<213> ORGANISM: Artificial Sequence
<220> FEATURE:
<223> OTHER INFORMATION: C6 of CDR-L2

<400> SEQUENCE: 153

Ser Thr Ser Ser Arg Tyr Thr
1               5

<210> SEQ ID NO 154
<211> LENGTH: 7
<212> TYPE: PRT
<213> ORGANISM: Artificial Sequence
<220> FEATURE:
<223> OTHER INFORMATION: A1 of CDR-L2

<400> SEQUENCE: 154

Ser Thr Ser Ser Arg Tyr Thr
1               5

<210> SEQ ID NO 155
<211> LENGTH: 7
<212> TYPE: PRT
<213> ORGANISM: Artificial Sequence
<220> FEATURE:
<223> OTHER INFORMATION: A2 of CDR-L2

<400> SEQUENCE: 155

Ser Thr Ser Ser Arg Tyr Thr
1               5

<210> SEQ ID NO 156
<211> LENGTH: 7
<212> TYPE: PRT
<213> ORGANISM: Artificial Sequence
<220> FEATURE:
<223> OTHER INFORMATION: A3 of CDR-L2

<400> SEQUENCE: 156

Ser Thr Ser Ser Arg Tyr Thr
1               5

<210> SEQ ID NO 157
<211> LENGTH: 9
```

```
<212> TYPE: PRT
<213> ORGANISM: Artificial Sequence
<220> FEATURE:
<223> OTHER INFORMATION: WT of CDR-L3

<400> SEQUENCE: 157

Gln Gln His Tyr Thr Thr Pro Leu Thr
1               5

<210> SEQ ID NO 158
<211> LENGTH: 9
<212> TYPE: PRT
<213> ORGANISM: Artificial Sequence
<220> FEATURE:
<223> OTHER INFORMATION: B3 of CDR-L3

<400> SEQUENCE: 158

Met Gln His Tyr Thr Thr Pro Leu Thr
1               5

<210> SEQ ID NO 159
<211> LENGTH: 9
<212> TYPE: PRT
<213> ORGANISM: Artificial Sequence
<220> FEATURE:
<223> OTHER INFORMATION: C4 of CDR-L3

<400> SEQUENCE: 159

Gln Gln His Ser Thr Thr Pro Leu Thr
1               5

<210> SEQ ID NO 160
<211> LENGTH: 9
<212> TYPE: PRT
<213> ORGANISM: Artificial Sequence
<220> FEATURE:
<223> OTHER INFORMATION: B1 of CDR-L3

<400> SEQUENCE: 160

Gln Gln His Tyr Thr Thr Pro Leu Thr
1               5

<210> SEQ ID NO 161
<211> LENGTH: 9
<212> TYPE: PRT
<213> ORGANISM: Artificial Sequence
<220> FEATURE:
<223> OTHER INFORMATION: B6 of CDR-L3

<400> SEQUENCE: 161

Gln Gln His Tyr Thr Thr Pro Leu Thr
1               5

<210> SEQ ID NO 162
<211> LENGTH: 9
<212> TYPE: PRT
<213> ORGANISM: Artificial Sequence
<220> FEATURE:
<223> OTHER INFORMATION: C3 of CDR-L3

<400> SEQUENCE: 162

Gln Gln His Tyr Thr Thr Pro Leu Thr
1               5

<210> SEQ ID NO 163
<211> LENGTH: 9
<212> TYPE: PRT
```

```
<213> ORGANISM: Artificial Sequence
<220> FEATURE:
<223> OTHER INFORMATION: C6 of CDR-L3

<400> SEQUENCE: 163

Gln Gln His Tyr Thr Thr Pro Leu Thr
1               5

<210> SEQ ID NO 164
<211> LENGTH: 9
<212> TYPE: PRT
<213> ORGANISM: Artificial Sequence
<220> FEATURE:
<223> OTHER INFORMATION: A1 of CDR-L3

<400> SEQUENCE: 164

Gln Gln His Tyr Thr Thr Pro Leu Thr
1               5

<210> SEQ ID NO 165
<211> LENGTH: 9
<212> TYPE: PRT
<213> ORGANISM: Artificial Sequence
<220> FEATURE:
<223> OTHER INFORMATION: A2 of CDR-L3

<400> SEQUENCE: 165

Gln Gln His Tyr Thr Thr Pro Leu Thr
1               5

<210> SEQ ID NO 166
<211> LENGTH: 9
<212> TYPE: PRT
<213> ORGANISM: Artificial Sequence
<220> FEATURE:
<223> OTHER INFORMATION: A3 of CDR-L3

<400> SEQUENCE: 166

Gln Gln His Ser Asp Ala Pro Leu Thr
1               5

<210> SEQ ID NO 167
<211> LENGTH: 119
<212> TYPE: PRT
<213> ORGANISM: Artificial Sequence
<220> FEATURE:
<223> OTHER INFORMATION: WT-VH

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110
```

```
Thr Thr Val Thr Val Ser Ser
        115

<210> SEQ ID NO 168
<211> LENGTH: 107
<212> TYPE: PRT
<213> ORGANISM: Artificial Sequence
<220> FEATURE:
<223> OTHER INFORMATION: WT- VK

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 169
<211> LENGTH: 119
<212> TYPE: PRT
<213> ORGANISM: Artificial Sequence
<220> FEATURE:
<223> OTHER INFORMATION: B3-VH

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 170
<211> LENGTH: 107
<212> TYPE: PRT
<213> ORGANISM: Artificial Sequence
<220> FEATURE:
<223> OTHER INFORMATION: B3-VK

<400> SEQUENCE: 170

Asp Ile Gln Met Thr Gln Ser Pro Ser Ser Leu Ser Ala Ser Val Gly
```

```
              1               5                  10                 15
Asp Arg Val Thr Ile Thr Cys Lys Ala Lys Gln Asp Val Thr Pro Ala
                20                  25                 30

Val Ala Trp Tyr Gln Gln Lys Pro Gly Lys Ala Pro Lys Leu Leu Ile
            35                  40                 45

Tyr Ser Thr Ser Ser Arg Tyr Thr Gly Val Pro Ser Arg Phe Ser Gly
        50                  55                 60

Ser Gly Ser Gly Thr Asp Phe Thr Phe Thr Ile Ser Ser Leu Gln Pro
65                  70                  75                 80

Glu Asp Ile Ala Thr Tyr Tyr Cys Met Gln His Tyr Thr Thr Pro Leu
                85                  90                 95

Thr Phe Gly Gln Gly Thr Lys Leu Glu Ile Lys
                100                 105
```

<210> SEQ ID NO 171
<211> LENGTH: 119
<212> TYPE: PRT
<213> ORGANISM: Artificial Sequence
<220> FEATURE:
<223> OTHER INFORMATION: C4-VH

<400> SEQUENCE: 171

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Ser Trp Gly Gln Gly
                100                 105                 110

Thr Thr Val Thr Val Ser Ser
        115
```

<210> SEQ ID NO 172
<211> LENGTH: 107
<212> TYPE: PRT
<213> ORGANISM: Artificial Sequence
<220> FEATURE:
<223> OTHER INFORMATION: C4-VK

<400> SEQUENCE: 172

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Trp Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln His Ser Thr Thr Pro Leu
                85                  90                  95

Thr Phe Gly Gln Gly Thr Lys Leu Glu Ile Lys
            100                 105

<210> SEQ ID NO 173
<211> LENGTH: 119
<212> TYPE: PRT
<213> ORGANISM: Artificial Sequence
<220> FEATURE:
<223> OTHER INFORMATION: B1-VH

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Ile Phe Asn Arg Tyr Ala Leu Asp Tyr Trp Gly Gln Gly
            100                 105                 110

Thr Thr Val Thr Val Ser Ser
        115

<210> SEQ ID NO 174
<211> LENGTH: 107
<212> TYPE: PRT
<213> ORGANISM: Artificial Sequence
<220> FEATURE:
<223> OTHER INFORMATION: B1-VK

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 175
<211> LENGTH: 119
<212> TYPE: PRT
<213> ORGANISM: Artificial Sequence
<220> FEATURE:
<223> OTHER INFORMATION: B6-VH
```

```
<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser
            115

<210> SEQ ID NO 176
<211> LENGTH: 107
<212> TYPE: PRT
<213> ORGANISM: Artificial Sequence
<220> FEATURE:
<223> OTHER INFORMATION: B6-VK

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 177
<211> LENGTH: 119
<212> TYPE: PRT
<213> ORGANISM: Artificial Sequence
<220> FEATURE:
<223> OTHER INFORMATION: C3-VH

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Leu His Phe Arg Tyr Ala Leu Asp Tyr Trp Gly Gln Gly
            100                 105                 110

Thr Thr Val Thr Val Ser Ser
            115

<210> SEQ ID NO 178
<211> LENGTH: 107
<212> TYPE: PRT
<213> ORGANISM: Artificial Sequence
<220> FEATURE:
<223> OTHER INFORMATION: C3-VK

<400> SEQUENCE: 178

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Thr Pro Ala
                 20                  25                  30

Val Ala Trp Tyr Gln Gln Lys Pro Gly Lys Ala Pro Lys Leu Leu Ile
             35                  40                  45

Tyr Ser Thr Ser Ser Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Thr Thr Pro Leu
                 85                  90                  95

Thr Phe Gly Gln Gly Thr Lys Leu Glu Ile Lys
            100                 105

<210> SEQ ID NO 179
<211> LENGTH: 119
<212> TYPE: PRT
<213> ORGANISM: Artificial Sequence
<220> FEATURE:
<223> OTHER INFORMATION: C6-VH

<400> SEQUENCE: 179

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Ser Leu Glu Trp Val
             35                  40                  45

Ala Thr Ile Ser Asp Ala Gly Gly Tyr Ile Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Leu Tyr Phe Arg Tyr Ala Leu Asp Tyr Trp Gly Gln Gly
            100                 105                 110

Thr Thr Val Thr Val Ser Ser
            115

<210> SEQ ID NO 180
```

```
<211> LENGTH: 107
<212> TYPE: PRT
<213> ORGANISM: Artificial Sequence
<220> FEATURE:
<223> OTHER INFORMATION: C6-VK

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 181
<211> LENGTH: 119
<212> TYPE: PRT
<213> ORGANISM: Artificial Sequence
<220> FEATURE:
<223> OTHER INFORMATION: A1-VH

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Leu His Arg Tyr Ala Leu Asp Tyr Trp Gly Gln Gly
            100                 105                 110

Thr Thr Val Thr Val Ser Ser
        115

<210> SEQ ID NO 182
<211> LENGTH: 107
<212> TYPE: PRT
<213> ORGANISM: Artificial Sequence
<220> FEATURE:
<223> OTHER INFORMATION: A1-VK

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30
```

```
Val Ala Trp Tyr Gln Gln Lys Pro Gly Lys Ala Pro Lys Leu Leu Ile
         35                  40                  45

Tyr Ser Thr Ser Ser Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Thr Thr Pro Leu
                 85                  90                  95

Thr Phe Gly Gln Gly Thr Lys Leu Glu Ile Lys
                100                 105
```

<210> SEQ ID NO 183
<211> LENGTH: 119
<212> TYPE: PRT
<213> ORGANISM: Artificial Sequence
<220> FEATURE:
<223> OTHER INFORMATION: A2-VH

<400> SEQUENCE: 183

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Ser Leu Glu Trp Val
         35                  40                  45

Ala Thr Ile Ser Asp Ala Gly Gly Tyr Ile Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Leu Arg Gly Arg Tyr Ala Leu Asp Tyr Trp Gly Gln Gly
                100                 105                 110

Thr Thr Val Thr Val Ser Ser
            115
```

<210> SEQ ID NO 184
<211> LENGTH: 107
<212> TYPE: PRT
<213> ORGANISM: Artificial Sequence
<220> FEATURE:
<223> OTHER INFORMATION: A2-VK

<400> SEQUENCE: 184

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Thr Pro Ala
             20                  25                  30

Val Ala Trp Tyr Gln Gln Lys Pro Gly Lys Ala Pro Lys Leu Leu Ile
         35                  40                  45

Tyr Ser Thr Ser Ser Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Thr Thr Pro Leu
                 85                  90                  95

Thr Phe Gly Gln Gly Thr Lys Leu Glu Ile Lys
                100                 105
```

<210> SEQ ID NO 185
<211> LENGTH: 119
<212> TYPE: PRT
<213> ORGANISM: Artificial Sequence
<220> FEATURE:
<223> OTHER INFORMATION: A3-VH

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 186
<211> LENGTH: 107
<212> TYPE: PRT
<213> ORGANISM: Artificial Sequence
<220> FEATURE:
<223> OTHER INFORMATION: A3-VK

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Asp Ala Pro Leu
                85                  90                  95

Thr Phe Gly Gln Gly Thr Lys Leu Glu Ile Lys
            100                 105

<210> SEQ ID NO 187
<211> LENGTH: 121
<212> TYPE: PRT
<213> ORGANISM: Artificial Sequence
<220> FEATURE:
<223> OTHER INFORMATION: heavy chain variable region of 41B01

<400> SEQUENCE: 187

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
            115                 120

<210> SEQ ID NO 188
<211> LENGTH: 121
<212> TYPE: PRT
<213> ORGANISM: Artificial Sequence
<220> FEATURE:
<223> OTHER INFORMATION: heavy chain variable region of 41B01.01

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
            115                 120

<210> SEQ ID NO 189
<211> LENGTH: 121
<212> TYPE: PRT
<213> ORGANISM: Artificial Sequence
<220> FEATURE:
<223> OTHER INFORMATION: heavy chain variable region of 41B01.02

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 190
<211> LENGTH: 121
<212> TYPE: PRT
<213> ORGANISM: Artificial Sequence
<220> FEATURE:
<223> OTHER INFORMATION: heavy chain variable region of 41B01.03

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 191
<211> LENGTH: 121
<212> TYPE: PRT
<213> ORGANISM: Artificial Sequence
<220> FEATURE:
<223> OTHER INFORMATION: heavy chain variable region of 41B01.04

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120
```

```
<210> SEQ ID NO 192
<211> LENGTH: 127
<212> TYPE: PRT
<213> ORGANISM: Artificial Sequence
<220> FEATURE:
<223> OTHER INFORMATION: heavy chain variable region of 41B02

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 193
<211> LENGTH: 110
<212> TYPE: PRT
<213> ORGANISM: Artificial Sequence
<220> FEATURE:
<223> OTHER INFORMATION: light chain variable region of 41B01

<400> SEQUENCE: 193

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 194
<211> LENGTH: 110
<212> TYPE: PRT
<213> ORGANISM: Artificial Sequence
<220> FEATURE:
<223> OTHER INFORMATION: light chain variable region of 41B01.01

<400> SEQUENCE: 194

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30
```

```
Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
                100                 105                 110

<210> SEQ ID NO 195
<211> LENGTH: 110
<212> TYPE: PRT
<213> ORGANISM: Artificial Sequence
<220> FEATURE:
<223> OTHER INFORMATION: light chain variable region of 41B01.02

<400> SEQUENCE: 195

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
                100                 105                 110

<210> SEQ ID NO 196
<211> LENGTH: 110
<212> TYPE: PRT
<213> ORGANISM: Artificial Sequence
<220> FEATURE:
<223> OTHER INFORMATION: light chain variable region of 41B01.03

<400> SEQUENCE: 196

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
                100                 105                 110
```

-continued

```
<210> SEQ ID NO 197
<211> LENGTH: 110
<212> TYPE: PRT
<213> ORGANISM: Artificial Sequence
<220> FEATURE:
<223> OTHER INFORMATION: light chain variable region of 41B01.04

<400> SEQUENCE: 197
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

```
<210> SEQ ID NO 198
<211> LENGTH: 110
<212> TYPE: PRT
<213> ORGANISM: Artificial Sequence
<220> FEATURE:
<223> OTHER INFORMATION: light chain variable region of 41B02

<400> SEQUENCE: 198
```

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

```
<210> SEQ ID NO 199
<211> LENGTH: 449
<212> TYPE: PRT
<213> ORGANISM: Artificial Sequence
<220> FEATURE:
<223> OTHER INFORMATION: Heavy chain of H12 in Heavy component of
      ABLPNB.01

<400> SEQUENCE: 199
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val

```
            35                  40                  45
Ala Thr Ile Ser Asp Ala Gly Gly Tyr Ile Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Phe Gly Lys Arg Tyr Ala Leu Asp Tyr Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

-continued

<210> SEQ ID NO 200
<211> LENGTH: 15
<212> TYPE: PRT
<213> ORGANISM: Artificial Sequence
<220> FEATURE:
<223> OTHER INFORMATION: Linker of Heavy component of ABLPNB.01

<400> SEQUENCE: 200

Gly Gly Gly Gly Ser Gly Gly Gly Gly Ser Gly Gly Gly Gly Ser
1               5                   10                  15

<210> SEQ ID NO 201
<211> LENGTH: 110
<212> TYPE: PRT
<213> ORGANISM: Artificial Sequence
<220> FEATURE:
<223> OTHER INFORMATION: VL of scFv of 41B01 in ABLPNB.01

<400> SEQUENCE: 201

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 202
<211> LENGTH: 20
<212> TYPE: PRT
<213> ORGANISM: Artificial Sequence
<220> FEATURE:
<223> OTHER INFORMATION: Linker of scFv of 41B01 in ABLPNB.01

<400> SEQUENCE: 202

Gly Gly Gly Gly Ser Gly Gly Gly Gly Ser Gly Gly Gly Gly Ser Gly
1               5                   10                  15

Gly Gly Gly Ser
            20

<210> SEQ ID NO 203
<211> LENGTH: 121
<212> TYPE: PRT
<213> ORGANISM: Artificial Sequence
<220> FEATURE:
<223> OTHER INFORMATION: VH of scFv of 41B01 in ABLPNB.01

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Cys Leu Glu Trp Val
            35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 204
<211> LENGTH: 2148
<212> TYPE: DNA
<213> ORGANISM: Artificial Sequence
<220> FEATURE:
<223> OTHER INFORMATION: Heavy component of ABLPNB.01

<400> SEQUENCE: 204

```
gaggtgcagc tggtggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgatg cgggcggcta catctattac     180
tccgacagcg tgaagggcag gttcaccatc agcagggaca cgccaagaa cagcctgtac      240 ctgcagatga acagcctgag gatgaggac accgccgtgt acatctgcgc cagggagttc      300
ggcaaaaggt acgccctgga ctactggggc cagggcacaa ccgtgaccgt gagcagcgct     360
agcaccaagg gcccctctgt gttccctctg gccccttcct ctaaatccac ctctggcgga     420
accgctgctc tgggctgtct ggtcaaggac tacttccctg agcccgtgac cgtgtcttgg     480
aattctggcg ctctgaccag cggagtgcac acctttccag ctgtgctgca gtcctccggc     540
ctgtactctc tgtcctctgt cgtgacagtg ccttccagct ctctgggcac ccagacctac     600
atctgcaacg tgaaccacaa gcccccaac accaaggtgg acaagaaggt ggaacccaag     660
tcctgcgaca gacccacac ctgtcctcca tgtcctgctc cagaactgct gggcggaccc      720
tccgtgttcc tgttccctcc aaagcctaag gacaccctga tgatctcccg gaccctgaa      780 gtgacctgcg tggtggtgga tgtgtcccac gaggatcccg aagtgaagtt caattggtac     840
gtggacggcg tggaagtgca caacgccaag accaagccta gaggaaca gtacgcctcc      900 acctaccggg tggtgtccgt gctgaccgtt ctgcaccagg attggctgaa cggcaaagag     960
tacaagtgca aggtgtccaa caaggccctg cctgcccta tcgaaaagac catctctaag    1020
gccaagggcc agccccggga acctcaagtg tacaccttgc ctcccagccg ggaagagatg    1080
accaagaacc aggtgtccct gacctgcctg gttaagggct tctacccctc cgatatcgcc    1140
gtggaatggg agtctaacgg ccagcccgag aacaactaca agaccacccc tcctgtgctg    1200
gactccgacg gctcattctt cctgtactcc aagctgaccg tggacaagtc tcggtggcag    1260
cagggcaacg tgttctcctg ctctgtgatg cacgaggccc tgcacaacca ctacacccag    1320
aagtccctgt ccctgtctcc cggcaaaggt gggggggat ctggtggtgg tggatcaggg     1380 ggtgggggt ctcaaagcgt actcacccaa cctccatctg catccggtac acctggtcgg     1440
cgagtaacca tctcctgctc tgggagctct tctaatattg gtaacaacta tgtcacctgg    1500
tatcagcagt gcctgggac agcacccaaa cttcttatat atgccgatag ccatcggcct    1560
tccggcgtac ccgatcgctt ctccgggtca aaatctggaa catctgcctc actcgcaatt    1620
```

```
agtggattgc gatctgagga tgaagcagat tattattgcg ctacctggga ttattcactt    1680
tctggctacg tctttggttg tggaacaaaa cttaccgtgt tgggcggcgg aggaagcgga    1740
ggcggcggtt ctggtggtgg cggtagcgga ggtggtggat ctgaagtaca gcttcttgag    1800
tctggcggag gattggtcca gccaggcggt tccctccgcc tgtcatgtgc cgcatccggc    1860
tttactttct ctagttatga tatgagctgg gttcgccaag ctcctggcaa atgcctggag    1920
tgggtctcct ggatttcata ctcaggtggc agcatctatt atgctgacag tgtgaaaggt    1980
cgctttacaa tctcccgaga taacagcaaa aacaccttgt acctgcaaat gaacagcctt    2040
cgcgcagagg acacagccgt atattattgc gctcgcgatg gacaacgtaa ttctatgcgt    2100
gagtttgact actggggaca ggggacattg gtcactgtat cttcctga                 2148
```

<210> SEQ ID NO 205
<211> LENGTH: 645
<212> TYPE: DNA
<213> ORGANISM: Artificial Sequence
<220> FEATURE:
<223> OTHER INFORMATION: Light component of ABLPNB.01

<400> SEQUENCE: 205

```
gacatccaga tgacccagag ccctagcagc ctgagcgcta gcgtgggcga cagggtgacc     60
atcacctgca aggccagcca ggatgtgacc cctgccgtgg cctggtacca gcagaagccc    120
ggcaaggccc ccaagctgct gatctacagc accagcagca ggtacaccgg cgtgcccagc    180
aggtttagcg gaagcggcag cggcaccgac ttcaccttca ccatcagcag cctgcagccc    240
gaggacatcg ccacctacta ctgccagcag cactacacca cccctctgac cttcggccag    300
ggcaccaagc tggagatcaa gagaaccgtg gccgctccct ccgtgttcat cttcccacca    360
tctgacgagc agctgaagtc cggcaccgct tctgtcgtgt gcctgctgaa caacttctac    420
cctcgggaag ccaaggtgca gtggaaggtg gacaatgccc tgcagtccgg caactcccaa    480
gagtctgtga ccgagcagga ctccaaggac agcacctact ccctgtcctc taccctgacc    540
ctgtccaagg ccgactacga gaagcacaag gtgtacgcct gcgaagtgac ccaccaggga    600
ctgtctagcc ccgtgaccaa gtccttcaac agaggcgagt gctga                   645
```

<210> SEQ ID NO 206
<211> LENGTH: 449
<212> TYPE: PRT
<213> ORGANISM: Artificial Sequence
<220> FEATURE:
<223> OTHER INFORMATION: Heavy chain of H12 in Heavy component of
      ABLPNB.02

<400> SEQUENCE: 206

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95
```

```
Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 207
<211> LENGTH: 15
<212> TYPE: PRT
<213> ORGANISM: Artificial Sequence
<220> FEATURE:
<223> OTHER INFORMATION: Linker of Heavy component of ABLPNB.02

<400> SEQUENCE: 207

Gly Gly Gly Gly Ser Gly Gly Gly Gly Ser Gly Gly Gly Gly Ser
```

-continued

<210> SEQ ID NO 208
<211> LENGTH: 110
<212> TYPE: PRT
<213> ORGANISM: Artificial Sequence
<220> FEATURE:
<223> OTHER INFORMATION: VL of scFv of 41B01.03 in ABLPNB.02

<400> SEQUENCE: 208

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 209
<211> LENGTH: 20
<212> TYPE: PRT
<213> ORGANISM: Artificial Sequence
<220> FEATURE:
<223> OTHER INFORMATION: Linker of scFv of 41B01.03 in ABLPNB.02

<400> SEQUENCE: 209

Gly Gly Gly Gly Ser Gly Gly Gly Ser Gly Gly Gly Gly Ser Gly
1               5                   10                  15

Gly Gly Gly Ser
            20

<210> SEQ ID NO 210
<211> LENGTH: 121
<212> TYPE: PRT
<213> ORGANISM: Artificial Sequence
<220> FEATURE:
<223> OTHER INFORMATION: VH of scFv of 41B01.03 in ABLPNB.02

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 211
<211> LENGTH: 2148
<212> TYPE: DNA
<213> ORGANISM: Artificial Sequence
<220> FEATURE:
<223> OTHER INFORMATION: Heavy component of ABLPNB.02

<400> SEQUENCE: 211

| | | | | | |
|---|---|---|---|---|---|
| gaggtgcagc | tggtggagag | cggaggagga | ctggtgcaac | ccggaggcag | cctgagactg | 60 |
| agctgcgctg | ccagcggctt | caccttcagc | agctacgaca | tgagctgggt | gagacaggcc | 120 |
| cctggcaaaa | gcctggagtg | ggtggccacc | atctccgatg | cgggcggcta | catctattac | 180 |
| tccgacagcg | tgaagggcag | gttcaccatc | agcagggaca | acgccaagaa | cagcctgtac | 240 |
| ctgcagatga | acagcctgag | ggatgaggac | accgccgtgt | acatctgcgc | cagggagttc | 300 |
| ggcaaaaggt | acgccctgga | ctactggggc | cagggcacaa | ccgtgaccgt | gagcagcgct | 360 |
| agcaccaagg | gcccctctgt | gttccctctg | gccccttcct | ctaaatccac | ctctggcgga | 420 |
| accgctgctc | tgggctgtct | ggtcaaggac | tacttccctg | agcccgtgac | cgtgtcttgg | 480 |
| aattctggcg | ctctgaccag | cggagtgcac | acctttccag | ctgtgctgca | gtcctccggc | 540 |
| ctgtactctc | tgtcctctgt | cgtgacagtg | ccttccagct | ctctgggcac | ccagacctac | 600 |
| atctgcaacg | tgaaccacaa | gcccctccaac | accaaggtgg | acaagaaggt | ggaacccaag | 660 |
| tcctgcgaca | gacccacac | ctgtcctcca | tgtcctgctc | cagaactgct | gggcggaccc | 720 |
| tccgtgttcc | tgttccctcc | aaagcctaag | gacaccctga | tgatctcccg | gacccctgaa | 780 |
| gtgacctgcg | tggtggtgga | tgtgtcccac | gaggatccag | aagtgaagtt | caattggtac | 840 |
| gtggacggcg | tggaagtgca | caatgccaag | accaagccta | gagaggaaca | gtacgcctcc | 900 |
| acctacagag | tggtgtccgt | gctgactgtg | ctgcaccagg | attggctgaa | cggcaaagag | 960 |
| tacaagtgca | aggtgtccaa | caaggccctg | cctgctccta | tcgaaaagac | catcagcaag | 1020 |
| gccaagggcc | agcctaggga | accccaggtt | tacaccctgc | ctccaagccg | ggaagagatg | 1080 |
| accaagaacc | aggtgtccct | gacctgcctc | gtgaagggct | tctaccctc | cgatatcgcc | 1140 |
| gtggaatggg | agagcaatgg | ccagcctgag | aacaactaca | agacaacccc | tcctgtgctg | 1200 |
| gactccgacg | gctcattctt | cctgtactcc | aagctgaccg | tggacaagtc | cagatggcag | 1260 |
| cagggcaacg | tgttcctg | ctccgtgatg | cacgaggccc | tgcacaatca | ctacacccag | 1320 |
| aagtccctgt | ctctgagccc | tggaaaaggc | ggcggaggat | ctggcggagg | tggtagcgga | 1380 |
| ggcggtggat | ctcagtctgt | tctgacccag | cctccttccg | cttctggcac | ccctggacag | 1440 |
| agagtgacca | tctcttgctc | cggctcctcc | tccaacatcg | gcaacaacta | cgtgacctgg | 1500 |
| tatcagcagc | tgcccggcac | agctcccaaa | ctgctgatct | acgccgactc | tcacagacct | 1560 |
| tccggcgtgc | ccgatagatt | ctccggctct | aagtctggca | cctctgccag | cctggctatc | 1620 |
| agcggcctga | gatctgagga | cgaggccgac | tactactgcg | ccacctggga | ttattccctg | 1680 |
| tccggctacg | tgttcggctg | cggcacaaaa | ctgacagtgc | tcgaggcgg | aggaagtggt | 1740 |
| ggcggaggtt | caggtggtgg | tggtagtggc | ggaggcggat | cagaagttca | gctgttggag | 1800 |
| tcaggtggcg | gcttggtgca | accaggtgga | agtctgagac | tcagctgtgc | tgccagcggc | 1860 |
| tttaccttca | gctcctacga | catgagctgg | gttcgacaag | ctcccggaaa | gtgcttggag | 1920 |
| tgggtttcct | ggatctccta | ctccggcggc | agcatctatt | acgccgacag | cgtgaaaggc | 1980 |

```
cggtttacca tctctcggga taacagcaag aatacccctct acctccaaat gaactctctg   2040
agagccgagg acactgctgt gtactattgc gccagagatg cccagcggaa ctccatgaga   2100
gagttcgact actggggaca aggcaccctg gtcaccgtgt ctagttga               2148
```

<210> SEQ ID NO 212
<211> LENGTH: 645
<212> TYPE: DNA
<213> ORGANISM: Artificial Sequence
<220> FEATURE:
<223> OTHER INFORMATION: Light component of ABLPNB.02

<400> SEQUENCE: 212

```
gacatccaga tgacccagag ccctagcagc ctgagcgcta gcgtgggcga cagggtgacc    60
atcacctgca aggccagcca ggatgtgacc cctgccgtgg cctggtacca gcagaagccc   120
ggcaaggccc ccaagctgct gatctacagc accagcagca ggtacaccgg cgtgcccagc   180
aggtttagcg gaagcggcag cggcaccgac ttcaccttca ccatcagcag cctgcagccc   240
gaggacatcg ccacctacta ctgccagcag cactacacca cccctctgac cttcggccag   300
ggcaccaagc tggagatcaa gagaaccgtg gccgctccct ccgtgttcat cttcccacca   360
tctgacgagc agctgaagtc cggcaccgct tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctact ccctgtcctc taccctgacc   540
ctgtccaagg ccgactacga gaagcacaag gtgtacgcct gcgaagtgac ccaccaggga   600
ctgtctagcc ccgtgaccaa gtccttcaac agaggcgagt gctga                  645
```

<210> SEQ ID NO 213
<211> LENGTH: 449
<212> TYPE: PRT
<213> ORGANISM: Artificial Sequence
<220> FEATURE:
<223> OTHER INFORMATION: Heavy chain of H12 in Heavy component of
      ABLPNB.03

<400> SEQUENCE: 213

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 214
<211> LENGTH: 15
<212> TYPE: PRT
<213> ORGANISM: Artificial Sequence
<220> FEATURE:
<223> OTHER INFORMATION: Linker of Heavy component of ABLPNB.03

<400> SEQUENCE: 214

Gly Gly Gly Gly Ser Gly Gly Gly Ser Gly Gly Gly Gly Ser
1               5                   10                  15

<210> SEQ ID NO 215
<211> LENGTH: 110
<212> TYPE: PRT
<213> ORGANISM: Artificial Sequence
<220> FEATURE:
<223> OTHER INFORMATION: VL of scFv of 41B02 in ABLPNB.03

<400> SEQUENCE: 215

```
Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 216
<211> LENGTH: 20
<212> TYPE: PRT
<213> ORGANISM: Artificial Sequence
<220> FEATURE:
<223> OTHER INFORMATION: Linker of scFv of 41B02 in ABLPNB.03

<400> SEQUENCE: 216

Gly Gly Gly Gly Ser Gly Gly Gly Gly Ser Gly Gly Gly Gly Ser Gly
1               5                   10                  15

Gly Gly Ser
        20

<210> SEQ ID NO 217
<211> LENGTH: 127
<212> TYPE: PRT
<213> ORGANISM: Artificial Sequence
<220> FEATURE:
<223> OTHER INFORMATION: VH of scFv of 41B02 in ABLPNB.03

<400> SEQUENCE: 217

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 218
<211> LENGTH: 2166
<212> TYPE: DNA
<213> ORGANISM: Artificial Sequence
<220> FEATURE:
<223> OTHER INFORMATION: Heavy component of ABLPNB.03
```

<400> SEQUENCE: 218

```
gaggtgcagc tggtggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgatg cgggcggcta catctattac     180
tccgacagcg tgaagggcag gttcaccatc agcagggaca cgccaagaa cagcctgtac      240
ctgcagatga acagcctgag ggatgaggac accgccgtgt acatctgcgc cagggagttc     300
ggcaaaaggt acgccctgga ctactggggc cagggcacaa ccgtgaccgt gagcagcgct     360
agcaccaagg gccctctgt gttccctctg gccccttcct ctaaatccac ctctggcgga      420
accgctgctc tgggctgtct ggtcaaggac tacttccctg agcccgtgac cgtgtcttgg     480
aattctggcg ctctgaccag cggagtgcac acctttccag ctgtgctgca gtcctccggc     540
ctgtactctc tgtcctctgt cgtgacagtg ccttccagct ctctgggcac ccagacctac     600
atctgcaacg tgaaccacaa gcccctccaac accaaggtgg acaagaaggt ggaacccaag    660
tcctgcgaca gacccacac ctgtcctcca tgtcctgctc cagaactgct gggcggaccc      720
tccgtgttcc tgttccctcc aaagcctaag gacaccctga tgatctcccg gacccctgaa     780
gtgacctgcg tggtggtgga tgtgtcccac gaggatcccg aagtgaagtt caattggtac     840
gtggacggcg tggaagtgca caacgccaag accaagccta gagaggaaca gtacgcctcc     900
acctaccggg tggtgtccgt gctgaccgtt ctgcaccagg attggctgaa cggcaaagag     960
tacaagtgca aggtgtccaa caaggccctg cctgccccta tcgaaaagac catctctaag    1020
gccaagggcc agccccggga acctcaagtg tacaccttgc ctcccagccg ggaagagatg    1080
accaagaacc aggtgtccct gacctgcctg gttaagggct tctaccccctc cgatatcgcc    1140
gtggaatggg agtctaacgg ccagcccgag aacaactaca agaccacccc tcctgtgctg    1200
gactccgacg gctcattctt cctgtactcc aagctgaccg tggacaagtc tcggtggcag    1260
cagggcaacg tgttctcctg ctctgtgatg cacgaggccc tgcacaacca ctacacccag    1320
aagtccctgt ccctgtctcc cggcaaaggt ggggggggat ctggtggtgg tggatcaggg    1380
ggtggggggt ctcaaagcgt actcacccaa cctccatctg catccggtac acctggtcgg    1440
cgagtaacca tctcctgctc tgggagctct tctaatattg gtaacaacta tgtcacctgg    1500
tatcagcagt tgcctgggac agcacccaaa cttcttatat atgccgatag ccatcggcct    1560
tccggcgtac ccgatcgctt ctccgggtca aaatctggaa catctgcctc actcgcaatt    1620
agtggattgc gatctgagga tgaagcagat tattattgcg ctacctggga ttattcactt    1680
tctggctacg tctttggttg tggaacaaaa cttaccgtgt gggcggcgg aggaagcgga     1740
ggcggcggtt ctggtggtgg cggtagcgga ggtggtggat ctgaggttca actgttggag    1800
tcaggtggcg gacttgtcca gcctggcggg tctctgaggc tgagttgcgc tgcttctggg    1860
tttactttt caggatatga catgagttgg gtacgtcagg ctccaggtaa gtgcctcgaa     1920
tgggtctccg ttatctatcc cgatgatgga aatacttact acgctgacag tgtgaaaggc    1980
aggttcacaa tcagtaggga caattctaaa aatacactct acctccagat gaactcactt    2040
cgagccgagg acgccgccgt atattactgt gccaaacacg gcgggcaaaa acccactact    2100
aaatccagta gtgcttacgg gatggatggc tggggacagg ggacattggt cactgtatct    2160
tcctga                                                              2166
```

<210> SEQ ID NO 219

```
<211> LENGTH: 645
<212> TYPE: DNA
<213> ORGANISM: Artificial Sequence
<220> FEATURE:
<223> OTHER INFORMATION: Light component of ABLPNB.03

<400> SEQUENCE: 219
gacatccaga tgacccagag ccctagcagc ctgagcgcta gcgtgggcga cagggtgacc        60
atcacctgca aggccagcca ggatgtgacc cctgccgtgg cctggtacca gcagaagccc       120
ggcaaggccc ccaagctgct gatctacagc accagcagca ggtacaccgg cgtgcccagc       180
aggtttagcg gaagcggcag cggcaccgac ttcaccttca ccatcagcag cctgcagccc       240
gaggacatcg ccacctacta ctgccagcag cactacacca cccctctgac cttcggccag       300
ggcaccaagc tggagatcaa gaaaccgtg gccgctccct ccgtgttcat cttcccacca       360
tctgacgagc agctgaagtc cggcaccgct tctgtcgtgt gcctgctgaa caacttctac       420
cctcgggaag ccaaggtgca gtggaaggtg gacaatgccc tgcagtccgg caactcccaa       480
gagtctgtga ccgagcagga ctccaaggac agcacctact ccctgtcctc taccctgacc       540
ctgtccaagg ccgactacga gaagcacaag gtgtacgcct gcgaagtgac ccaccaggga       600
ctgtctagcc ccgtgaccaa gtccttcaac agaggcgagt gctga                      645

<210> SEQ ID NO 220
<211> LENGTH: 449
<212> TYPE: PRT
<213> ORGANISM: Artificial Sequence
<220> FEATURE:
<223> OTHER INFORMATION: Heavy chain of B6 in Heavy component of
      ABLPNB.04

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 221
<211> LENGTH: 15
<212> TYPE: PRT
<213> ORGANISM: Artificial Sequence
<220> FEATURE:
<223> OTHER INFORMATION: Linker of Heavy component of ABLPNB.04

<400> SEQUENCE: 221

Gly Gly Gly Gly Ser Gly Gly Gly Ser Gly Gly Gly Gly Ser
1               5                   10                  15

<210> SEQ ID NO 222
<211> LENGTH: 110
<212> TYPE: PRT
<213> ORGANISM: Artificial Sequence
<220> FEATURE:
<223> OTHER INFORMATION: VL of scFv of 41B01 in ABLPNB.04

<400> SEQUENCE: 222

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

```
Ile Tyr Ala Asp Ser His Arg Pro Ser Gly Val Pro Asp Arg Phe Ser
 50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Thr Trp Asp Tyr Ser Leu
                 85                  90                  95
Ser Gly Tyr Val Phe Gly Cys Gly Thr Lys Leu Thr Val Leu
            100                 105                 110
```

<210> SEQ ID NO 223
<211> LENGTH: 20
<212> TYPE: PRT
<213> ORGANISM: Artificial Sequence
<220> FEATURE:
<223> OTHER INFORMATION: Linker of scFv of 41B01 in ABLPNB.04

<400> SEQUENCE: 223

```
Gly Gly Gly Gly Ser Gly Gly Gly Ser Gly Gly Gly Gly Ser Gly
 1               5                   10                  15
Gly Gly Gly Ser
            20
```

<210> SEQ ID NO 224
<211> LENGTH: 121
<212> TYPE: PRT
<213> ORGANISM: Artificial Sequence
<220> FEATURE:
<223> OTHER INFORMATION: VH of scFv of 41B01 in ABLPNB.04

<400> SEQUENCE: 224

```
Glu Val Gln Leu Leu Glu Ser Gly Gly Gly Leu Val Gln Pro Gly Gly
 1               5                   10                  15
Ser Leu Arg Leu Ser Cys Ala Ala Ser Gly Phe Thr Phe Ser Ser Tyr
             20                  25                  30
Asp Met Ser Trp Val Arg Gln Ala Pro Gly Lys Cys Leu Glu Trp Val
         35                  40                  45
Ser Trp Ile Ser Tyr Ser Gly Gly Ser Ile Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Gly Gln Arg Asn Ser Met Arg Glu Phe Asp Tyr Trp Gly
            100                 105                 110
Gln Gly Thr Leu Val Thr Val Ser Ser
        115                 120
```

<210> SEQ ID NO 225
<211> LENGTH: 2148
<212> TYPE: DNA
<213> ORGANISM: Artificial Sequence
<220> FEATURE:
<223> OTHER INFORMATION: Heavy component of ABLPNB.04

<400> SEQUENCE: 225
gaagtgcagc tggttgaatc tggcggcgga ttggttcagc ctggcggatc tctgagactg      60
tcttgtgccg cctccggctt caccttctcc agctacgata tgtcctgggt ccgacaggcc     120
cctggcaagt cttttgaatg ggtcgccacc atctctgacg ctggcggcta catctactac     180

```
cgggactctg tgaagggcag attcaccatc agccgggaca cgccaagaa ctccctgtac     240 ctgcagatga acagcctgcg cgacgaggat accgccgtgt acatctgtgc tagagagctg    300
ccttggagat acgccctgga ttattggggc agggcacca cagtgaccgt gtcctctgct     360
tctaccaagg gacccagcgt gttccctctg gctccttcca gcaagtctac ctctggcgga    420
acagctgctc tgggctgcct ggtcaaggac tactttcctg agcctgtgac agtgtcctgg    480
aactctggcg ctctgacatc tggcgtgcac acctttccag cagtgctgca gtcctccggc    540
ctgtactctc tgtcctctgt cgtgaccgtg ccttccagct ctctgggaac ccagacctac    600
atctgcaatg tgaaccacaa gccttccaac accaaggtgg acaagaaggt ggaacccaag    660
tcctgcgaca gacccacac ctgtcctcca tgtcctgctc cagaactgct cggcggacct     720
tccgtgttcc tgtttcctcc aaagcctaag gacaccctga tgatctctcg gacccctgaa    780
gtgacctgcg tggtggtgga tgtgtcccac gaggatccaa agtgaagtt caattggtac     840 gtggacggcg tggaagtgca caatgccaag accaagccta gagaggaaca gtacgcctcc    900
acctacagag tggtgtccgt gctgactgtg ctgcaccagg attggctgaa cggcaaagag    960
tacaagtgca aggtgtccaa caaggccctg cctgctccta tcgaaaagac catcagcaag    1020
gccaagggcc agcctaggga accccaggtt tacaccctgc ctccaagccg gaagagatg    1080 accaagaacc aggtgtccct gacctgcctc gtgaagggct ctacccttc cgatatcgcc    1140 gtggaatggg agagcaatgg ccagcctgag aacaactaca agcaaccccc tcctgtgctg    1200
gactccgacg gctcattctt cctgtactcc aagctgaccg tggacaagtc cagatggcag    1260
cagggcaacg tgttctcctg ctccgtgatg cacgaggccc tgcacaatca ctacacccag    1320
aagtccctgt ctctgagccc tggaaaaggc ggcggaggat ctggcggagg tggtagcgga    1380
ggcggtggat ctcagtctgt tctgacccag cctccttccg cttctggcac ccctggaaga    1440
agagtgacca tctcttgctc cggctcctcc tccaacatcg caacaacta cgtgacctgg    1500 tatcagcagc tgcccggcac agctcccaaa ctgctgatct acgccgactc tcacagacct    1560
tccggcgtgc ccgatagatt ctccggctct aagtctggca cctctgccag cctggctatc    1620
agcggcctga tctgagga cgaggccgac tactactgcg ccacctggga ttattccctg    1680
tccggctacg tgttcggctg cggcacaaaa ctgacagtgc tcggaggcgg aggaagtggt    1740
ggcggaggtt caggtggtgg tggtagtggc ggaggcggat cagaagttca gctgttggag    1800
tcaggtggcg gcttggtgca accaggtgga agtctgagac tcagctgtgc tgccagcggc    1860
tttaccttca gctcctacga catgagctgg gttcgacaag ctcccggaaa gtgcttggag    1920
tgggtttcct ggatctccta ctccggcggc agcatctatt acgccgacag cgtgaaaggc    1980
cggtttacca tctctcggga taacagcaag aatacctct acctccaaat gaactctctg    2040
agagccgagg acactgctgt gtactattgc gccagagatg gccagcggaa ctccatgaga    2100
gagttcgact actggggaca aggcaccctg gtcaccgtgt ctagttga                2148
```

<210> SEQ ID NO 226
<211> LENGTH: 645
<212> TYPE: DNA
<213> ORGANISM: Artificial Sequence
<220> FEATURE:
<223> OTHER INFORMATION: Light component of ABLPNB.04

<400> SEQUENCE: 226

```
gacatccaga tgacccagag ccctagcagc ctgagcgcta gcgtgggcga cagggtgacc     60
atcacctgca aggccagcca ggatgtgacc cctgccgtgg cctggtacca gcagaagccc    120
```

```
ggcaaggccc ccaagctgct gatctacagc accagcagca ggtacaccgg cgtgcccagc    180
aggtttagcg gaagcggcag cggcaccgac ttcaccttca ccatcagcag cctgcagccc    240
gaggacatcg ccacctacta ctgccagcag cactacacca cccctctgac cttcggccag    300
ggcaccaagc tggagatcaa agaaccgtg gccgctccct ccgtgttcat cttcccacca    360
tctgacgagc agctgaagtc cggcaccgct tctgtcgtgt gcctgctgaa caacttctac    420
cctcgggaag ccaaggtgca gtggaaggtg gacaatgccc tgcagtccgg caactcccaa    480
gagtctgtga ccgagcagga ctccaaggac agcacctact ccctgtcctc taccctgacc    540
ctgtccaagg ccgactacga gaagcacaag gtgtacgcct gcgaagtgac ccaccaggga    600
ctgtctagcc ccgtgaccaa gtccttcaac agaggcgagt gctga                    645
```

<210> SEQ ID NO 227
<211> LENGTH: 449
<212> TYPE: PRT
<213> ORGANISM: Artificial Sequence
<220> FEATURE:
<223> OTHER INFORMATION: Heavy chain of B6 in Heavy component of
      ABLPNB.05

<400> SEQUENCE: 227

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                  260                 265                 270
Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 228
<211> LENGTH: 15
<212> TYPE: PRT
<213> ORGANISM: Artificial Sequence
<220> FEATURE:
<223> OTHER INFORMATION: Linker of Heavy component of ABLPNB.05

<400> SEQUENCE: 228

Gly Gly Gly Gly Ser Gly Gly Gly Gly Ser Gly Gly Gly Gly Ser
1               5                   10                  15

<210> SEQ ID NO 229
<211> LENGTH: 110
<212> TYPE: PRT
<213> ORGANISM: Artificial Sequence
<220> FEATURE:
<223> OTHER INFORMATION: VL of scFv of 41B01.01 in ABLPNB.05

<400> SEQUENCE: 229

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
```

<210> SEQ ID NO 230
<211> LENGTH: 20
<212> TYPE: PRT
<213> ORGANISM: Artificial Sequence
<220> FEATURE:
<223> OTHER INFORMATION: Linker of scFv of 41B01.01 in ABLPNB.05

<400> SEQUENCE: 230

Gly Gly Gly Gly Ser Gly Gly Gly Ser Gly Gly Gly Gly Ser Gly
1               5                   10                  15

Gly Gly Gly Ser
            20

<210> SEQ ID NO 231
<211> LENGTH: 121
<212> TYPE: PRT
<213> ORGANISM: Artificial Sequence
<220> FEATURE:
<223> OTHER INFORMATION: VH of scFv of 41B01.01 in ABLPNB.05

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 232
<211> LENGTH: 2148
<212> TYPE: DNA
<213> ORGANISM: Artificial Sequence
<220> FEATURE:
<223> OTHER INFORMATION: Heavy component of ABLPNB.05

<400> SEQUENCE: 232
gaagtgcagc tggttgaatc tggcggcgga ttggttcagc ctggcggatc tctgagactg      60
tcttgtgccg cctccggctt caccttctcc agctacgata tgtcctgggt ccgacaggcc     120
cctggcaagt ctttgaatg ggtcgccacc atctctgacg ctggcggcta catctactac     180
cgggactctg tgaagggcag attcaccatc agccgggaca cgccaagaa ctccctgtac     240 ctgcagatga acagcctgcg cgacgaggat accgccgtgt acatctgtgc tagagagctg     300
ccttggagat acgccctgga ttattgggc cagggcacca cagtgaccgt gtcctctgct     360
tctaccaagg gacccagcgt gttccctctg gctccttcca gcaagtctac ctctggcgga     420
acagctgctc tgggctgcct ggtcaaggac tactttcctg agcctgtgac agtgtcctgg     480
aactctggcg ctctgacatc tggcgtgcac accttccagc agtgctgca gtcctccggc     540

```
ctgtactctc tgtcctctgt cgtgaccgtg ccttccagct ctctgggaac ccagacctac      600
atctgcaatg tgaaccacaa gccttccaac accaaggtgg acaagaaggt ggaacccaag      660
tcctgcgaca agacccacac ctgtcctcca tgtcctgctc cagaactgct cggcggacct      720
tccgtgttcc tgtttcctcc aaagcctaag acaccctga tgatctctcg accccctgaa       780
gtgacctgcg tggtggtgga tgtgtcccac gaggatccag aagtgaagtt caattggtac      840
gtggacggcg tggaagtgca caatgccaag accaagccta gagaggaaca gtacgcctcc      900
acctacagag tggtgtccgt gctgactgtg ctgcaccagg attggctgaa cggcaaagag      960
tacaagtgca aggtgtccaa caaggccctg cctgctccta tcgaaaagac catcagcaag     1020
gccaagggcc agcctaggga accccaggtt tacaccctgc ctccaagccg gaagagatg      1080 accaagaacc aggtgtccct gacctgcctc gtgaagggct ctacccttc cgatatcgcc      1140 gtggaatggg agagcaatgg ccagcctgag aacaactaca agacaacccc tcctgtgctg     1200
gactccgacg gctcattctt cctgtactcc aagctgaccg tggacaagtc cagatggcag     1260
cagggcaacg tgttctcctg ctccgtgatg cacgaggccc tgcacaatca ctacacccag     1320
aagtccctgt ctctgagccc tggaaaaggc ggcggaggat ctggcggagg tggtagcgga     1380
ggcggtggat ctcagtctgt tctgacccag cctccttccg cttctggcac ccctggaaga     1440
agagtgacca tctcttgctc cggctcctcc tccaacatcg caacaacta cgtgacctgg     1500 tatcagcagc tgcccggcac agctcccaaa ctgctgatct acgccgactc tcacagacct     1560
tccggcgtgc ccgatagatt ctccggctct aagtctggca cctctgccag cctggctatc     1620
agcggcctga gatctgagga cgaggccgac tactactgcg ccacctggga ttattccctg     1680
tccggctacg tgttcggctg cggcacaaaa ctgacagtgc tcggaggcgg aggaagtggt     1740
ggcggaggtt caggtggtgg tggtagtggc ggaggcggat cagaagttca gctgttggag     1800
tcaggtggcg gcttggtgca accaggtgga agtctgagac tcagctgtgc tgccagcggc     1860
tttaccttca gctcctacga catgagctgg gttcgacaag ctcccggaaa gtgcttggag     1920
tgggtttcct ggatctccta ctccggcggc agcatctatt acgccgacag cgtgaaaggc     1980
cggtttacca tctctcggga taacagcaag aataccctct acctccaaat gaactctctg     2040
agagccgagg acactgctgt gtactattgc gccagagatg cccagcggaa ctccatgaga     2100
gagttcgact actgggggaca aggcacccctg gtcaccgtgt ctagttga                2148

<210> SEQ ID NO 233
<211> LENGTH: 645
<212> TYPE: DNA
<213> ORGANISM: Artificial Sequence
<220> FEATURE:
<223> OTHER INFORMATION: Light component of ABLPNB.05

<400> SEQUENCE: 233
gacatccaga tgacccagag ccctagcagc ctgagcgcta gcgtgggcga cagggtgacc       60
atcacctgca aggccagcca ggatgtgacc cctgccgtgg cctggtacca gcagaagccc      120
ggcaaggccc ccaagctgct gatctacagc accagcagca ggtacaccgg cgtgcccagc      180
aggtttagcg gaagcggcag cggcaccgac ttcaccttca ccatcagcag cctgcagccc      240
gaggacatcg ccacctacta ctgccagcag cactacacca cccctctgac cttcggccag      300
ggcaccaagc tggagatcaa gagaaccgtg gccgctccct ccgtgttcat cttcccacca      360
tctgacgagc agctgaagtc cggcaccgct tctgtcgtgt gcctgctgaa caacttctac      420
```

```
cctcgggaag ccaaggtgca gtggaaggtg acaatgccc tgcagtccgg caactcccaa      480
gagtctgtga ccgagcagga ctccaaggac agcacctact ccctgtcctc taccctgacc      540
ctgtccaagg ccgactacga gaagcacaag gtgtacgcct gcgaagtgac caccaggga      600 ctgtctagcc ccgtgaccaa gtccttcaac agaggcgagt gctga                     645
```

<210> SEQ ID NO 234
<211> LENGTH: 449
<212> TYPE: PRT
<213> ORGANISM: Artificial Sequence
<220> FEATURE:
<223> OTHER INFORMATION: Heavy chain of B6 in Heavy component of
      ABLPNB.06

<400> SEQUENCE: 234

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 235
<211> LENGTH: 15
<212> TYPE: PRT
<213> ORGANISM: Artificial Sequence
<220> FEATURE:
<223> OTHER INFORMATION: Linker of Heavy component of ABLPNB.06

<400> SEQUENCE: 235

Gly Gly Gly Gly Ser Gly Gly Gly Gly Ser Gly Gly Gly Gly Ser
1               5                   10                  15

<210> SEQ ID NO 236
<211> LENGTH: 110
<212> TYPE: PRT
<213> ORGANISM: Artificial Sequence
<220> FEATURE:
<223> OTHER INFORMATION: VL of scFv of 41B01.02 in ABLPNB.06

<400> SEQUENCE: 236

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 237
<211> LENGTH: 20
<212> TYPE: PRT
<213> ORGANISM: Artificial Sequence
<220> FEATURE:
<223> OTHER INFORMATION: Linker of scFv of 41B01.02 in ABLPNB.06

<400> SEQUENCE: 237

Gly Gly Gly Gly Ser Gly Gly Gly Ser Gly Gly Gly Ser Gly
1               5               10              15

Gly Gly Gly Ser
        20

<210> SEQ ID NO 238
<211> LENGTH: 121
<212> TYPE: PRT
<213> ORGANISM: Artificial Sequence
<220> FEATURE:
<223> OTHER INFORMATION: VH of scFv of 41B01.02 in ABLPNB.06

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 239
<211> LENGTH: 2145
<212> TYPE: DNA
<213> ORGANISM: Artificial Sequence
<220> FEATURE:
<223> OTHER INFORMATION: Heavy component of ABLPNB.06

<400> SEQUENCE: 239
gtgcagctgg ttgaatctgg cggcggattg gttcagcctg gcggatctct gagactgtct      60
tgtgccgcct ccggcttcac cttctccagc tacgatatgt cctgggtccg acaggccccc     120
ggcaagtctt ggaatgggt cgccaccatc tctgacgctg gcggctacat ctactaccgg      180
gactctgtga agggcagatt caccatcagc cgggacaacg ccaagaactc cctgtacctg     240
cagatgaaca gcctgcgcga cgaggatacc gccgtgtaca tctgtgctag agagctgcct     300
tggagatacg ccctggatta ttggggccag ggcaccacag tgaccgtgtc ctctgcttct     360
accaagggac ccagcgtgtt ccctctggct ccttccagca gtctacctc tggcggaaca      420 gctgctctgg gctgcctggt caaggactac tttcctgagc tgtgacagt gtcctggaac      480 tctggcgctc tgacatctgg cgtgcacacc tttccagcag tgctgcagtc ctccggcctg     540
tactctctgt cctctgtcgt gaccgtgcct tccagctctc tgggaaccca gacctacatc     600
tgcaatgtga accacaagcc ttccaacacc aaggtggaca gaaggtgga acccaagtcc      660 tgcgacaaga cccacacctg tcctccatgt cctgctccag aactgctcgg cggaccttcc     720
gtgttcctgt tcctccaaa gcctaaggac ccctgatga tctctcggac ccctgaagtg      780
acctgcgtgg tggtggatgt gtcccacgag gatccagaag tgaagttcaa ttggtacgtg     840

```
gacggcgtgg aagtgcacaa tgccaagacc aagcctagag aggaacagta cgcctccacc    900
tacagagtgg tgtccgtgct gactgtgctg caccaggatt ggctgaacgg caaagagtac    960
aagtgcaagg tgtccaacaa ggccctgcct gctcctatcg aaaagaccat cagcaaggcc   1020
aagggccagc ctagggaacc ccaggtttac accctgcctc aagccgggga agagatgacc   1080
aagaaccagg tgtccctgac ctgcctcgtg aagggcttct acccttccga tatcgccgtg   1140 gaatggggaga gcaatggcca gcctgagaac aactacaaga caaccccctcc tgtgctggac   1200 tccgacggct cattcttcct gtactccaag ctgaccgtgg acaagtccag atggcagcag   1260
ggcaacgtgt tctcctgctc cgtgatgcac gaggccctgc acaatcacta cacccagaag   1320
tccctgtctc tgagccctgg aaaaggcggc ggaggatctg gcggaggtgg tagcggaggc   1380
ggtggatctc agtctgttct gacccagcct ccttccgctt ctggcacccc tggaagaaga   1440
gtgaccatct cttgctccgg ctcctcctcc aacatcggca caactacgt gacctggtat    1500 cagcagctgc ccggcacagc tcccaaactg ctgatctacg ccgactctca cagaccttcc   1560
ggcgtgcccg atagattctc cggctctaag tctggcacct ctgccagcct ggctatcagc   1620
ggcctgagat ctgaggacga ggccgactac tactgcgcca cctgggatta ttccctgtcc   1680
ggctacgtgt tcggctgcgg cacaaaactg acagtgctcg gaggcggagg aagtggtggc   1740
ggaggttcag gtggtggtgg tagtggcgga ggcggatcag aagttcagct gttggagtca   1800
ggtggcggct tggtgcaacc aggtggaagt ctgagactca gctgtgctgc cagcggcttt   1860
accttcagct cctacgacat gagctgggtt cgacaagctc ccggaaagtg cttggagtgg   1920
gtttcctgga tctcctactc cggcggcagc atctattacg ccgacagcgt gaaaggccgg   1980
tttaccatct ctcgggataa cagcaagaat accctctacc tccaaatgaa ctctctgaga   2040
gccgaggaca ctgctgtgta ctattgcgcc agagatgccc agcggcaatc catgagagag   2100
ttcgactact ggggacaagg caccctggtc accgtgtcta gttga                  2145
```

<210> SEQ ID NO 240
<211> LENGTH: 645
<212> TYPE: DNA
<213> ORGANISM: Artificial Sequence
<220> FEATURE:
<223> OTHER INFORMATION: Light component of ABLPNB.06

<400> SEQUENCE: 240

```
gacatccaga tgacccagag ccctagcagc ctgagcgcta gcgtgggcga cagggtgacc     60
atcacctgca aggccagcca ggatgtgacc cctgccgtgg cctggtacca gcagaagccc    120
ggcaaggccc ccaagctgct gatctacagc accagcagca ggtacaccgg cgtgcccagc    180
aggtttagcg gaagcggcag cggcaccgac ttcaccttca ccatcagcag cctgcagccc    240
gaggacatcg ccacctacta ctgccagcag cactacacca cccctctgac cttcggccag    300
ggcaccaagc tggagatcaa gagaaccgtg gccgctccct ccgtgttcat cttcccacca    360
tctgacgagc agctgaagtc cggcaccgct tctgtcgtgt gcctgctgaa caacttctac    420
cctcgggaag ccaaggtgca gtggaaggtg gacaatgccc tgcagtccgg caactcccaa    480
gagtctgtga ccgagcagga ctccaaggac agcacctact ccctgtcctc taccctgacc    540
ctgtccaagg ccgactacga aagcacaag gtgtacgcct gcgaagtgac ccaccaggga    600
ctgtctagcc ccgtgaccaa gtccttcaac agaggcgagt gctga                   645
```

<210> SEQ ID NO 241
<211> LENGTH: 449

```
<212> TYPE: PRT
<213> ORGANISM: Artificial Sequence
<220> FEATURE:
<223> OTHER INFORMATION: Heavy chain of B6 in Heavy component of
      ABLPNB.07

<400> SEQUENCE: 241
```

| | | | | | | | | | | | | | | | |
|---|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly|
|1| | | |5| | | | |10| | | | |15| |

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
 145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
 210                 215                 220

Thr His Thr Cys Pro Pro Cys Pro Ala Pro Glu Leu Leu Gly Gly Pro
 225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
 290                 295                 300

Val Ser Val Leu Thr Val Leu His Gln Asp Trp Leu Asn Gly Lys Glu
 305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

```
Ser Asn Gly Gln Pro Glu Asn Tyr Lys Thr Thr Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 242
<211> LENGTH: 15
<212> TYPE: PRT
<213> ORGANISM: Artificial Sequence
<220> FEATURE:
<223> OTHER INFORMATION: Linker of Heavy component of ABLPNB.07

<400> SEQUENCE: 242

Gly Gly Gly Gly Ser Gly Gly Gly Gly Ser Gly Gly Gly Gly Ser
1               5                   10                  15

<210> SEQ ID NO 243
<211> LENGTH: 110
<212> TYPE: PRT
<213> ORGANISM: Artificial Sequence
<220> FEATURE:
<223> OTHER INFORMATION: VL of scFv of 41B01.03 in ABLPNB.07

<400> SEQUENCE: 243

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 244
<211> LENGTH: 20
<212> TYPE: PRT
<213> ORGANISM: Artificial Sequence
<220> FEATURE:
<223> OTHER INFORMATION: Linker of scFv of 41B01.03 in ABLPNB.07

<400> SEQUENCE: 244

Gly Gly Gly Gly Ser Gly Gly Gly Gly Ser Gly Gly Gly Gly Ser Gly
1               5                   10                  15

Gly Gly Gly Ser
            20

<210> SEQ ID NO 245
<211> LENGTH: 121
<212> TYPE: PRT
```

<213> ORGANISM: Artificial Sequence
<220> FEATURE:
<223> OTHER INFORMATION: VH of scFv of 41B01.04 in ABLPNB.07

<400> SEQUENCE: 245

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Asp | Met | Ser | Trp | Val | Arg | Gln | Ala | Pro | Gly | Lys | Cys | Leu | Glu | Trp | Val |
|---|---|---|---|---|---|---|---|---|---|---|---|---|---|---|---|
| | | 35 | | | | | 40 | | | | | 45 | | | |

| Ser | Trp | Ile | Ser | Tyr | Ser | Gly | Gly | Ser | Ile | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Ala | Gln | Arg | Asn | Ser | Met | Arg | Glu | Phe | Tyr | Trp | Gly |
|---|---|---|---|---|---|---|---|---|---|---|---|---|---|---|
| | | | 100 | | | | | 105 | | | | | 110 | |

| Gln | Gly | Thr | Leu | Val | Thr | Val | Ser | Ser |
|---|---|---|---|---|---|---|---|---|
| | | | 115 | | | | 120 | |

<210> SEQ ID NO 246
<211> LENGTH: 2148
<212> TYPE: DNA
<213> ORGANISM: Artificial Sequence
<220> FEATURE:
<223> OTHER INFORMATION: Heavy component of ABLPNB.07

<400> SEQUENCE: 246

```
gaagtgcagc tggttgaatc tggcggcgga ttggttcagc ctggcggatc tctgagactg      60
tcttgtgccg cctccggctt caccttctcc agctacgata tgtcctgggt ccgacaggcc     120
cctggcaagt ctttggaatg gtcgccacc atctctgacg ctggcggcta catctactac      180
cgggactctg tgaagggcag attcaccatc agccgggaca cgccaagaa ctccctgtac      240
ctgcagatga acagcctgcg cgacgaggat accgccgtgt acatctgtgc tagagagctg     300
ccttggagat acgccctgga ttattgggc agggcacca cagtgaccgt gtcctctgct       360
tctaccaagg gacccagcgt gttccctctg gctccttcca gcaagtctac ctctggcgga     420
acagctgctc tgggctgcct ggtcaaggac tactttcctg agcctgtgac agtgtcctgg     480
aactctggcg ctctgacatc tggcgtgcac acctttccag cagtgctgca gtcctccggc     540
ctgtactctc tgtcctctgt cgtgaccgtg ccttccagct ctctgggaac ccagacctac     600
atctgcaatg tgaaccacaa gccttccaac accaaggtgg acaagaaggt ggaacccaag     660
tcctgcgaca gacccacac ctgtcctcca tgtcctgctc agaactgct cggcggacct       720
tccgtgttcc tgtttcctcc aaagcctaag acaccctga tgatctctcg gaccccctgaa     780
gtgacctgcg tggtggtgga tgtgtcccac gaggatccag aagtgaagtt caattggtac     840
gtggacggcg tggaagtgca caatgccaag accaagccta gagaggaaca gtacgcctcc     900
acctacagag tggtgtccgt gctgactgtg ctgcaccagg attggctgaa cggcaaagag     960
tacaagtgca aggtgtccaa caaggccctg cctgctccta tcgaaaagac catcagcaag    1020
gccaagggcc agcctaggga accccaggtt tacaccctgc ctccaagccg ggaagagatg    1080
accaagaacc aggtgtccct gacctgcctc gtgaagggct tctacccttc gatatcgcc     1140
gtggaatggg agagcaatgg ccagcctgag aacaactaca gacaacccc tcctgtgctg    1200
```

```
gactccgacg gctcattctt cctgtactcc aagctgaccg tggacaagtc cagatggcag    1260
cagggcaacg tgttctcctg ctccgtgatg cacgaggccc tgcacaatca ctacacccag    1320
aagtccctgt ctctgagccc tggaaaaggc ggcggaggat ctggcggagg tggtagcgga    1380
ggcggtggat ctcagtctgt tctgacccag cctccttccg cttctggcac ccctggacag    1440
agagtgacca tctcttgctc cggctcctcc tccaacatcg gcaacaacta cgtgacctgg    1500
tatcagcagc tgcccggcac agctcccaaa ctgctgatct acgccgactc tcacagacct    1560
tccggcgtgc ccgatagatt ctccggctct aagtctggca cctctgccag cctggctatc    1620
agcggcctga gatctgagga cgaggccgac tactactgcg ccacctggga ttattccctg    1680
tccggctacg tgttcggctg cggcacaaaa ctgacagtgc tcggaggcgg aggaagtggt    1740
ggcggaggtt caggtggtgg tggtagtggc ggaggcggat cagaagttca gctgttggag    1800
tcaggtggcg gcttggtgca accaggtgga agtctgagac tcagctgtgc tgccagcggc    1860
tttaccttca gctcctacga catgagctgg gttcgacaag ctcccggaaa gtgcttggag    1920
tgggtttcct ggatctccta ctccggcggc agcatctatt acgccgacag cgtgaaaggc    1980
cggtttacca tctctcggga taacagcaag aataccctct acctccaaat gaactctctg    2040
agagccgagg acactgctgt gtactattgc gccagagatg cccagcggaa ctccatgaga    2100
gagttcgact actggggaca aggcaccctg gtcaccgtgt ctagttga              2148
```

<210> SEQ ID NO 247
<211> LENGTH: 645
<212> TYPE: DNA
<213> ORGANISM: Artificial Sequence
<220> FEATURE:
<223> OTHER INFORMATION: Light component of ABLPNB.07

<400> SEQUENCE: 247

```
gacatccaga tgacccagag ccctagcagc ctgagcgcta gcgtgggcga cagggtgacc     60
atcacctgca aggccagcca ggatgtgacc cctgccgtgg cctggtacca gcagaagccc    120
ggcaaggccc ccaagctgct gatctacagc accagcagca ggtacaccgg cgtgcccagc    180
aggtttagcg gaagcggcag cggcaccgac ttcaccttca ccatcagcag cctgcagccc    240
gaggacatcg ccacctacta ctgccagcag cactacacca cccctctgac cttcggccag    300
ggcaccaagc tggagatcaa gagaaccgtg gccgctccct ccgtgttcat cttcccacca    360
tctgacgagc agctgaagtc cggcaccgct tctgtcgtgt gcctgctgaa caacttctac    420
cctcgggaag ccaaggtgca gtggaaggtg gacaatgccc tgcagtccgg caactcccaa    480
gagtctgtga ccgagcagga ctccaaggac agcacctact ccctgtcctc tacgctgacc    540
ctgtccaagg ccgactacga gaagcacaag gtgtacgcct gcgaagtgac ccaccaggga    600
ctgtctagcc ccgtgaccaa gtccttcaac agaggcgagt gctga                   645
```

<210> SEQ ID NO 248
<211> LENGTH: 449
<212> TYPE: PRT
<213> ORGANISM: Artificial Sequence
<220> FEATURE:
<223> OTHER INFORMATION: Heavy chain of B6 in Heavy component of
      ABLPNB.08

<400> SEQUENCE: 248

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly

-continued

```
              435                 440                 445

Lys

<210> SEQ ID NO 249
<211> LENGTH: 15
<212> TYPE: PRT
<213> ORGANISM: Artificial Sequence
<220> FEATURE:
<223> OTHER INFORMATION: Linker of Heavy component of ABLPNB.08

<400> SEQUENCE: 249

Gly Gly Gly Gly Ser Gly Gly Gly Gly Ser Gly Gly Gly Gly Ser
1               5                   10                  15

<210> SEQ ID NO 250
<211> LENGTH: 110
<212> TYPE: PRT
<213> ORGANISM: Artificial Sequence
<220> FEATURE:
<223> OTHER INFORMATION: VL of scFv of 41B01.04 in ABLPNB.08

<400> SEQUENCE: 250

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 251
<211> LENGTH: 20
<212> TYPE: PRT
<213> ORGANISM: Artificial Sequence
<220> FEATURE:
<223> OTHER INFORMATION: Linker of scFv of 41B01.04 in ABLPNB.08

<400> SEQUENCE: 251

Gly Gly Gly Gly Ser Gly Gly Gly Gly Ser Gly Gly Gly Gly Ser Gly
1               5                   10                  15

Gly Gly Gly Ser
                20

<210> SEQ ID NO 252
<211> LENGTH: 121
<212> TYPE: PRT
<213> ORGANISM: Artificial Sequence
<220> FEATURE:
<223> OTHER INFORMATION: VH of scFv of 41B01.04 in ABLPNB.08

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30
```

```
Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120
```

<210> SEQ ID NO 253
<211> LENGTH: 2148
<212> TYPE: DNA
<213> ORGANISM: Artificial Sequence
<220> FEATURE:
<223> OTHER INFORMATION: Heavy component of ABLPNB.08

<400> SEQUENCE: 253

```
gaagtgcagc tggttgaatc tggcggcgga ttggttcagc ctggcggatc tctgagactg      60
tcttgtgccg cctccggctt caccttctcc agctacgata tgtcctgggt ccgacaggcc     120
cctggcaagt cttttggaatg gtcgccacc atctctgacg ctggcggcta catctactac     180
cgggactctg tgaagggcag attcaccatc agccgggaca cgccaagaa ctccctgtac     240 ctgcagatga acagcctgcg cgacgaggat accgccgtgt acatctgtgc tagagagctg     300
ccttggagat acgccctgga ttattggggc cagggcacca cagtgaccgt gtcctctgct     360
tctaccaagg gacccagcgt gttccctctg gctccttcca gcaagtctac ctctggcgga     420
acagctgctc tgggctgcct ggtcaaggac tactttcctg agcctgtgac agtgtcctgg     480
aactctggcg ctctgacatc tggcgtgcac acctttccag cagtgctgca gtcctccggc     540
ctgtactctc tgtcctctgt cgtgaccgtg ccttccagct ctctgggaac ccagacctac     600
atctgcaatg tgaaccacaa gccttccaac accaaggtgg acaagaaggt ggaacccaag     660
tcctgcgaca gacccacac ctgtcctcca tgtcctgctc cagaactgct cggcggacct     720
tccgtgttcc tgtttcctcc aaagcctaag gacaccctga tgatctctcg gaccccctgaa     780 gtgacctgcg tggtggtgga tgtgtcccac gaggatccag aagtgaagtt caattggtac     840
gtggacggcg tggaagtgca caatgccaag accaagccta gaggaacaa gtacgcctcc     900 acctacagag tggtgtccgt gctgactgtg ctgcaccagg attggctgaa cggcaaagag     960
tacaagtgca aggtgtccaa caaggccctg cctgctccta tcgaaaagac catcagcaag    1020
gccaagggcc agcctaggga acccagggtt tacaccctgc ctccaagccg ggaagagatg    1080
accaagaacc aggtgtccct gacctgcctc gtgaagggct ctaccccttc cgatatcgcc    1140
gtggaatggg agagcaatgg ccagcctgag aacaactaca agacaacccc tcctgtgctg    1200
gactccgacg gctcattctt cctgtactcc aagctgaccg tggacaagtc cagatggcag    1260
cagggcaacg tgttctcctg ctccgtgatg cacgaggccc tgcacaatca ctacacccag    1320
aagtccctgt ctctgagccc tggaaaaggc ggcggaggat ctggcggagg tggtagcgga    1380
ggcggtggat ctcagtctgt tctgacccag cctccttccg cttctggcac ccctggacag    1440
agagtgacca tctcttgctc cggctcctcc tccaacatcg caacaactaa cgtgacctgg    1500
```

```
tatcagcagc tgcccggcac agctcccaaa ctgctgatct acgccgactc tcacagacct   1560
tccggcgtgc ccgatagatt ctccggctct aagtctggca cctctgccag cctggctatc   1620
agcggcctga gatctgagga cgaggccgac tactactgcg ccacctggga ttattccctg   1680
tccggctacg tgttcggctg cggcacaaaa ctgacagtgc tcggaggcgg aggaagtggt   1740
ggcggaggtt caggtggtgg tggtagtggc ggaggcggat cagaagttca gctgttggag   1800
tcaggtggcg gcttggtgca accaggtgga agtctgagac tcagctgtgc tgccagcggc   1860
tttaccttca gctcctacga catgagctgg gttcgacaag ctcccggaaa gtgcttggag   1920
tgggtttcct ggatctccta ctccggcggc agcatctatt acgccgacag cgtgaaaggc   1980
cggtttacca tctctcggga taacagcaag aataccctct acctccaaat gaactctctg   2040
agagccgagg acactgctgt gtactattgc gccagagatg cccagcggca atccatgaga   2100
gagttcgact actggggaca aggcaccctg gtcaccgtgt ctagttga              2148
```

<210> SEQ ID NO 254
<211> LENGTH: 645
<212> TYPE: DNA
<213> ORGANISM: Artificial Sequence
<220> FEATURE:
<223> OTHER INFORMATION: Light component of ABLPNB.08

<400> SEQUENCE: 254

```
gacatccaga tgacccagag ccctagcagc ctgagcgcta gcgtgggcga cagggtgacc    60
atcacctgca aggccagcca ggatgtgacc cctgccgtgg cctggtacca gcagaagccc   120
ggcaaggccc ccaagctgct gatctacagc accagcagca ggtacaccgg cgtgcccagc   180
aggtttagcg gaagcggcag cggcaccgac ttcaccttca ccatcagcag cctgcagccc   240
gaggacatcg ccacctacta ctgccagcag cactacacca cccctctgac cttcggccag   300
ggcaccaagc tggagatcaa gagaaccgtg gccgctccct ccgtgttcat cttcccacca   360
tctgacgagc agctgaagtc cggcaccgct tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctact ccctgtcctc taccctgacc   540
ctgtccaagg ccgactacga aagcacaag gtgtacgcct gcgaagtgac ccaccaggga   600
ctgtctagcc ccgtgaccaa gtccttcaac agaggcgagt gctga                 645
```

<210> SEQ ID NO 255
<211> LENGTH: 449
<212> TYPE: PRT
<213> ORGANISM: Artificial Sequence
<220> FEATURE:
<223> OTHER INFORMATION: Heavy chain of B6 in Heavy component of
      ABLPNB.09

<400> SEQUENCE: 255

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 256
<211> LENGTH: 15
<212> TYPE: PRT
<213> ORGANISM: Artificial Sequence
<220> FEATURE:
<223> OTHER INFORMATION: Linker of Heavy component of ABLPNB.09
```

-continued

<400> SEQUENCE: 256

Gly Gly Gly Gly Ser Gly Gly Gly Gly Ser Gly Gly Gly Gly Ser
1               5                   10                  15

<210> SEQ ID NO 257
<211> LENGTH: 110
<212> TYPE: PRT
<213> ORGANISM: Artificial Sequence
<220> FEATURE:
<223> OTHER INFORMATION: VL of scFv of 41B02 in ABLPNB.09

<400> SEQUENCE: 257

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 258
<211> LENGTH: 20
<212> TYPE: PRT
<213> ORGANISM: Artificial Sequence
<220> FEATURE:
<223> OTHER INFORMATION: Linker of scFv of 41B02 in ABLPNB.09

<400> SEQUENCE: 258

Gly Gly Gly Gly Ser Gly Gly Gly Gly Ser Gly Gly Gly Gly Ser Gly
1               5                   10                  15

Gly Gly Gly Ser
            20

<210> SEQ ID NO 259
<211> LENGTH: 127
<212> TYPE: PRT
<213> ORGANISM: Artificial Sequence
<220> FEATURE:
<223> OTHER INFORMATION: VH of scFv of 41B02 in ABLPNB.09

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys 85                  90                  95
Ala Lys His Gly Gly Gln Lys Pro Thr Thr Lys Ser Ser Ser Ala Tyr
                100                 105                 110

Gly Met Asp Gly Trp Gly Gln Gly Thr Leu Val Thr Val Ser Ser
            115                 120                 125

<210> SEQ ID NO 260
<211> LENGTH: 2166
<212> TYPE: DNA
<213> ORGANISM: Artificial Sequence
<220> FEATURE:
<223> OTHER INFORMATION: Heavy component of ABLPNB.09

<400> SEQUENCE: 260

| | | | | | |
|---|---|---|---|---|---|
| gaagtgcagc | tggttgaatc | tggcggcgga | ttggttcagc | ctggcggatc | tctgagactg | 60 |
| tcttgtgccg | cctccggctt | caccttctcc | agctacgata | tgtcctgggt | ccgacaggcc | 120 |
| cctggcaagt | ctttggaatg | ggtcgccacc | atctctgacg | ctggcggcta | catctactac | 180 |
| cgggactctg | tgaagggcag | attcaccatc | agccgggaca | acgccaagaa | ctccctgtac | 240 |
| ctgcagatga | acagcctgcg | cgacgaggat | accgccgtgt | acatctgtgc | tagagagctg | 300 |
| ccttggagat | acgccctgga | ttattggggc | cagggcacca | cagtgaccgt | gtcctctgct | 360 |
| tctaccaagg | gacccagcgt | gttccctctg | gctccttcca | gcaagtctac | ctctggcgga | 420 |
| acagctgctc | tgggctgcct | ggtcaaggac | tactttcctg | agcctgtgac | agtgtcctgg | 480 |
| aactctggcg | ctctgacatc | tggcgtgcac | acctttccag | cagtgctgca | gtcctccggc | 540 |
| ctgtactctc | tgtcctctgt | cgtgaccgtg | ccttccagct | ctctgggcac | ccagacctac | 600 |
| atctgcaacg | tgaaccacaa | gccctccaac | accaaggtgg | acaagaaggt | ggaacccaag | 660 |
| tcctgcgaca | agacccacac | ctgtcctcca | tgtcctgctc | cagaactgct | gggcggaccc | 720 |
| tccgtgttcc | tgttccctcc | aaagcctaag | gacaccctga | tgatctcccg | gacccctgaa | 780 |
| gtgacctgcg | tggtggtgga | tgtgtcccac | gaggatcccg | aagtgaagtt | caattggtac | 840 |
| gtggacggcg | tggaagtgca | caacgccaag | accaagccta | gagaggaaca | gtacgcctcc | 900 |
| acctaccggg | tggtgtccgt | gctgaccgtt | ctgcaccagg | attggctgaa | cggcaaagag | 960 |
| tacaagtgca | aggtgtccaa | caaggccctg | cctgcccta | tcgaaaagac | catctctaag | 1020 |
| gccaagggca | gccccggga | acctcaagtg | tacaccttgc | ctcccagccg | ggaagagatg | 1080 |
| accaagaacc | aggtgtccct | gacctgcctg | gttaagggct | tctacccctc | cgatatcgcc | 1140 |
| gtggaatggg | agtctaacgg | ccagcccgag | aacaactaca | agaccacccc | tcctgtgctg | 1200 |
| gactccgacg | gctcattctt | cctgtactcc | aagctgaccg | tggacaagtc | cggtggcag | 1260 |
| cagggcaacg | tgttctcctg | ctctgtgatg | cacgaggccc | tgcacaacca | ctacacccag | 1320 |
| aagtccctgt | ccctgtctcc | cggcaaaggt | gggggggat | ctggtggtgg | tggatcaggg | 1380 |
| ggtgggggt | ctcaaagcgt | actcacccaa | cctccatctg | catccggtac | acctggtcgg | 1440 |
| cgagtaacca | tctcctgctc | tgggagctct | tctaatattg | gtaacaacta | tgtcacctgg | 1500 |
| tatcagcagt | tgcctgggac | agcacccaaa | cttcttatat | atgccgatag | ccatcggcct | 1560 |
| tccggcgtac | ccgatcgctt | ctccgggtca | aaatctggaa | catctgcctc | actcgcaatt | 1620 |
| agtggattgc | gatctgagga | tgaagcagat | tattattgcg | ctacctggga | ttattcactt | 1680 |
| tctggctacg | tctttggttg | tggaacaaaa | cttaccgtgt | tgggcggcgg | aggaagcgga | 1740 |
| ggcggcggtt | ctggtggtgg | cggtagcgga | ggtggtggat | ctgaggttca | actgttggag | 1800 |
| tcaggtggcg | gacttgtcca | gcctggcggg | tctctgaggc | tgagttgcgc | tgcttctggg | 1860 |

```
tttactttttt caggatatga catgagttgg gtacgtcagg ctccaggtaa gtgcctcgaa    1920
tgggtctccg ttatctatcc cgatgatgga aatacttact acgctgacag tgtgaaaggc    1980
aggttcacaa tcagtaggga caattctaaa aatacactct acctccagat gaactcactt    2040
cgagccgagg acgccgccgt atattactgt gccaaacacg gcgggcaaaa acccactact    2100
aaatccagta gtgcttacgg gatggatggc tggggacagg ggacattggt cactgtatct    2160
tcctga                                                               2166
```

<210> SEQ ID NO 261
<211> LENGTH: 645
<212> TYPE: DNA
<213> ORGANISM: Artificial Sequence
<220> FEATURE:
<223> OTHER INFORMATION: Light component of ABLPNB.09

<400> SEQUENCE: 261

```
gacatccaga tgacccagag ccctagcagc ctgagcgcta gcgtgggcga cagggtgacc     60
atcacctgca aggccagcca ggatgtgacc cctgccgtgg cctggtacca gcagaagccc    120
ggcaaggccc ccaagctgct gatctacagc accagcagca gtacaccggg cgtgcccagc    180
aggtttagcg gaagcggcag cggcaccgac ttcaccttca ccatcagcag cctgcagccc    240
gaggacatcg ccacctacta ctgccagcag cactacacac ccctctgac cttcggccag    300 ggcaccaagc tggagatcaa gagaaccgtg gccgctccct ccgtgttcat cttcccacca    360
tctgacgagc agctgaagtc cggcaccgct tctgtcgtgt gcctgctgaa caacttctac    420
cctcgggaag ccaaggtgca gtggaaggtg gacaatgccc tgcagtccgg caactcccaa    480
gagtctgtga ccgagcagga ctccaaggac agcacctact ccctgtcctc taccctgacc    540
ctgtccaagg ccgactacga gaagcacaag gtgtacgcct gcgaagtgac ccaccaggga    600
ctgtctagcc ccgtgaccaa gtccttcaac agaggcgagt gctga                   645
```

<210> SEQ ID NO 262
<211> LENGTH: 10
<212> TYPE: PRT
<213> ORGANISM: Artificial Sequence
<220> FEATURE:
<223> OTHER INFORMATION: VH CDR3 of anti-PD-L1 antibody
<400> SEQUENCE: 262

Glu Phe Gly Lys Arg Tyr Ala Leu Asp Ser
1               5                   10

<210> SEQ ID NO 263
<211> LENGTH: 10
<212> TYPE: PRT
<213> ORGANISM: Artificial Sequence
<220> FEATURE:
<223> OTHER INFORMATION: VH CDR3 of anti-PD-L1 antibody
<400> SEQUENCE: 263

Glu Ile Phe Asn Arg Tyr Ala Leu Asp Tyr
1               5                   10

<210> SEQ ID NO 264
<211> LENGTH: 10
<212> TYPE: PRT
<213> ORGANISM: Artificial Sequence
<220> FEATURE:
<223> OTHER INFORMATION: VH CDR3 of anti-PD-L1 antibody

```
<400> SEQUENCE: 264

Glu Leu His Phe Arg Tyr Ala Leu Asp Tyr
1               5                   10

<210> SEQ ID NO 265
<211> LENGTH: 10
<212> TYPE: PRT
<213> ORGANISM: Artificial Sequence
<220> FEATURE:
<223> OTHER INFORMATION: VH CDR3 of anti-PD-L1 antibody

<400> SEQUENCE: 265

Glu Leu Tyr Phe Arg Tyr Ala Leu Asp Tyr
1               5                   10

<210> SEQ ID NO 266
<211> LENGTH: 10
<212> TYPE: PRT
<213> ORGANISM: Artificial Sequence
<220> FEATURE:
<223> OTHER INFORMATION: VH CDR3 of anti-PD-L1 antibody

<400> SEQUENCE: 266

Glu Leu Leu His Arg Tyr Ala Leu Asp Tyr
1               5                   10

<210> SEQ ID NO 267
<211> LENGTH: 10
<212> TYPE: PRT
<213> ORGANISM: Artificial Sequence
<220> FEATURE:
<223> OTHER INFORMATION: VH CDR3 of anti-PD-L1 antibody

<400> SEQUENCE: 267

Glu Leu Arg Gly Arg Tyr Ala Leu Asp Tyr
1               5                   10

<210> SEQ ID NO 268
<211> LENGTH: 11
<212> TYPE: PRT
<213> ORGANISM: Artificial Sequence
<220> FEATURE:
<223> OTHER INFORMATION: VL CDR1 of anti-PD-L1 antibody

<400> SEQUENCE: 268

Lys Ala Lys Gln Asp Val Thr Pro Ala Val Ala
1               5                   10

<210> SEQ ID NO 269
<211> LENGTH: 11
<212> TYPE: PRT
<213> ORGANISM: Artificial Sequence
<220> FEATURE:
<223> OTHER INFORMATION: VL CDR1 of anti-PD-L1 antibody

<400> SEQUENCE: 269

Lys Ala Ser Gln Asp Val Trp Pro Ala Val Ala
1               5                   10

<210> SEQ ID NO 270
<211> LENGTH: 9
<212> TYPE: PRT
<213> ORGANISM: Artificial Sequence
<220> FEATURE:
<223> OTHER INFORMATION: VL CDR3 of anti-PD-L1 antibody

<400> SEQUENCE: 270
```

```
Met Gln His Tyr Thr Thr Pro Leu Thr
1               5
```

<210> SEQ ID NO 271
<211> LENGTH: 9
<212> TYPE: PRT
<213> ORGANISM: Artificial Sequence
<220> FEATURE:
<223> OTHER INFORMATION: VL CDR3 of anti-PD-L1 antibody

<400> SEQUENCE: 271

```
Gln Gln His Ser Thr Thr Pro Leu Thr
1               5
```

<210> SEQ ID NO 272
<211> LENGTH: 9
<212> TYPE: PRT
<213> ORGANISM: Artificial Sequence
<220> FEATURE:
<223> OTHER INFORMATION: VL CDR3 of anti-PD-L1 antibody

<400> SEQUENCE: 272

```
Gln Gln His Ser Asp Ala Pro Leu Thr
1               5
```

ANTI-PD-L1/ANTI-4-1BB BISPECIFIC ANTIBODIES AND USES THEREOF

CROSS REFERENCE TO RELATED APPLICATIONS

This application is a National Stage of International Application No. PCT/CN2019/075180 filed Feb. 15, 2019, claiming priority based on U.S. Patent Application No. 62/773,239 filed Nov. 30, 2018, the entire disclosures of which are incorporated herein by reference.

BACKGROUND

Programmed death-ligand 1 (PD-L1), also known as cluster of differentiation 274 (CD274) or B7 homolog 1 (B7-H1), is a 40 kDa type 1 transmembrane protein believed to play a major role in suppressing the immune system during particular events such as pregnancy, tissue allografts, autoimmune disease and other disease states such as hepatitis. The binding of PD-L1 to PD-1 or B7.1 transmits an inhibitory signal which reduces the proliferation of CD8+ T cells at the lymph nodes and supplementary to that PD-1 is also able to control the accumulation of foreign antigen specific T cells in the lymph nodes through apoptosis which is further mediated by a lower regulation of the gene Bcl-2.

It has been shown that upregulation of PD-L1 may allow cancers to evade the host immune system. An analysis of tumor specimens from patients with renal cell carcinoma found that high tumor expression of PD-L1 was associated with increased tumor aggressiveness and an increased risk of death. Many PD-L1 inhibitors are in development as immuno-oncology therapies and are showing good results in clinical trials.

4-1BB is a member of TNF-receptor superfamily (TNFRSF) and is a costimulatory molecule which is expressed following the activation of immune cells, both innate and adaptive immune cells. 4-1BB plays important role in modulate the activity of various immune cells. 4-1BB agonists enhance immune cell proliferation, survival, secretion of cytokines and cytolytic activity CD8 T cells. Many other studies showed that activation of 4-1BB enhances immune response to eliminate tumors in mice. Therefore, it suggests that 4-1BB is a promising target molecule in cancer immunology. Despite of their anti-tumor efficacy, anti-4-1BB antibody induced severe liver toxicity in clinical application.

SUMMARY

The present disclosure provides an anti-PD-L1/anti-4-1BB bispecific antibody capable to effectively block the interactions between PD-L1 and its receptor PD-1 and between 4-1BB and its ligand. The bispecific antibody may have high binding affinity to both of a PD-L1 protein (e.g., a human PD-L1 protein) and a 4-1BB protein (e.g., a human 4-1BB protein).

The anti-PD-L1/anti-4-1BB bispecific antibody may comprise an anti-PD-L1 antibody or an antigen-binding fragment thereof as a PD-L1 targeting moiety, which is capable of specifically recognizing and/or binding to a PD-L1 protein, and an anti-4-1BB antibody or an antigen-binding fragment thereof as a 4-1BB targeting moiety, which is capable of specifically recognizing and/or binding to a 4-1BB protein.

The anti-PD-L1/anti-4-1BB bispecific antibody may comprise an anti-PD-L1 antibody or an antigen-binding fragment thereof as a PD-L1 targeting moiety.

In an embodiment, the anti-PD-L1 antibody or fragment thereof comprised in the bispecific antibody can specifically bind to an immunoglobulin C (IgC) domain of PD-L1 (e.g., human PD-L1) protein. In some embodiments, the IgC domain consists of amino acid residues 133-225 of a human PD-L1 protein. In some embodiments, the anti-PD-L1 antibody or fragment thereof can bind to at least one of amino acid residues Y134, K162, and N183 of a human PD-L1 protein. In some embodiments, the anti-PD-L1 antibody or fragment thereof does not bind to an immunoglobulin V (IgV) domain of the PD-L1 protein, and for example, the IgV domain consists of amino acid residues 19-127 of a human PD-L1 protein. For example, the human PD-L1 protein may be selected from the group consisting of proteins represented by GenBank Accession No. NP_001254635.1 NP_001300958.1, NP_054862.1, etc., but may not be limited thereto. These anti-PD-L1 antibodies may be useful for therapeutic purposes such as treating various types of cancer, etc., and can also be used for diagnostic and prognostic purposes. In an embodiment, the anti-PD-L1 antibody or fragment thereof is capable of specificity to a human PD-L1 protein.

The anti-PD-L1/anti-4-1BB bispecific antibody comprise an anti-PD-L1 antibody or an antigen-binding fragment thereof and an anti-4-1BB antibody or an antigen-binding fragment thereof, wherein the anti-PD-L1 antibody or antigen-binding fragment thereof is capable of specifically binding to an immunoglobulin C (Ig C) domain of a human Programmed death-ligand 1 (PD-L1) protein, wherein the Ig C domain consists of amino acid residues 133-225;

the anti-PD-L1 antibody or antigen-binding fragment thereof comprises a VH CDR1 having an amino acid sequence of SEQ ID NO: 1; a VH CDR2 having an amino acid sequence selected from the group consisting of SEQ ID NOS: 2 and 3; a VH CDR3 having an amino acid sequence selected from the group consisting of SEQ ID NOS: 4, 5, 262, 263, 264, 265, 266, and 267; a VL CDR1 having an amino acid sequence of SEQ ID NOS: 6, 268, and 269; a VL CDR2 having an amino acid sequence of SEQ ID NO: 7; and a VL CDR3 having an amino acid sequence of SEQ ID NOS: 8, 270, 271, and 272; and the anti-4-1BB antibody or antigen-binding fragment thereof comprises a VH CDR1 having an amino acid sequence selected from the group consisting of SEQ ID NOS: 10 and 11; a VH CDR2 having an amino acid sequence selected from the group consisting of SEQ ID NOS: 12 and 13; a VH CDR3 having an amino acid sequence selected from the group consisting of SEQ ID NOS: 14, 15, 16 and 17; a VL CDR1 having an amino acid sequence of SEQ ID NO: 18; a VL CDR2 having an amino acid sequence of SEQ ID NO: 19; and a VL CDR3 having an amino acid sequence of SEQ ID NO: 20.

In an embodiment, the anti-PD-L1 antibody or antigen-binding fragment thereof comprises a VH CDR1 having an amino acid sequence of SEQ ID NO: 1; a VH CDR2 having an amino acid sequence selected from the group consisting of SEQ ID NOS: 2 and 3; a VH CDR3 having an amino acid sequence selected from the group consisting of SEQ ID NOS: 4 and 5; a VL CDR1 having an amino acid sequence of SEQ ID NO: 6; a VL CDR2 having an amino acid sequence of SEQ ID NO: 7; and a VL CDR3 having an amino acid sequence of SEQ ID NO: 8.

In an embodiment, the anti-PD-L1 antibody or antigen-binding fragment thereof is capable of binding to at least one of amino acid residues Y134, K162, or N183 of the PD-L1 protein.

In an embodiment, the anti-PD-L1 antibody or antigen-binding fragment thereof is capable of binding to amino acid residues Y134, K162, and N183 of the PD-L1 protein.

In an embodiment, the anti-PD-L1 antibody or antigen-binding fragment thereof does not bind to an immunoglobulin V (Ig V) domain of the PD-L1 protein, wherein the Ig V domain consists of amino acid residues 19-127.

In an embodiment, the anti-PD-L1/anti-4-1BB bispecific antibody activates 4-1BB signaling, or immune response, depending on PD-L1 expressed on cell surfaces.

In an embodiment, each of the anti-PD-L1 antibody or antigen-binding fragment thereof and the anti-4-1BB antibody or antigen-binding fragment thereof is independently a chimeric antibody, a humanized antibody, or a fully human antibody.

The anti-PD-L1/anti-4-1BB bispecific antibody comprise an anti-PD-L1 antibody or an antigen-binding fragment thereof and an anti-4-1BB antibody or an antigen-binding fragment thereof, wherein the anti-PD-L1 antibody or antigen-binding fragment thereof comprises:

(1) a VH CDR1 having an amino acid sequence of SEQ ID NO: 1;
(2) a VH CDR2 having an amino acid sequence selected from the group consisting of SEQ ID NOS: 2 and 3;
(3) a VH CDR3 having an amino acid sequence selected from the group consisting of SEQ ID NOS: 4, 5, 262, 263, 264, 265, 266 and 267;
(4) a VL CDR1 having an amino acid sequence of SEQ ID NOS: 6, 268, and 269;
(5) a VL CDR2 having an amino acid sequence of SEQ ID NO: 7; and
(6) a VL CDR3 having an amino acid sequence of SEQ ID NOS: 8, 270, 271, and 272, and the anti-4-1BB antibody or antigen-binding fragment thereof comprises:

(i) a VH CDR1 having an amino acid sequence selected from the group consisting of SEQ ID NOS: 10 and 11;
(ii) a VH CDR2 having an amino acid sequence selected from the group consisting of SEQ ID NOS: 12 and 13;
(iii) a VH CDR3 having an amino acid sequence selected from the group consisting of SEQ ID NOS: 14, 15, 16 and 17;
(iv) a VL CDR1 having an amino acid sequence of SEQ ID NO: 18;
(v) a VL CDR2 having an amino acid sequence of SEQ ID NO: 19; and
(vi) a VL CDR3 having an amino acid sequence of SEQ ID NO: 20.

The anti-PD-L1 antibody or fragment thereof may comprise (1) a VH CDR1 having an amino acid sequence of SEQ ID NO: 1; (2) a VH CDR2 having an amino acid sequence selected from the group consisting of SEQ ID NOS: 2 and 3; (3) a VH CDR3 having an amino acid sequence selected from the group consisting of SEQ ID NOS: 4, 5, 262, 263, 264, 265, 266 and 267; (4) a VL CDR1 having an amino acid sequence of SEQ ID NOS: 6, 268 and 269; (5) a VL CDR2 having an amino acid sequence of SEQ ID NO: 7; and (6) a VL CDR3 having an amino acid sequence of SEQ ID NOS: 8, 270, 271 and 272. For example, the anti-PD-L1 antibody or fragment thereof may comprise a VH CDR1 having an amino acid sequence of SEQ ID NO: 1; a VH CDR2 having an amino acid sequence of SEQ ID NO: 2 or 3; (3) a VH CDR3 having an amino acid sequence of SEQ ID NO: 4, 5, 262, 263, 264, 265, 266, or 267; a VL CDR1 having an amino acid sequence of SEQ ID NO: 6, 268 or 269; a VL CDR2 having an amino acid sequence of SEQ ID NO: 7; and a VL CDR3 having an amino acid sequence of SEQ ID NO: 8, 270, 271 or 272.

In an embodiment, the anti-PD-L1 antibody or antigen-binding fragment thereof comprises a VH CDR1 having an amino acid sequence of SEQ ID NO: 1; a VH CDR2 having an amino acid sequence selected from the group consisting of SEQ ID NOS: 2 and 3; a VH CDR3 having an amino acid sequence selected from the group consisting of SEQ ID NOS: 4 and 5; a VL CDR1 having an amino acid sequence of SEQ ID NO: 6; a VL CDR2 having an amino acid sequence of SEQ ID NO: 7; and a VL CDR3 having an amino acid sequence of SEQ ID NO: 8.

The anti-PD-L1/anti-4-1BB bispecific antibody may comprise an anti-4-1BB antibody or an antigen-binding fragment thereof as a 4-1BB targeting moiety. In an embodiment, the anti-4-1BB antibody or fragment thereof can specifically bind to 4-1BB (e.g., human 4-1BB) protein.

The anti-4-1BB antibody or an antigen-binding fragment thereof is capable of enhancing immune response and/or treating tumor (cancer) in a mammal. The anti-4-1BB antibody or an antigen-binding fragment thereof is characterized by localizing and/or activating only in tumor microenvironment (TME) and/or considerably reducing liver toxicities compared to pre-existing anti-4-1BB antibodies, with maintaining the efficacies of enhancing immune response enhancement and/or tumor treatment.

For example, the human 4-1BB protein may be selected from the group consisting of proteins represented by NCBI Accession No. NP_001552, etc., but may not be limited thereto. These anti-4-1BB antibodies may be useful for therapeutic purposes such as treating various types of cancer, etc., and can also be used for diagnostic and prognostic purposes.

In an embodiment, the anti-4-1BB antibody or fragment thereof is capable of specificity to a human 4-1BB protein. The anti-4-1BB antibody or fragment thereof may comprise (i) a VH CDR1 having an amino acid sequence selected from the group consisting of SEQ ID NOS: 10 and 11; (ii) a VH CDR2 having an amino acid sequence selected from the group consisting of SEQ ID NOS: 12 and 13; (iii) a VH CDR3 having an amino acid sequence selected from the group consisting of SEQ ID NOS: 14, 15, 16 and 17; (iv) a VL CDR1 having an amino acid sequence of SEQ ID NO: 18; (v) a VL CDR2 having an amino acid sequence of SEQ ID NO: 19; and (vi) a VL CDR3 having an amino acid sequence of SEQ ID NO: 20. For example, the anti-4-1BB antibody or fragment thereof may comprise a VH CDR1 having an amino acid sequence of SEQ ID NO: 10 or 11; a VH CDR2 having an amino acid sequence of SEQ ID NO: 12 or 13; a VH CDR3 having an amino acid sequence of SEQ ID NO: 14, 15, 16, or 17; a VL CDR1 having an amino acid sequence of SEQ ID NO: 18; a VL CDR2 having an amino acid sequence of SEQ ID NO: 19; and a VL CDR3 having an amino acid sequence of SEQ ID NO: 20.

In an embodiment, each of the anti-PD-L1 antibody or antigen-binding fragment thereof and the anti-4-1BB antibody or antigen-binding fragment thereof is independently a chimeric antibody, a humanized antibody, or a fully human antibody.

In an embodiment, wherein the anti-PD-L1 antibody or antigen-binding fragment thereof and the anti-4-1BB antibody or antigen-binding fragment thereof are humanized antibodies.

In an embodiment, the anti-PD-L1 antibody or antigen-binding fragment thereof comprises a heavy chain variable region comprising an amino acid sequence selected from the group consisting of SEQ ID NOS: 103 and 104, or a polypeptide having at least 90% sequence identity to an amino acid sequence selected from the group consisting of SEQ ID NOS: 103 and 104.

In an embodiment, the anti-PD-L1 antibody or antigen-binding fragment thereof comprises a light chain variable region comprising an amino acid sequence selected from the group consisting of SEQ ID NOS: 105 and 106, or a peptide having at least 90% sequence identity to an amino acid sequence selected from the group consisting of SEQ ID NOS: 105 and 106.

In an embodiment, the anti-4-1BB antibody or antigen-binding fragment thereof comprises a heavy chain variable region comprising an amino acid sequence selected from the group consisting of SEQ ID NOS: 21, 22, 23 and 24, or a polypeptide having at least 90% sequence identity to an amino acid sequence selected from the group consisting of SEQ ID NOS: 21, 22, 23 and 24.

In an embodiment, the anti-4-1BB antibody or antigen-binding fragment thereof comprises a light chain variable region comprising an amino acid sequence selected from the group consisting of SEQ ID NOS: 25 and 26, or a peptide having at least 90% sequence identity to an amino acid sequence selected from the group consisting of SEQ ID NOS: 25 and 26.

In an embodiment, the anti-PD-L1/anti-4-1BB bispecific antibody activates 4-1BB signaling depending on PD-L1 expressed on cell surfaces.

In an embodiment, the anti-PD-L1/anti-4-1BB bispecific antibody is in the form of IgG-scFv form.

The anti-PD-L1/anti-4-1BB bispecific antibody may comprise a heavy component comprising an amino acid sequence selected from the group consisting of SEQ ID NOS: 27, 29, 31, 33, 35, 37, 39, 41 and 43; and a light component an amino acid sequence selected from the group consisting of SEQ ID NOS: 28, 30, 32, 34, 36, 38, 40, 42 and 44.

Another embodiment provides a pharmaceutical composition comprising the bispecific antibody as described above. The pharmaceutical composition may further comprise a pharmaceutically acceptable carrier. The pharmaceutical composition may be used for treating and/or preventing a cancer.

Another embodiment provides a method of treating and/or preventing a cancer in a subject in need thereof, comprising administering to the subject a pharmaceutically effective amount of the bispecific antibody or the pharmaceutical composition. The method may further step of identifying the subject in need of treating and/or preventing a cancer, prior to the administering step.

Another embodiment provides a use of the bispecific antibody or the pharmaceutical composition in treating and/or preventing a cancer. Another embodiment provides a use of the bispecific antibody in preparing a pharmaceutical composition for treating and/or preventing a cancer.

In the pharmaceutical compositions, methods and/or uses provided herein, the cancer may be a solid cancer or blood cancer, preferably a solid cancer.

Another embodiment provides a composition for detection of PD-L1, 4-1BB, or both thereof simultaneously, in a biological sample, the composition comprising the bispecific antibody. Another embodiment provides a method of detection of PD-L1, 4-1BB, or both thereof simultaneously, in a biological sample, the method comprising contacting the biological sample with the bispecific antibody; and detecting (measuring) an antigen-antibody reaction (binding) between the bispecific antibody and PD-L1, 4-1BB, or both thereof.

The method of detection may further comprise, after the detecting step, determining that PD-L1, 4-1BB, or both thereof are present in the biological sample when an antigen-antibody reaction is detected, and/or that PD-L1, 4-1BB, or both thereof are absent (not present) in the biological sample, when an antigen-antibody reaction is not detected.

Another embodiment provides a pharmaceutical composition for diagnosing a disease associated with PD-L1, 4-1BB, or both thereof, the composition comprising the bispecific antibody. In another embodiment, provided is a use of the bispecific antibody for diagnosing a disease associated with PD-L1, 4-1BB, or both thereof.

Another embodiment provides a method of diagnosing a disease associated with PD-L1, 4-1BB, or both thereof, the method comprising contacting a biological sample obtained from a patient with the bispecific antibody, and detecting antigen-antibody reaction or measuring a level of antigen-antibody reaction in the biological sample. In some embodiments, the method may further comprise contacting a normal sample with the bispecific antibody, and measuring a level of an antigen-antibody reaction in the normal sample. In addition, the method may further comprise comparing the level of the antigen-antibody reaction in the biological sample and in the normal sample, after the measuring step. In addition, after the detecting step or comparing step, the method may further comprise determining the patient as a patient with a disease associated with PD-L1, 4-1BB, or both thereof, when the antigen-antibody reaction is detected in the biological sample or the level of the antigen-antibody reaction in the biological sample is higher than that of the normal sample.

The disease associated with PD-L1, 4-1BB, or both thereof may be one associated with activation (e.g., abnormal activation or over-activation) and/or overproduction (overexpression) of PD-L1, 4-1BB, or both thereof. For example, the disease may be a cancer, as described above.

An embodiment provides a polynucleotide encoding the bispecific antibody. In particular, an embodiment provides a polynucleotide encoding a heavy chain of the bispecific antibody in an IgG-scFv form which comprises a full-length IgG and a scFv linked to a C-terminus and/or N-terminus of the full-length IgG. Other embodiment provides a polynucleotide encoding a light chain of the bispecific antibody in an IgG-scFv form. Another embodiment provides a recombinant vector comprising the polynucleotide encoding a heavy chain of the bispecific antibody, the polynucleotide encoding a light chain of the bispecific antibody, or both thereof. Another embodiment provides a recombinant cell transfected with the recombinant vector.

Another embodiment provides a method of preparing the bispecific antibody, comprising expressing the polynucleotide encoding a heavy chain of the bispecific antibody, the polynucleotide encoding a light chain of the bispecific antibody in a cell. The step of expressing the polynucleotide may be conducted by culturing the cell comprising the polynucleotide (for example, in a recombinant vector) under a condition allowing the expression of the polynucleotide. The method may further comprise isolating and/or purifying the bispecific antibody from the cell culture, after the step of expressing or culturing.

DETAILED DESCRIPTION

Definitions

Figure 1A:
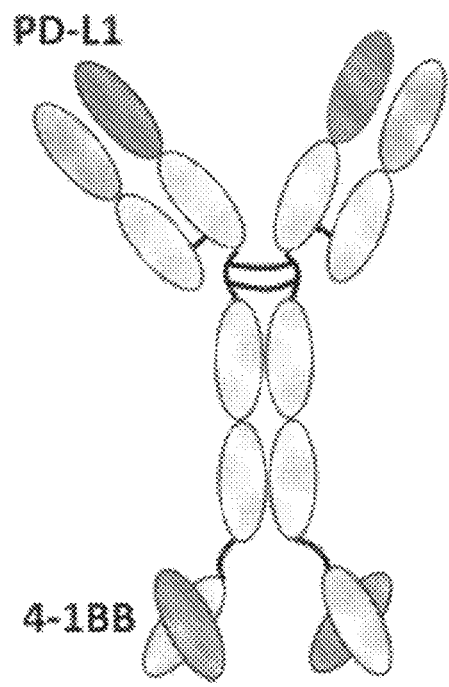
FIGS. 1A and 1B schematically illustrate an anti-PD-L1/anti-4-1BB bispecific antibody according to an embodiment.

It is to be noted that the term "a" or "an" entity refers to one or more of that entity for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides are meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least 70%, at least 75%, at least 80%, at least 85%, at least 90%, at least 95%, at least 98%, or at least 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency." In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene." A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γI-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')₂, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see www.bioinf.org.uk: Dr. Andrew C. R. Martin's Group; "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." Preferably, the antibody binds to an antigen (or epitope) with "high affinity", namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $25\times10^{-9}$ M or less or even more preferably $1\times10^{-9}$ M or less.

As used herein, the terms "treat" or "treatment" may refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," may refer to any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

The present disclosure provides an anti-PD-L1/anti-4-1BB bispecific antibody capable to effectively block the interactions between PD-L1 and its receptor PD-1 and between 4-1BB and its ligand. The bispecific antibody may have high binding affinity to both of a PD-L1 protein (e.g., a human PD-L1 protein) and a 4-1BB protein (e.g., a human 4-1BB protein).

The anti-PD-L1/anti-4-1BB bispecific antibody may comprise an anti-PD-L1 antibody or an antigen-binding fragment thereof as a PD-L1 targeting moiety, which is capable of specifically recognizing and/or binding to a PD-L1 protein, and an anti-4-1BB antibody or an antigen-binding fragment thereof as a 4-1BB targeting moiety, which is capable of specifically recognizing and/or binding to a 4-1BB protein.

Anti-PD-L1 Antibody

The anti-PD-L1/anti-4-1BB bispecific antibody may comprise an anti-PD-L1 antibody or an antigen-binding fragment thereof as a PD-L1 targeting moiety. The anti-PD-L1 antibody or antigen-binding fragment thereof may exhibit potent binding and inhibitory activities to PD-L1, and be useful for therapeutic and diagnostics uses.

The PD-L1 protein is a 40 kDa type 1 transmembrane protein. The PD-L1 protein may be a human PD-L1 protein, and the human PD-L1 protein may be selected from the group consisting of proteins represented by GenBank Accession No. NP_001254635.1, NP_001300958.1, NP_054862.1, etc., but may not be limited thereto. The human PD-L1 protein includes an extracellular portion including an N-terminal immunoglobulin V (IgV) domain (amino acids 19-127) and a C-terminal immunoglobulin C (IgC) domain (amino acids 133-225). Unlike pre-existing anti-PD-L1 antibodies, which bind to the IgV domain of PD-L1, thereby disrupting the binding between PD-1 and PD-L1, the anti-PD-L1 antibody or fragment thereof comprised in the bispecific antibody may not bind to an immunoglobulin V (IgV) domain of the PD-L1 protein but bind to the IgC domain of PD-L1, to effectively inhibit PD-L1, thereby improving therapeutic effects.

In particular, the anti-PD-L1 antibody or fragment thereof comprised in the bispecific antibody can specifically bind to an immunoglobulin C (IgC) domain of PD-L1 protein. In the case of human PD-L1 protein, the Ig C domain comprises or consists essentially of amino acid residues 133-225 of full-length of the human PD-L1 protein. More specifically, the anti-PD-L1 antibody or fragment thereof can bind to at least one selected from the amino acid residues Y134, K162, and N183 of human PD-L1 protein. In some embodiments, the anti-PD-L1 antibody or fragment thereof can bind to at least two selected from the amino acid residues Y134, K162, and N183 of human PD-L1 protein. In some embodiments, the anti-PD-L1 antibody or fragment thereof does not bind to an immunoglobulin V (IgV) domain of the PD-L1 protein, wherein the IgV domain consists of amino acid residues 19-127 of human PD-L1 protein.

In an embodiment, the anti-PD-L1 antibody or fragment thereof is capable of specificity to a human PD-L1 protein.

The anti-PD-L1 antibody or fragment thereof may comprise (1) a VH CDR1 having an amino acid sequence of SEQ ID NO: 1; (2) a VH CDR2 having an amino acid sequence selected from the group consisting of SEQ ID NO: 2 and SEQ ID NO: 3; (3) a VH CDR3 having an amino acid sequence selected from the group consisting of SEQ ID NOS: 4, 5, 262, 263, 264, 265, 266 and 267; (4) a VL CDR1 having an amino acid sequence of SEQ ID NO: 6, 268 and 269; (5) a VL CDR2 having an amino acid sequence of SEQ ID NO: 7; and (6) a VL CDR3 having an amino acid sequence of SEQ ID NO: 8, 270, 271 and 272.

TABLE 2

CDRs of anti-PD-L1 antibodies

| Name | Sequence | SEQ ID NO: |
|---|---|---|
| VH CDR1 | SYDMS | 1 |
| VH CDR2 | TISDAGGYIYYSDSVKG | 2 |
|  | TISDAGGYIYYRDSVKG | 3 |
| VH CDR3 | EFGKRYALDY | 4 |
|  | ELPWRYALDY | 5 |
|  | EFGKRYALDS | 262 |
|  | EIFNRYALDY | 263 |
|  | ELHFRYALDY | 264 |
|  | ELYFRYALDY | 265 |
|  | ELLHRYALDY | 266 |
|  | ELRGRYALDY | 267 |
| VL CDR1 | KASQDVTPAVA | 6 |
|  | KAKQDVTPAVA | 268 |
|  | KASQDVWPAVA | 269 |
| VL CDR2 | STSSRYT | 7 |
| VL CDR3 | QQHYTTPLT | 8 |
|  | MQHYTTPLT | 270 |
|  | QQHSTTPLT | 271 |
|  | QQHSDAPLT | 272 |

In some embodiments, an antibody or fragment thereof includes no more than one, no more than two, or no more than three of the above substitutions. In some embodiments, the antibody or fragment thereof includes a VH CDR1 of SEQ ID NO: 1, a VH CDR2 of SEQ ID NO: 2 or 3, a VH CDR3 of SEQ ID NO: 4, 5, 262, 263, 264, 265, 266 or 267, a VL CDR1 of SEQ ID NO: 6, 268 or 269, a VL CDR2 of SEQ ID NO: 7, and a VL CDR3 of SEQ ID NO: 8, 270, 271 or 272.

For example, the anti-PD-L1 antibody or fragment thereof may comprise a VH CDR1 having an amino acid sequence of SEQ ID NO: 1; a VH CDR2 having an amino acid sequence of SEQ ID NO: 2 or 3; a VH CDR3 having an amino acid sequence of SEQ ID NO: 4 or 5; a VL CDR1 having an amino acid sequence of SEQ ID NO: 6; a VL CDR2 having an amino acid sequence of SEQ ID NO: 7; and a VL CDR3 having an amino acid sequence of SEQ ID NO: 8.

The back-mutations may be useful for retaining certain characteristics of the anti-PD-L1 antibodies. In some embodiments, the anti-PD-L1 antibodies of the present disclosure, in particular the human or humanized ones, may include one or more of the back-mutations. In some embodiments, the back-mutation (i.e., included amino acid at the specified position) in a heavy chain variable region (VH) is one or more selected from (a) Ser at position 44, (b) Ala at position 49, (c) Ala at position 53, (d) Ile at position 91, (e) Glu at position 1, (f) Val at position 37, (g) Thr at position 40, (h) Val at position 53, (i) Glu at position 54, (j) Asn at position 77, (k) Arg at position 94, and (l) Thr at position 108, of the heavy chain variable region, according to Kabat numbering, and combinations thereof. In some embodiments, the VH back-mutations are selected from (a) Ser at position 44, (b) Ala at position 49, (c) Ala at position 53, and/or (d) Ile at position 91, of the heavy chain variable region, according to Kabat numbering, and combinations thereof.

In some embodiments, the back-mutation in a light chain variable region (VL) is one or more selected from (a) Ser at position 22, (b) Gln at position 42, (c) Ser at position 43, (d) Asp at position 60, and (e) Thr at position 63, of the light chain variable region, according to Kabat numbering, and combinations thereof.

In some embodiments, the anti-PD-L1 antibody or fragment thereof further comprises a heavy chain constant region, a light chain constant region, an Fc region, or the combination thereof. In some embodiments, the light chain constant region may be a kappa or lambda chain constant region. In some embodiments, the antibody is of an isotype of IgG, IgM, IgA, IgE or IgD, for example, human IgG, human IgM, human IgA, human IgE, or human IgD. In some embodiments, the isotype may be IgG, for example human IgG, such as, IgG1, IgG2, IgG3, or IgG4. In some embodiments, the fragment (antigen-binding fragment of the anti-PD-L1 antibody) may be any fragment comprising heavy chain CDRs and/or light chain CDRs of the antibody, and for example, it may be selected from the group consisting of Fab, Fab', F(ab')$_2$, Fd (comprising a heavy chain variable region and a CH1 domain), Fv (a heavy chain variable region and/or a light chain variable region), single-chain Fv (scFv; comprising or consisting essentially of a heavy chain variable region and a light chain variable region, in any order, and a peptide linker between the heavy chain variable region and the light chain variable region), single-chain antibodies, disulfide-linked Fvs (sdFv), and the like.

Without limitation, the anti-PD-L1 antibody or fragment thereof is a chimeric antibody, a humanized antibody, or a fully human antibody. In one aspect, antibody or fragment thereof is not naturally occurring, or chemically or recombinantly synthesized.

The binding of an antibody of the disclosure to PD-L1 can be assessed using one or more techniques well established in the art. For example, in a preferred embodiment, an antibody can be tested by a flow cytometry assay in which the antibody is reacted with a cell line that expresses human PD-L1, such as CHO cells that have been transfected to express PD-L1, e.g., human PD-L1, or monkey PD-L1, e.g., rhesus or cynomolgus monkey or mouse PD-L1 on their cell surface. Other suitable cells for use in flow cytometry assays include anti-CD3-stimulated CD4$^+$ activated T cells, which express native PD-L1. Still other suitable binding assays include ELISA assays, for example using a recombinant PD-L1 protein. Additionally, or alternatively, the binding of the antibody, including the binding kinetics (e.g., KD value) can be tested in Biacore analysis. Preferred binding affinities of an antibody of the disclosure include those with a dissociation constant or KD of $4.25 \times 10^{-9}$ M or less.

Given that each of these antibodies can bind to PD-L1 such as human PD-L1, the CDR sequences or $V_H$ and $V_L$ sequences can be "mixed and matched" to create other anti-PD-L1 binding molecules of the disclosure. Preferably, when the CDR sequences or $V_H$ and $V_L$ chains are mixed and matched, for example, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Anti-4-1BB Antibody

The anti-PD-L1/anti-4-1BB bispecific antibody may comprise an anti-4-1BB antibody or an antigen-binding fragment thereof as a 4-1BB targeting moiety.

In an embodiment, the anti-4-1BB antibody or fragment thereof can specifically bind to 4-1BB (e.g., human 4-1BB) protein.

For example, the human 4-1BB protein may be selected from the group consisting of proteins represented by NCBI Accession No. NP_001552, etc., but may not be limited thereto. These anti-4-1BB antibodies or antigen-binding fragments thereof are capable of enhancing immune response and/or treating tumor (cancer) in a mammal. The anti-4-1BB antibody or an antigen-binding fragment thereof is characterized by localizing and/or activating only in tumor microenvironment (TME) and/or considerably reducing liver toxicities compared to pre-existing anti-4-1BB antibodies, with maintaining the efficacies of enhancing immune response enhancement and/or tumor treatment.

The term "4-1BB" refers to CD137, or TNFRSF9 (TNF Receptor 25 Superfamily Member 9), is a member of TNF-receptor superfamily (TNFRSF) and is a co-stimulatory molecule which is expressed following the activation of immune cells, both innate and adaptive immune cells. As used herein, 4-1BB may be originated from a mammal, for example, *Homo sapiens* (human) (NCBI Accession No. NP_001552). For example, the human 4-1BB protein (NP_001552) may be represented by the amino acid sequence (SEQ ID NO: 9), as follows:

1 mgnscyniva tillvlnfer trslqdpcsn cpagtfcdnn mqicspcpp
   nsfssaggqr 61 tcdicrqckg   vfrtrkecss   tsnaecdctp   gfhclgagcs
   mceqdckqgq eltkkgckdc 121 cfgtfndqkr gicrpwtncs ldgksvlvng tkerdvvcgp spadl-
   spgas svtppapare 181 pghspqiisf flaltstall fllfltirf svvkrgrkkl lyifkqpfmr
   pvqttqeedg 241 cscrfpeeee ggcel As described herein, the term "4-1BB" includes variants, isoforms, homologs, orthologs, and paralogs. For example, antibodies specific for a human 4-1BB protein may, in certain cases, cross-react with a 4-1BB protein from a species other than human. In other embodiments, the antibodies specific for a human 4-1BB protein may be completely specific for the human 4-1BB protein and may exhibit species or other types of cross-reactivity, or may cross-react with 4-1BB from certain other species but not all other species (e.g., cross-react with monkey 4-1BB, but not mouse 4-1BB). The term "human 4-1BB" refers to human sequence 4-1BB, such as the complete amino acid sequence of human 4-1BB having NCBI Accession No. NP_001552. The term "mouse 4-1BB" refers to mouse sequence 4-1BB, such as the complete amino acid sequence of mouse 4-1BB having NCBI Accession No. NP 033430.1. 4-1BB also can be known in the art as, for example, CD137. The human 4-1BB sequence in the disclosure may differ from human 4-1BB of NCBI Accession No. NP_001552 by having, e.g., conserved mutations or mutations in non-conserved regions and the 4-1BB in the disclosure has substantially the same biological function as the human 4-1BB of NCBI Accession No. NP_001552.

As demonstrated in the experimental examples, the anti-4-1BB antibodies disclosure herein show 4-1BB binding abilities, binding abilities to 4-1BB which expressed on cell surface, and high 4-1BB binding affinities. In addition, as demonstrated in the experimental example, the anti-4-1BB antibody disclosure herein, particularly when combined with anti-PD-L1 antibody disclosure herein, is capable of activation T cell. Furthermore, as demonstrated in the experimental example, the anti-4-1BB antibody disclosure herein has increased in vivo antitumor effect.

These anti-4-1BB antibodies may be useful for therapeutic purposes such as treating various types of cancer, etc., and can also be used for diagnostic and prognostic purposes.

In an embodiment, the anti-4-1BB antibody or fragment thereof is capable of specificity to a human 4-1BB protein. The anti-4-1BB antibody or fragment thereof may comprise (i) a VH CDR1 having an amino acid sequence selected from the group consisting of SEQ ID NOS: 10 and 11; (ii) a VH CDR2 having an amino acid sequence selected from the group consisting of SEQ ID NOS: 12 and 13; (iii) a VH CDR3 having an amino acid sequence selected from the group consisting of SEQ ID NOS: 14, 15, 16 and 17; (iv) a VL CDR1 having an amino acid sequence of SEQ ID NO: 18; (v) a VL CDR2 having an amino acid sequence of SEQ ID NO: 19; and (vi) a VL CDR3 having an amino acid sequence of SEQ ID NO: 20. For example, the anti-4-1BB antibody or fragment thereof may comprise a VH CDR1 having an amino acid sequence of SEQ ID NO: 10 or 11; a VH CDR2 having an amino acid sequence of SEQ ID NO: 12 or 13; a VH CDR3 having an amino acid sequence of SEQ ID NO: 14, 15, 16, or 17; a VL CDR1 having an amino acid sequence of SEQ ID NO: 18; a VL CDR2 having an amino acid sequence of SEQ ID NO: 19; and a VL CDR3 having an amino acid sequence of SEQ ID NO: 20.

TABLE 3

CDRs of anti-4-1BB antibodies

| Name | Sequence | SEQ ID NO: |
|---|---|---|
| VH CDR1 | SYDMS | 10 |
|  | GYDMS | 11 |
| VH CDR2 | WISYSGGSIYYADSVKG | 12 |
|  | VIYPDDGNTYYADSVKG | 13 |
| VH CDR3 | DGQRNSMREFDY | 14 |
|  | HGGQKPTTKSSSAYGMDG | 15 |
|  | DAQRNSMREFDY | 16 |
|  | DAQRQSMREFDY | 17 |
| VL CDR1 | SGSSSNIGNNYVT | 18 |

TABLE 3-continued

CDRs of anti-4-1BB antibodies

| Name | Sequence | SEQ ID NO: |
|---|---|---|
| VL CDR2 | ADSHRPS | 19 |
| VL CDR3 | ATWDYSLSGYV | 20 |

In non-limiting examples of the anti-4-1BB antibody or fragment thereof,
(1) the heavy chain variable region may comprise or consist essentially of a polypeptide having an amino acid sequence selected from the group consisting of SEQ ID NOS: 21, 22, 23 and 24, or a polypeptide having a sequence identity of at least 80%, at least 85%, at least 90%, at least 95%, at least 96%, at least 97%, at least 98%, or at least 99% to the above described amino acid sequences; and/or
(2) the light chain variable region may comprise or consist essentially of a polypeptide having an amino acid sequence selected from the group consisting of SEQ ID NOS: 25 and 26, or a polypeptide having a sequence identity of at least 80%, at least 85%, at least 90%, at least 95%, at least 96%, at least 97%, at least 98%, or at least 99% to the above described amino acid sequences.

Non-limiting examples of the anti-4-1BB antibody or fragment thereof may comprise a heavy chain variable region comprising or consisting essentially of the amino acid sequence of SEQ ID NO: 21, 22, 23 or 24.

(SEQ ID NO: 21)
EVQLLESGGGLVQPGGSLRLSCAASGFTFSSYDMSWVRQAPGKCLEWVS

WISYSGGSIYYADSVKGRFTISRDNSKNTLYLQMNSLRAEDTAVYYCAR

DGQRNSMREFDYWGQGTLVTVSS (SEQ ID NO: 22)
EVQLLESGGGLVQPGGSLRLSCAASGFTFSGYDMSWVRQAPGKCLEWVS

VIYPDDGNTYYADSVKGRFTISRDNSKNTLYLQMNSLRAEDAAVYYCAK

HGGQKPTTKSSSAYGMDGWGQGTLVTVSS (SEQ ID NO: 23)
EVQLLESGGGLVQPGGSLRLSCAASGFTFSSYDMSWVRQAPGKCLEWVS

WISYSGGSIYYADSVKGRFTISRDNSKNTLYLQMNSLRAEDTAVYYCAR

DAQRNSMREFDYWGQGTLVTVSS (SEQ ID NO: 24)
EVQLLESGGGLVQPGGSLRLSCAASGFTFSSYDMSWVRQAPGKCLEWVS

WISYSGGSIYYADSVKGRFTISRDNSKNTLYLQMNSLRAEDTAVYYCAR

DAQRQSMREFDYWGQGTLVTVSS

Non-limiting examples of the anti-4-1BB antibody or fragment thereof may comprise a light chain variable region comprising or consisting essentially of the amino acid sequence of SEQ ID NO: 25 or 26.

(SEQ ID NO: 25)
QSVLTQPPSASGTPGRRVTISGSGSSSNIGNNYVTWYQQLPGTAPKLLI

YADSHRPSGVPDRFSGSKSGTSASLAISGLRSEDEADYYCATWDYSLSG

YVFGCGTKLTVL

-continued (SEQ ID NO: 26)
QSVLTQPPSASGTPGQRVTISGSGSSSNIGNNYVTWYQQLPGTAPKLLI

YADSHRPSGVPDRFSGSKSGTSASLAISGLRSEDEADYYCATWDYSLSG

YVFGCGTKLTVL

The antibodies of the disclosure are characterized by particular functional features or properties of the antibodies. For example, the antibodies specifically bind to human 4-1BB and may bind to 4-1BB from certain other species, e.g., monkey 4-1BB, e.g., cynomolgus monkey, rhesus monkey, but may not substantially bind to 4-1BB from certain other species, e.g., mouse 4-1BB. Preferably, an antibody of the disclosure binds to human 4-1BB with high affinity.

Further, the antibody of the disclosure, particularly as bispecific antibody comprising an anti-PD-L1 antibody of the disclosure herein, has the ability to enhance immune cell proliferation, survival, secretion of cytokines and cytolytic activity CD8 T cells. In certain embodiments, an antibody of the disclosure, particularly as bispecific antibody comprising an anti-PD-L1 antibody, binds to human 4-1BB and exhibits an ability to activate T cells.

Other means by which to evaluate the ability of the antibody to stimulate an immune response include the ability of the antibody to inhibit tumor growth, such as in an in vivo tumor graft model.

The binding of an antibody of the disclosure to 4-1BB can be assessed using one or more techniques well established in the art. For example, in a preferred embodiment, an antibody can be tested by a flow cytometry assay in which the antibody is reacted with a cell line that expresses human 4-1BB, such as CHO cells that have been transfected to express 4-1BB, e.g., human 4-1BB, or monkey 4-1BB, e.g., rhesus or cynomolgus monkey or mouse 4-1BB on their cell surface. Other suitable cells for use in flow cytometry assays include anti-CD3-stimulated CD4+ activated T cells, which express native 4-1BB. Still other suitable binding assays include ELISA assays, for example using a recombinant 4-1BB protein. Additionally, or alternatively, the binding of the antibody, including the binding kinetics (e.g., KD value) can be tested in Octet analysis. Preferred binding affinities of an antibody of the disclosure include those with a dissociation constant or KD of $1.80 \times 10^{-10}$ M or less.

In some embodiments, the anti-4-1BB antibody or fragment thereof further comprises a heavy chain constant region, a light chain constant region, an Fc region, or the combination thereof. In some embodiments, the light chain constant region may be a kappa or lambda chain constant region. In some embodiments, the antibody is of an isotype of IgG, IgM, IgA, IgE or IgD, for example, human IgG, human IgM, human IgA, human IgE, or human IgD. In some embodiments, the isotype may be IgG, for example human IgG, such as, IgG1, IgG2, IgG3, or IgG4. In some embodiments, the fragment (antigen-binding fragment of the anti-PD-L1 antibody) may be any fragment comprising heavy chain CDRs and/or light chain CDRs of the antibody, and for example, it may be selected from the group consisting of Fab, Fab', F(ab')$_2$, Fd (comprising a heavy chain variable region and a CH1 domain), Fv (a heavy chain variable region and/or a light chain variable region), single-chain Fv (scFv; comprising or consisting essentially of a heavy chain variable region and a light chain variable region, in any order, and a peptide linker between the heavy chain variable region and the light chain variable region), single-chain antibodies, disulfide-linked Fvs (sdFv), and the like.

Without limitation, the anti-4-1BB antibody or fragment thereof is a chimeric antibody, a humanized antibody, or a fully human antibody. In one aspect, antibody or fragment thereof is not naturally occurring, or chemically or recombinantly synthesized.

Given that each of these antibodies can bind to 4-1BB such as human 4-1BB, the CDR sequences or the $V_H$ and $V_L$ sequences can be "mixed and matched" to create other anti-4-1BB binding molecules of the disclosure. Preferably, when the CDRs sequences or $V_H$ and $V_L$ chains are mixed and matched, for example, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Anti-PD-L1/Anti-4-1BB Bispecific Antibody

Figure 1B:
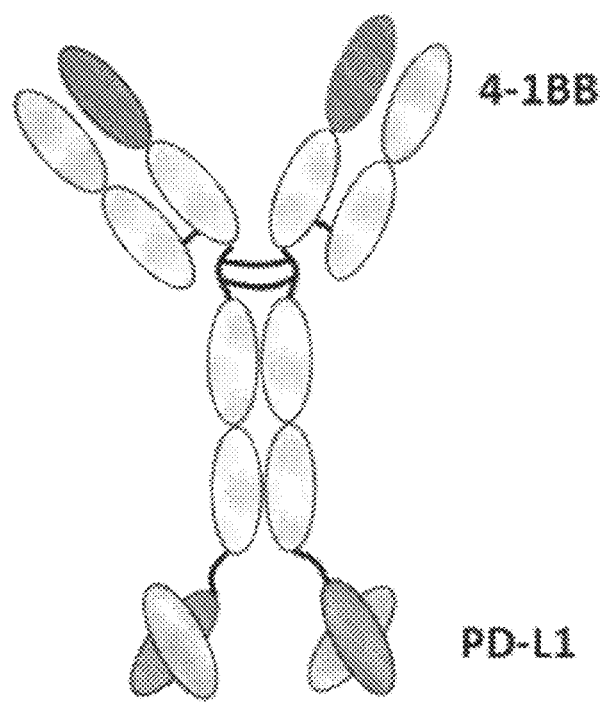

In the bispecific antibody comprising the PD-L1 targeting moiety and the 4-1BB targeting moiety, one of the PD-L1 targeting moiety and the 4-1BB targeting moiety can be a full-length antibody, and the other can be an antigen-binding fragment (e.g., scFv) comprising heavy chain CDRs, light chain CDRs, or a combination thereof. The full-length antibody targeting one of PD-L1 and 4-1BB proteins, and the antigen-binding fragment targeting the other protein may be chemically linked (e.g., covalently linked) directly or via a peptide linker. The antigen-binding fragment (e.g., scFv) may be linked directly or via a peptide linker to N-terminus of the full-length antibody (e.g., N-terminus of a light chain or a heavy chain of the full-length antibody), C-terminus of the full-length antibody (e.g., C-terminus of a heavy chain (or Fc or CH3 domain) of the full-length antibody), or both thereof (see FIGS. 1A and 1B).

In an embodiment, the bispecific antibody may comprise a full-length anti-PD-L1 antibody, an antigen-binding fragment (e.g., scFv) of an anti-4-1BB antibody, and a peptide linker therebetween. In other embodiment, the bispecific antibody may comprise a full-length anti-4-1BB antibody, an antigen-binding fragment (e.g., scFv) of an anti-PD-L1 antibody, and a peptide linker therebetween.

In an embodiment, the scFv contained in the bispecific antibody may comprise a heavy chain variable region and a light chain variable region in any order. For example, the scFv contained in the bispecific antibody may comprise a heavy chain variable region and a light chain variable, in a direction from N-terminus to C-terminus, and optionally a peptide linker therebetween, or alternatively, the scFv contained in the bispecific antibody may comprise a light chain variable region and a heavy chain variable, in a direction from N-terminus to C-terminus, and optionally a peptide linker therebetween.

In an embodiment, the anti-PD-L1/anti-4-1BB bispecific antibody activates 4-1BB signaling, and as a result immune response, depending on PD-L1 expressed on cell surfaces.

The use of a peptide linker for the bispecific antibody may lead to a high purity of the antibody.

As used herein, the term "peptide linker" may be those including any amino acids of 1 to 100, particularly 2 to 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the relevant art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as $(G_mS_l)_n$ (m, l, and n, are independently an integer of about 1 to about 10, particularly an integer of about 2 to about 5). For example, the examples of the peptide liners are summarized as follows:

| Linker Function | Fusion Proteis | Linker Type | Sequence[a] | Ref. |
|---|---|---|---|---|
| Increase Stability/ Folding | scFv | flexible | (GGGGS)₃ | [46] |
| | G-CSF-Tf | flexible | (GGGGS)₃ | [20] |
| | HBsAg preS1 | flexible | (GGGGS)₃ | [85] |
| | Myc- Est2p | flexible | (Gly)₆ | [30] |
| | albumin-ANF | flexible | (Gly)₆ | [31] |
| | virus coat protein | rigid | (EAAAK)₃ | [50] |
| | beta-glucannase-xylanase | rigid | (EAAAK)ₙ (n = 1-3) | [52] |
| Increase expression | hGH-Tf and Tf-hGH | rigid | A(EAAAK)₄ALEA(EAAAK)₄A | [18] |
| | G-CSF-Tf and Tf-F-CSF | rigid | A(EAAAK)₄ALEA(EAAAK)₄A | [18] |
| Improve biological activity | G-CSF-Tf | flexible | (GGGGS)₃ | [20] |
| | G-CSF-Tf | sigid | A(EAAAK)₄ALEA(EAAAK)₄A | [20] |
| | hGH-Tf | digid | A(EAAAK)₄ALEA(EAAAK)₄A | [40] |
| | HSA-IFN-α2b | flexible | GGGGS | [17] |
| | HSA-IFN-α2b | rigid | PAPAP | [17] |
| | HSA-IFN-α2b | rigid | AEAAAKEAAAKA | [17] |
| | PGA-rTHS | flexible | (GGGGS)ₙ (n = 1, 2, 4) | [55] |
| | interferon- -gp120 | rigid | (Als-Pro)ₙ (10-34 aa) | [54] |
| | GSF-S-S-Tf | cleavable | disulfide | [39] |
| | IFN-α2b-HSA | cleavable | disulfide | [42] |
| Enable targeting | FIX-albumin | cleavable | VSQTSKLTR AETVFPDV[b] | [59] |
| | LAP-IFN- | cleavable | PLG LWA[c] | [64] |
| | MazE-MazF | cleavable | RVL AEA; EDVVCC SMSY; GGIEGR GS[c] | [68] |
| | Immunotoxins | cleavable | TRHRQPR GWE; AGNRVRR SVG; RRRRRRR R R[d] | [72] |
| | Immunotoxin | cleavable | GFLG[c] | [77] |
| Alter PK | G-CSF-Tf and hGH-TF | dipeptide | LE | [79] |
| | | rigid | A(EAAAK)₄ALEA(EAAAK)₄A | |
| | | cleavable | Disulfide | |

In another embodiment, both of the PD-L1 targeting moiety and the 4-1BB targeting moiety may be a full-length antibody or an antigen-binding fragment comprising heavy chain CDRs, light chain CDRs, or a combination thereof.

In another embodiment, the bispecific antibody may be in a heterodimeric form, which comprises a first arm including a pair of a first heavy chain and a first light chain targeting one of PD-L1 and 4-1BB, and a second arm including a pair of a second heavy chain and a second light chain targeting the other one.

In an embodiment, the full-length antibody may be in a full-length immunoglobulin form (e.g., IgG, IgM, IgA, IgE or IgD, such as, human IgG, human IgM, human IgA, human IgE, or human IgD), and the antigen-binding fragment may be selected from the group consisting of Fab, Fab', F(ab')₂, Fd, Fv, scFv, single-chain antibodies, sdFv, and the like, as described above. For example, the full-length antibody may be in a full-length human IgG (human IgG1, human IgG2, human IgG3, or human IgG4) form, and the antigen-binding fragment may be scFv.

For example, an antibody described herein may comprise a flexible linker sequence, or may be modified to add a functional moiety (e.g., PEG, a drug, a toxin, or a label).

Antibodies or variants described herein may comprise derivatives that are modified, e.g., by the covalent attachment of any type of molecule to the antibody such that covalent attachment does not prevent the antibody from binding to the antigen (e.g., an epitope). For example, but not by way of limitation, the antibodies can be modified, e.g., by at least one selected from the group consisting of glycosylation, acetylation, pegylation, phosphorylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

The antibodies or fragments thereof can be detectably labeled by tagging (coupling) with a conventional labeling material selected from chemiluminescent compounds, fluorescent compounds (e.g., fluorescence emitting metals), radioisotopes, dyes, etc. The presence of the tagged antibodies or fragments thereof can be detected by measuring a signal arising during a chemical reaction between the antibody (or fragment thereof) and the labeling material. Examples of particularly useful labeling material may be at least one selected from the group consisting of luminol, isoluminol, theromatic acridinium ester, imidazole, acridinium salt, oxalate ester, fluorescence emitting metals, and the like. For example, the fluorescence emitting metals may be $^{152}$Eu, or others of the lanthanide series. These metals can be attached to the antibody using such metal chelating groups as diethylenetriaminepentacetic acid (DTPA) or ethylenediaminetetraacetic acid (EDTA).

In certain embodiments, the prepared bispecific antibodies will not elicit a deleterious immune response in the animal to be treated, e.g., in a human. In one embodiment, the bispecific antibody may be modified to reduce their immunogenicity using any conventional techniques. For example, the bispecific antibody may be a humanized, primatized, deimmunized, or chimeric antibody. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues.

De-immunization can also be used to decrease the immunogenicity of an antibody. As used herein, the term "de-immunization" may include alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V (variable) region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity and/or affinity of the bispecific antibody to each target protein can be determined by any conventional assay, for example, in vitro assays such as immunoprecipitation, radioimmunoassay (RIA), or enzyme-linked immunoabsorbent assay (ELISA), but not be limited thereto.

Alternatively, techniques described for the production of single-chain units (U.S. Pat. No. 4,694,778, etc.) can be adapted to produce single-chain units of the present disclosure. Single-chain units are formed by linking the heavy and light chain fragments of the Fv region via an amino acid bridge (peptide linker), resulting in a single-chain fusion peptide (scFv). Techniques for the assembly of functional Fv fragments in E. coli may also be used.

Examples of techniques which can be used to produce single-chain Fvs (scFvs) and antibodies include those described in U.S. Pat. Nos. 4,946,778, 5,258,498, etc.). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., U.S. Pat. Nos. 5,807,715, 4,816,567, and 4,816,397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions (See, e.g., Queen et al., U.S. Pat. No. 5,585,089, which are incorporated herein by reference in their entireties). Antibodies can be humanized using a variety of techniques known in the art including, for example, CDR-grafting (U.S. Pat. Nos. 5,225,539, 5,530,101, 5,585,089, etc., each of which is incorporated by reference in its entirety), veneering or resurfacing (EP 592,106; EP 519,596, each of which is incorporated by reference in its entirety), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887, 4,716,111, etc., each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the bisprcific antibody may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). For example, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen (or epitope). Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Alternatively, antibody-producing cell lines may be selected and cultured using techniques well known to the skilled artisan. Such techniques are described in a variety of laboratory manuals and primary publications.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Non-limiting examples of Anti-PD-L1/anti-4-1BB bispecific antibody are provided in Table 4 below.

As used herein, "Heavy Component" means a component of anti-PD-L1/anti-4-1BB bispecific antibody of the present disclosure, which comprises (1) heavy chain of anti-PD-L1 antibody and (2) heavy chain and light chain of anti-4-1BB antibody.

As used herein, "Light Component" means a component of anti-PD-L1/anti-4-1BB bispecific antibody of the present disclosure, which comprises light chain of anti-PD-L1 antibody.

TABLE 4

Examples of Anti-PD-L1/anti-4-1BB bispecific antibody

| ABLPNB.01 | Heavy Component | EVOLVESGGGLVQPGGSLRLSCAASGFTFSSYDMS WVRQAPGKSLEWVATISDAGGYIYYSDSVKGRFTISR DNAKNSLYLQMNSLRDEDTAVYICAREFGKRYALDY WGQGTTVTVSSASTKGPSVFPLAPSSKSTSGGTAAL GCLVKDYFPEPVTVSWNSGALTSGVHTFPAVLQSSG LYSLSSWTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAK TKPREEQYASTYRVVSVLTVLHQDWLNGKEYKCKVS NKALPAPIEKTISKAKGQPREPQVYTLPPSREEMTKN QVSLTCLVKGFYPSDIAVEWESNGQPENNYKTTPPVL DSDGSFFLYSKLTVDKSRWQQGNVFSCSVMHEALH NHYTQKSLSLSPGKGGGGSGGGGSGGGGSQSVLTQ PPSASGTPGRRVTISGSGSSSNIGNNYVTWYQQLPG TAPKLLIYADSHRPSGVPDRFSGSKSGTSASLAISGLR SEDEADYYCATWDYSLSGYVFGCGTKLTVLGGGGS GGGGSGGGGSGGGGSEVQLLESGGGLVQPGGSLR | SEQ ID NO: 27 |

TABLE 4-continued

Examples of Anti-PD-L1/anti-4-1BB bispecific antibody

| | | | |
|---|---|---|---|
| | | LSCAASGFTFSSYDMSWVRQAPGKCLEWVSWISYSGGSIYYADSVKGRFTISRDNSKNTLYLQMNSLRAEDTAVYYCARDGQRNSMREFDYWGQGTLVTVSS | |
| | Light Component | DIQMTQSPSSLSASVGDRVTITCKASQDVTPAVAWYQQKPGKAPKLLIYSTSSRYTGVPSRFSGSGSGTDFTFTISSLQPEDIATYYCQQHYTTPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 28 |
| ABLPNB.02 | Heavy Component | EVQLVESGGGLVQPGGSLRLSCAASGFTFSSYDMSWVRQAPGKSLEWVATISDAGGYIYYSDSVKGRFTISRDNAKNSLYLQMNSLRDEDTAVYICAREFGKRYALDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGGGSGGGGSGGGGSQSVLTQPPSASGTPGQRVTISGSGSSSNIGNNYVTWYQQLPGTAPKLLIYADSHRPSGVPDRFSGSKSGTSASLAISGLRSEDEADYYCATWDYSLSGYVFGCGTKLTVLGGGGSGGGGGGGGSGGGGSEVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS | SEQ ID NO: 29 |
| | Light Component | DIQMTQSPSSLSASVGDRVTITCKASQDVTPAVAWYQQKPGKAPKLLIYSTSSRYTGVPSRFSGSGSGTDFTFTISSLQPEDIATYYCQQHYTTPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 30 |
| ABLPNB.03 | Heavy Component | EVQLVESGGGLVQPGGSLRLSCAASGFTFSSYDMSWVRQAPGKSLEWVATISDAGGYIYYSDSVKGRFTISRDNAKNSLYLQMNSLRDEDTAVYICAREFGKRYALDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGGGSGGGGSGGGGSQSVLTQPPSASGTPGRRVTISGSGSSSNIGNNYVTWYQQLPGTAPKLLIYADSHRPSGVPDRFSGSKSGTSASLAISGLRSEDEADYYCATWDYSLSGYVFGCGTKLTVLGGGGSGGGGSGGGGSGGGGSEVQLLESGGGLVQPGGSLRLSCAASGFTFSGYDMSWVRQAPGKCLEWVSVIYPDDGNTYYADSVKGRFTISRDNSKNTLYLQMNSLRAEDAAVYYCAKHGGQKPTTKSSSAYGMDGWGQGTLVTVSS | SEQ ID NO: 31 |
| | Light Component | DIQMTQSPSSLSASVGDRVTITCKASQDVTPAVAWYQQKPGKAPKLLIYSTSSRYTGVPSRFSGSGSGTDFTFTISSLQPEDIATYYCQQHYTTPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 32 |
| ABLPNB.04 | Heavy Component | EVQLVESGGGLVQPGGSLRLSCAASGFTFSSYDMSWVRQAPGKSLEWVATISDAGGYIYYRDSVKGRFTISRDNAKNSLYLQMNSLRDEDTAVYICARELPWRYALDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKN | SEQ ID NO: 33 |

TABLE 4-continued

Examples of Anti-PD-L1/anti-4-1BB bispecific antibody

|  |  |  |  |
|---|---|---|---|
|  |  | QVSLTCLVKGFYPSDIAVEWESNGQPENNYKTTPPVL<br>DSDGSFFLYSKLTVDKSRWQQGNVFSCSVMHEALH<br>NHYTQKSLSLSPGKGGGGSGGGGSGGGGSQSVLTQ<br>PPSASGTPGRRVTISGSGSSSNIGNNYVTWYQQLPG<br>TAPKLLIYADSHRPSGVPDRFSGSKSGTSASLAISGLR<br>SEDEADYYCATWDYSLSGYVFGCGTKLTVLGGGGS<br>GGGGSGGGGSGGGGSEVQLLESGGGLVQPGGSLR<br>LSCAASGFTFSSYDMSWVRQAPGKCLEWVSWISYS<br>GGSIYYADSVKGRFTISRDNSKNTLYLQMNSLRAEDT<br>AVYYCARDGQRNSMREFDYWGQGTLVTVSS |  |
|  | Light<br>Component | DIQMTQSPSSLSASVGDRVTITCKASQDVTPAVAWY<br>QQKPGKAPKLLIYSTSSRYTGVPSRFSGSGSGTDFTF<br>TISSLQPEDIATYYCQQHYTTPLTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC | SEQ<br>ID<br>NO:<br>34 |
| ABLPNB.05 | Heavy<br>Component | EVQLVESGGGLVQPGGSLRLSCAASGFTFSSYDMS<br>WVRQAPGKSLEWVATISDAGGYIYYRDSVKGRFTISR<br>DNAKNSLYLQMNSLRDEDTAVYICARELPWRYALDY<br>WGQGTTVTVSSASTKGPSVFPLAPSSKSTSGGTAAL<br>GCLVKDYFPEPVTVSWNSGALTSGVHTFPAVLQSSG<br>LYSLSSVVTVPSSSLGTQTYICNVNHKPSNTKVDKKV<br>EPKSCDKTHTCPPCPAPELLGGPSVFLFPPKPKDTLM<br>ISRTPEVTCVVVDVSHEDPEVKFNWYVDGVEVHNAK<br>TKPREEQYASTYRVVSVLTVLHQDWLNGKEYKCKVS<br>NKALPAPIEKTISKAKGQPREPQVYTLPPSREEMTKN<br>QVSLTCLVKGFYPSDIAVEWESNGQPENNYKTTPPVL<br>DSDGSFFLYSKLTVDKSRWQQGNVFSCSVMHEALH<br>NHYTQKSLSLSPGKGGGGSGGGGSGGGGSQSVLTQ<br>PPSASGTPGRRVTISGSGSSSNIGNNYVTWYQQLPG<br>TAPKLLIYADSHRPSGVPDRFSGSKSGTSASLAISGLR<br>SEDEADYYCATWDYSLSGYVFGCGTKLTVLGGGGS<br>GGGGSGGGGSGGGGSEVQLLESGGGLVQPGGSLR<br>LSCAASGFTFSSYDMSWVRQAPGKCLEWVSWISYS<br>GGSIYYADSVKGRFTISRDNSKNTLYLQMNSLRAEDT<br>AVYYCARDAQRNSMREFDYWGQGTLVTVSS | SEQ<br>ID<br>NO:<br>35 |
|  | Light<br>Component | DIQMTQSPSSLSASVGDRVTITCKASQDVTPAVAWY<br>QQKPGKAPKLLIYSTSSRYTGVPSRFSGSGSGTDFTF<br>TISSLQPEDIATYYCQQHYTTPLTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC | SEQ<br>ID<br>NO:<br>36 |
| ABLPNB.06 | Heavy<br>Component | EVQLVESGGGLVQPGGSLRLSCAASGFTFSSYDMS<br>WVRQAPGKSLEWVATISDAGGYIYYRDSVKGRFTISR<br>DNAKNSLYLQMNSLRDEDTAVYICARELPWRYALDY<br>WGQGTTVTVSSASTKGPSVFPLAPSSKSTSGGTAAL<br>GCLVKDYFPEPVTVSWNSGALTSGVHTFPAVLQSSG<br>LYSLSSVVTVPSSSLGTQTYICNVNHKPSNTKVDKKV<br>EPKSCDKTHTCPPCPAPELLGGPSVFLFPPKPKDTLM<br>ISRTPEVTCVVVDVSHEDPEVKFNWYVDGVEVHNAK<br>TKPREEQYASTYRVVSVLTVLHQDWLNGKEYKCKVS<br>NKALPAPIEKTISKAKGQPREPQVYTLPPSREEMTKN<br>QVSLTCLVKGFYPSDIAVEWESNGQPENNYKTTPPVL<br>DSDGSFFLYSKLTVDKSRWQQGNVFSCSVMHEALH<br>NHYTQKSLSLSPGKGGGGSGGGGSGGGGSQSVLTQ<br>PPSASGTPGRRVTISGSGSSSNIGNNYVTWYQQLPG<br>TAPKLLIYADSHRPSGVPDRFSGSKSGTSASLAISGLR<br>SEDEADYYCATWDYSLSGYVFGCGTKLTVLGGGGS<br>GGGGGGGGSGGGGSEVQLLESGGGLVQPGGSLR<br>LSCAASGFTFSSYDMSWVRQAPGKCLEWVSWISYS<br>GGSIYYADSVKGRFTISRDNSKNTLYLQMNSLRAEDT<br>AVYYCARDAQRQSMREFDYWGQGTLVTVSS | SEQ<br>ID<br>NO:<br>37 |
|  | Light<br>Component | DIQMTQSPSSLSASVGDRVTITCKASQDVTPAVAWY<br>QQKPGKAPKLLIYSTSSRYTGVPSRFSGSGSGTDFTF<br>TISSLQPEDIATYYCQQHYTTPLTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC | SEQ<br>ID<br>NO:<br>38 |
| ABLPNB.07 | Heavy<br>Component | EVQLVESGGGLVQPGGSLRLSCAASGFTFSSYDMS<br>WVRQAPGKSLEWVATISDAGGYIYYRDSVKGRFTISR<br>DNAKNSLYLQMNSLRDEDTAVYICARELPWRYALDY<br>WGQGTTVTVSSASTKGPSVFPLAPSSKSTSGGTAAL | SEQ<br>ID<br>NO:<br>39 |

TABLE 4-continued

Examples of Anti-PD-L1/anti-4-1BB bispecific antibody

|  |  |  |  |
|---|---|---|---|
|  |  | GCLVKDYFPEPVTVSWNSGALTSGVHTFPAVLQSSG<br>LYSLSSWTVPSSSLGTQTYICNVNHKPSNTKVDKKV<br>EPKSCDKTHTCPPCPAPELLGGPSVFLFPPKPKDTLM<br>ISRTPEVTCVVVDVSHEDPEVKFNWYVDGVEVHNAK<br>TKPREEQYASTYRVVSVLTVLHQDWLNGKEYKCKVS<br>NKALPAPIEKTISKAKGQPREPQVYTLPPSREEMTKN<br>QVSLTCLVKGFYPSDIAVEWESNGQPENNYKTTPPVL<br>DSDGSFFLYSKLTVDKSRWQQGNVFSCSVMHEALH<br>NHYTQKSLSLSPGKGGGGSGGGGSGGGGSQSVLTQ<br>PPSASGTPGQRVTISGSGSSSNIGNNYVTWYQQLPG<br>TAPKLLIYADSHRPSGVPDRFSGSKSGTSASLAISGLR<br>SEDEADYYCATWDYSLSGYVFGCGTKLTVLGGGGS<br>GGGGSGGGGSGGGGSEVQLLESGGGLVQPGGSLR<br>LSCAASGFTFSSYDMSWVRQAPGKCLEWVSWISYS<br>GGSIYYADSVKGRFTISRDNSKNTLYLQMNSLRAEDT<br>AVYYCARDAQRNSMREFDYWGQGTLVTVSS |  |
|  | Light<br>Component | DIQMTQSPSSLSASVGDRVTITCKASQDVTPAVAWY<br>QQKPGKAPKLLIYSTSSRYTGVPSRFSGSGSGTDFTF<br>TISSLQPEDIATYYCQQHYTTPLTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC | SEQ<br>ID<br>NO:<br>40 |
| ABLPNB.08 | Heavy<br>Component | EVQLVESGGGLVQPGGSLRLSCAASGFTFSSYDMS<br>WVRQAPGKSLEWVATISDAGGYIYYRDSVKGRFTISR<br>DNAKNSLYLQMNSLRDEDTAVYICARELPWRYALDY<br>WGQGTTVTVSSASTKGPSVFPLAPSSKSTSGGTAAL<br>GCLVKDYFPEPVTVSWNSGALTSGVHTFPAVLQSSG<br>LYSLSSWTVPSSSLGTQTYICNVNHKPSNTKVDKKV<br>EPKSCDKTHTCPPCPAPELLGGPSVFLFPPKPKDTLM<br>ISRTPEVTCVVVDVSHEDPEVKFNWYVDGVEVHNAK<br>TKPREEQYASTYRVVSVLTVLHQDWLNGKEYKCKVS<br>NKALPAPIEKTISKAKGQPREPQVYTLPPSREEMTKN<br>QVSLTCLVKGFYPSDIAVEWESNGQPENNYKTTPPVL<br>DSDGSFFLYSKLTVDKSRWQQGNVFSCSVMHEALH<br>NHYTQKSLSLSPGKGGGGSGGGGSGGGGSQSVLTQ<br>PPSASGTPGQRVTISGSGSSSNIGNNYVTWYQQLPG<br>TAPKLLIYADSHRPSGVPDRFSGSKSGTSASLAISGLR<br>SEDEADYYCATWDYSLSGYVFGCGTKLTVLGGGGS<br>GGGGSGGGGSGGGGSEVQLLESGGGLVQPGGSLR<br>LSCAASGFTFSSYDMSWVRQAPGKCLEWVSWISYS<br>GGSIYYADSVKGRFTISRDNSKNTLYLQMNSLRAEDT<br>AVYYCARDAQRQSMREFDYWGQGTLVTVSS | SEQ<br>ID<br>NO:<br>41 |
|  | Light<br>Component | DIQMTQSPSSLSASVGDRVTITCKASQDVTPAVAWY<br>QQKPGKAPKLLIYSTSSRYTGVPSRFSGSGSGTDFTF<br>TISSLQPEDIATYYCQQHYTTPLTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC | SEQ<br>ID<br>NO:<br>42 |
| ABLPNB.09 | Heavy<br>Component | EVQLVESGGGLVQPGGSLRLSCAASGFTFSSYDMS<br>WVRQAPGKSLEWVATISDAGGYIYYRDSVKGRFTISR<br>DNAKNSLYLQMNSLRDEDTAVYICARELPWRYALDY<br>WGQGTTVTVSSASTKGPSVFPLAPSSKSTSGGTAAL<br>GCLVKDYFPEPVTVSWNSGALTSGVHTFPAVLQSSG<br>LYSLSSWTVPSSSLGTQTYICNVNHKPSNTKVDKKV<br>EPKSCDKTHTCPPCPAPELLGGPSVFLFPPKPKDTLM<br>ISRTPEVTCVVVDVSHEDPEVKFNWYVDGVEVHNAK<br>TKPREEQYASTYRVVSVLTVLHQDWLNGKEYKCKVS<br>NKALPAPIEKTISKAKGQPREPQVYTLPPSREEMTKN<br>QVSLTCLVKGFYPSDIAVEWESNGQPENNYKTTPPVL<br>DSDGSFFLYSKLTVDKSRWQQGNVFSCSVMHEALH<br>NHYTQKSLSLSPGKGGGGSGGGGSGGGGSQSVLTQ<br>PPSASGTPGRRVTISGSGSSSNIGNNYVTWYQQLPG<br>TAPKLLIYADSHRPSGVPDRFSGSKSGTSASLAISGLR<br>SEDEADYYCATWDYSLSGYVFGCGTKLTVLGGGGS<br>GGGGSGGGGSGGGGSEVQLLESGGGLVQPGGSLR<br>LSCAASGFTFSGYDMSWVRQAPGKCLEWVSVIYPDD<br>GNTYYADSVKGRFTISRDNSKNTLYLQMNSLRAEDA<br>AVYYCAKHGGQKPTTKSSSAYGMDGWGQGTLVTVS<br>S | SEQ<br>ID<br>NO:<br>43 |

TABLE 4-continued

Examples of Anti-PD-L1/anti-4-1BB bispecific antibody

| Light Component | DIQMTQSPSSLSASVGDRVTITCKASQDVTPAVAWY QQKPGKAPKLLIYSTSSRYTGVPSRFSGSGSGTDFTF TISSLQPEDIATYYCQQHYTTPLTFGQGTKLEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC | SEQ ID NO: 44 |

Therapeutic Use of the Bispecific Antibody

Figure 2:
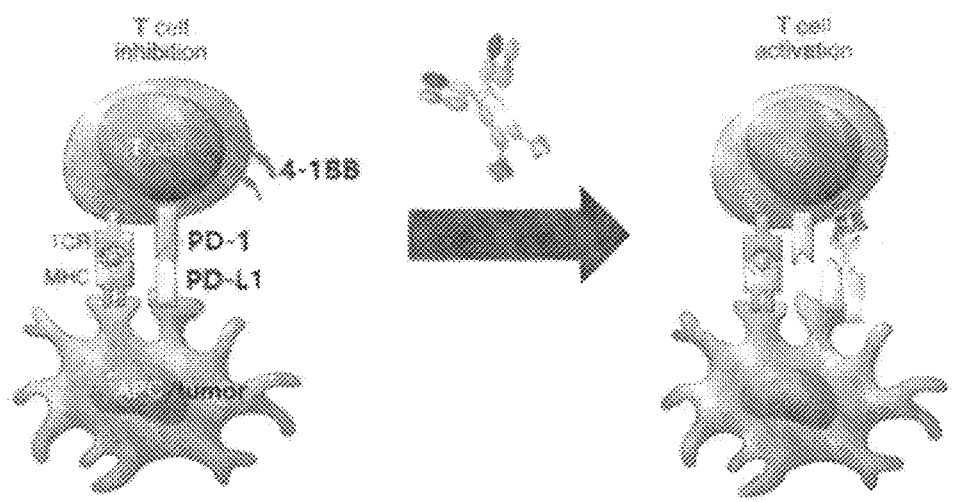
FIG. 2 schematically illustrates the mechanism of action of an anti-PD-L1/anti-4-1BB bispecific antibody according to an embodiment.

The bispecific antibody provided herein is capable of simultaneously blocking the activities of PD-L1 and 4-1BB, thereby exhibiting improved effects in immunotherapies and/or cancer therapies, for example, by activating immune response (see FIG. 2). Given the ability of the bispecific antibodies of the disclosure to inhibit the binding of PD-L1 to PD-1 molecules and to stimulate antigen-specific T cell responses, the disclosure also provides a composition or in vitro and in vivo methods of using the antibodies of the disclosure to stimulate, enhance or upregulate antigen-specific T cell responses.

An embodiment provides a pharmaceutical composition comprising the bispecific antibody as described above. The pharmaceutical composition may further comprise a pharmaceutically acceptable carrier. The pharmaceutical composition may be used for stimulating an immune response (e.g., an antigen-specific T cell response), and/or treating and/or preventing a disease associated with PD-L1, 4-1BB, or both thereof.

Another embodiment provides a method of stimulating an immune response (e.g., an antigen-specific T cell response), and/or treating and/or preventing a disease associated with PD-L1, 4-1BB, or both thereof, in a subject in need thereof, comprising administering to the subject a pharmaceutically effective amount of the bispecific antibody or the pharmaceutical composition. The method may further step of identifying the subject in need of treating and/or preventing a disease associated with PD-L1, 4-1BB, or both thereof, prior to the administering step.

The disease associated with PD-L1, 4-1BB, or both thereof may be selected from cancers (or tumors), infectious diseases, autoimmune reactions, nervous system disorders, and the like.

In an embodiment, the subject may be selected from mammals including humans, for example, a mammal (e.g., a human) suffering from a cancer mammalian cells. In other embodiment, the subject may be a cell separated (isolated) from a mammal, for example, a mammal suffering from the disease selected from cancers infectious diseases, autoimmune reactions, nervous system disorders, and the like (e.g., a cancer cell or a cell separated (isolated) from an infectious region in the mammal, or a T cell, such as a tumor-infiltrating T lymphocyte, a CD4+ T cell, a CD8+ T cell, or the combination thereof).

Another embodiment provides a use of the bispecific antibody or the pharmaceutical composition in treating and/or preventing a cancer. Another embodiment provides a use of the bispecific antibody in preparing a pharmaceutical composition for treating and/or preventing a cancer.

In the pharmaceutical compositions, methods and/or uses provided herein, the disease associated with PD-L1, 4-1BB, or both thereof may be one associated with activation (e.g., abnormal activation or over-activation) and/or overproduction (overexpression) of PD-L1, 4-1BB, or both thereof. For example, the disease may be a cancer.

The cancer may be a solid cancer or blood cancer, preferably a solid cancer.

The administration of the bispecific antibody may be conducted by one or more techniques well established in the art.

A "therapeutically effective dosage" of the antibody of the disclosure preferably results in a decrease in severity of disease symptoms, an increase infrequency and duration of disease symptom-free periods, or a prevention of impairment or disability due to the disease affliction. For example, for the treatment of tumor bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical compositions may comprise an effective amount of the bispecific antibody, and an acceptable carrier. In some embodiments, the composition further includes a second anticancer agent (e.g., an immune checkpoint inhibitor).

In a specific embodiment, the term "pharmaceutically acceptable" may refer to approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The composition comprising the antibody or the antigen-binding fragment thereof of the present disclosure may further comprise a pharmaceutically acceptable carrier. The pharmaceutically acceptable carrier is the one conventionally used in preparing a formulation.

Diagnostic Use of the Bispecific Antibody

Over-expression and/or over-activation of PD-L1 and/or 4-1BB is observed in a biological sample (e.g., cells, tissues, blood, serum, etc.) from a patient suffering from a certain cancer (for example, tumor cell), and/or patients having PD-L1- and/or 4-1BB-over-expressing cells are likely responsive to treatments with the bispecific antibody. Accordingly, the bispecific antibody of the present disclosure can also be used for diagnostic and prognostic purposes.

An embodiment provides a pharmaceutical composition for diagnosing a disease associated with PD-L1, 4-1BB, or both thereof, the composition comprising the bispecific antibody. In another embodiment, provided is a use of the bispecific antibody for diagnosing a disease associated with PD-L1, 4-1BB, or both thereof.

Another embodiment provides a method of diagnosing a disease associated with PD-L1, 4-1BB, or both thereof, the method comprising contacting a biological sample obtained from a patient with the bispecific antibody, and detecting antigen-antibody reaction or measuring a level of antigen-antibody reaction in the biological sample. In this method, when the antigen-antibody reaction is detected in the biological sample or the level of the antigen-antibody reaction in the biological sample is higher than that of a normal sample, the patient from whom the biological sample is obtained may be determined as a patient with a disease associated with PD-L1, 4-1BB, or both thereof. Therefore, in some embodiments, the method may further comprise contacting a normal sample with the bispecific antibody, and measuring a level of an antigen-antibody reaction in the normal sample. In addition, the method may further comprise comparing the level of the antigen-antibody reaction in the biological sample and in the normal sample, after the measuring step. In addition, after the detecting step or comparing step, the method may further comprise determining the patient as a patient with a disease associated with PD-L1, 4-1BB, or both thereof, when the antigen-antibody reaction is detected in the biological sample or the level of the antigen-antibody reaction in the biological sample is higher than that of the normal sample.

The disease associated with PD-L1, 4-1BB, or both thereof may be one associated with activation (e.g., abnormal activation or over-activation) and/or overproduction (overexpression) of PD-L1, 4-1BB, or both thereof. For example, the disease may be a cancer, as described above.

In the diagnosing composition and method, the biological sample may be at least one selected from the group consisting of a cell, a tissue, body fluid (e.g., blood, serum, lymph, etc.) and the like, obtained (separated) from a patient to be diagnosed. The normal sample may be at least one selected from the group consisting of a cell, a tissue, body fluid (e.g., blood, serum, lymph, urine, etc.) and the like, obtained (separated) from a patient having no disease associated with PD-L1, 4-1BB, or both thereof. The patient may be selected from a mammal, such as a human. Upon optional pre-treatment of the sample, the sample can be incubated with the bispecific antibody of the present disclosure under conditions allowing the antibody to interact with a PD-L1 and/or 4-1BB protein potentially present in the sample.

Presence and/or level (concentration) of the PD-L1 and/or 4-1BB protein in the sample can be used for identifying a patient who is suitable for a treatment with the bispecific antibody, or a patient who is responsive or susceptive to the treatment with the bispecific antibody.

An embodiment provides a pharmaceutical composition identifying a patient who is suitable for a treatment with the bispecific antibody, or a patient who is responsive or susceptive to the treatment with the bispecific antibody, the composition comprising the bispecific antibody. In another embodiment, provided is a use of the bispecific antibody for identifying a patient who is suitable for a treatment with the bispecific antibody, or a patient who is responsive or susceptive to the treatment with the bispecific antibody. Another embodiment provides a method of identifying a patient who is suitable for a treatment with the bispecific antibody, or a patient who is responsive or susceptive to the treatment with the bispecific antibody, the method comprising contacting a biological sample obtained from a patient with the bispecific antibody, and detecting antigen-antibody reaction or measuring a level of antigen-antibody reaction in the biological sample.

An embodiment provides a composition for detection of PD-L1, 4-1BB, or both thereof simultaneously, in a biological sample, the composition comprising the bispecific antibody. Another embodiment provides a method of detection of PD-L1, 4-1BB, or both thereof simultaneously, in a biological sample, the method comprising contacting the biological sample with the bispecific antibody; and detecting (measuring) an antigen-antibody reaction (binding) between the bispecific antibody and PD-L1, 4-1BB, or both thereof.

In the detecting composition and the detecting method, the term "detection of PD-L1, 4-1BB, or both thereof" may refer to, but not be limited to, detection of presence (and/or absence) and/or level of PD-L1, 4-1BB, or both thereof in the biological sample.

In the method of detection, when an antigen-antibody reaction is detected, it can be determined that PD-L1, 4-1BB, or both thereof are present in the biological sample, and when an antigen-antibody reaction is not detected, it can be determined that PD-L1, 4-1BB, or both thereof are absent (not present) in the biological sample. Therefore, the method of detection may further comprise, after the detecting step, determining that PD-L1, 4-1BB, or both thereof are present in the biological sample when an antigen-antibody reaction is detected, and/or that PD-L1, 4-1BB, or both thereof are absent (not present) in the biological sample, when an antigen-antibody reaction is not detected.

In the method of detection, the level of PD-L1, 4-1BB, or both thereof may be determined according to the degree of the antigen-antibody reaction (e.g., the amount of antigen-antibody complex formed by the antigen-antibody reaction, the intensity of any signal obtained by the antigen-antibody reaction, and the like, which can be measured by any conventional means).

The biological sample may comprise at least one selected from the group consisting of a cell (e.g., a tumor cell), a tissue (e.g., a tumor tissue), body fluid (e.g., blood, serum, etc.), and the like, obtained or isolated from a mammal such as a human. The steps of the method of detection may be conducted in virto.

In the diagnosing method and/or detecting method, the step of detecting the antigen-antibody reaction or measuring a level of the antigen-antibody reaction may be performed by any general method known to the relevant art, such as general enzymatic reactions, fluorescent reactions, luminescent reactions, and/or detection of radiation. For example, the step may be performed by a method selected from, but not limited to, the group consisting of immunochromatography, immunohistochemistry (IHC), enzyme linked immunosorbent assay (ELISA), radioimmunoassay (RIA), enzyme immunoassay (EIA), fluorescence immunoassay (FIA), luminescence immunoassay (LIA), western blotting, microarray, flow cytometry, surface plasmon resonance (SPR), and the like, but not be limited thereto.

Polynucleotides Encoding the Antibodies and Methods of Preparing the Antibodies

An embodiment provides a polynucleotide encoding the bispecific antibody. In particular, an embodiment provides a polynucleotide encoding a heavy chain of the bispecific antibody in an IgG-scFv form. Other embodiment provides a polynucleotide encoding a light chain of the bispecific antibody in the IgG-scFv form. The IgG-scFv form may refer to a kind of a bispecific antibody comprising a full-length IgG antibody targeting (binding to) one of PD-L1 and 4-1BB proteins and a scFv fragment targeting (binding to) the other one, wherein the scFv is linked to a C-terminus and/or N-terminus of the full-length IgG antibody directly (without a peptide linker) or via a peptide linker.

In an embodiment, when the bispecific antibody in an IgG-scFv form comprises a full-length IgG antibody against PD-L1 and a scFv fragment against 4-1BB, the polynucleotide encoding a heavy chain of the bispecific antibody may encode a heavy chain of the full-length IgG antibody against PD-L1 and a scFv fragment against 4-1BB that is linked to a C-terminus and/or N-terminus of the full-length IgG antibody directly or via a peptide linker; and the polynucleotide encoding a light chain of the bispecific antibody may encode a light chain of the full-length IgG antibody against PD-L1.

In another embodiment, when the bispecific antibody in an IgG-scFv form comprises a full-length IgG antibody against 4-1BB and a scFv fragment against PD-L1, the polynucleotide encoding a heavy chain of the bispecific antibody may encode a heavy chain of the full-length IgG antibody against 4-1BB and a scFv fragment against PD-L1 that is linked to a C-terminus and/or N-terminus of the full-length IgG antibody directly or via a peptide linker; and the polynucleotide encoding a light chain of the bispecific antibody may encode a light chain of the full-length IgG antibody against 4-1BB.

Another embodiment provides a recombinant vector comprising the polynucleotide encoding a heavy chain of the bispecific antibody, the polynucleotide encoding a light chain of the bispecific antibody, or both thereof. Another embodiment provides a recombinant cell transfected with the recombinant vector.

Another embodiment provides a method of preparing the bispecific antibody, comprising expressing the polynucleotide encoding a heavy chain of the bispecific antibody, the polynucleotide encoding a light chain of the bispecific antibody in a cell. The step of expressing the polynucleotide may be conducted by culturing the cell comprising the polynucleotide (for example, in a recombinant vector) under a condition allowing the expression of the polynucleotide. The method may further comprise isolating and/or purifying the bispecific antibody from the cell culture, after the step of expressing or culturing.

EXAMPLES

Hereafter, the present invention will be described in detail by examples.

The following examples are intended merely to illustrate the invention and are not construed to restrict the invention.

Example 1: Preparation of Anti-PD-L1 Monoclonal Antibodies 1.1. Preparation of Anti-Human-PD-L1 Mouse Monoclonal Antibodies and Analysis Thereof Anti-human-PD-L1 mouse monoclonal antibodies were generated using the hybridoma technology, as disclosed in International Application Publication WO2017-215590.

The amino acid and polynucleotide sequences of the variable regions of the hybridoma supernatants, named Hybridoma HL1210-3, are provided in Table 5 below.

TABLE 5

| | HL1210-3 variable sequences | |
|---|---|---|
| Name | Sequence | SEQ ID NO: |
| HL1210-3 VH | GAAGTGAAACTGGTGGAGTCTGGGGGAGACTTAGTG AAGCCTGGAGGGTCCCTGAAACTCTCCTGTGCAGCC TCTGGATTCACTTTCAGTAGCTATGACATGTCTTGGG TTCGCCAGACTCCGGAGAAGAGTCTGGAGTGGGTCG CAACCATTAGTGATGGTGGTGGTTACATCTACTATTC AGACAGTGTGAAGGGGCGATTTACCATCTCCAGAGA CAATGCCAAGAACAACCTGTACCTGCAAATGAGCAGT CTGAGGTCTGAGGACACGGCCTTGTATATTTGTGCAA GAGAATTTGGTAAGCGCTATGCTTTGGACTACTGGG GTCAAGGAACCTCAGTCACCGTCTCCTCA | 45 |
| HL1210-3 VH | EVKLVESGGDLVKPGGSLKLSCAASGFTFSSYDMSWV RQTPEKSLEWVATISDGGGYIYYSDSVKGRFTISRDNAK NNLYLQMSSLRSEDTALYICAREFGKRYALDYWGQGTS VT | 46 |
| HL1210-3 VL | GACATTGTGATGACCCAGTCTCACAAATTCATGTCCA CATCGGTAGGAGACAGGGTCAGCATCTCCTGCAAGG CCAGTCAGGATGTGACTCCTGCTGTCGCCTGGTATC AACAGAAGCCAGGACAATCTCCTAAACTACTGATTTA CTCCACATCCTCCCGGTACACTGGAGTCCCTGATCG CTTCACTGGCAGTGGATCTGGGACGGATTTCACTTTC ACCATCAGCAGTGTGCAGGCTGAAGACCTGGCAGTT TATTACTGTCAGCAACATTATACTACTCCGCTCACGTT CGGTGCTGGGACCAAGCTGGAGCTGAAA | 47 |
| HL1210-3 VL | DIVMTQSHKFMSTSVGDRVSISCKASQDVTPAVAWYQQ KPGQSPKLLIYSTSSRYTGVPDRFTGSGSGTDFTFTISS VQAEDLAVYYCQQHYTTPLTFGAGTKLELK | 48 |

1.2. Humanization of the HL1210-3 Mouse mAb

The mAb HL1210-3 variable region genes were employed to create a humanized Mab, per the methods commonly employed in the art and as disclosed in International Application Publication WO 2017-215590.

The amino acid and nucleotide sequences of some of the resultant humanized antibody are listed in Table 6 below.

TABLE 6

| Humanized antibody sequences (bold indicates CDR) | | |
|---|---|---|
| Name | Amino Acid Sequence | SEQ ID NO: |
| HL1210-VH | EVKLVESGGDLVKPGGSLKLSCAASGFTFSSYDMSWVRQTPEKSLEWVATISDGGGYIYYSDSVKGRFTISRDNAKNNLYLQMSSLRSEDTALYICAREFGKRYALDYWGQGTSVTVSS | 49 |
| Hu1210 VH.1 | EVQLVESGGGLVKPGGSLRLSCAASGFTFSSYDMSWVRQAPGKGLEWVSTISDGGGYIYYSDSVKGRFTISRDNAKNSLYLQMNSLRAEDTAVYYCAREFGKRYALDYWGQGTTVTVSS | 50 |
| Hu1210 VH.1a | EVQLVESGGGLVKPGGSLRLSCAASGFTFSSYDMSWVRQAPGKGLEWVATISDGGGYIYYSDSVKGRFTISRDNAKNSLYLQMNSLRAEDTAVYYCAREFGKRYALDYWGQGTTVTVSS | 51 |
| Hu1210 VH.1b | EVQLVESGGGLVKPGGSLRLSCAASGFTFSSYDMSWVRQAPGKSLEWVATISDGGGYIYYSDSVKGRFTISRDNAKNSLYLQMNSLRAEDTAVYICAREFGKRYALDYWGQGTTVTVSS | 52 |
| Hu1210 VH.2 | EVQLVESGGGLVKPGGSLRLSCAASGFTFSSYDMSWIRQAPGKGLEWVSTISDGGGYIYYSDSVKGRFTISRDNAKNSLYLQMNSLRAEDTAVYYCAREFGKRYALDYWGQGTTVTVSS | 53 |
| Hu1210 VH.2a | EVQLVESGGGLVKPGGSLRLSCAASGFTFSSYDMSWIRQAPGKGLEWVATISDGGGYIYYSDSVKGRFTISRDNAKNSLYLQMNSLRAEDTAVYYCAREFGKRYALDYWGQGTTVTVSS | 54 |
| Hu1210 VH.2b | EVQLVESGGGLVKPGGSLRLSCAASGFTFSSYDMSWVRQAPGKSLEWVATISDGGGYIYYSDSVKGRFTISRDNAKNSLYLQMNSLRAEDTAVYICAREFGKRYALDYWGQGTTVTVSS | 55 |
| Hu1210 VH.3 | EVQLLESGGGLVQPGGSLRLSCAASGFTFSSYDMSWVRQAPGKGLEWVSTISDGGGYIYYSDSVKGRFTISRDNSKNTLYLQMNSLRAEDTAVYYCAREFGKRYALDYWGQGTTVTVSS | 56 |
| Hu1210 VH.3a | EVQLLESGGGLVQPGGSLRLSCAASGFTFSSYDMSWVRQAPGKSLEWVATISDGGGYIYYSDSVKGRFTISRDNSKNTLYLQMNSLRAEDTAVYICAREFGKRYALDYWGQGTTVTVSS | 57 |
| Hu1210 VH.4 | EVQLVESGGGLVQPGGSLRLSCAASGFTFSSYDMSWVRQAPGKGLEWVSTISDGGGYIYYSDSVKGRFTISRDNAKNSLYLQMNSLRDEDTAVYYCAREFGKRYALDYWGQGTTVTVSS | 58 |
| Hu1210 VH.4a | EVQLVESGGGLVQPGGSLRLSCAASGFTFSSYDMSWVRQAPGKGLEWVATISDGGGYIYYSDSVKGRFTISRDNAKNSLYLQMNSLRDEDTAVYYCAREFGKRYALDYWGQGTTVTVSS | 59 |
| Hu1210 VH.4b | EVQLVESGGGLVQPGGSLRLSCAASGFTFSSYDMSWVRQAPGKSLEWVATISDGGGYIYYSDSVKGRFTISRDNAKNSLYLQMNSLRDEDTAVYICAREFGKRYALDYWGQGTTVTVSS | 60 |
| Hu1210 VH.4c | EVQLVESGGGLVQPGGSLRLSCAASGFTFSSYDMSWVRQAPGKSLEWVATISEGGGYIYYSDSVKGRFTISRDNAKNSLYLQMNSLRDEDTAVYICAREFGKRYALDYWGQGTTVTVSS | 61 |

TABLE 6-continued

| Humanized antibody sequences (bold indicates CDR) | | |
|---|---|---|
| Hu1210 VH.4d (H12 VH) | EVQLVESGGGLVQPGGSLRLSCAASGFTFSSYDMSWVRQAPGKSLEWVATISDAGGYIYYSDSVKGRFTISRDNAKNSLYLQMNSLRDEDTAVYICAREFGKRYALDYWGQGTTVTVSS | 62 |
| Hu1210 VH.4e | EVQLVESGGGLVQPGGSLRLSCAASGFTFSSYDMSWVRQAPGKSLEWVATISDVGGYIYYSDSVKGRFTISRDNAKNSLYLQMNSLRDEDTAVYICAREFGKRYALDYWGQGTTVTVSS | 63 |
| Hu1210 VH.5 | EVQLVESGGGLVQPGGSLRLSCAASGFTFSSYDMSWVRQAPGKGLEWVATISDGGGYIYYSDSVKGRFTISRDNAKNSLYLQMNSLRAEDTAVYYCAREFGKRYALDYWGQGTLVTVSS | 64 |
| HU1210 VH.5a | EVQLVESGGGLVQPGGSLRLSCAASGFTFSSYDMSWVRQAPGKGLEWVATISDGGGYIYYSDSVKGRFTISRDNAKNSLYLQMNSLRAEDTAVYICAREFGKRYALDYWGQGTLVTVSS | 65 |
| HU1210 VH.5b | EVQLVESGGGLVQPGGSLRLSCAASGFTFSSYDMSWVRQAPGKGLEWVATISDGGGYIYYSDSVKGRFTISRDNAKNSLYLQMNSLRAEDTAVYICAREFGKRYALDYWGQGTTVTVSS | 66 |
| HU1210 VH.5C | EVQLVESGGGLVQPGGSLRLSCAASGFTFSSYDMSWVRQAPGKGLEWVATISDGGGYIYYSDSVKGRFTISRDNAKNNLYLQMNSLRAEDTAVYICAREFGKRYALDYWGQGTLVTVSS | 67 |
| HU1210 VH.5d | EVQLVESGGGLVQPGGSLRLSCAASGFTFSSYDMSWVRQTPEKSLEWVATISDGGGYIYYSDSVKGRFTISRDNAKNNLYLQMNSLRAEDTAVYICAREFGKRYALDYWGQGTLVTVSS | 68 |
| HL1210-VK | DIVMTQSHKFMSTSVGDRVSISCKASQDVTPAVAWYQQKPGQSPKLLIYSTSSRYTGVPDRFTGSGSGTDFTFTISSVQAEDLAVYYCQQHYTTPLTFGAGTKLELK | 69 |
| Hu1210 VK.1 (H12 VL) | DIQMTQSPSSLSASVGDRVTITCKASQDVTPAVAWYQQKPGKAPKLLIYSTSSRYTGVPSRFSGSGSGTDFTFTISSLQPEDIATYYCQQHYTTPLTFGQGTKLEIK | 70 |
| Hu1210 VL.1a | DIQMTQSPSSLSASVGDRVTITCKASQDVTPAVAWYQQKPGKSPKLLIYSTSSRYTGVPSRFSGSGSGTDFTFTISSLQPEDIATYYCQQHYTTPLTFGQGTKLEIK | 71 |
| Hu1210 VK.2 | DIQMTQSPSSLSASVGDRVTITCKASQDVTPAVAWYQQKPGKAPKLLIYSTSSRYTGVPSRFSGSGSGTDFTLTISSLQPEDFATYYCQQHYTTPLTFGQGTKLEIKR | 72 |
| Hu1210 VK.2a | DIQMTQSPSSLSASVGDRVTITCKASQDVTPAVAWYQQKPGKAPKLLIYSTSSRYTGVPDRFTGSGSGTDFTLTISSLQPEDFATYYCQQHYTTPLTFGQGTKLEIKR | 73 |
| Hu1210 VK.2b | DIQMTQSPSSLSASVGDRVTITCKASQDVTPAVAWYQQKPGQSPKLLIYSTSSRYTGVPDRFTGSGSGTDFTLTISSLQPEDFATYYCQQHYTTPLTFGQGTKLEIKR | 74 |
| Hu1210 VK.2c | DIQMTQSPSSLSASVGDRVTISCKASQDVTPAVAWYQQKPGQSPKLLIYSTSSRYTGVPDRFTGSGSGTDFTLTISSLQPEDFATYYCQQHYTTPLTFGQGTKLEIKR | 75 |

| Name | Nucleic Acid Sequence | SEQ ID NO: |
|---|---|---|
| HL1210 VH | GAGGTGAAGCTGGTGGAGAGCGGCGGAGATCTGGTGAAGCCTGGCGGCAGCCTGAAGCTGAGCTGTGCCGCCAGCGGCTTCACCTTCAGCAGCTACGACATGAGCTGGGTGAGGCAGACCCCCGAGAAGAGCCTGGAGTGGGTGGCCACCATCAGCGATGGCGGCGGCTACATCTACTACAGCGACAGCGTGAAGGGCAGGTTCACCATCAGCAGGGACAACGCCAAGAACAACCTGTACCTGCAGATGAGCAGCCTGAGGAGCGAGGACACCGCCCTGTACATCTGCGCCAGGGAGTTCGGCAAGAGGTACGCCCTGGACTACTGGGGACAGGGCACCAGCGTGACCGTGAGCAGC | 76 |

TABLE 6-continued

Humanized antibody sequences (bold indicates CDR)

| | | |
|---|---|---|
| Hu1210 VH.1 | GAGGTGCAGCTGGTGGAGAGCGGAGGAGGACTGGTG<br>AAGCCCGGAGGCAGCCTGAGACTGAGCTGCGCTGCCA<br>GCGGCTTCACCTTCAGCAGCTACGACATGAGCTGGGT<br>GAGACAGGCCCCTGGCAAAGGCCTGGAGTGGGTGAGC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGCCGAGGACACCGCCGTGTACTACTGCGCCAGGGAG<br>TTCGGCAAAAGGTACGCCCTGGACTACTGGGGCCAGG<br>GCACAACCGTGACCGTGAGCAGC | 77 |
| Hu1210 VH.1a | GAGGTGCAGCTGGTGGAGAGCGGAGGAGGACTGGTG<br>AAGCCCGGAGGCAGCCTGAGACTGAGCTGCGCTGCCA<br>GCGGCTTCACCTTCAGCAGCTACGACATGAGCTGGGT<br>GAGACAGGCCCCTGGCAAAGGCCTGGAGTGGGTGGCC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGCCGAGGACACCGCCGTGTACTACTGCGCCAGGGAG<br>TTCGGCAAAAGGTACGCCCTGGACTACTGGGGCCAGG<br>GCACAACCGTGACCGTGAGCAGC | 78 |
| Hu1210 VH.1b | GAGGTGCAGCTGGTGGAGAGCGGAGGAGGACTGGTG<br>AAGCCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGCCGAGGACACCGCCGTGTACATCTGCGCCAGGGAG<br>TTCGGCAAAAGGTACGCCCTGGACTACTGGGGCCAGG<br>GCACAACCGTGACCGTGAGCAGC | 79 |
| Hu1210 VH.2 | GAGGTGCAGCTGGTGGAGAGCGGAGGAGGACTGGTG<br>AAGCCCGGAGGCAGCCTGAGACTGAGCTGCGCTGCCA<br>GCGGCTTCACCTTCAGCAGCTACGACATGAGCTGGATC<br>AGACAGGCCCCTGGCAAAGGCCTGGAGTGGGTGAGCA<br>CCATCTCCGATGGCGGCGGCTACATCTATTACTCCGAC<br>AGCGTGAAGGGCAGGTTCACCATCAGCAGGGACAACG<br>CCAAGAACAGCCTGTACCTGCAGATGAACAGCCTGAGG<br>GCCGAGGACACCGCCGTGTACTACTGCGCCAGGGAGT<br>TCGGCAAAAGGTACGCCCTGGACTACTGGGGCCAGGG<br>CACAACCGTGACCGTGAGCAGC | 80 |
| Hu1210 VH.2a | GAGGTGCAGCTGGTGGAGAGCGGAGGAGGACTGGTG<br>AAGCCCGGAGGCAGCCTGAGACTGAGCTGCGCTGCCA<br>GCGGCTTCACCTTCAGCAGCTACGACATGAGCTGGATC<br>AGACAGGCCCCTGGCAAAGGCCTGGAGTGGGTGGCCA<br>CCATCTCCGATGGCGGCGGCTACATCTATTACTCCGAC<br>AGCGTGAAGGGCAGGTTCACCATCAGCAGGGACAACG<br>CCAAGAACAGCCTGTACCTGCAGATGAACAGCCTGAGG<br>GCCGAGGACACCGCCGTGTACTACTGCGCCAGGGAGT<br>TCGGCAAAAGGTACGCCCTGGACTACTGGGGCCAGGG<br>CACAACCGTGACCGTGAGCAGC | 81 |
| Hu1210 VH.2b | GAGGTGCAGCTGGTGGAGAGCGGAGGAGGACTGGTG<br>AAGCCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGCCGAGGACACCGCCGTGTACATCTGCGCCAGGGAG<br>TTCGGCAAAAGGTACGCCCTGGACTACTGGGGCCAGG<br>GCACAACCGTGACCGTGAGCAGC | 82 |
| Hu1210 VH.3 | GAGGTGCAGCTGCTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAGGCCTGGAGTGGGTGAGC<br>ACCATCTCCGATGGCGGCGGCTACATCTATTACTCCGA<br>CAGCGTGAAGGGCAGGTTCACCATCAGCAGGGACAAC<br>AGCAAGAACACCCTGTACCTGCAGATGAACAGCCTGAG<br>GGCCGAGGACACCGCCGTGTACTACTGCGCCAGGGAG<br>TTCGGCAAAAGGTACGCCCTGGACTACTGGGGCCAGG<br>GCACAACCGTGACCGTGAGCAGC | 83 |

TABLE 6-continued

Humanized antibody sequences (bold indicates CDR)

| | | |
|---|---|---|
| Hu1210 VH.3a | GAGGTGCAGCTGCTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGATGGCGGCGGCTACATCTATTACTCCGA<br>CAGCGTGAAGGGCAGGTTCACCATCAGCAGGGACAAC<br>AGCAAGAACACCCTGTACCTGCAGATGAACAGCCTGAG<br>GGCCGAGGACACCGCCGTGTACATCTGCGCCAGGGAG<br>TTCGGCAAAAGGTACGCCCTGGACTACTGGGGCCAGG<br>GCACAACCGTGACCGTGAGCAGC | 84 |
| Hu1210 VH.4 | GAGGTGCAGCTGGTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAGGCCTGGAGTGGGTGAGC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGATGAGGACACCGCCGTGTACTACTGCGCCAGGGAG<br>TTCGGCAAAAGGTACGCCCTGGACTACTGGGGCCAGG<br>GCACAACCGTGACCGTGAGCAGC | 85 |
| Hu1210 VH.4a | GAGGTGCAGCTGGTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAGGCCTGGAGTGGGTGGCC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGATGAGGACACCGCCGTGTACTACTGCGCCAGGGAG<br>TTCGGCAAAAGGTACGCCCTGGACTACTGGGGCCAGG<br>GCACAACCGTGACCGTGAGCAGC | 86 |
| Hu1210 VH.4b | GAGGTGCAGCTGGTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGATGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGATGAGGACACCGCCGTGTACATCTGCGCCAGGGAG<br>TTCGGCAAAAGGTACGCCCTGGACTACTGGGGCCAGG<br>GCACAACCGTGACCGTGAGCAGC | 87 |
| Hu1210 VH.4c | GAGGTGCAGCTGGTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGAAGGCGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGATGAGGACACCGCCGTGTACATCTGCGCCAGGGAG<br>TTCGGCAAAAGGTACGCCCTGGACTACTGGGGCCAGG<br>GCACAACCGTGACCGTGAGCAGC | 88 |
| Hu1210 VH.4d | GAGGTGCAGCTGGTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGATGCGGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGATGAGGACACCGCCGTGTACTACTGCGCCAGGGAG<br>TTCGGCAAAAGGTACGCCCTGGACTACTGGGGCCAGG<br>GCACAACCGTGACCGTGAGCAGC | 89 |
| Hu1210 VH.4e | GAGGTGCAGCTGGTGGAGAGCGGAGGAGGACTGGTG<br>CAACCCGGAGGCAGCCTGAGACTGAGCTGCGCTGCCA<br>GCGGCTTCACCTTCAGCAGCTACGACATGAGCTGGGT<br>GAGACAGGCCCCTGGCAAAAGCCTGGAGTGGGTGGCC<br>ACCATCTCCGATGTTGGCGGCTACATCTATTACTCCGA<br>CAGCGTGAAGGGCAGGTTCACCATCAGCAGGGACAAC<br>GCCAAGAACAGCCTGTACCTGCAGATGAACAGCCTGAG<br>GGATGAGGACACCGCCGTGTACATCTGCGCCAGGGAG<br>TTCGGCAAAAGGTACGCCCTGGACTACTGGGGCCAGG<br>GCACAACCGTGACCGTGAGCAGC | 90 |

TABLE 6-continued

Humanized antibody sequences (bold indicates CDR)

| | | |
|---|---|---|
| Hu1210 VH.5 | GAGGTGCAGCTGGTGGAGTCCGGAGGAGGCCTGGTG<br>CAACCTGGAGGCTCCCTGAGGCTGTCCTGTGCCGCTT<br>CCGGCTTCACCTTCAGCTCCTACGATATGAGCTGGGTG<br>AGGCAGGCTCCTGGAAAGGGCCTGGAGTGGGTGGCCA<br>CCATCTCCGACGGAGGCGGCTACATCTACTACTCCGAC<br>TCCGTGAAGGGCAGGTTCACCATCTCCCGGGACAACG<br>CCAAGAACTCCCTGTACCTGCAGATGAACTCTCTCAGG<br>GCTGAGGACACCGCCGTGTATTACTGCGCCAGGGAGT<br>TTGGCAAGAGGTACGCCCTGGATTACTGGGGCCAGGG<br>CACACTGGTGACAGTGAGCTCC | 91 |
| Hu1210 VH.5a | GAGGTGCAGCTGGTGGAGTCCGGAGGAGGCCTGGTG<br>CAACCTGGAGGCTCCCTGAGGCTGTCCTGTGCCGCTT<br>CCGGCTTCACCTTCAGCTCCTACGATATGAGCTGGGTG<br>AGGCAGGCTCCTGGAAAGGGCCTGGAGTGGGTGGCCA<br>CCATCTCCGACGGAGGCGGCTACATCTACTACTCCGAC<br>TCCGTGAAGGGCAGGTTCACCATCTCCCGGGACAACG<br>CCAAGAACTCCCTGTACCTGCAGATGAACTCTCTCAGG<br>GCTGAGGACACCGCCGTGTATATCTGCGCCAGGGAGT<br>TTGGCAAGAGGTACGCCCTGGATTACTGGGGCCAGGG<br>CACACTGGTGACAGTGAGCTCC | 92 |
| Hu1210 VH.5b | GAGGTGCAGCTGGTGGAGTCCGGAGGAGGCCTGGTG<br>CAACCTGGAGGCTCCCTGAGGCTGTCCTGTGCCGCTT<br>CCGGCTTCACCTTCAGCTCCTACGATATGAGCTGGGTG<br>AGGCAGGCTCCTGGAAAGGGCCTGGAGTGGGTGGCCA<br>CCATCTCCGACGGAGGCGGCTACATCTACTACTCCGAC<br>TCCGTGAAGGGCAGGTTCACCATCTCCCGGGACAACG<br>CCAAGAACAACCTGTACCTGCAGATGAACTCTCTCAGG<br>GCTGAGGACACCGCCGTGTATATCTGCGCCAGGGAGT<br>TTGGCAAGAGGTACGCCCTGGATTACTGGGGCCAGGG<br>CACACTGGTGACAGTGAGCTCC | 93 |
| Hu1210 VH.5c | GAGGTGCAGCTGGTGGAGTCCGGAGGAGGCCTGGTG<br>CAACCTGGAGGCTCCCTGAGGCTGTCCTGTGCCGCTT<br>CCGGCTTCACCTTCAGCTCCTACGATATGAGCTGGGTG<br>AGGCAGACCCCTGAGAAGAGCCTGGAGTGGGTGGCCA<br>CCATCTCCGACGGAGGCGGCTACATCTACTACTCCGAC<br>TCCGTGAAGGGCAGGTTCACCATCTCCCGGGACAACG<br>CCAAGAACAACCTGTACCTGCAGATGAACTCTCTCAGG<br>GCTGAGGACACCGCCGTGTATATCTGCGCCAGGGAGT<br>TTGGCAAGAGGTACGCCCTGGATTACTGGGGCCAGGG<br>CACACTGGTGACAGTGAGCTCC | 94 |
| Hu1210 VH.5d | GAGGTGCAGCTGGTGGAGTCCGGAGGAGGCCTGGTG<br>CAACCTGGAGGCTCCCTGAGGCTGTCCTGTGCCGCTT<br>CCGGCTTCACCTTCAGCTCCTACGATATGAGCTGGGTG<br>AGGCAGGCTCCTGGAAAGGGCCTGGAGTGGGTGGCCA<br>CCATCTCCGACGGAGGCGGCTACATCTACTACTCCGAC<br>TCCGTGAAGGGCAGGTTCACCATCTCCCGGGACAACG<br>CCAAGAACTCCCTGTACCTGCAGATGAACTCTCTCAGG<br>GCTGAGGACACCGCCGTGTATATCTGCGCCAGGGAGT<br>TTGGCAAGAGGTACGCCCTGGATTACTGGGGCCAGGG<br>CACAACCGTGACAGTGAGCTCC | 95 |
| HL1210 VK | GACATCGTGATGACCCAGAGCCACAAGTTCATGAGCAC<br>CAGCGTGGGCGATAGGGTGAGCATCAGCTGCAAGGCC<br>AGCCAGGATGTGACCCCTGCCGTGGCCTGGTACCAGC<br>AGAAGCCCGGCCAGAGCCCCAAGCTGCTGATCTACAG<br>CACCAGCAGCAGGTACACCGGCGTGCCCGACAGGTTC<br>ACAGGAAGCGGCAGCGGCACCGACTTCACCTTCACCA<br>TCAGCAGCGTGCAGGCCGAGGACCTGGCCGTGTACTA<br>CTGCCAGCAGCACTACACCACCCCTCTGACCTTCGGCG<br>CCGGCACCAAGCTGGAGCTGAAG | 96 |
| Hu1210 VK.1 | GACATCCAGATGACCCAGAGCCCTAGCAGCCTGAGCG<br>CTAGCGTGGGCGACAGGGTGACCATCACCTGCAAGGC<br>CAGCCAGGATGTGACCCCTGCCGTGGCCTGGTACCAG<br>CAGAAGCCCGGCAAGGCCCCCAAGCTGCTGATCTACA<br>GCACCAGCAGCAGGTACACCGGCGTGCCCAGCAGGTT<br>TAGCGGAAGCGGCAGCGGCACCGACTTCACCTTCACC<br>ATCAGCAGCCTGCAGCCCGAGGACATCGCCACCTACTA<br>CTGCCAGCAGCACTACACCACCCCTCTGACCTTCGGCC<br>AGGGCACCAAGCTGGAGATCAAG | 97 |

TABLE 6-continued

| Humanized antibody sequences (bold indicates CDR) | | |
|---|---|---|
| Hu1210 VK.1a | GACATCCAGATGACCCAGAGCCCTAGCAGCCTGAGCG<br>CTAGCGTGGGCGACAGGGTGACCATCACCTGCAAGGC<br>CAGCCAGGATGTGACCCCTGCCGTGGCCTGGTACCAG<br>CAGAAGCCCGGCAAGTCCCCCAAGCTGCTGATCTACA<br>GCACCAGCAGCAGGTACACCGGCGTGCCCAGCAGGTT<br>TAGCGGAAGCGGCAGCGGCACCGACTTCACCTTCACC<br>ATCAGCAGCCTGCAGCCCGAGGACATCGCCACCTACTA<br>CTGCCAGCAGCACTACACCACCCCTCTGACCTTCGGCC<br>AGGGCACCAAGCTGGAGATCAAG | 98 |
| Hu1210 VK.2 | GACATTCAGATGACCCAGTCCCCTAGCAGCCTGTCCGC<br>TTCCGTGGGCGACAGGGTGACCATCACCTGCAAGGCC<br>AGCCAGGACGTGACACCTGCTGTGGCCTGGTATCAACA<br>GAAGCCTGGCAAGGCTCCTAAGCTCCTGATCTACAGCA<br>CATCCTCCCGGTACACCGGAGTGCCCTCCAGGTTTAGC<br>GGCAGCGGCTCCGGCACCGATTTCACCCTGACCATTTC<br>CTCCCTGCAGCCCGAGGACTTCGCCACCTACTACTGCC<br>AGCAGCACTACACCACACCCCTGACCTTCGGCCAGGG<br>CACCAAGCTGGAGATCAAGCGG | 99 |
| Hu1210 VK.2a | GACATTCAGATGACCCAGTCCCCTAGCAGCCTGTCCGC<br>TTCCGTGGGCGACAGGGTGACCATCACCTGCAAGGCC<br>AGCCAGGACGTGACACCTGCTGTGGCCTGGTATCAACA<br>GAAGCCTGGCAAGGCTCCTAAGCTCCTGATCTACAGCA<br>CATCCTCCCGGTACACCGGAGTGCCCGACAGGTTTACC<br>GGCAGCGGCTCCGGCACCGATTTCACCCTGACCATTTC<br>CTCCCTGCAGCCCGAGGACTTCGCCACCTACTACTGCC<br>AGCAGCACTACACCACACCCCTGACCTTCGGCCAGGG<br>CACCAAGCTGGAGATCAAGCGG | 100 |
| Hu1210 VK.2b | GACATTCAGATGACCCAGTCCCCTAGCAGCCTGTCCGC<br>TTCCGTGGGCGACAGGGTGACCATCACCTGCAAGGCC<br>AGCCAGGACGTGACACCTGCTGTGGCCTGGTATCAACA<br>GAAGCCTGGCAGAGCCCTAAGCTCCTGATCTACAGCA<br>CATCCTCCCGGTACACCGGAGTGCCCGACAGGTTTACC<br>GGCAGCGGCTCCGGCACCGATTTCACCCTGACCATTTC<br>CTCCCTGCAGCCCGAGGACTTCGCCACCTACTACTGCC<br>AGCAGCACTACACCACACCCCTGACCTTCGGCCAGGG<br>CACCAAGCTGGAGATCAAGCGG | 101 |
| Hu1210 VK.2c | GACATTCAGATGACCCAGTCCCCTAGCAGCCTGTCCGC<br>TTCCGTGGGCGACAGGGTGACCATCAGCTGCAAGGCC<br>AGCCAGGACGTGACACCTGCTGTGGCCTGGTATCAACA<br>GAAGCCTGGCCAGAGCCCTAAGCTCCTGATCTACAGCA<br>CATCCTCCCGGTACACCGGAGTGCCCGACAGGTTTACC<br>GGCAGCGGCTCCGGCACCGATTTCACCCTGACCATTTC<br>CTCCCTGCAGCCCGAGGACTTCGCCACCTACTACTGCC<br>AGCAGCACTACACCACACCCCTGACCTTCGGCCAGGG<br>CACCAAGCTGGAGATCAAGCGG | 102 |

The humanized VH and VK genes were produced synthetically and then respectively cloned into vectors containing the human gamma 1 and human kappa constant domains. The pairing of the human VH and the human VK created the 40 humanized antibodies (see Table 7).

TABLE 7

| Humanized antibodies with their VH an VL regions | | | | | | | |
|---|---|---|---|---|---|---|---|
| VH<br>VK | Hu1210<br>VH.1 | Hu1210<br>VH.1a | Hu1210<br>VH.1b | Hu1210<br>VH.2 | Hu1210<br>VH.2a | Hu1210<br>VH 2.b | Hu1210<br>VH |
| Hu1210 VK.1 | Hu1210-1 | Hu1210-2 | Hu1210-3 | Hu1210-4 | Hu1210-5 | | |
| Hu1210 VK.1a | Hu1210-7 | Hu1210-8 | Hu1210-9 | Hu1210-10 | Hu1210-11 | | |
| Hu1210 VK | | | | | | | H1210 chimera |

TABLE 7-continued

Humanized antibodies with their VH an VL regions

| VH<br>VK | Hu1210 VH.3 | Hu1210 VH.3a | Hu1210 VH.4 | Hu1210 VH.4a | Hu1210 VH.4b |
|---|---|---|---|---|---|
| Hu1210 VK.1 | Hu1210-13 | Hu1210-14 | Hu1210-15 | Hu1210-16 | Hu1210-17 |
| Hu1210 VK.1a | Hu1210-18 | Hu1210-19 | Hu1210-20 | Hu1210-21 | Hu1210-22 |

Humanized antibodies with their VH an VL regions

| VH<br>VK | Hu1210 VH.5 | HU1210 VH.5a | Hu1210 VH.5b | HU1210 VH.5c | HU1210 VH.5d |
|---|---|---|---|---|---|
| Hu1210 VK.2 | Hu1210-23 | Hu1210-27 | Hu1210-31 | Hu1210-32 | Hu1210-36 |
| Hu1210 VK.2a | Hu1210-24 | Hu1210-28 | | Hu1210-33 | Hu1210-37 |
| Hu1210 VK.2b | Hu1210-25 | Hu1210-29 | | Hu1210-34 | Hu1210-38 |
| Hu1210 VK.2c | Hu1210-26 | Hu1210-30 | | Hu1210-35 | Hu1210-39 |

Humanized antibodies with their VH an VL regions

| VH<br>VK | Hu1210 VH.4c | Hu1210 VH.4d | Hu1210 VH.4e |
|---|---|---|---|
| Hu1210 VK.1 | Hu1210-40 | Hu1210-41 | Hu1210-42 |

1.3. Identification of PD-L1 Epitope

This study was conducted to identify amino acid residues involved in the binding of PD-L1 to the antibodies of the present disclosure.

Figure 3:
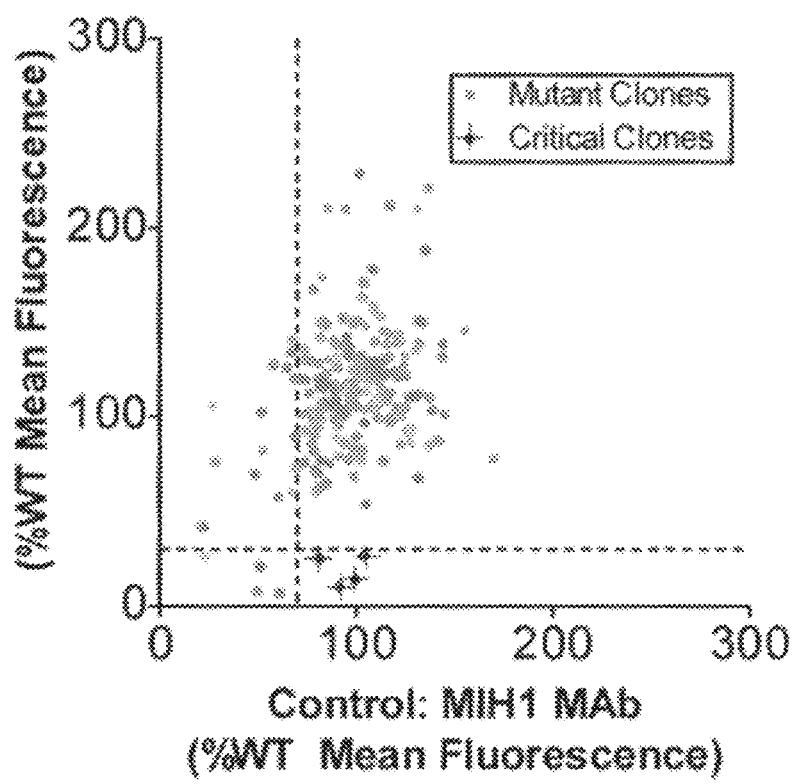
FIG. 3 plots demonstrated selection criteria for PD-L1 variants in order to identify required residues for Hu1210-41 binding.

An alanine-scan library of PD-L1 was constructed. Briefly, 217 mutant clones of PD-L1 were generated on Integral Molecular's protein engineering platform. Binding of Hu1210-41 Fab to each variant in the PD-L1 mutation library was determined, in duplicate, by high-throughput flow cytometry. Each raw data point had background fluorescence subtracted and was normalized to reactivity with PD-L1 wild-type (WT). For each PD-L1 variant, the mean binding value was plotted as a function of expression. To identify preliminary critical clones (circles with crosses), thresholds (dashed lines) of >70% WT binding to control MAb (MIH1 Mab, in house prepared) and <30% WT reactivity to Hu1210-41 Fab were applied (FIG. 3). Y134, K162, and N183 of PD-L1 were identified as required residues for Hu1210-41 binding. The low reactivity of N183A clone with Hu1210-41 Fab suggests that it is the major energetic contributor to Hu1210-41 binding, with lesser contributions by Y134 and K162.

Figure 4:
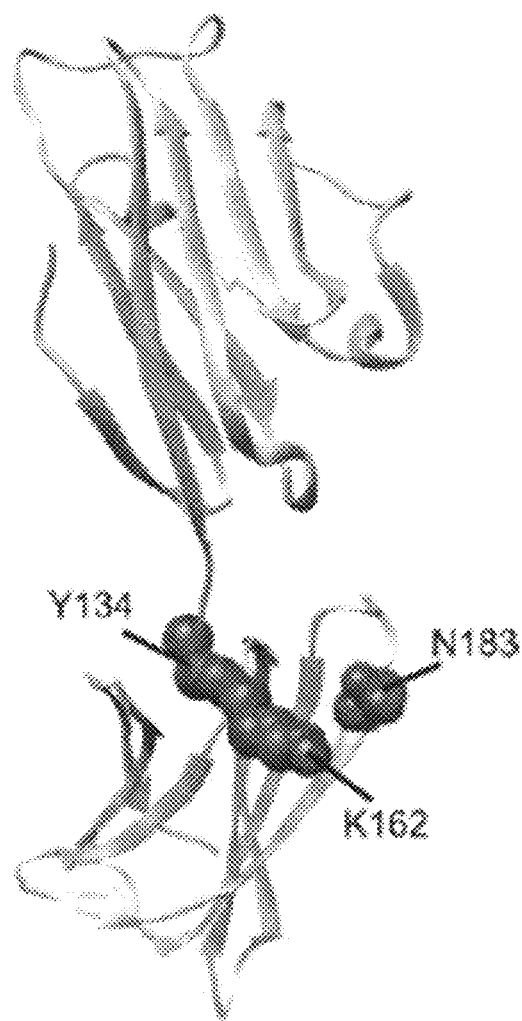
FIG. 4 illustrates the locations of Y134, K162, and N183, the residues (spheres) involved in binding to the anti-PD-L1 antibody according to an embodiment.

The critical residues (spheres) were identified on a 3D PD-L1 structure, as illustrated in FIG. 4. These residues, Y134, K162, and N183, therefore, constitute epitopes of PD-L1 responsible for binding to antibodies of various embodiments of the present disclosure.

It is interesting to note that Y134, K162, and N183 are all located within the IgC domain of the PD-L1 protein. Both PD-1 and PD-L1's extracellular portions have an IgV domain and an IgC domain. It is commonly known that PD-L1 binds to PD-1 through bindings between their IgV domains. Unlike such conventional antibodies, however, Hu1210-41 binds to the IgC domain, which would have been expected to be ineffective in inhibiting PD-1/PD-L1 binding. This different epitope of Hu1210-41, surprisingly, likely contributes to the excellent activities of Hu1210-41.

1.4. Antibody Engineering of Anti-PD-L1 Antibody

Examples 1.4 attempted to identify further improved antibodies based on Hu1210-41 using mutagenesis.

Four sub-libraries were constructed for antibody engineering of anti-PD-L1 monoclonal antibody, using either of the following strategies. In strategy 1, mutagenesis of heavy chain variable domain VH CDR3 or VL-CDR3 was perform by highly random mutation. In strategy 2, two CDR combination libraries composed of (VH-CDR3, VL-CDR3 and VL-CDR1) or (VH-CDR1, VH-CDR2 and VL-CDR2) were generated by CDR walking with controlled mutation rates.

Bio-Panning: the phage panning methods were adapted by shortening the incubation/binding time prior to the harsh washing condition. Briefly, 100 µl magnetic streptavidin beads (Invitrogen, USA) were blocked with 1 ml of MPBS for 1 hr at room temperature. In another tube, library phage was pre-incubated (5×10^11~12 for each round) with 100 µl magnetic streptavidin beads in 1 ml of MPBS to remove unwanted binders. Magnet particle concentrator was used to separate the phage and beads. The biotinylated PD-L1 protein was added to the phage and incubated 2 h at room temperature, and gently mixed using an over-head shaker. Beads carrying phage from the solution were separated in the magnetic particle concentrator and the supernatant was discarded. The beads were washed with fresh wash buffer, ten times with PBST and ten times with PBS (pH7.4). 0.8 ml, 0.25% Trypsin in PBS (Sigma, USA) was added and incubated for 20 min at 37° C. to elute the phage. The output phage was titrated and rescued for next round panning, decreasing antigen concentration round by round.

ELISA Screening and on/Off Rate Ranking

Clones were picked and induced from the desired panning output; phage ELISA was conducted for primary screening; positive clones were analyzed by sequencing; unique hotspots were found.

Table 8 shows the mutations identified. As shown below, the hotpot mutation residues and/or their substitutes are underlined.

TABLE 8

| | CDR-H1 (SEQ ID No.) | CDR-H2 (SEQ ID No.) | CDR-H3 (SEQ ID No.) |
|---|---|---|---|
| WT (H12) | SYDMS (107) | TISDAGGYIYYSDSVKG (117) | EFGKRYALDY (127) |
| B3 | SYDMS (108) | TISDAGGYIYYRDSVKG (118) | EFGKRYALDY (128) |
| C4 | SYDMS (109) | TISDAGGYIYYRDSVKG (119) | EFGKRYALDS (129) |
| B1 | SYDMS (110) | TISDAGGYIYYRDSVKG (120) | EIFNRYALDY (130) |
| B6 | SYDMS (111) | TISDAGGYIYYRDSVKG (121) | ELPWRYALDY (131) |
| C3 | SYDMS (112) | TISDAGGYIYYRDSVKG (122) | ELHFRYALDY (132) |
| C6 | SYDMS (113) | TISDAGGYIYYRDSVKG (123) | ELYFRYALDY (133) |
| A1 | SYDMS (114) | TISDAGGYIYYRDSVKG (124) | ELLHRYALDY (134) |
| A2 | SYDMS (115) | TISDAGGYIYYRDSVKG (125) | ELRGRYALDY (135) |
| A3 | SYDMS (116) | TISDAGGYIYYRDSVKG (126) | EFGKRYALDY (136) |

| | CDR-L1 (SEQ ID No.) | CDR-L2 (SEQ ID No.) | CDR-L3 (SEQ ID No.) |
|---|---|---|---|
| WT | KASQDVTPAVA (137) | STSSRYT (147) | QQHYTTPLT (157) |
| B3 | KAKQDVTPAVA (138) | STSSRYT (148) | MQHYTTPLT (158) |
| C4 | KASQDVWPAVA (139) | STSSRYT (149) | QQHSTTPLT (159) |
| B1 | KASQDVTPAVA (140) | STSSRYT (150) | QQHYTTPLT (160) |
| B6 | KASQDVTPAVA (141) | STSSRYT (151) | QQHYTTPLT (161) |
| C3 | KASQDVTPAVA (142) | STSSRYT (152) | QQHYTTPLT (162) |
| C6 | KASQDVTPAVA (143) | STSSRYT (153) | QQHYTTPLT (163) |
| A1 | KASQDVTPAVA (144) | STSSRYT (154) | QQHYTTPLT (164) |
| A2 | KASQDVTPAVA (145) | STSSRYT (155) | QQHYTTPLT (165) |
| A3 | KASQDVTPAVA (146) | STSSRYT (156) | QQHSDAPLT (166) |

The amino acid sequences of the variable regions of these antibodies are shown in Table 9 below.

TABLE 9

Antibody sequences

| Name Sequence | SEQ ID NO: |
|---|---|
| WT-VHEVQLVESGGGLVQPGGSLRLSCAASGFTFSSYDMSWVRQ APGKSLEWVATISDAGGYIYYRDSVKGRFTISRDNAKNSLY LQMNSLRDEDTAVYICAREFGKRYALDYWGQGTTVTVSS | 167 |
| WT-VKDIQMTQSPSSLSASVGDRVTITCKASQDVTPAVAWYQQKP GKAPKLLIYSTSSRYTGVPSRFSGSGSGTDFTFTISSLQPE DIATYYCQQHYTTPLTFGQGTKLEIK | 168 |
| B3-VHEVQLVESGGGLVQPGGSLRLSCAASGFTFSSYDMSWVRQ APGKSLEWVATISDAGGYIYYRDSVKGRFTISRDNAKNSLY LQMNSLRDEDTAVYICAREFGKRYALDYWGQGTTVTVSS | 169 |
| B3-VKDIQMTQSPSSLSASVGDRVTITCKAKQDVTPAVAWYQQKP GKAPKLLIYSTSSRYTGVPSRFSGSGSGTDFTFTISSLQPE DIATYYCMQHYTTPLTFGQGTKLEIK | 170 |
| C4-VHEVQLVESGGGLVQPGGSLRLSCAASGFTFSSYDMSWVRQ APGKSLEWVATISDAGGYIYYRDSVKGRFTISRDNAKNSLY LQMNSLRDEDTAVYICAREFGKRYALDSWGQGTTVTVSS | 171 |

TABLE 9-continued

Antibody sequences

| Name Sequence | SEQ ID NO: |
|---|---|
| C4-VKDIQMTQSPSSLSASVGDRVTITCKASQDVWPAVAWYQQK PGKAPKLLIYSTSSRYTGVPSRFSGSGSGTDFTFTISSLQP EDIATYYCQQHSTTPLTFGQGTKLEIK | 172 |
| B1-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICAREIFNRYALDYWGQGTTVTVS S | 173 |
| B1-VKDIQMTQSPSSLSASVGDRVTITCKASQDVTPAVAWYQQK PGKAPKLLIYSTSSRYTGVPSRFSGSGSGTDFTFTISSLQP EDIATYYCQQHYTTPLTFGQGTKLEIK | 174 |
| B6-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICARELPWRYALDYWGQGTTVTV SS | 175 |
| B6-VKDIQMTQSPSSLSASVGDRVTITCKASQDVTPAVAWYQQK PGKAPKLLIYSTSSRYTGVPSRFSGSGSGTDFTFTISSLQP EDIATYYCQQHYTTPLTFGQGTKLEIK | 176 |
| C3-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICARELHFRYALDYWGQGTTVTV SS | 177 |
| C3-VKDIQMTQSPSSLSASVGDRVTITCKASQDVTPAVAWYQQK PGKAPKLLIYSTSSRYTGVPSRFSGSGSGTDFTFTISSLQP EDIATYYCQQHYTTPLTFGQGTKLEIK | 178 |
| C6-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICARELYFRYALDYWGQGTTVTV SS | 179 |
| C6-VKDIQMTQSPSSLSASVGDRVTITCKASQDVTPAVAWYQQK PGKAPKLLIYSTSSRYTGVPSRFSGSGSGTDFTFTISSLQP EDIATYYCQQHYTTPLTFGQGTKLEIK | 180 |
| A1-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICARELLHRYALDYWGQGTTVTV SS | 181 |
| A1-VKDIQMTQSPSSLSASVGDRVTITCKASQDVTPAVAWYQQK PGKAPKLLIYSTSSRYTGVPSRFSGSGSGTDFTFTISSLQP EDIATYYCQQHYTTPLTFGQGTKLEIK | 182 |
| A2-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICARELRGRYALDYWGQGTTVTV SS | 183 |
| A2-VKDIQMTQSPSSLSASVGDRVTITCKASQDVTPAVAWYQQK PGKAPKLLIYSTSSRYTGVPSRFSGSGSGTDFTFTISSLQP EDIATYYCQQHYTTPLTFGQGTKLEIK | 184 |
| A3-VHEVQLVESGGGLVQPGGSLRLSCAASGFTFSSYDMSWVR QAPGKSLEWVATISDAGGYIYYRDSVKGRFTISRDNAKNS LYLQMNSLRDEDTAVYICAREFGKRYALDYWGQGTTVTV SS | 185 |
| A3-VKDIQMTQSPSSLSASVGDRVTITCKASQDVTPAVAWYQQK PGKAPKLLIYSTSSRYTGVPSRFSGSGSGTDFTFTISSLQP EDIATYYCQQHSDAPLTFGQGTKLEIK | 186 |

TABLE 10

Heavy chain variable regions for H12 and B6 clones

| Antibody No. | VH | SEQ ID NO: |
|---|---|---|
| H12 | EVQLVESGGGLVQPGGSLRLSCAASGFTFSSYDMSWVRQAPGKSLEWV ATISDAGGYIYYSDSVKGRFTISRDNAKNSLYLQMNSLRDEDTAVYICARE FGKRYALDYWGQGTTVTVSS | 103 |
| B6 | EVQLVESGGGLVQPGGSLRLSCAASGFTFSSYDMSWVRQAPGKSLEWV ATISDAGGYIYYRDSVKGRFTISRDNAKNSLYLQMNSLRDEDTAVYICARE LPWRYALDYWGQGTTVTVSS | 104 |

TABLE 11

Light chain variable regions for H12 and B6 clones

| Antibody No. | VL | SEQ ID NO: |
|---|---|---|
| H12 | DIQMTQSPSSLSASVGDRVTITCKASQDVTPAVAWYQQKPGKAPKLLIYST SSRYTGVPSRFSGSGSGTDFTFTISSLQPEDIATYYCQQHYTTPLTFGQGT KLEIK | 105 |
| B6 | DIQMTQSPSSLSASVGDRVTITCKASQDVTPAVAWYQQKPGKAPKLLIYST SSRYTGVPSRFSGSGSGTDFTFTISSLQPEDIATYYCQQHYTTPLTFGQGT KLEIK | 106 |

1.5. Protein Kinetic for PD-L1

To explore the binding kinetics of the humanized antibody, this example performed the affinity ranking by using Biacore. As shown in Table 12 below, H12 and B6.

TABLE 12

| Antibody | KD (M) | kon(1/Ms) | kdis(1/s) | Chi |
|---|---|---|---|---|
| H12 | 6.122E−09 | 7.124E+04 | 4.361E−04 | 0.0415 |
| B6 | 4.248E−09 | 9.827E+04 | 4.175E−04 | 0.0766 |

As shown in Table 12, the anti-PD-L1 antibodies tested show high PD-L1 binding affinities.

Example 2. Preparation of Anti-4-1BB Monoclonal Antibodies 2.1. Screening of Full Human Monoclonal Antibodies Against 4-1BB Phage Library Immunotube Panning Against 4-1BB For panning of the library against target molecules, four rounds of panning were carried out in total using 4-1BB coated immunotubes.

Bacterial colonies from the 3 rounds of panning output were grown in SB-Carbenicilin in 96 deepwell plate until turbid, at which point 1011 pfu of VCSM13 helper phage was added to each well. After 1 h infection at 37° C. with gentle shaking (80 rpm), 70 μg/mL of kanamycin was added and the cells were cultured overnight at 30° C. with shaking at 200 rpm.

Next day, the plates were centrifuged and the supernatants containing the phages were added to 4-1BB antigen-coated ELISA plates blocked with 3% BSA in PBST. After 1 h incubation at room temperature, the plates were washed three times with PBST and anti M13 antibody was added. The plates were incubated for 1 h, washed three times with PBST, and the binding activity was measured using tetramethylbenzidine (TMB).

The 4-1BB specific binders were amplified for plasmid DNA sequencing. Ig light chain V genes (VL) and VH sequences were analyzed to identify unique sequences and determine sequence diversity.

TABLE 13 heavy chain variable regions

| Antibody No. | VH | SEQ ID NO: |
|---|---|---|
| 41B01 | EVQLLESGGGLVQPGGSLRLSCAASGFTFSSYDMSWVRQAPGKGLEWVS WISYSGGSIYYADSVKGRFTISRDNSKNTLYLQMNSLRAEDTAVYYCARDG QRNSMREFDYWGQGTLVTVSS | 187 |
| 41B01.01 | EVQLLESGGGLVQPGGSLRLSCAASGFTFSSYDMSWVRQAPGKGLEWVS WISYSGGSIYYADSVKGRFTISRDNSKNTLYLQMNSLRAEDTAVYYCARDAQ RNSMREFDYWGQGTLVTVSS | 188 |
| 41B01.02 | EVQLLESGGGLVQPGGSLRLSCAASGFTFSSYDMSWVRQAPGKGLEWVS WISYSGGSIYYADSVKGRFTISRDNSKNTLYLQMNSLRAEDTAVYYCARDAQ RQSMREFDYWGQGTLVTVSS | 189 |

TABLE 13-continued heavy chain variable regions

| Antibody No. | VH | SEQ ID NO: |
|---|---|---|
| 41B01.03 | EVQLLESGGGLVQPGGSLRLSCAASGFTFSSYDMSWVRQAPGKGLEWVS WISYSGGSIYYADSVKGRFTISRDNSKNTLYLQMNSLRAEDTAVYYCARDAQ RNSMREFDYWGQGTLVTVSS | 190 |
| 41B01.04 | EVQLLESGGGLVQPGGSLRLSCAASGFTFSSYDMSWVRQAPGKGLEWVS WISYSGGSIYYADSVKGRFTISRDNSKNTLYLQMNSLRAEDTAVYYCARDAQ RQSMREFDYWGQGTLVTVSS | 191 |
| 41B02 | EVQLLESGGGLVQPGGSLRLSCAASGFTFSGYDMSWVRQAPGKGLEWVS VIYPDDGNTYYADSVKGRFTISRDNSKNTLYLQMNSLRAEDAAVYYCAKHG GQKPTTKSSSAYGMDGWGQGTLVTVSS | 192 |

TABLE 14

Heavy Chain CDRs

| Antibody No. | CDR H1 | SEQ ID NO: | CDR H2 | SEQ ID NO: | CDR H3 | SEQ ID NO: |
|---|---|---|---|---|---|---|
| 41B01 | SYDMS | 10 | WISYSGGSIYYADSVKG | 12 | DGQRNSMREFDY | 14 |
| 41B01.01 | SYDMS | 10 | WISYSGGSIYYADSVKG | 12 | DAQRNSMREFDY | 16 |
| 41B01.02 | SYDMS | 10 | WISYSGGSIYYADSVKG | 12 | DAQRQSMREFDY | 17 |
| 41B01.03 | SYDMS | 10 | WISYSGGSIYYADSVKG | 12 | DAQRNSMREFDY | 16 |
| 41B01.04 | SYDMS | 10 | WISYSGGSIYYADSVKG | 12 | DAQRQSMREFDY | 17 |
| 41B02 | GYDMS | 11 | VIYPDDGNTYYADSVKG | 13 | HGGQKPTTKSSSAYGMDG | 15 |

TABLE 15

Light chain variable regions

| Antibody No. | VL | SEQ ID NO: |
|---|---|---|
| 41B01 | QSVLTQPPSASGTPGRRVTISCSGSSSNIGNNYVTWYQQLPGTAPKLLIYADSHRP SGVPDRFSGSKSGTSASLAISGLRSEDEADYYCATWDYSLSGYVFGGGTKLTVL | 193 |
| 41B01.01 | QSVLTQPPSASGTPGRRVTISCSGSSSNIGNNYVTWYQQLPGTAPKLLIYADSHRP SGVPDRFSGSKSGTSASLAISGLRSEDEADYYCATWDYSLSGYVFGGGTKLTVL | 194 |
| 41B01.02 | QSVLTQPPSASGTPGRRVTISCSGSSSNIGNNYVTWYQQLPGTAPKLLIYA DSHRPSGVPDRFSGSKSGTSASLAISGLRSEDEADYYCATWDYSLSGYVF GGGTKLTVL | 195 |
| 41B01.03 | QSVLTQPPSASGTPGQRVTISCSGSSSNIGNNYVTWYQQLPGTAPKLLIYA DSHRPSGVPDRFSGSKSGTSASLAISGLRSEDEADYYCATWDYSLSGYVF GGGTKLTVL | 196 |
| 41B01.04 | QSVLTQPPSASGTPGQRVTISCSGSSSNIGNNYVTWYQQLPGTAPKLLIYA DSHRPSGVPDRFSGSKSGTSASLAISGLRSEDEADYYCATWDYSLSGYVF GGGTKLTVL | 197 |
| 41B02 | QSVLTQPPSASGTPGRRVTISCSGSSSNIGNNYVTWYQQLPGTAPKLLIYA DSHRPSGVPDRFSGSKSGTSASLAISGLRSEDEADYYCATWDYSLSGYVF GGGTKLTVL | 198 |

TABLE 16

Light Chain CDRs

| Antibody No. | CDR L1 | SEQ ID NO: | CDR L2 | SEQ ID NO: | CDR L3 | SEQ ID NO: |
|---|---|---|---|---|---|---|
| 41B01 | SGSSSNIGNNYVT | 18 | ADSHRPS | 19 | ATWDYSLSGYV | 20 |
| 41B01.01 | SGSSSNIGNNYVT | 18 | ADSHRPS | 19 | ATWDYSLSGYV | 20 |
| 41B01.02 | SGSSSNIGNNYVT | 18 | ADSHRPS | 19 | ATWDYSLSGYV | 20 |
| 41B01.03 | SGSSSNIGNNYVT | 18 | ADSHRPS | 19 | ATWDYSLSGYV | 20 |
| 41B01.04 | SGSSSNIGNNYVT | 18 | ADSHRPS | 19 | ATWDYSLSGYV | 20 |
| 41B02 | SGSSSNIGNNYVT | 18 | ADSHRPS | 19 | ATWDYSLSGYV | 20 |

Figure 5:
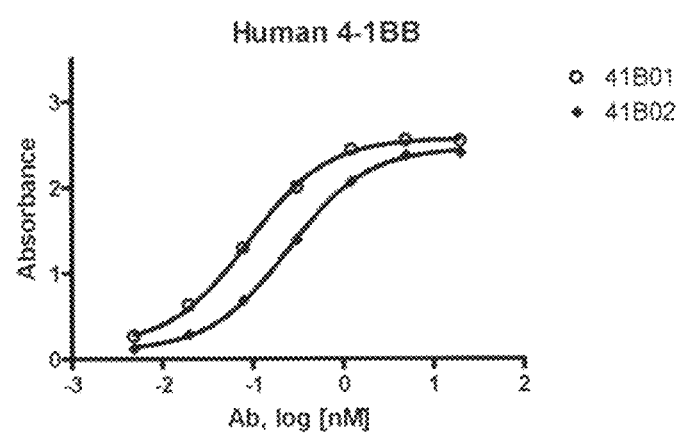
FIG. 5 show that the anti-4-1BB antibodies according to embodiments can bind to human 4-1BB with high affinity.

2.2. Antigen Binding Abilities of Anti-4-1BB Antibodies to Human 4-1BB (1) Antigen Binding Measured by ELISA To evaluate the antigen binding activity, the antibody candidates were subjected to ELISA test. Briefly, microtiter plates were coated with human 4-1BB-Fc protein at 0.1 µg/ml in PBS, 100 µl/well at 4° C. overnight, then blocked with 100 µl/well of 5% BSA. Five-fold dilutions of humanized antibodies {41B01 and 41B02} starting from 10 µg/ml were added to each well and incubated for 1-2 hours at RT. The plates were washed with PBS/Tween and then incubate with goat-anti-human IgG antibody conjugated with Horse Radish Peroxidase (HRP) for 1 hour at RT. After washing, the plates were developed with TMB substrate and analyzed by spectrophotometer at OD 450-630 nm. As shown in FIG. 5, the anti-4-1BB antibodies tested show 4-1BB binding abilities.

(2) Cell Binding Measured by FACS

Figure 6:
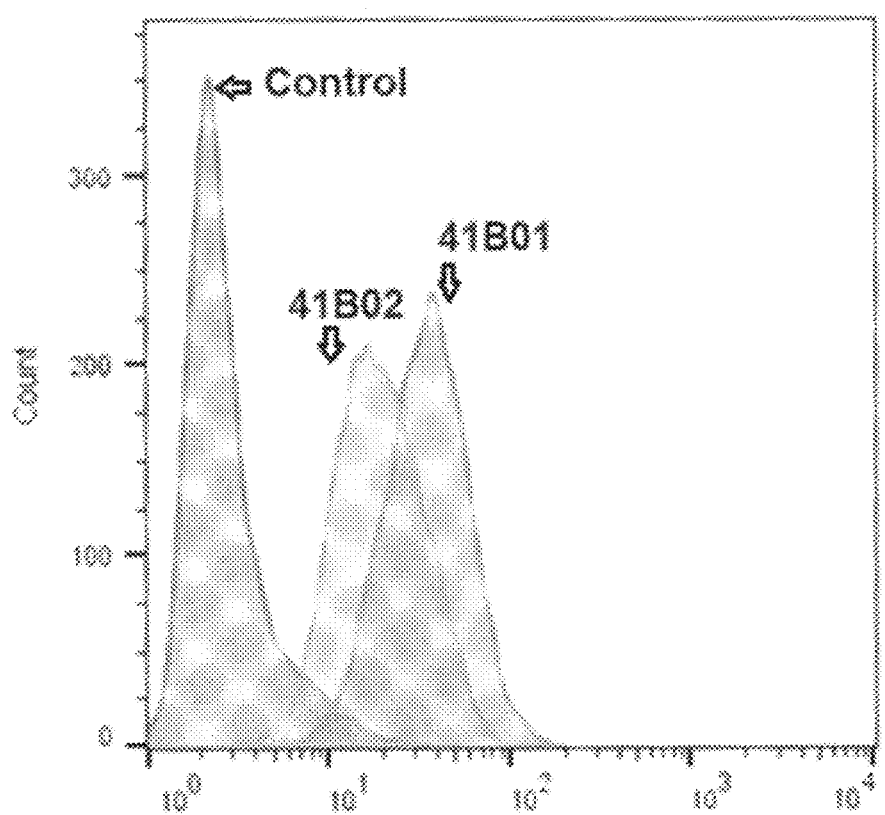
FIG. 6 shows that the anti-4-1BB antibodies according to embodiments can efficiently bind to 4-1BB expressed on mammalian cells.

To evaluate the antigen binding property, the antibody candidates were analyzed for its binding to mammalian expressed 4-1BB by FACS. Briefly, 4-1BB-Jurkat cells were incubated with antibodies (41B01 and 41B02). After wash by FACS buffer (1% BSA in PBS), the FITC-anti-human IgG antibody was added to each well and incubated at 4° C. for 1 hour. The MFI of FITC was evaluated by FACS Caliber. As shown in FIG. 6, the anti-4-1BB antibodies tested show binding abilities to 4-1BB which expressed on cell surface and can efficiently bind to 4-1BB expressed on mammalian cells.

(3) Protein Kinetic for 4-1BB

To explore the binding kinetics of the humanized antibody, this example performed the affinity ranking by using Octet Red 96. As shown in Table 17 below, 41B01 and 41B02.

TABLE 17

| Antibody | KD (M) | kon(1/Ms) | kdis(1/s) | Chi | R$^2$ |
|---|---|---|---|---|---|
| 41B01 | 1.80E−10 | 6.58E+05 | 1.19E−04 | 0.0392 | 0.9987 |
| 41B02 | 1.01E−09 | 5.95E+05 | 6.03E−04 | 0.0525 | 0.9973 |

As shown in Table 17, the anti-4-1BB antibodies tested show high 4-1BB binding affinities.

Example 3. Preparation of Anti-PD-L1/Anti-4-1BB Bispecific Antibodies

Hu1210-41 (Hu1210 VH.4d×Hu1210 VK.1, see Table 6; hereinafter, "H12") and B6 (see Table 12) clones among the anti-PD-L1 clones prepared in Example 1 and 41B01, 41B01.01, 41B01.02, 41B01.03, 41B01.04, and 41B02 clones among the anti-4-1BB clones prepared in Example 2 were exemplarily selected, to prepare anti-PD-L1/anti-4-1BB bispecific antibodies in a full-length IgG X scFv form. When PD-L1 is placed in full IgG part, IgG1 with ADCC reduced mutant backbone (N297A mutation; U.S. Pat. Nos. 7,332,581, 8,219,149, etc.) was used, and when 4-1BB is placed in full IgG part, IgG4 was used.

A DNA segment 1 having a nucleotide sequence encoding a heavy chain of an IgG antibody of the anti-PD-L1/anti-4-1BB bispecific antibody was inserted into pcDNA 3.4 (Invitrogen, A14697; plasmid 1), and a DNA segment 2 having a nucleotide sequence encoding a light chain of an IgG antibody of the anti-PD-L1/anti-4-1BB bispecific antibody was inserted into pcDNA 3.4 (Invitrogen, A14697; plasmid 2). Thereafter, a DNA segment 3 encoding a scFv was fused at a part of the DNA segment 1 corresponding to the c-terminus of the Fc region of the IgG antibody inserted into the plasmid 1, using a DNA segment 4 encoding a linker peptide having 10 amino acid lengths consisting of (GGGGS)2, to construct vectors for the expression of bispecific antibodies. Furthermore, in order to stabilize scFv, additional modification was applied to generate disulfide bridge fusing VL103-VH44 to C-terminus of light chain and C-terminus of heavy chain, respectively.

The sequences of the heavy chain, light chain, scFv and DNA segments were summarized in Table 18:

TABLE 18

Bispecific antibody comprising the anti-PD-L1 clone in IgG form
and the anti-4-1BB clone in scFv form (PD-L1x4-1BB)

| | | | Amino acid sequence (N' → C') (Seq ID No.) | Nucleotide Sequence (5' → 3') (Seq ID No.) |
|---|---|---|---|---|

ABLPNB.01
(bispecific antibody comprising the anti-PD-L1 H12 clone in
IgG form and the anti-4-1BB 41B01 clone in scFv form)

| | | | Amino acid sequence | Nucleotide Sequence |
|---|---|---|---|---|
| Heavy component | Heavy chain of H12 | | EVQLVESGGGLV QPGGSLRLSCAA SGFTFSSYDMSW VRQAPGKSLEWV ATISDAGGYIYYS DSVKGRFTISRDN AKNSLYLQMNSL RDEDTAVYICARE FGKRYALDYWG QGTTVTVSSASTK GPSVFPLAPSSKS TSGGTAALGCLV KDYFPEPVTVSW NSGALTSGVHTF PAVLQSSGLYSLS SVVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (199) | GAGGTGCAGCTGGTGGAGAGCGGAGGA GGACTGGTGCAACCCGGAGGCAGCCTG AGACTGAGCTGCGCTGCCAGCGGCTTCA CCTTCAGCAGCTACGACATGAGCTGGGT GAGACAGGCCCCTGGCAAAAGCCTGGA GTGGGTGGCCACCATCTCCGATGCGGGC GGCTACATCTATTACTCCGACAGCGTGA AGGGCAGGTTCACCATCAGCAGGGACA ACGCCAAGAACAGCCTGTACCTGCAGAT GAACAGCCTGAGGGATGAGGACACCGC CGTGTACATCTGCGCCAGGGAGTTCGGC AAAAGGTACGCCCTGGACTACTGGGGCC AGGGCACAACCGTGACCGTGAGCAGCgc tAgcAccAAgGGCCCCTCTGTGTTCCCTCT GGCCCCTTCCTCTAAATCCACCTCTGGCG GAACCGCTGCTCTGGGCTGTCTGGTCAA GGACTACTTCCCTGAGCCCGTGACCGTG TCTTGGAATTCTGGCGCTCTGACCAGCG GAGTGCACACCTTTCCAGCTGTGCTGCA GTCCTCCGGCCTGTACTCTCTGTCCTCTG TCGTGACAGTGCCTTCCAGCTCTCTGGGC ACCCAGACCTACATCTGCAACGTGAACC ACAAGCCCTCCAACACCAAGGTGGACAA GAAGGTGGAACCCAAGTCCTGCGACAA GACCCACACCTGTCCTCCATGTCCTGCTC CAGAACTGCTGGGCGGACCCTCCGTGTT CCTGTTCCCTCCAAAGCCTAAGGACACC CTGATGATCTCCCGGACCCCTGAAGTGA CCTGCGTGGTGGTGGATGTGTCCCACGA GGATCCCGAAGTGAAGTTCAATTGGTAC GTGGACGGCGTGGAAGTGCACAACGCC AAGACCAAGCCTAGAGAGGAACAGTAC gccTCCACCTACCGGGTGGTGTCCGTGCT GACCGTTCTGCACCAGGATTGGCTGAAC GGCAAAGAGTACAAGTGCAAGGTGTCCA ACAAGGCCCTGCCTGCCCCTATCGAAAA GACCATCTCTAAGGCCAAGGGCCAGCCC CGGGAACCTCAAGTGTACACCTTGCCTC CCAGCCGGGAAGAGATGACCAAGAACC AGGTGTCCCTGACCTGCCTGGTTAAGGG CTTCTACCCCTCCGATATCGCCGTGGAAT GGGAGTCTAACGGCCAGCCCGAGAACA ACTACAAGACCACCCCTCCTGTGCTGGA CTCCGACGGCTCATTCTTCCTGTACTCCA AGCTGACCGTGGACAAGTCTCGGTGGCA GCAGGGCAACGTGTTCTCCTGCTCTGTG ATGCACGAGGCCCTGCACAACCACTACA CCCAGAAGTCCCTGTCCCTGTCTCCCGG CAAAGGTGGGGGGGGATCTGGTGGTGG TGGATCAGGGGGTGGGGGTCTCAAAG CGTACTCACCCAACCTCCATCTGCATCCG GTACACCTGGTCGGCGAGTAACCATCTC |
| | Linker | | GGGGSGGGGSG GGGS (200) | |
| | scFv of 41B01 | VL | QSVLTQPPSASG TPGRRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (201) | |
| | | Linker | GGGGSGGGGS GGGSGGGGS (202) | |
| | | VH | EVQLLESGGGLV QPGGSLRLSCAA SGFTFSSYDMSW VRQAPGKCLEWV SWISYSGGSIYYA DSVKGRFTISRDN SKNTLYLQMNSL RAEDTAVYYCAR DGQRNSMREFDY WGQGTLVTVSS (203) | CTGCTCTGGGAGCTCTTCTAATATTGGTA ACAACTATGTCACCTGGTATCAGCAGTTG CCTGGGACAGCACCCAAACTTCTTATATA TGCCGATAGCCATCGGCCTTCCGGCGTA CCCGATCGCTTCTCCGGGTCAAAATCTG GAACATCTGCCTCACTCGCAATTAGTGG ATTGCGATCTGAGGATGAAGCAGATTATT ATTGCGCTACCTGGGATTATTCACTTTCT GGCTACGTCTTTGGTtgtggaACAAAACTT ACCGTGTTGGGGGGGAGGAAGCGGA GGCGGCGGTTCTGGTGGTGGCGGTAGCG GAGGTGGTGGATCTGAAGTACAGCTTCT TGAGTCTGGCGGAGGATTGGTCCAGCCA GGCGGTTCCCTCCGCCTGTCATGTGCCG CATCCGGCTTTACTTTCTCTAGTTATGATA TGAGCTGGGTTCGCCAAGCTCCTGGCAA |

TABLE 18-continued

Bispecific antibody comprising the anti-PD-L1 clone in IgG form
and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | | | AtgcCTGGAGTGGGTCTCCTGGATTTCAT ACTCAGGTGGCAGCATCTATTATGCTGA CAGTGTGAAAGGTCGCTTTACAATCTCCC GAGATAACAGCAAAAACACCTTGTACCT GCAAATGAACAGCCTTCGCGCAGAGGAC ACAGCCGTATATTATTGCGCTCGCGATG GACAACGTAATTCTATGCGTGAGTTTGAC TACTGGGGACAGGGGACATTGGTCACTG TATCTTCCtga (204) |
| Light component | Light chain of H12 | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (28) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (205) |

ABLPNB.02
(bispecific antibody comprising the anti-PD-L1 H12 clone in
IgG form and the anti-4-1BB 41B01.03 clone in scFv form)

| | | | |
|---|---|---|---|
| Heavy component | Heavy chain of H12 | EVQLVESGGGLV QPGGSLRLSCAA SGFTFSSYDMSW VRQAPGKSLEWV ATISDAGGYIYYS DSVKGRFTISRDN AKNSLYLQMNSL RDEDTAVYICARE FGKRYALDYWG QGTTVTVSSASTK GPSVFPLAPSSKS TSGGTAALGCLV KDYFPEPVTVSW NSGALTSGVHTF PAVLQSSGLYSLS SVVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG | GAGGTGCAGCTGGTGGAGAGCGGA GGAGGACTGGTGCAACCCGGAGGC AGCCTGAGACTGAGCTGCGCTGCCA GCGGCTTCACCTTCAGCAGCTACGA CATGAGCTGGGTGAGACAGGCCCCT GGCAAAAGCCTGGAGTGGGTGGCCA CCATCTCCGATGCGGGCGGCTACAT CTATTACTCCGACAGCGTGAAGGGC AGGTTCACCATCAGCAGGGACAACG CCAAGAACAGCCTGTACCTGCAGAT GAACAGCCTGAGGGATGAGGACACC GCCGTGTACATCTGCGCCAGGGAGT TCGGCAAAAGGTACGCCCTGGACTA CTGGGGCCAGGGCACAACCGTGACC GTGAGCAGCgctAgcAccAAgGGCCCC TCTGTGTTCCCTCTGGCCCCTTCCTC TAAATCCACCTCTGGCGGAACCGCT GCTCTGGGCTGTCTGGTCAAGGACT ACTTCCCTGAGCCCGTGACCGTGTC TTGGAATTCTGGCGCTCTGACCAGC GGAGTGCACACCTTTCCAGCTGTGC TGCAGTCCTCCGGCCTGTACTCTCT GTCCTCTGTCGTGACAGTGCCTTCCA GCTCTCTGGGCACCCAGACCTACAT CTGCAACGTGAACCACAAGCCCTCC AACAACAAGGTGGACAAGAAGGTGG AACCCAAGTCCTGCGACAAGACCCA CACCTGTCCTCCATGTCCTGCTCCAG AACTGCTGGGCGGACCCTCCGTGTT CCTGTTCCCTCCAAAGCCTAAGGACA CCCTGATGATCTCCCGGACCCCTGA |

TABLE 18-continued

Bispecific antibody comprising the anti-PD-L1 clone in IgG form and the anti-4-1BB clone in scFv form (PD-L1x4-1BB)

| | | | Amino acid sequence (N' → C') (Seq ID No.) | Nucleotide Sequence (5' → 3') (Seq ID No.) |
|---|---|---|---|---|
| | | | QPENNYKTTPPVL DSDGSFFLYSKLT VDKSRWQQGNV FSCSVMHEALHN HYTQKSLSLSPGK (206) | AGTGACCTGCGTGGTGGTGGATGTG TCCCACGAGGATCCAGAAGTGAAGT TCAATTGGTACGTGGACGGCGTGGA AGTGCACAATGCCAAGACCAAGCCT AGAGAGGAACAGTACGCCTCCACCT ACAGAGTGGTGTCCGTGCTGACTGT |
| | Linker | | GGGGSGGGGSG GGGS (207) | GCTGCACCAGGATTGGCTGAACGGC AAAGAGTACAAGTGCAAGGTGTCCA |
| | scFv of 41B0 1.03 | VL | QSVLTQPPSASG TPGQRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (208) | ACAAGCCCTGCCTGCCTCCTATCGA AAAGACCATCAGCAAGGCCAAGGGC CAGCCTAGGGAACCCCAGGTTTACA CCCTGCCTCCAAGCCGGGAAGAGAT GACCAAGAACCAGGTGTCCCTGACC TGCCTCGTGAAGGGCTTCTACCCTTC CGATATCGCCGTGGAATGGGAGAGC AATGGCCAGCCTGAGAACAACTACA AGACAACCCCTCCTGTGCTGGACTC CGACGGCTCATTCTTCCTGTACTCCA |
| | Linker | | GGGGSGGGGSG GGGSGGGGS (209) | AGCTGACCGTGGACAAGTCCAGATG GCAGCAGGGCAACGTGTTCTCCTGC TCCGTGATGCACGAGGCCCTGCACA |
| | | VH | EVQLLESGGGLV QPGGSLRLSCAA SGFTFSSYDMSW VRQAPGKCLEWV SWISYSGGSIYYA DSVKGRFTISRDN SKNTLYLQMNSL RAEDTAVYYCAR DAQRNSMREFDY WGQGTLVTVSS (210) | ATCACTACACCCAGAAGTCCCTGTCT CTGAGCCCTGGAAAAGGCGGCGGA GGATCTGGCGGAGGTGGTAGCGGA GGCGGTGGATCTCAGTCTGTTCTGA CCCAGCCTCCTTCCGCTTCTGGCAC CCCTGGACAGAGAGTGACCATCTCTT GCTCCGGCTCCTCCTCCAACATCGG CAACAACTACGTGACCTGGTATCAGC AGCTGCCCGGCACAGCTCCCAAACT GCTGATCTACGCCGACTCTCACAGA CCTTCCGGCGTGCCCGATAGATTCT CCGGCTCTAAGTCTGGCACCTCTGC CAGCCTGGCTATCAGCGGCCTGAGA TCTGAGGACGAGGCCGACTACTACT GCGCCACCTGGGATTATTCCCTGTC CGGCTACGTGTTCGGCTGCGGCACA AAACTGACAGTGCTCGGAGGCGGAG GAAGTGGTGGCGGAGGTTCAGGTGG TGGTGGTAGTGGCGGAGGCGGATCA GAAGTTCAGCTGTTGGAGTCAGGTG GCGGCTTGGTGCAACCAGGTGGAAG TCTGAGACTCAGCTGTGCTGCCAGC GGCTTTACCTTCAGCTCCTACGACAT GAGCTGGGTTCGACAAGCTCCCGGA AAGTGCTTGGAGTGGGTTTCCTGGA TCTCCTACTCCGGCGGCAGCATCTAT TACGCCGACAGCGTGAAAGGCCGGT TTACCATCTCTCGGGATAACAGCAAG AATACCCTCTACCTCCAAATGAACTC TCTGAGAGCCGAGGACACTGCTGTG TACTATTGCGCCAGAGATGccCAGCG GAACTCCATGAGAGAGTTCGACTACT GGGGACAAGGCACCCTGGTCACCGT GTCTAGTTGA (211) |
| Light component | Light chain of H12 | | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT |

TABLE 18-continued

Bispecific antibody comprising the anti-PD-L1 clone in IgG form
and the anti-4-1BB clone in scFv form (PD-L1x4-1BB)

| | | | Amino acid sequence (N' → C') (Seq ID No.) | Nucleotide Sequence (5' → 3') (Seq ID No.) |
|---|---|---|---|---|
| | | | KVYACEVTHQGL SSPVTKSFNRGE C (30) | GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (212) |

ABLPNB.03
(bispecific antibody comprising the anti-PD-L1 H12 clone in
IgG form and the anti-4-1BB 41B02 clone in scFv form

| Heavy component | Heavy chain of H12 | | | EVQLVESGGGLV QPGGSLRLSCAA SGFTFSSYDMSW VRQAPGKSLEWV ATISDAGGYIYYS DSVKGRFTISRDN AKNSLYLQMNSL RDEDTAVYICARE FGKRYALDYWG QGTTVTVSSASTK GPSVFPLAPSSKS TSGGTAALGCLV KDYFPEPVTVSW NSGALTSGVHTF PAVLQSSGLYSLS SVVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (213) | GAGGTGCAGCTGGTGGAGAGCGGA GGAGGACTGGTGCAACCCGGAGGC AGCCTGAGACTGAGCTGCGCTGCCA GCGGCTTCACCTTCAGCAGCTACGA CATGAGCTGGGTGAGACAGGCCCCT GGCAAAAGCCTGGAGTGGGTGGCCA CCATCTCCGATGCGGGCGGCTACAT CTATTACTCCGACAGCGTGAAGGGC AGGTTCACCATCAGCAGGGACAACG CCAAGAACAGCCTGTACCTGCAGAT GAACAGCCTGAGGGATGAGGACACC GCCGTGTACATCTGCGCCAGGGAGT TCGGCAAAAGGTACGCCCTGGACTA CTGGGGCCAGGGCACAACCGTGACC GTGAGCAGCgctAgcAccAAgGGCCCC TCTGTGTTCCCTCTGGCCCCTTCCTC TAAATCCACCTCTGGCGGAACCGCT GCTCTGGGCTGTCTGGTCAAGGACT ACTTCCCTGAGCCCGTGACCGTGTC TTGGAATTCTGGCGCTCTGACCAGC GGAGTGCACACCTTTCCAGCTGTGC TGCAGTCCTCCGGCCTGTACTCTCT GTCCTCTGTCGTGACAGTGCCTTCCA GCTCTCTGGGCACCCAGACCTACAT CTGCAACGTGAACCACAAGCCCTCC AACACCAAGGTGGACAAGAAGGTGG AACCCAAGTCCTGCGACAAGACCCA CACCTGTCCTCCATGTCCTGCTCCAG AACTGCTGGGCGGACCCTCCGTGTT CCTGTTCCCTCCAAAGCCTAAGGACA CCCTGATGATCTCCCGGACCCCTGA AGTGACCTGCGTGGTGGTGGATGTG TCCCACGAGGATCCCGAAGTGAAGT TCAATTGGTACGTGGACGGCGTGGA AGTGCACAACGCCAAGACCAAGCCT AGAGAGGAACAGTACgccTCCACCTA CCGGGTGGTGTCCGTGCTGACCGTT |
| | Linker | | | GGGGSGGGGSG GGGS (214) | CTGCACCAGGATTGGCTGAACGGCA AAGAGTACAAGTGCAAGGTGTCCAA |
| scFv of 41B0 2 | | VL | | QSVLTQPPSASG TPGRRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (215) | CAAGGCCCTGCCTGCCCCTATCGAA AAGACCATCTCTAAGGCCAAGGGCC AGCCCCGGGAACCTCAAGTGTACAC CTTGCCTCCCAGCCGGGAAGAGATG ACCAAGAACCAGGTGTCCCTGACCT GCCTGGTTAAGGGCTTCTACCCCTC CGATATCGCCGTGGAATGGGAGTCT AACGGCCAGCCCGAGAACAACTACA AGACCACCCCTCCTGTGCTGGACTC CGACGGCTCATTCTTCCTGTACTCCA |
| | Linker | | | GGGGSGGGGSG GGGSGGGGS (216) | AGCTGACCGTGGACAAGTCTCGGTG GCAGCAGGGCAACGTGTTCTCCTGC TCTGTGATGCACGAGGCCCTGCACA |
| | | VH | | EVQLLESGGGLV QPGGSLRLSCAA SGFTFSGYDMSW VRQAPGKCLEWV SVIYPDDGNTYYA | ACCACTACACCCAGAAGTCCCTGTC CCTGTCTCCCGGCAAAGGTGGGGGG GGATCTGGTGGTGGTGGATCAGGGG GTGGGGGGTCTCAAAGCGTACTCAC CCAACCTCCATCTGCATCCGGTACAC |

TABLE 18-continued

Bispecific antibody comprising the anti-PD-L1 clone in IgG form and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | | DSVKGRFTISRDN SKNTLYLQMNSL RAEDAAVYYCAK HGGQKPTTKSSS AYGMDGWGQGT LVTVSS (217) | CTGGTCGGCGAGTAACCATCTCCTG CTCTGGGAGCTCTTCTAATATTGGTA ACAACTATGTCACCTGGTATCAGCAG TTGCCTGGGACAGCACCCAAACTTCT TATATATGCCGATAGCCATCGGCCTT CCGGCGTACCCGATCGCTTCTCCGG GTCAAAATCTGGAACATCTGCCTCAC TCGCAATTAGTGGATTGCGATCTGAG GATGAAGCAGATTATTATTGCGCTAC CTGGGATTATTCACTTTCTGGCTACG TCTTTGGTtgtGGAACAAAACTTACCG TGTTGGGCGGCGGAGGAAGCGGAG GCGGCGGTTCTGGTGGTGGCGGTA GCGGAGGTGGTGGATCTGAGGTTCA ACTGTTGGAGTCAGGTGGCGGACTT GTCCAGCCTGGCGGGTCTCTGAGGC TGAGTTGCGCTGCTTCTGGGTTTACT TTTTCAGGATATGACATGAGTTGGGT ACGTCAGGCTCCAGGTAAGtgcCTCG AATGGGTCTCCGTTATCTATCCCGAT GATGGAAATACTTACTACGCTGACAG TGTGAAAGGCAGGTTCACAATCAGTA GGGACAATTCTAAAAATACACTCTAC CTCCAGATGAACTCACTTCGAGCCG AGGACGCCGCCGTATATTACTGTGC CAAACACGGCGGGCAAAAACCCACT ACTAAATCCAGTAGTGCTTACGGGAT GGATGGCTGGGGACAGGGGACATTG GTCACTGTATCTTCCtga (218) |
| Light component | Light chain of H12 | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (32) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTA GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (219) |

ABLPNB.04
(bispecific antibody comprising the anti-PD-L1 B6 clone in IgG form and the anti-4-1BB 41B01 clone in scFv form)

| Heavy component | Heavy chain of B6 | EVQLVESGGGLV QPGGSLRLSCAA SGFTFSSYDMSW VRQAPGKSLEWV ATISDAGGYIYYR DSVKGRFTISRDN AKNSLYLQMNSL RDEDTAVYICARE LPWRYALDYWG QGTTVTVSSASTK GPSVFPLAPSSKS | GAAGTGCAGCTGGTTGAATCTGGCG GCGGATTGGTTCAGCCTGGCGGATC TCTGAGACTGTCTTGTGCCGCCTCC GGCTTCACCTTCTCCAGCTACGATAT GTCCTGGGTCCGACAGGCCCCTGGC AAGTCTTTGGAATGGGTCGCCACCAT CTCTGACGCTGGCGGCTACATCTAC TACCGGGACTCTGTGAAGGGCAGAT TCACCATCAGCCGGGACAACGCCAA GAACTCCCTGTACCTGCAGATGAACA GCCTGCGCGACGAGGATACCGCCGT |

TABLE 18-continued

Bispecific antibody comprising the anti-PD-L1 clone in IgG form
and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | | TSGGTAALGCLV KDYFPEPVTVSW NSGALTSGVHTF PAVLQSSGLYSLS SWVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (220) | GTACATCTGTGCTAGAGAGCTGCCTT GGAGATACGCCCTGGATTATTGGGG CCAGGGCACCACAGTGACCGTGTCC TCTGCTTCTACCAAGGGACCCAGCG TGTTCCCTCTGGCTCCTTCCAGCAAG TCTACCTCTGGCGAACAGCTGCTC TGGGCTGCCTGGTCAAGGACTACTT TCCTGAGCCTGTGACAGTGTCCTGG AACTCTGGCGCTCTGACATCTGGCG TGCACACCTTTCCAGCAGTGCTGCA GTCCTCCGGCCTGTACTCTCTGTCCT CTGTCGTGACCGTGCCTTCCAGCTC TCTGGGAACCCAGACCTACATCTGC AATGTGAACCACAAGCCTTCCAACAC CAAGGTGGACAAGAAGGTGGAACCC AAGTCCTGCGACAAGACCCACACCT GTCCTCCATGTCCTGCTCCAGAACTG CTCGGCGGACCTTCCGTGTTCCTGT TTCCTCCAAAGCCTAAGGACACCCTG ATGATCTCTCGGACCCCTGAAGTGA CCTGCGTGGTGGTGGATGTGTCCCA CGAGGATCCAGAAGTGAAGTTCAATT GGTACGTGGACGGCGTGGAAGTGCA CAATGCCAAGACCAAGCCTAGAGAG GAACAGTACGCCTCCACCTACGAG TGGTGTCCGTGCTGACTGTGCTGCA CCAGGATTGGCTGAACGGCAAAGAG TACAAGTGCAAGGTGTCCAACAAGG |
| Linker | | GGGGSGGGGSG GGGS (221) | CCCTGCCTGCTCCTATCGAAAAGAC |
| scFv of 41B01 | VL | QSVLTQPPSASG TPGRRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (222) | CATCAGCAAGGCCAAGGGCCAGCCT AGGGAACCCCAGGTTTACACCCTGC CTCCAAGCGGGAAGAGATGACCAA GAACCAGGTGTCCCTGACCTGCCTC GTGAAGGGCTTCTACCCTTCCGATAT CGCCGTGGAATGGGAGAGCAATGGC CAGCCTGAGAACAACTACAAGACAA CCCCTCCTGTGCTGGACTCCGACGG CTCATTCTTCCTGTACTCCAAGCTGA |
| | Linker | GGGGSGGGGSG GGGSGGGGS (223) | CCGTGGACAAGTCCAGATGGCAGCA GGGCAACGTGTTCTCCTGCTCCGTG ATGCACGAGGCCCTGCACAATCACT |
| | VH | EVQLLESGGGLV QPGGSLRLSCAA SGFTFSSYDMSW VRQAPGKCLEWV SWISYSGGSIYYA DSVKGRFTISRDN SKNTLYLQMNSL RAEDTAVYYCAR DGQRNSMREFDY WGQGTLVTVSS (224) | ACACCCAGAAGTCCCTGTCTCTGAG CCCTGGAAAAGGCGGCGGAGGATCT GGCGGAGGTGGTAGCGGAGGCGGT GGATCTCAGTCTGTTCTGACCCAGC CTCCTTCCGCTTCTGGCACCCCTGG AAGAAGAGTGACCATCTCTTGCTCCG GCTCCTCCTCCAACATCGGCAACAA CTACGTGACCTGGTATCAGCAGCTG CCCGGCACAGCTCCCAAACTGCTGA TCTACGCCGACTCTCACAGACCTTCC GGCGTGCCCGATAGATTCTCCGGCT CTAAGTCTGGCACCTCTGCCAGCCT GGCTATCAGCGGCCTGAGATCTGAG GACGAGGCCGACTACTACTGCGCCA CCTGGGATTATTCCCTGTCCGGCTAC GTGTTCGGCTGCGGCACAAAACTGA CAGTGCTCGGAGGCGGAGGAAGTG GTGGCGGAGGTTCAGGTGGTGGTG GTAGTGGCGGAGGCGGATCAGAAGT TCAGCTGTTGGAGTCAGGTGGCGGC TTGGTGCAACCAGGTGGAAGTCTGA GACTCAGCTGTGCTGCCAGCGGCTT TACCTTCAGCTCCTACGACATGAGCT GGGTTCGACAAGCTCCCGGAAAGTG CTTGGAGTGGGTTTCCTGGATCTCCT ACTCCGGCGGCAGCATCTATTACGC CGACAGCGTGAAAGGCCGGTTTACC ATCTCTCGGGATAACAGCAAGAATAC CCTCTACCTCCAAATGAACTCTCTGA GAGCCGAGGACACTGCTGTGTACTA TTGCGCCAGAGATGGCCAGCGGAAC |

TABLE 18-continued

Bispecific antibody comprising the anti-PD-L1 clone in IgG form
and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | | | TCCATGAGAGAGTTCGACTACTGGG GACAAGGCACCCTGGTCACCGTGTC TAGTTGA (225) |
| Light component | Light chain of B6 | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (34) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (226) |

ABLPNB.05
(bispecific antibody comprising the anti-PD-L1 B6 clone in
IgG form and the anti-4-1BB 41B01.01 clone in scFv form)

| | | | |
|---|---|---|---|
| Heavy component | Heavy chain of B6 | EVQLVESGGGLV QPGGSLRLSCAA SGFTFSSYDMSW VRQAPGKSLEWV ATISDAGGYIYYR DSVKGRFTISRDN AKNSLYLQMNSL RDEDTAVYICARE LPWRYALDYWG QGTTVTVSSASTK GPSVFPLAPSSKS TSGGTAALGCLV KDYFPEPVTVSW NSGALTSGVHTF PAVLQSSGLYSLS SVVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (227) | GAAGTGCAGCTGGTTGAATCTGGCG GCGGATTGGTTCAGCCTGGCGGATC TCTGAGACTGTCTTGTGCCGCCTCC GGCTTCACCTTCTCCAGCTACGATAT GTCCTGGGTCCGACAGGCCCCTGGC AAGTCTTTGGAATGGGTCGCCACCAT CTCTGACGCTGGCGGCTACATCTAC TACCGGGACTCTGTGAAGGGCAGAT TCACCATCAGCCGGGACAACGCCAA GAACTCCCTGTACCTGCAGATGAACA GCCTGCGCGACGAGGATACCGCCGT GTACATCTGTGCTAGAGAGCTGCCTT GGAGATACGCCCTGGATTATTGGGG CCAGGGCACCACAGTGACCGTGTCC TCTGCTTCTACCAAGGGACCCAGCG TGTTCCCTCTGGCTCCTTCCAGCAAG TCTACCTCTGGCGGAACAGCTGCTC TGGGCTGCCTGGTCAAGGACTACTT TCCTGAGCCTGTGACAGTGTCCTGG AACTCTGGCGCTCTGACATCTGGCG TGCACACCTTTCCAGCAGTGCTGCA GTCCTCCGGCCTGTACTCTCTGTCCT CTGTCGTGACCGTGCCTTCCAGCTC TCTGGGAACCCAGACCTACATCTGC AATGTGAACCACAAGCCTTCCAACAC CAAGGTGGACAAGAAGGTGGAACCC AAGTCCTGCGACAAGACCCACACCT GTCCTCCATGTCCTGCTCCAGAACTG CTCGGCGGACCTTCCGTGTTCCTGT TTCCTCCAAAGCCTAAGGACACCCTG ATGATCTCTCGGACCCCTGAAGTGA CCTGCGTGGTGGTGGATGTGTCCCA CGAGGATCCAGAAGTGAAGTTCAATT GCTACGTGGACGGCGTGGAAGTGCA CAATGCCAAGACCAAGCCTAGAGAG GAACAGTACGCCTCCACCTACAGAG TGGTGTCCGTGCTGACTGTGCTGCA |

TABLE 18-continued

Bispecific antibody comprising the anti-PD-L1 clone in IgG form
and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | Linker | GGGGSGGGGSGGGGS (228) | CCAGGATTGGCTGAACGGCAAAGAGTACAAGTGCAAGGTGTCCAACAAGG |
| scFv of 41B0 1.01 | VL | QSVLTQPPSASGTPGRRVTISCSGSSSNIGNNYVTWYQQLPGTAPKLLIYADSHRPSGVPDRFSGSKSGTSASLAISGLRSEDEADYYCATWDYSLSGYVFGCGTKLTVL (229) | CCCTGCCTGCTCCTATCGAAAAGACCATCAGCAAGGCCAAGGGCCAGCCTAGGGAACCCCAGGTTTACACCCTGCCTCCAAGCCGGGAAGAGATGACCAAGAACCAGGTGTCCCTGACCTGCCTCGTGAAGGGCTTCTACCCTTCCGATATCGCCGTGGAATGGGAGAGCAATGGCCAGCCTGAGAACAACTACAAGACAACCCCTCCTGTGCTGGACTCCGACGGCTCATTCTTCCTGTACTCCAAGCTGA |
| | Linker | GGGGSGGGGSGGGSGGGGS (230) | CCGTGGACAAGTCCAGATGGCAGCAGGGCAACGTGTTCTCCTGCTCCGTGATGCACGAGGCCCTGCACAATCACT |
| | VH | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (231) | ACACCCAGAAGTCCCTGTCTCTGAGCCCTGGAAAAGGCGGCGGAGGATCTGGCGGAGGTGGTAGCGGAGGCGGTGGATCTCAGTCTGTTCTGACCCAGCCTCCTTCCGCTTCTGGCACCCCTGGAAGAAGAGTGACCATCTCTTGCTCCGGCTCCTCCTCCAACATCGGCAACAACTACGTGACCTGGTATCAGCAGCTGCCCGGCACAGCTCCCAAACTGCTGATCTACGCCGACTCTCACAGACCTTCCGGCGTGCCCGATAGATTCTCCGGCTCTAAGTCTGGCACCTCTGCCAGCCTGGCTATCAGCGGCCTGAGATCTGAGGACGAGGCCGACTACTACTGCGCCACCTGGGATTATTCCCTGTCCGGCTACGTGTTCGGCTGCGGCACAAAACTGACAGTGCTCGGAGGCGGAGGAAGTGGTGGCGGAGGTTCAGGTGGTGGTGGTAGTGGCGGAGGCGGATCAGAAGTTCAGCTGTTGGAGTCAGGTGGCGGCTTGGTGCAACCAGGTGGAAGTCTGAGACTCAGCTGTGCTGCCAGCGGCTTTACCTTCAGCTCCTACGACATGAGCTGGGTTCGACAAGCTCCCGGAAAGTGCTTGGAGTGGGTTTCCTGGATCTCCTACTCCGGCGGCAGCATCTATTACGCCGACAGCGTGAAAGGCCGGTTTACCATCTCTCGGGATAACAGCAAGAATACCCTCTACCTCCAAATGAACTCTCTGAGAGCCGAGGACACTGCTGTGTACTATTGCGCCAGAGATGccCAGCGGAACTCCATGAGAGAGTTCGACTACTGGGGACAAGGCACCCTGGTCACCGTGTCTAGTTGA (232) |
| Light component | Light chain of B6 | DIQMTQSPSSLSASVGDRVTITCKASQDVTPAVAWYQQKPGKAPKLLIYSTSSRYTGVPSRFSGSGSGTDFTFTISSLQPEDIATYYCQQHYTTPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNREC (36) | GACATCCAGATGACCCAGAGCCCTAGCAGCCTGAGCGCTAGCGTGGGCGACAGGGTGACCATCACCTGCAAGGCCAGCCAGGATGTGACCCCTGCCGTGGCCTGGTACCAGCAGAAGCCCGGCAAGGCCCCCAAGCTGCTGATCTACAGCACCAGCAGCAGGTACACCGGCGTGCCCAGCAGGTTTAGCGGAAGCGGCAGCGGCACCGACTTCACCTTCACCATCAGCAGCCTGCAGCCCGAGGACATCGCCACCTACTACTGCCAGCAGCACTACACCACCCCTCTGACCTTCGGCCAGGGCACCAAGCTGGAGATCAAGAGAACCGTGGCCGCTCCCTCCGTGTTCATCTTCCCACCATCTGACGAGCAGCTGAAGTCCGGCACCGCTTCTGTCGTGTGCCTGCTGAACAACTTCTACCCTCGGGAAGCCAAGGTGCAGTGGAAGGTGGACAATGCCCTGCAGTCCGGCAACTCCCAAGAGTCTGTGACCGAGCAGGACTCCAAGGACAGCACCTACTCCCTGTCCTCTACCCTGACCCTGTCCAAGG |

TABLE 18-continued

Bispecific antibody comprising the anti-PD-L1 clone in IgG form
and the anti-4-1BB clone in scFv form (PD-L1x4-1BB)

| | | | Amino acid sequence (N' → C') (Seq ID No.) | Nucleotide Sequence (5' → 3') (Seq ID No.) |
|---|---|---|---|---|
| | | | | CCGACTACGAGAAGCACAAGGTGTA CGCCTGCGAAGTGACCCACCAGGGA CTGTCTAGCCCCGTGACCAAGTCCTT CAACAGAGGCGAGTGCTGA (233) |

ABLPNB.06
(bispecific antibody comprising the anti-PD-L1 B6 clone in
IgG form and the anti-4-1BB 41B01.02 clone in scFv form)

| Heavy compo nent | Heavy chain of B6 | | EVQLVESGGGLV QPGGSLRLSCAA SGFTFSSYDMSW VRQAPGKSLEWV ATISDAGGYIYYR DSVKGRFTISRDN AKNSLYLQMNSL RDEDTAVYICARE LPWRYALDYWG QGTTVTVSSASTK GPSVFPLAPSSKS TSGGTAALGCLV KDYFPEPVTVSW NSGALTSGVHTF PAVLQSSGLYSLS SVVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (234) | GTGCAGCTGGTTGAATCTGGCGGCG GATTGGTTCAGCCTGGCGGATCTCT GAGACTGTCTTGTGCCGCCTCCGGC TTCACCTTCTCCAGCTACGATATGTC CTGGGTCCGACAGGCCCCTGGCAAG TCTTTGGAATGGGTCGCCACCATCTC TGACGCTGGCGGCTACATCTACTAC CGGGACTCTGTGAAGGGCAGATTCA CCATCAGCCGGGACAACGCCAAGAA CTCCCTGTACCTGCAGATGAACAGC CTGCGCGACGAGGATACCGCCGTGT ACATCTGTGCTAGAGAGCTGCCTTG GAGATACGCCCTGGATTATTGGGGC CAGGGCACCACAGTGACCGTGTCCT CTGCTTCTACCAAGGGACCCAGCGT GTTCCCTCTGGCTCCTTCCAGCAAGT CTACCTCTGGCGGAACAGCTGCTCT GGGCTGCCTGGTCAAGGACTACTTT CCTGAGCCTGTGACAGTGTCCTGGA ACTCTGGCGCTCTGACATCTGGCGT GCACACCTTTCCAGCAGTGCTGCAG TCCTCCGGCCTGTACTCTCTGTCCTC TGTCGTGACCGTGCCTTCCAGCTCT CTGGGAACCCAGACCTACATCTGCA ATGTGAACCACAAGCCTTCCAACACC AAGGTGGACAAGAAGGTGGAACCCA AGTCCTGCGACAAGACCCACACCTG TCCTCCATGTCCTGCTCCAGAACTGC TCGGCGGACCTTCCGTGTTCCTGTTT CCTCCAAAGCCTAAGGACACCCTGA TGATCTCTCGGACCCCTGAAGTGAC CTGCGTGGTGGTGGATGTGTCCCAC GAGGATCCAGAAGTGAAGTTCAATTG GTACGTGGACGGCGTGGAAGTGCAC AATGCCAAGACCAAGCCTAGAGAGG AACAGTACGCCTCCACCTACAGAGT GGTGTCCGTGCTGACTGTGCTGCAC |
| | Linker | | GGGGSGGGGSG GGGS (235) | CAGGATTGGCTGAACGGCAAAGAGT ACAAGTGCAAGGTGTCCAACAAGGC |
| | scFv of 41B0 1.02 | VL | QSVLTQPPSASG TPGRRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (236) | CCTGCCTGCTCCTATCGAAAAGACCA TCAGCAAGGCCAAGGGCCAGCCTAG GGAACCCCAGGTTTACACCCTGCCT CCAAGCCGGGAAGAGATGACCAAGA ACCAGGTGTCCCTGACCTGCCTCGT GAAGGGCTTCTACCCTTCCGATATCG CCGTGGAATGGGAGAGCAATGGCCA GCCTGAGAACAACTACAAGACAACC CCTCCTGTGCTGGACTCCGACGGCT CATTCTTCCTGTACTCCAAGCTGACC |
| | | Linker | GGGGSGGGGSG GGGSGGGGS (237) | GTGGACAAGTCCAGATGGCAGCAGG GCAACGTGTTCTCCTGCTCCGTGAT GCACGAGGCCCTGCACAATCACTAC |
| | | VH | EVQLLESGGGLV QPGGSLRLSCAA SGFTFSSYDMSW VRQAPGKCLEWV SWISYSGGSIYYA DSVKGRFTISRDN SKNTLYLQMNSL RAEDTAVYYCAR DAQRQSMREFDY WGQGTLVTVSS (238) | ACCCAGAAGTCCCTGTCTCTGAGCC CTGGAAAAGGCGGCGGAGGATCTGG CGGAGGTGGTAGCGGAGGCGGTGG ATCTCAGTCTGTTCTGACCCAGCCTC CTTCCGCTTCTGGCACCCCTGGAAG AAGAGTGACCATCTCTTGCTCCGGT CCTCCTCCAACATCGGCAACAACTAC GTGACCTGGTATCAGCAGCTGCCCG GCACAGCTCCCAAACTGCTGATCTAC GCCGACTCTCACAGACCTTCCGGCG TGCCCGATAGATTCTCCGGCTCTAAG |

TABLE 18-continued

Bispecific antibody comprising the anti-PD-L1 clone in IgG form
and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | | | TCTGGCACCTCTGCCAGCCTGGCTA TCAGCGGCCTGAGATCTGAGGACGA GGCCGACTACTACTGCGCCACCTGG GATTATTCCCTGTCCGGCTACGTGTT CGGCTGCGGCACAAAACTGACAGTG CTCGGAGGCGGAGGAAGTGGTGGC GGAGGTTCAGGTGGTGGTGGTAGTG GCGGAGGCGGATCAGAAGTTCAGCT GTTGGAGTCAGGTGGCGGCTTGGTG CAACCAGGTGGAAGTCTGAGACTCA GCTGTGCTGCCAGCGGCTTTACCTT CAGCTCCTACGACATGAGCTGGGTT CGACAAGCTCCCGGAAAGTGCTTGG AGTGGGTTTCCTGGATCTCCTACTCC GGCGGCAGCATCTATTACGCCGACA GCGTGAAAGGCCGGTTTACCATCTC TCGGGATAACAGCAAGAATACCCTCT ACCTCCAAATGAACTCTCTGAGAGCC GAGGACACTGCTGTGTACTATTGCG CCAGAGATGccCAGCGGCAATCCATG AGAGAGTTCGACTACTGGGGACAAG GCACCCTGGTCACCGTGTCTAGTTG A (239) |
| Light compo nent | Light chain of B6 | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (38) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (240) |

ABLPNB.07
(bispecific antibody comprising the anti-PD-L1 B6 clone in
IgG form and the anti-4-1BB 41B01.03 clone in scFv form)

| | | | |
|---|---|---|---|
| Heavy compo nent | Heavy chain of B6 | EVQLVESGGGLV QPGGSLRLSCAA SGFTFSSYDMSW VRQAPGKSLEWV ATISDAGGYIYYR DSVKGRFTISRDN AKNSLYLQMNSL RDEDTAVYICARE LPWRYALDYWG QGTTVTVSSASTK GPSVFPLAPSSKS TSGGTAALGCLV KDYFPEPVTVSW NSGALTSGVHTF PAVLQSSGLYSLS SWVTVPSSSLGTQ TYICNVNHKPSNT | GAAGTGCAGCTGGTTGAATCTGGCG GCGGATTGGTTCAGCCTGGCGGATC TCTGAGACTGTCTTGTGCCGCCTCC GGCTTCACCTTCTCCAGCTACGATAT GTCCTGGGTCCGACAGGCCCCTGGC AAGTCTTTGGAATGGGTCGCCACCAT CTCTGACGCTGGCGGCTACATCTAC TACCGGGACTCTGTGAAGGGCAGAT TCACCATCAGCCGGGACAACGCCAA GAACTCCCTGTACCTGCAGATGAACA GCCTGCGCGACGAGGATACCGCCGT GTACATCTGTGCTAGAGAGCTGCCTT GGAGATACGCCCTGGATTATTGGGG CCAGGGCACCACAGTGACCGTGTCC TCTGCTTCTACCAAGGGACCCAGCG TGTTCCCTCTGGCTCCTTCCAGCAAG TCTACCTCTGGCGGAACAGCTGCTC |

TABLE 18-continued

Bispecific antibody comprising the anti-PD-L1 clone in IgG form and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| | | KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (241) | TGGGCTGCCTGGTCAAGGACTACTT TCCTGAGCCTGTGACAGTGTCCTGG AACTCTGGCGCTCTGACATCTGGCG TGCACACCTTTCCAGCAGTGCTGCA GTCCTCCGGCCTGTACTCTCTGTCCT CTGTCGTGACCGTGCCTTCCAGCTC TCTGGGAACCCAGACCTACATCTGC AATGTGAACCACAAGCCTTCCAACAC CAAGGTGGACAAGAAGGTGGAACCC AAGTCCTGCGACAAGACCCACACCT GTCCTCCATGTCCTGCTCCAGAACTG CTCGGCGGACCTTCCGTGTTCCTGT TTCCTCCAAAGCCTAAGGACACCCTG ATGATCTCTCGGACCCCTGAAGTGA CCTGCGTGGTGGTGGATGTGTCCCA CGAGGATCCAGAAGTGAAGTTCAATT GGTACGTGGACGGCGTGGAAGTGCA CAATGCCAAGACCAAGCCTAGAGAG GAACAGTACGCCTCCACCTACAGAG TGGTGTCCGTGCTGACTGTGCTGCA |
| Linker | | GGGGSGGGGSG GGGS (242) | CCAGGATTGGCTGAACGGCAAAGAG TACAAGTGCAAGGTGTCCAACAAGG |
| | scFv VL of 41B0 1.03 | QSVLTQPPSASG TPGQRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (243) | CCCTGCCTGCTCCTATCGAAAAGAC CATCAGCAAGGCCAAGGGCCAGCCT AGGGAACCCCAGGTTTACACCCTGC CTCCAAGCCGGGAAGAGATGACCAA GAACCAGGTGTCCCTGACCTGCCTC GTGAAGGGCTTCTACCCTTCCGATAT CGCCGTGGAATGGGAGAGCAATGGC CAGCCTGAGAACAACTACAAGACAA CCCCTCCTGTGCTGGACTCCGACGG CTCATTCTTCCTGTACTCCAAGCTGA |
| | Linker | GGGGSGGGGSG GGGSGGGGS (244) | CCGTGGACAAGTCCAGATGGCAGCA GGGCAACGTGTTCTCCTGCTCCGTG ATGCACGAGGCCCTGCACAATCACT |
| | VH | EVQLLESGGGLV QPGGSLRLSCAA SGFTFSSYDMSW VRQAPGKCLEWV SWISYSGGSIYYA DSVKGRFTISRDN SKNTLYLQMNSL RAEDTAVYYCAR DAQRNSMREFDY WGQGTLVTVSS (245) | ACACCCAGAAGTCCCTGTCTCTGAG CCCTGGAAAAGGCCGGAGGATCT GGCGGAGGTGGTAGCGGAGGCGGT GGATCTCAGTCTGTTCTGACCCAGC CTCCTTCCGCTTCTGGCACCCCTGG AcAGAGAGTGACCATCTCTTGCTCCG GCTCCTCCTCCAACATCGGCAACAA CTACGTGACCTGGTATCAGCAGCTG CCCGGCACAGCTCCCAAACTGCTGA TCTACGCCGACTCTCACAGACCTTCC GGCGTGCCCGATAGATTCTCCGGCT CTAAGTCTGGCACCTCTGCCAGCCT GGCTATCAGCGGCCTGAGATCTGAG GACGAGGCCGACTACTACTGCGCCA CCTGGGATTATTCCCTGTCCGGCTAC GTGTTCGGCTGCGGCACAAAACTGA CAGTGCTCGGAGGCGGAGGAAGTG GTGGCGGAGGTTCAGGTGGTGGTG GTAGTGGCGGAGGCGGATCAGAAGT TCAGCTGTTGGAGTCAGGTGGCGGC TTGGTGCAACCAGGTGGAAGTCTGA GACTCAGCTGTGCTGCCAGCGGCTT TACCTTCAGCTCCTACGACATGAGCT GGGTTCGACAAGCTCCCGGAAAGTG CTTGGAGTGGGTTTCCTGGATCTCCT ACTCCGGCGGCAGCATCTATTACGC CGACAGCGTGAAAGGCCGGTTTACC ATCTCTCGGGATAACAGCAAGAATAC CCTCTACCTCCAAATGAACTCTCTGA GAGCCGAGGACACTGCTGTGTACTA TTGCGCCAGAGATGcCAGCGGAACT CCATGAGAGAGTTCGACTACTGGGG ACAAGGCACCCTGGTCACCGTGTCT AGTTGA (246) |

TABLE 18-continued

Bispecific antibody comprising the anti-PD-L1 clone in IgG form
and the anti-4-1BB clone in scFv form (PD-L1x4-1BB)

| | | Amino acid sequence (N' → C') (Seq ID No.) | Nucleotide Sequence (5' → 3') (Seq ID No.) |
|---|---|---|---|
| Light component | Light chain of B6 | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (40) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (247) |

ABLPNB.08
(bispecific antibody comprising the anti-PD-L1 B6 clone in
IgG form and the anti-4-1BB 41B01.04 clone in scFv form)

| | | | |
|---|---|---|---|
| Heavy component | Heavy chain of B6 | EVQLVESGGGLV QPGGSLRLSCAA SGFTFSSYDMSW VRQAPGKSLEWV ATISDAGGYIYYR DSVKGRFTISRDN AKNSLYLQMNSL RDEDTAVYICARE LPWRYALDYWG QGTTVTVSSASTK GPSVFPLAPSSKS TSGGTAALGCLV KDYFPEPVTVSW NSGALTSGVHTF PAVLQSSGLYSLS SWVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (248) | GAAGTGCAGCTGGTTGAATCTGGCG GCGGATTGGTTCAGCCTGGCGGATC TCTGAGACTGTCTTGTGCCGCCTCC GGCTTCACCTTCTCCAGCTACGATAT GTCCTGGGTCCGACAGGCCCCTGGC AAGTCTTTGGAATGGGTCGCCACCAT CTCTGACGCTGGCGGCTACATCTAC TACCGGGACTCTGTGAAGGGCAGAT TCACCATCAGCCGGGACAACGCCAA GAACTCCCTGTACCTGCAGATGAACA GCCTGCGCGACGAGGATACCGCCGT GTACATCTGTGCTAGAGAGCTGCCTT GGAGATACGCCCTGGATTATTGGGG CCAGGGCACCACAGTGACCGTGTCC TCTGCTTCTACCAAGGGACCCAGCG TGTTCCCTCTGGCTCCTTCCAGCAAG TCTACCTCTGGCGGAACAGCTGCTC TGGGCTGCCTGGTCAAGGACTACTT TCCTGAGCCTGTGACAGTGTCCTGG AACTCTGGCGCTCTGACATCTGGCG TGCACACCTTTCCAGCAGTGCTGCA GTCCTCCGGCCTGTACTCTCTGTCCT CTGTCGTGACCGTGCCTTCCAGCTC TCTGGGAACCCAGACCTACATCTGC AATGTGAACCACAAGCCTTCCAACAC CAAGGTGGACAAGAAGGTGGAACCC AAGTCCTGCGACAAGACCCACACCT GTCCTCCATGTCCTGCTCCAGAACTG CTCGGCGGACCTTCCGTGTTCCTGT TTCCTCCAAAGCCTAAGGACACCCTG ATGATCTCTCGGACCCCTGAAGTGA CCTGCGTGGTGGTGGATGTGTCCCA CGAGGATCCAGAAGTGAAGTTCAATT GGTACGTGGACGGCGTGGAAGTGCA CAATGCCAAGACCAAGCCTAGAGAG GAACAGTACGCCTCCACCTACAGAG TGGTGTCCGTGCTGACTGTGCTGCA |

TABLE 18-continued

Bispecific antibody comprising the anti-PD-L1 clone in IgG form and the anti-4-1BB clone in scFv form (PD-L1x4-1BB)

| | | | Amino acid sequence (N' → C') (Seq ID No.) | Nucleotide Sequence (5' → 3') (Seq ID No.) |
|---|---|---|---|---|
| | Linker | | GGGGSGGGGSG GGGS (249) | CCAGGATTGGCTGAACGGCAAAGAG TACAAGTGCAAGGTGTCCAACAAGG |
| | scFv of 41B0 1.04 | VL | QSVLTQPPSASG TPGQRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (250) | CCCTGCCTGCTCCTATCGAAAAGAC CATCAGCAAGGCCAAGGGCCAGCCT AGGGAACCCCAGGTTTACACCCTGC CTCCAAGCGGGAAGAGATGACCAA GAACCAGGTGTCCCTGACCTGCCTC GTGAAGGGCTTCTACCCTTCCGATAT CGCCGTGGAATGGGAGAGCAATGGC CAGCCTGAGAACAACTACAAGACAA CCCCTCCTGTGCTGGACTCCGACGG CTCATTCTTCCTGTACTCCAAGCTGA |
| | | Linker | GGGGSGGGGSG GGGSGGGGS (251) | CCGTGGACAAGTCCAGATGGCAGCA GGGCAACGTGTTCTCCTGCTCCGTG ATGCACGAGGCCCTGCACAATCACT |
| | | VH | EVQLLESGGGLV QPGGSLRLSCAA SGFTFSSYDMSW VRQAPGKCLEWV SWISYSGGSIYYA DSVKGRFTISRDN SKNTLYLQMNSL RAEDTAVYYCAR DAQRQSMREFDY WGQGTLVTVSS (252) | ACACCCAGAAGTCCCTGTCTCTGAG CCCTGGAAAAGGCGGCGGAGGATCT GGCGGAGGTGGTAGCGGAGGCGGT GGATCTCAGTCTGTTCTGACCCAGC CTCCTTCCGCTTCTGGCACCCCTGG AcAGAGAGTGACCATCTCTTGCTCCG GCTCCTCCTCCAACATCGGCAACAA CTACGTGACCTGGTATCAGCAGCTG CCCGGCACAGCTCCCAAACTGCTGA TCTACGCCGACTCTCACAGACCTTCC GGCGTGCCCGATAGATTCTCCGGCT CTAAGTCTGGCACCTCTGCCAGCCT GGCTATCAGCGGCCTGAGATCTGAG GACGAGGCCGACTACTACTGCGCCA CCTGGGATTATTCCCTGTCCGGCTAC GTGTTCGGCTGCGGCACAAAACTGA CAGTGCTCGGAGGCGGAGGAAGTG GTGGCGGAGGTTCAGGTGGTGGTG GTAGTGGCGGAGGCGGATCAGAAGT TCAGCTGTTGGAGTCAGGTGGCGGC TTGGTGCAACCAGGTGGAAGTCTGA GACTCAGCTGTGCTGCCAGCGGCTT TACCTTCAGCTCCTACGACATGAGCT GGGTTCGACAAGCTCCCGGAAAGTG CTTGGAGTGGGTTTCCTGGATCTCCT ACTCCGGCGGCAGCATCTATTACGC CGACAGCGTGAAAGGCCGGTTTACC ATCTCTCGGGATAACAGCAAGAATAC CCTCTACCTCCAAATGAACTCTCTGA GAGCCGAGGACACTGCTGTGTACTA TTGCGCCAGAGATGccCAGCGGCAAT CCATGAGAGAGTTCGACTACTGGGG ACAAGGCACCCTGGTCACCGTGTCT AGTTGA (253) |
| Light component | Light chain of B6 | | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (42) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG |

TABLE 18-continued

Bispecific antibody comprising the anti-PD-L1 clone in IgG form
and the anti-4-1BB clone in scFv form (PD-L1x4-1BB)

| | | | Amino acid sequence (N' → C') (Seq ID No.) | Nucleotide Sequence (5' → 3') (Seq ID No.) |
|---|---|---|---|---|
| | | | | CCGACTACGAGAAGCACAAGGTGTA CGCCTGCGAAGTGACCCACCAGGGA CTGTCTAGCCCCGTGACCAAGTCCTT CAACAGAGGCGAGTGCTGA (254) |

ABLPNB.09
(bispecific antibody comprising the anti-PD-L1 B6 clone in
IgG form and the anti-4-1BB 41B02 clone in scFv form)

| Heavy component | Heavy chain of B6 | | EVQLVESGGGLV QPGGSLRLSCAA SGFTFSSYDMSW VRQAPGKSLEWV ATISDAGGYIYYR DSVKGRFTISRDN AKNSLYLQMNSL RDEDTAVYICARE LPWRYALDYWG QGTTVTVSSASTK GPSVFPLAPSSKS TSGGTAALGCLV KDYFPEPVTVSW NSGALTSGVHTF PAVLQSSGLYSLS SVVTVPSSSLGTQ TYICNVNHKPSNT KVDKKVEPKSCD KTHTCPPCPAPEL LGGPSVFLFPPKP KDTLMISRTPEVT CVVVDVSHEDPE VKFNWYVDGVEV HNAKTKPREEQY ASTYRVVSVLTVL HQDWLNGKEYKC KVSNKALPAPIEK TISKAKGQPREPQ VYTLPPSREEMTK NQVSLTCLVKGFY PSDIAVEWESNG QPENNYKTTPPVL DSDGSFFLYSKLT VDKSRWQQGNV FSCSVMHEALHN HYTQKSLSLSPGK (255) | GAAGTGCAGCTGGTTGAATCTGGCG GCGGATTGGTTCAGCCTGGCGGATC TCTGAGACTGTCTTGTGCCGCCTCC GGCTTCACCTTCTCCAGCTACGATAT GTCCTGGGTCCGACAGGCCCCTGGC AAGTCTTTGGAATGGGTCGCCACCAT CTCTGACGCTGGCGGCTACATCTAC TACCGGGACTCTGTGAAGGGCAGAT TCACCATCAGCCGGGACAACGCCAA GAACTCCCTGTACCTGCAGATGAACA GCCTGCGCGACGAGGATACCGCCGT GTACATCTGTGCTAGAGAGCTGCCTT GGAGATACGCCCTGGATTATTGGGG CCAGGGCACCACAGTGACCGTGTCC TCTGCTTCTACCAAGGGACCCAGCG TGTTCCCTCTGGCTCCTTCCAGCAAG TCTACCTCTGGCGGAACAGCTGCTC TGGGCTGCCTGGTCAAGGACTACTT TCCTGAGCCTGTGACAGTGTCCTGG AACTCTGGCGCTCTGACATCTGGCG TGCACACCTTTCCAGCAGTGCTGCA GTCCTCCGGCCTGTACTCTCTGTCCT CTGTCGTGACCGTGCCTTCCAGCTC TCTGGGCACCCAGACCTACATCTGC AACGTGAACCACAAGCCCTCCAACA CCAAGGTGGACAAGAAGGTGGAACC CAAGTCCTGCGACAAGACCCACACC TGTCCTCCATGTCCTGCTCCAGAACT GCTGGGCGGACCCTCCGTGTTCCTG TTCCCTCCAAAGCCTAAGGACACCCT GATGATCTCCCGGACCCCTGAAGTG ACCTGCGTGGTGGTGGATGTGTCCC ACGAGGATCCCGAAGTGAAGTTCAA TTGGTACGTGGACGGCGTGGAAGTG CACAACGCCAAGACCAAGCCTAGAG AGGAACAGTACgccTCCACCTACCGG GTGGTGTCCGTGCTGACCGTTCTGC |
| | | Linker | GGGGGGGGSG GGGS (256) | ACCAGGATTGGCTGAACGGCAAAGA GTACAAGTGCAAGGTGTCCAACAAG |
| | scFv of 41B0 2 | VL | QSVLTQPPSASG TPGRRVTISCSGS SSNIGNNYVTWY QQLPGTAPKLLIY ADSHRPSGVPDR FSGSKSGTSASLA ISGLRSEDEADYY CATWDYSLSGYV FGCGTKLTVL (257) | GCCCTGCCTGCCCCTATCGAAAAGA CCATCTCTAAGGCCAAGGGCCAGCC CCGGGAACCTCAAGTGTACACCTTG CCTCCCAGCCGGGAAGAGATGACCA AGAACCAGGTGTCCCTGACCTGCCT GGTTAAGGGCTTCTACCCCTCCGATA TCGCCGTGGAATGGGAGTCTAACGG CCAGCCCGAGAACAACTACAAGACC ACCCCTCCTGTGCTGGACTCCGACG GCTCATTCTTCCTGTACTCCAAGCTG ACCGTGGACAAGTCTCGGTGGCAGC |
| | | Linker | GGGGSGGGGSG GGGSGGGGS (258) | AGGGCAACGTGTTCTCCTGCTCTGT GATGCACGAGGCCCTGCACAACCAC TACACCCAGAAGTCCCTGTCCCTGTC |
| | | VH | EVQLLESGGGLV QPGGSLRLSCAA SGFTFSGYDMSW VRQAPGKCLEWV SVIYPDDGNTYYA DSVKGRFTISRDN SKNTLYLQMNSL | TCCCGGCAAAGGTGGGGGGGATCT GGTGGTGGTGGATCAGGGGGTGGG GGGTCTCAAAGCGTACTCACCCAAC CTCCATCTGCATCCGGTACACCTGGT CGGCGAGTAACCATCTCCTGCTCTG GGAGCTCTTCTAATATTGGTAACAAC TATGTCACCTGGTATCAGCAGTTGCC |

TABLE 18-continued

Bispecific antibody comprising the anti-PD-L1 clone in IgG form
and the anti-4-1BB clone in scFv form (PD-L1x4-1BB)

|  |  | Amino acid sequence (N' → C') (Seq ID No.) | Nucleotide Sequence (5' → 3') (Seq ID No.) |
|---|---|---|---|
|  |  | RAEDAAVYYCAK HGGQKPTTKSSS AYGMDGWGQGT LVTVSS (259) | TGGGACAGCACCCAAACTTCTTATAT ATGCCGATAGCCATCGGCCTTCCGG CGTACCCGATCGCTTCTCCGGGTCA AAATCTGGAACATCTGCCTCACTCGC AATTAGTGGATTGCGATCTGAGGATG AAGCAGATTATTATTGCGCTACCTGG GATTATTCACTTTCTGGCTACGTCTTT GGTtgtGGAACAAAACTTACCGTGTTG GGCGGCGGAGGAAGCGGAGGCGGC GGTTCTGGTGGTGGCGGTAGCGGAG GTGGTGGATCTGAGGTTCAACTGTT GGAGTCAGGTGGCGGACTTGTCCAG CCTGGCGGGTCTCTGAGGCTGAGTT GCGCTGCTTCTGGGTTTACTTTTTCA GGATATGACATGAGTTGGGTACGTC AGGCTCCAGGTAAGtgcCTCGAATGG GTCTCCGTTATCTATCCCGATGATGG AAATACTTACTACGCTGACAGTGTGA AAGGCAGGTTCACAATCAGTAGGGA CAATTCTAAAAATACACTCTACCTCC AGATGAACTCACTTCGAGCCGAGGA CGCCGCCGTATATTACTGTGCCAAAC ACGGCGGGCAAAAACCCACTACTAA ATCCAGTAGTGCTTACGGGATGGAT GGCTGGGGACAGGGGACATTGGTCA CTGTATCTTCCtga (260) |
| Light component | Light chain of B6 | DIQMTQSPSSLSA SVGDRVTITCKAS QDVTPAVAWYQ QKPGKAPKLLIYS TSSRYTGVPSRF SGSGSGTDFTFTI SSLQPEDIATYYC QQHYTTPLTFGQ GTKLEIKRTVAAP SVFIFPPSDEQLK SGTASVVCLLNNF YPREAKVQWKVD NALQSGNSQESV TEQDSKDSTYSLS STLTLSKADYEKH KVYACEVTHQGL SSPVTKSFNRGE C (44) | GACATCCAGATGACCCAGAGCCCTA GCAGCCTGAGCGCTAGCGTGGGCG ACAGGGTGACCATCACCTGCAAGGC CAGCCAGGATGTGACCCCTGCCGTG GCCTGGTACCAGCAGAAGCCCGGCA AGGCCCCCAAGCTGCTGATCTACAG CACCAGCAGCAGGTACACCGGCGTG CCCAGCAGGTTTAGCGGAAGCGGCA GCGGCACCGACTTCACCTTCACCAT CAGCAGCCTGCAGCCCGAGGACATC GCCACCTACTACTGCCAGCAGCACT ACACCACCCCTCTGACCTTCGGCCA GGGCACCAAGCTGGAGATCAAGAGA ACCGTGGCCGCTCCCTCCGTGTTCA TCTTCCCACCATCTGACGAGCAGCT GAAGTCCGGCACCGCTTCTGTCGTG TGCCTGCTGAACAACTTCTACCCTCG GGAAGCCAAGGTGCAGTGGAAGGTG GACAATGCCCTGCAGTCCGGCAACT CCCAAGAGTCTGTGACCGAGCAGGA CTCCAAGGACAGCACCTACTCCCTG TCCTCTACCCTGACCCTGTCCAAGG CCGACTACGAGAAGCACAAGGTGTA CGCCTGCGAAGTGACCCACCAGGGA CTGTCTAGCCCCGTGACCAAGTCCTT CAACAGAGGCGAGTGCTGA (261) |

The constructed vectors were transiently expressed in ExpiCHO-S™ cells (Thermo Fisher, A29127) using (ExpiFectamine™ CHO Kit, Thermo, A29129), cultured in ExpiCHO™ Expression medium (Thermo, A29100-01) under the conditions of 30 to 37° C. for 7 to 15 days in a $CO_2$ incubator equipped with rotating shaker. Plasmid DNA (250 μg) and ExpiFectamin CHO Reagent (800 μL) were mixed with Opti-MEM® I medium (20 mL final volume) and allowed to stand at room temperature for 5 min. The mixed solution was added to $6 \times 10^6$ ExpiCHO cells cultured in ExpiCHO Expression Medium and gently mixed in a shaker incubator at 37° C. with a humidified atmosphere of 8% CO2 in air. At 18 hours post-transfection, 1.5 mL of ExpiFectamin CHO Transfection Enhancer 1 and 60 mL of ExpiFectamin CHO Transfection Feed were added to each flask.

Each BsAb was purified from the cell culture supernatant by recombinant Protein A affinity chromatography (Hitrap Mabselect Sure, GE Healthcare, 28-4082-55) and gel filtration chromatography with a HiLoad 26/200 Superdex200 prep grade column (GE Healthcare, 28-9893-36). SDS-PAGE (NuPage 4-12% Bis-Tris gel, NP0321) and size exclusion HPLC (Agilent, 1200 series) analysis with SE-HPLC column (SWXL SE-HPLC column, TOSOH, G3000SWXL) were performed to detect and confirm the size and purity of each BsAb. Purified proteins were concentrated in PBS by ultrafiltration using a Amicon Ultra 15 30K device (Merck, UFC903096), and protein concentrations were estimated using a nanodrop (Thermo, Nanodrop One). When a two-vector system is applied, the ratio between light to heavy chain could be 1:1 to 1:3 by weight. Alternatively, a one-vector system that contains both chains in one single vector can also be used.

The prepared anti-PD-L1/anti-4-1BB bispecific antibodies are named as H12×41B01 (ABLPNB.01), H12×41B01.03 (ABLPNB.02), H12×41B02 (ABLPNB.03), B6×41B01 (ABLPNB.04), B6×41B01.01 (ABLPNB.05), B6×41B01.01 (ABLPNB.06), B6×41B01.03 (ABLPNB.07), B6×41B01.04 (ABLPNB.08), and B6×41B02 (ABLPNB.09), respectively, wherein the former refers to the clone in the IgG form and the latter refers to the clone in the scFv form.

Figure 7A:
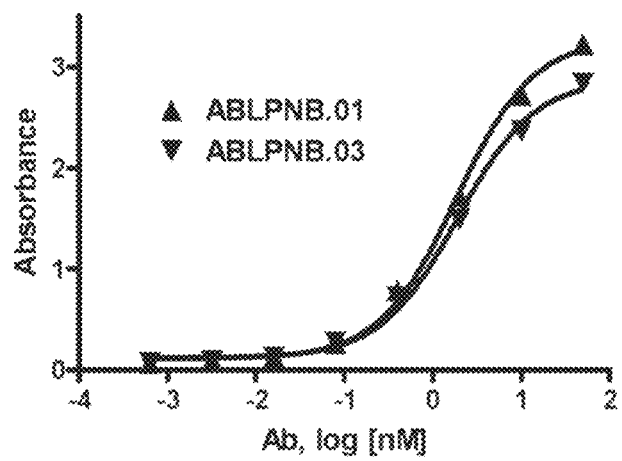
FIGS. 7A-7B show graphs illustrating the binding of the anti-PD-L1/anti-4-1BB bispecific antibody according to an embodiment to human PD-L1 and human 4-1BB, measured by DACE (dual antigen capture ELISA).
Figure 7B:
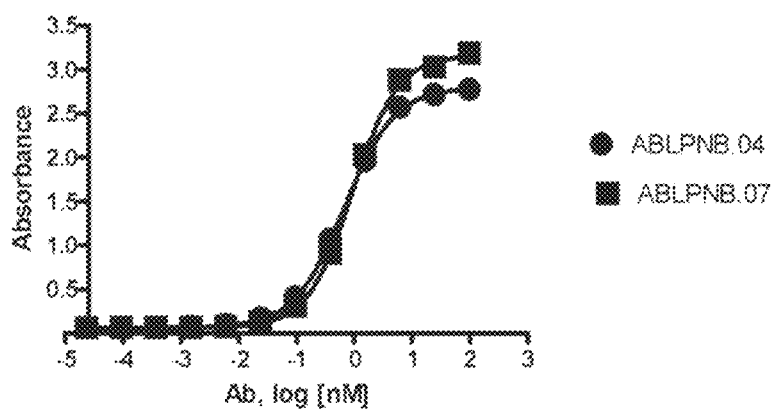

Example 4. Characterization of Bispecific Antibodies PD-L1×4-1BB 4.1. Binding of the Bispecific Antibodies To evaluate the binding activity to PD-L1 and 4-1BB of the bispecific antibodies prepared in Example 3, the BsAbs (ABLPNB.01, ABLPNB.03, ABLPNB.04 and ABLPNB.07), were subjected to DACE (Dual antigen captured ELISA) test. Briefly, microtiter plates were coated with 100 ng/well of human PD-L1-Fc protein (Sinobio, 10084-H02H) in PBS at 4° C. overnight, then blocked with 100 μl/well of 1% BSA for 2 hours at 37° C. Three-fold dilutions of each of the BsAbs starting from 100 nM were added to each well and incubated for 2 hours at 37° C. The plates were washed with PBS/Tween and then incubate with 50 ng/well of human 4-1BB-His protein (Sinobio, 16498-H08H) in 1% BSA for 1 hour at 37° C. The plates were washed with PBS/Tween and then incubate with Anti-His HRP (Roche, Cat: 11965085001) for 1 hour at 37° C. After washing, the plates were developed with TMB substrate and analyzed by spectrophotometer at OD 450-650 nm. The results are shown in FIGS. 7A and 7B. As shown in FIGS. 7A and 7B, all the BsAbs tested can bind to both of human PD-L1 and human 4-1BB proteins with high activities.

4.2 Serum Stability of Bispecific Antibody

Figure 8:
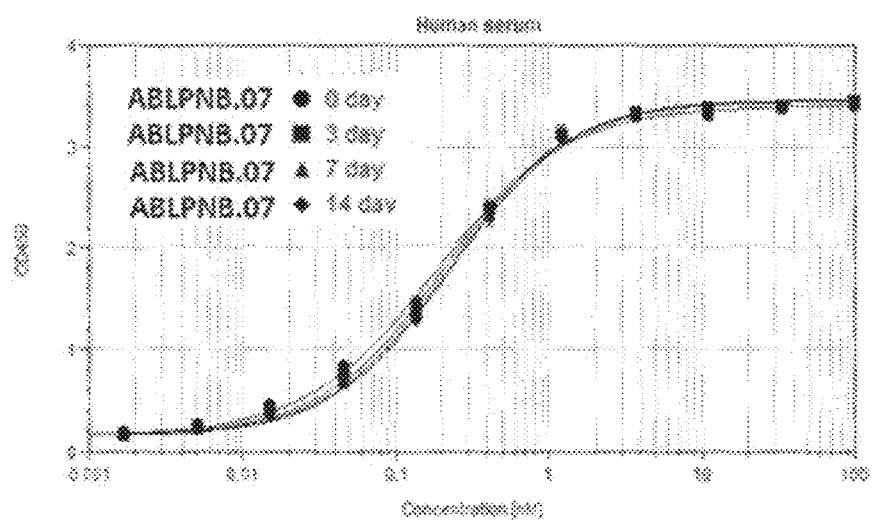
FIG. 8 show the anti-PD-L1/anti-4-1BB bispecific antibodies according to an embodiment are stable in human serum.

To evaluate the serum stability to PD-L1 and 4-1BB of the BsAb (ABLPNB.05, ABLPNB.06, ABLPNB.07 and ABLPNB.08), BsAb was incubated in human serum for 3, 7, 14 days at 37° C. Binding activity was analyzed to DACE (Dual antigen captured ELISA) test. Briefly, microtiter plates were coated with 100 ng/well of human PD-L1-Fc protein (Sinobio, 10084-H02H) in PBS at 4° C. overnight, then blocked with 100 μl/well of 1% BSA for 2 hours at 37° C. Three-fold dilutions of each of the BsAbs starting from 100 nM were added to each well and incubated for 2 hours at 37° C. The plates were washed with PBS/Tween and then incubate with 50 ng/well of human 4-1BB-His protein (Sinobio, 16498-H08H) in 1% BSA for 1 hour at 37° C. The plates were washed with PBS/Tween and then incubate with Anti-His HRP (Roche, Cat: 11965085001) for 1 hour at 37° C. After washing, the plates were developed with TMB substrate and analyzed by spectrophotometer at OD 450-650 nm. The binding activity of each of the BsAbs (ABLPNB.05 to ABLPNB.08) to both antigens was comparable to each sample. It means that BsAbs are stable in human serum for 2 weeks at 37° C. The representative date is as shown in FIG. 8.

4.3. Developability of Bispecific Antibodies

The developability regarding the physicochemical properties to PD-L1 and 4-1BB of the BsAbs (ABLPNB.02 and ABLPNB.07) was assessed. The quality attributes for the BsAbs were evaluated by several analytical methods. Briefly, the purity was measured by Size exclusion-high performance liquid chromatography (SE-HPCL) and both of the BsAb showed the high purity over 99%. The thermal stability by Protein thermal shift (PTS) with fluorescence labeled Real time-polymerase chain reaction (RT-PCR) was analyzed. Their melting temperature was observed over 67° C. which indicated that the test articles have stable structural integrity. To evaluate solubility of the molecules, the proteins were concentrated to 20 mg/mL using ultrafiltration (Amicon Ultra-15 spin concentrator). As a result, the visible particles were not observed by visual inspection and no increment of aggregates was confirmed by SE-HPLC. The Isoelectric point (pI) of ABLPNB.02 and ABLPNB.07 measured by capillary isoelectric focusing (cIEF) were 8.26 and 8.35, respectively. This pI range is appropriate to proceed downstream process and formulation development. Overall, as shown in Table 19. It showed that the tested BsAbs (ABLPNB.02 and ABLPNB.07) have proper physicochemical properties for the successful development.

TABLE 19

| Content | Method | ABLPNB.07 | ABLPNB.02 |
|---|---|---|---|
| Purity | SEC | 99.6 | 99.8 |
| Thermal Stability | PTS | 67.0 76.8 | 67.1 80.5 |
| Solubility | Visual inspection | Easy to concentrate upto 20 mg/mL, clear | Easy to concentrate upto 20 mg/mL, clear |
| pI | cIEF | 8.26 | 8.35 |

4.4. Activity of the Bispecific Antibodies to Promote 4-1BB Signal

Figure 9A:
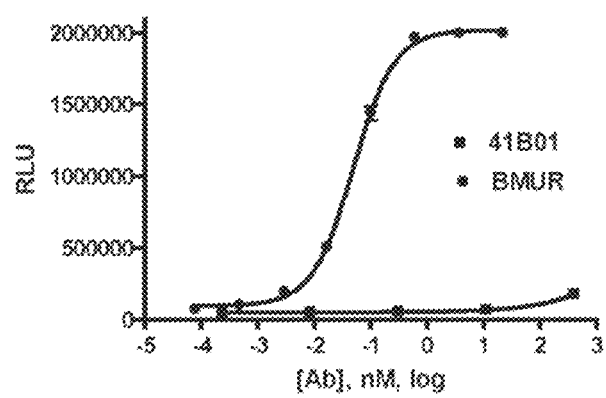
FIGS. 9A-9F show that bispecific antibodies PD-L1×4-1BB according to embodiment activate 4-1BB signaling depending on PD-L1 expression on target cells.
Figure 9B:
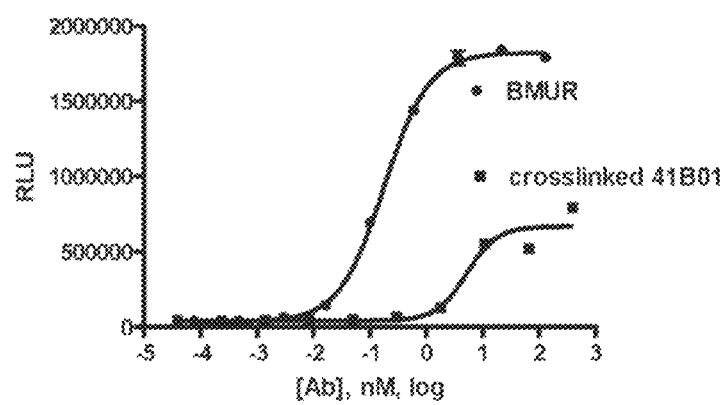
Figure 9C:
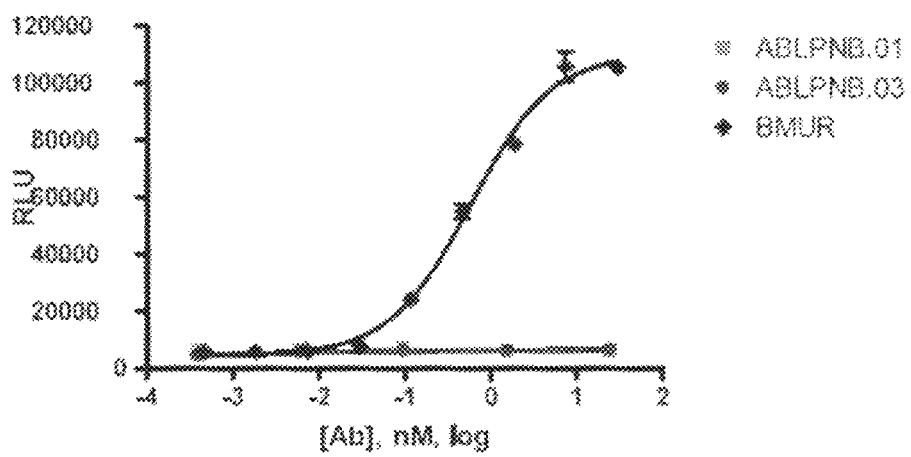
Figure 9D:
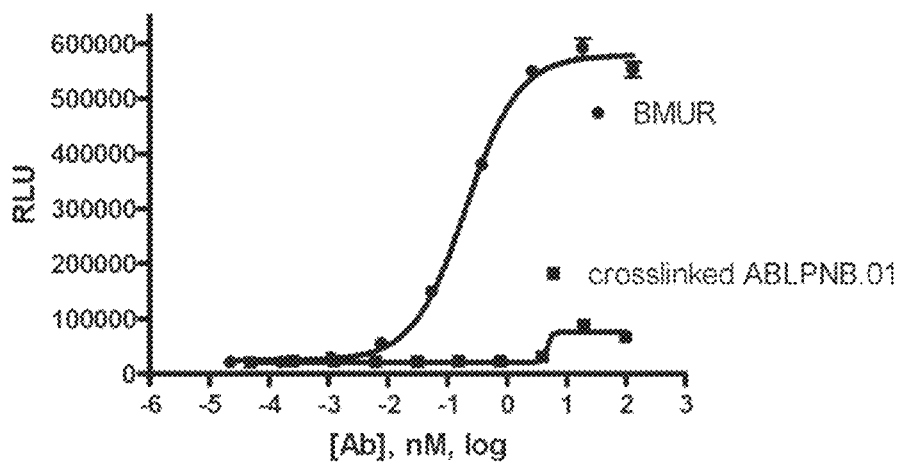
Figure 9E:
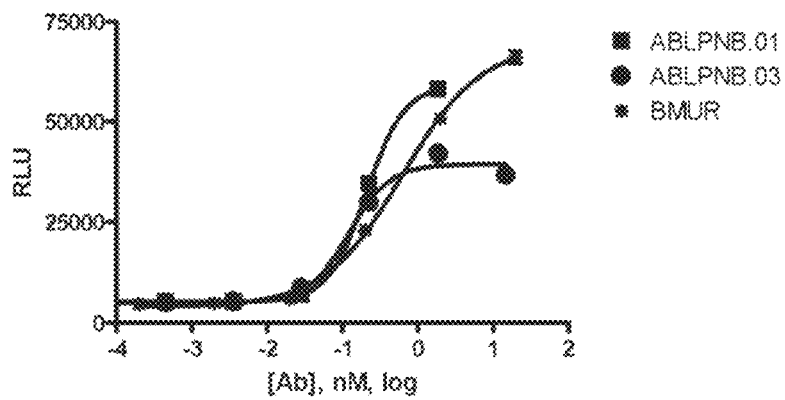
Figure 9F:
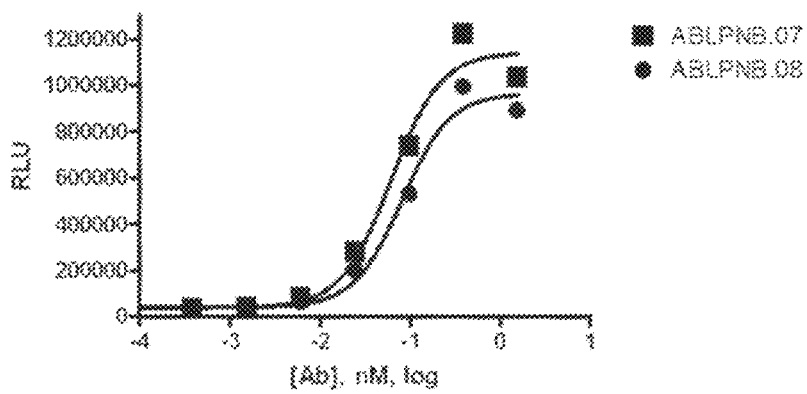

To test the ability of bispecific antibodies (ABLPNB.01, ABLPNB.03, ABLPNB.07 and ABLPNB.08) to promote 4-1BB signal, cell-based 4-1BB assay was used. In this assay, GloResponse™ NFκB-luc2/4-1BB Jurkat cell line (Promega, cat #CS196004) was used as effector cells and PD-L1-expressing or not expressing cancer cell line as target cells. GloResponse™ NFκB-luc2/4-1BB Jurkat cell line is genetically modified to stably express 4-1BB and luciferase downstream of a response element. Luciferase expression is induced upon antibody binding to the 4-1BB receptor. In brief, plate HCC1954 (expressing PD-L1) or BT474 or NCI-N87 (not expressing PD-L1) at $2.5 \times 10^4$ cells per well in a white 96-well assay plate in 100 μL culture medium (RPMI1640+10% FBS). Culture overnight in 37° C.+5% $CO_2$ humidified incubator. After overnight culture, remove 100 μL of culture medium and dispense 25 μL of Assay Medium (RPMI1640+1% FBS) to pre-plated target cells. 25 μL of bispecific antibodies (starting from 15 nM diluted for 8-fold or 1.5 nM diluted for 4-fold) and BMUR or monoclonal antibody 41B01 (starting from 20 nM for 10-fold or 133 nM for 6-fold) were added to the plate. Harvest GloResponse™ NFκB-luc2/4-1BB Jurkat cell line and resuspend with Assay Medium. Dispense 25 μL of GloResponse™ NFκB-luc2/4-1BB Jurkat cell line per well to make $2.5 \times 10^4$ cells per well to plate. Culture 6 hrs in 37° C.+5% $CO_2$ humidified incubator. During incubation time reconstitute Bio-Glo™ reagent according to the manufacturer's instruction. After 6 hrs incubation, add 75 per well of Bio-Glo™ Reagent to the assay plate. Wait 5 minutes and measure luminescence using microplate reader. Four-parameter logistic curve analysis was performed with GraphPad software. The results are shown in FIGS. 9A-9F. As shown in FIGS. 9A-9B, anti-4-1BB monoclonal antibody showed very limited 4-1BB signal activation comparing to BUMR. "41B01 (assayed in Fc-cross linked form) showed only weak activation of 4-1BB signal (FIG. 9B). In case of bispecific antibody, co-cultured with PD-L1 negative cancer cells (FIGS. 9C and 9D), PD-L1×4-1BB bispecific antibody showed no activation of 4-1BB signal (FIG. 9C) and weak 4-1BB signal upon Fc-cross linking as presented in FIGS. 9C and 9D, respectively. In the presence of PD-L1, i.e., when co-cultured with PD-L1 positive target cells (FIGS. 9E and 9F), PD-L1×4-1BB bispecific antibody showed 4-1BB signal activation, which was depending on the presence of tumor antigen (PD-L1).

Figure 10A:
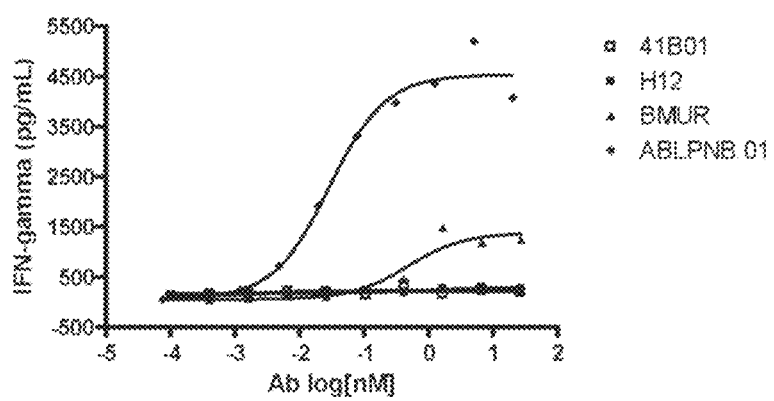
FIGS. 10A and 10B show the PBMC assay results for the anti-PD-L1/anti-4-1BB bispecific antibodies according to embodiments. It also shows graphs illustrating the T-cell promoting activities of the anti-PD-L1/anti-4-1BB bispecific antibodies according to embodiments.
Figure 10B:
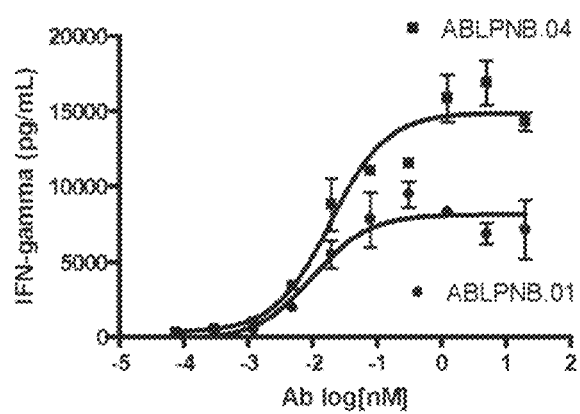

4.5. Activity of the Bispecific Antibodies to Promote Human T Cell Immune Response To test the ability of bispecific antibodies to stimulated human PBMCs response, cytokine production assay was used. Human PBMCs stimulated with human anti-CD3 antibody were used as the effector cells. HCC1954 cells which express PD-L1 was used as the target cells. In this system, PBMCs ($3 \times 10^4$) were co-cultured with HCC1954 ($1 \times 10^4$) in the presence of human anti-CD3 antibody. Bispecific antibodies (ABLPNB.01 and ABLPNB.04) (starting from 20 nM (=4 μg/mL) diluted for 10 dose) and their counterpart monoclonal antibodies (41B01 and H12) (starting from 26.67 nM (=4 μg/mL) diluted for 10 dose) were added to the mixed culture. As shown in FIGS. 10A and 10B, only bispecific antibody can activate T cell in the presence of PD-L1 expressing tumor cells (See FIG. 10A). Moreover, bispecific antibodies activated T-cell in dose dependent manner (See FIG. 10B).

4.6. Tumor Growth Inhibition of the Bispecific Antibodies (In Vivo Assay)

Figure 11:
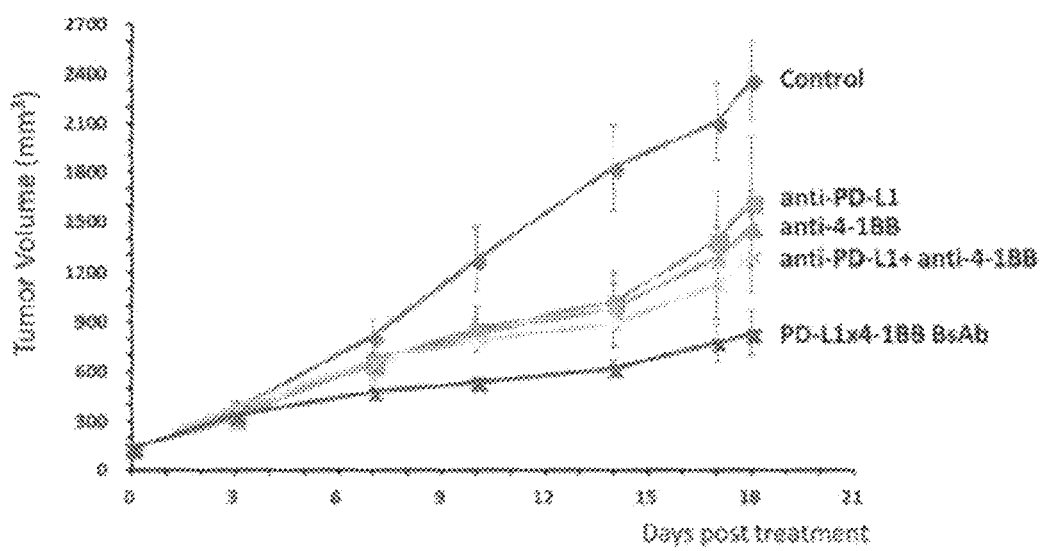
FIG. 11 shows a graph illustrating tumor growth inhibition effect of the anti-PD-L1/anti-4-1BB bispecific antibody according to an embodiment.

Humanized mice that express the extracellular domain of human 4-1BB were used. Mouse colon adenocarcinoma cells (MC38) were engineered to express human PD-L1. Humanized mice (h4-1BB) were subcutaneously implanted with MC38-hPD-L1 cells. Mouse were intraperitoneally administered Q3D for 5 times (five time injection of the antibody every three days) with following antibodies: isotype control (10 mg/kg), anti-PD-L1 antibody (H12, 10 mg/kg), anti-4-1BB antibody (41B01, 10 mg/kg), combination of anti-PD-L1 (H12, 10 mg/kg) and anti-4-1BB (41B01, 10 mg/kg) and PD-L1×4-1BB Bispecific antibody (BsAb) {BLPNB.01, 13.3 mg/kg}. Tumor volumes were monitored by caliper measurement twice per week for the duration of the experiment. Tumor growth inhibition induced by ABLPNB.01 was significantly greater than that observed with the combination of each targeting monoclonal antibodies (See FIG. 11).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. An anti-PD-L1/anti-4-1BB bispecific antibody, comprising an anti-PD-L1 antibody or an antigen-binding fragment thereof and an anti-4-1BB antibody or an antigen-binding fragment thereof, wherein the anti-PD-L1 antibody or antigen-binding fragment thereof comprises a VH CDR1 comprising the amino acid sequence of SEQ ID NO: 1; a VH CDR2 comprising the amino acid sequence selected from the group consisting of SEQ ID NOS: 2 and 3; a VH CDR3 comprising the amino acid sequence selected from the group consisting of SEQ ID NOS: 4, 5, 262, 263, 264, 265, 266 and 267; a VL CDR1 comprising the amino acid sequence selected from the group consisting of SEQ ID NOS: 6, 268 and 269; a VL CDR2 comprising the amino acid sequence of SEQ ID NO: 7; and a VL CDR3 comprising the amino acid sequence selected from the group consisting of SEQ ID NOS: 8, 270, 271 and 272; and the anti-4-1BB antibody or antigen-binding fragment thereof comprises a VH CDR1 comprising the amino acid sequence selected from the group consisting of SEQ ID NOS: 10 and 11; a VH CDR2 comprising the amino acid sequence selected from the group consisting of SEQ ID NOS: 12 and 13; a VH CDR3 comprising the amino acid sequence selected from the group consisting of SEQ ID NOS: 14, 15, 16 and 17; a VL CDR1 comprising the amino acid sequence of SEQ ID NO: 18; a VL CDR2 comprising the amino acid sequence of SEQ ID NO: 19; and a VL CDR3 comprising the amino acid sequence of SEQ ID NO: 20.

2. The anti-PD-L1/anti-4-1BB bispecific antibody of claim 1, wherein the anti-PD-L1 antibody or antigen-binding fragment thereof is capable of specifically binding to an immunoglobulin C (Ig C) domain of a human Programmed death-ligand 1 (PD-L1) protein, wherein the Ig C domain consists of amino acid residues 133-225.

3. The anti-PD-L1/anti-4-1BB bispecific antibody of claim 1, wherein the anti-PD-L1 antibody or antigen-binding fragment thereof does not bind to an immunoglobulin V (Ig V) domain of the PD-L1 protein, wherein the Ig V domain consists of amino acid residues 19-127.

4. The anti-PD-L1/anti-4-1BB bispecific antibody of claim 1, wherein the anti-PD-L1 antibody or antigen-binding fragment thereof comprises a heavy chain variable region comprising an amino acid sequence selected from the group consisting of SEQ ID NOS: 103, and 104, or a polypeptide having at least 90% sequence identity to an amino acid sequence selected from the group consisting of SEQ ID NOS: 103, and 104.

5. The anti-PD-L1/anti-4-1BB bispecific antibody of claim 1, wherein the anti-PD-L1 antibody or antigen-binding fragment thereof comprises a light chain variable region comprising an amino acid sequence selected from the group consisting of SEQ ID NOS: 105, and 106, or a peptide having at least 90% sequence identity to an amino acid sequence selected from the group consisting of SEQ ID NOS: 105, and 106.

6. The anti-PD-L1/anti-4-1BB bispecific antibody of claim 1, wherein the anti-4-1BB antibody or antigen-binding fragment thereof comprises a heavy chain variable region comprising an amino acid sequence selected from the group consisting of SEQ ID NOS: 21, 22, 23, and 24, or a polypeptide having at least 90% sequence identity to an amino acid sequence selected from the group consisting of SEQ ID NOS: 21, 22, 23, and 24.

7. The anti-PD-L1/anti-4-1BB bispecific antibody of claim 1, wherein the anti-4-1BB antibody or antigen-binding fragment thereof comprises a light chain variable region comprising an amino acid sequence selected from the group consisting of SEQ ID NOS: 25 and 26, or a peptide having at least 90% sequence identity to an amino acid sequence selected from the group consisting of SEQ ID NOS: 25 and 26.

8. The anti-PD-L1/anti-4-1BB bispecific antibody of claim 1, which is in the form of IgG-scFv form.

9. A method for treating a disease associated with PD-L1, 4-1BB, or both thereof, comprising administering to the patient a composition comprising the anti-PD-L1/anti-4-1BB bispecific antibody of claim 1 and a pharmaceutically acceptable carrier.

10. The method of claim 9, wherein the disease associated with PD-L1, 4-1BB, or both thereof is cancer.

* * * * *